(12) United States Patent
Tong

(10) Patent No.: US 9,216,957 B2
(45) Date of Patent: Dec. 22, 2015

(54) ANDROGEN RECEPTOR ANTAGONISTS AND USES THEREOF

(75) Inventor: Youzhi Tong, Jiangsu (CN)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 0 days.

(21) Appl. No.: 14/003,547

(22) PCT Filed: Mar. 8, 2012

(86) PCT No.: PCT/CN2012/072091
§ 371 (c)(1),
(2), (4) Date: Nov. 18, 2013

(87) PCT Pub. No.: WO2012/119559
PCT Pub. Date: Sep. 13, 2012

(65) Prior Publication Data
US 2014/0066425 A1   Mar. 6, 2014

Related U.S. Application Data

(60) Provisional application No. 61/451,120, filed on Mar. 10, 2011.

(51) Int. Cl.
| | | |
|---|---|---|
| *C07D 413/10* | (2006.01) | |
| *C07D 413/14* | (2006.01) | |
| *C07D 417/14* | (2006.01) | |
| *C07D 403/10* | (2006.01) | |
| *C07D 235/02* | (2006.01) | |
| *A61K 31/415* | (2006.01) | |
| *A61K 31/00* | (2006.01) | |
| *A61K 31/445* | (2006.01) | |
| *A61K 31/44* | (2006.01) | |
| *A61K 31/535* | (2006.01) | |
| *A61K 31/42* | (2006.01) | |
| *C07D 239/22* | (2006.01) | |
| *C07D 233/86* | (2006.01) | |
| *C07D 401/04* | (2006.01) | |
| *C07D 401/10* | (2006.01) | |
| *C07D 401/14* | (2006.01) | |

(52) U.S. Cl.
CPC ............ *C07D 239/22* (2013.01); *C07D 233/86* (2013.01); *C07D 235/02* (2013.01); *C07D 401/04* (2013.01); *C07D 401/10* (2013.01); *C07D 401/14* (2013.01); *C07D 403/10* (2013.01); *C07D 413/10* (2013.01); *C07D 413/14* (2013.01); *C07D 417/14* (2013.01)

(58) Field of Classification Search
USPC ............ 548/312.4, 317.1, 235; 544/139, 124; 546/271.4, 187; 514/210.18, 326, 341, 514/235.8, 374, 397, 391
See application file for complete search history.

(56) References Cited

U.S. PATENT DOCUMENTS

| | | |
|---|---|---|
| 5,434,176 A | 7/1995 | Claussner et al. |
| 5,589,497 A | 12/1996 | Claussner et al. |
| 5,646,172 A | 7/1997 | Claussner et al. |
| 5,705,654 A | 1/1998 | Claussner et al. |
| 5,750,553 A | 5/1998 | Claussner et al. |
| 6,087,509 A | 7/2000 | Claussner et al. |
| 6,242,611 B1 | 6/2001 | Claussner et al. |
| 6,982,265 B1 | 1/2006 | Hunt et al. |
| 7,112,675 B2 | 9/2006 | Hunt et al. |
| 7,244,733 B2 | 7/2007 | Hunt et al. |
| 7,709,516 B2 | 5/2010 | Labrie et al. |
| 7,709,517 B2 | 5/2010 | Sawyers et al. |
| 7,803,826 B2 | 9/2010 | Tachibana et al. |
| 8,168,627 B2 | 5/2012 | Labrie et al. |
| 8,470,829 B2 | 6/2013 | Tachibana et al. |
| 2006/0287327 A1 | 12/2006 | Labrie et al. |
| 2010/0063120 A1 | 3/2010 | Nique et al. |
| 2011/0306615 A1 | 12/2011 | Tachibana et al. |

FOREIGN PATENT DOCUMENTS

| | | |
|---|---|---|
| CA | 2579886 | 3/2006 |
| CA | 2608436 | 11/2006 |
| CA | 2648139 | 11/2007 |
| CA | 2703635 | 4/2009 |
| CA | 2790924 | 9/2011 |
| CN | 101048381 A | 10/2007 |
| CN | 101222922 A | 7/2008 |
| CN | 101460467 A | 6/2009 |
| CN | 101817787 | 9/2010 |
| CN | 102884057 A | 1/2013 |
| EP | 1775289 | 4/2007 |
| EP | 1790640 | 5/2007 |
| JP | H08-99977 | 4/1996 |

(Continued)

OTHER PUBLICATIONS

Jung et al., "Structure-activity relationship for thiohydantoin androgen receptor antagonists for castration-resistant prostate cancer (CRPC)," *Journal of Medicinal Chemistry*, 53(7):2779-2796, 2010.
PCT International Search Report and Written Opinion issued in International Patent Application No. PCT/CN2012/072091, dated May 31, 2012.
Yoshino et al., "Design and synthesis of an androgen receptor pure antognist (CH5137293) for the treatment of castration-resistant prostate cancer," *Bioorganic & Medicinal Chemistry*, 18(23):8150-8157, 2010.
Extended European Search Report issued in European Patent Application No. 10814994.9, dated Feb. 21, 2013.

(Continued)

*Primary Examiner* — Nyeemah A Grazier
(74) *Attorney, Agent, or Firm* — Parker Highlander PLLC

(57) ABSTRACT

Disclosed are substituted thioimidazolidinone compounds and pharmaceutical compositions comprising such compounds. The compounds and compositions can be used for treatment of androgen receptor-associated diseases or disorders, such as prostate cancer, benign prostatic hypertrophy, male hair loss and hypertrichosis.

14 Claims, No Drawings

(56) References Cited

FOREIGN PATENT DOCUMENTS

| | | |
|---|---|---|
| JP | H09-507241 | 7/1997 |
| JP | 2000502053 | 2/2000 |
| JP | 2000502669 | 3/2000 |
| JP | 2008543792 | 12/2008 |
| JP | 2009-531449 | 9/2009 |
| JP | 2011-500813 | 1/2011 |
| JP | 2013-504522 | 2/2013 |
| KR | 20070106969 | 11/2007 |
| KR | 20080014039 | 2/2008 |
| WO | WO 95/18794 | 7/1995 |
| WO | WO 97/19064 | 5/1997 |
| WO | WO 97/23464 | 7/1997 |
| WO | WO 2004/031160 | 4/2004 |
| WO | WO 2004/111012 | 12/2004 |
| WO | WO 2006/013887 | 2/2006 |
| WO | WO 2006/028226 | 3/2006 |
| WO | WO 2006/124118 | 11/2006 |
| WO | WO 2006/133567 | 12/2006 |
| WO | WO 2007/127010 | 11/2007 |
| WO | WO 2007/137874 | 12/2007 |
| WO | WO 2008/093838 | 8/2008 |
| WO | WO 2009/055053 | 4/2009 |
| WO | WO 2010/029119 | 3/2010 |
| WO | WO 2010/118354 | 10/2010 |
| WO | WO 2011/029329 | 3/2011 |
| WO | WO 2011/029392 | 3/2011 |
| WO | WO 2011/103202 | 8/2011 |
| WO | WO 2012/011840 | 1/2012 |

OTHER PUBLICATIONS

Office Communication issued in Canadian Patent Application No. 2,772,579, dated Feb. 13, 2013.
Office Communication issued in Japanese Patent Application No. 2012-528220, dated Oct. 22, 2013. (English translation of Japanese text).
Office Communication issued in Korean Patent Application No. 10-2012-7007933, dated Sep. 16, 2013. (English translation of Korean text).
Silva et al., "Advances in prodrug design," *Mini-Reviews in Medicinal Chemistry*, 5: 893-914, 2005.
Tran et al., "Development of a Second-Generation Antiandrogen for Treatment of Advanced Prostate Cancer," *Science*, 324:787-790., 2009.
Tran et al., Supporting Online Material for "Development of a Second-Generation Antiandrogen for Treatment of Advanced Prostate Cancer," 19 pages, 2009.
Trump et al., "Design and Synthesis of an Array of Selective Androgen," *J. Comb. Chem.*, 9:107-114, 2007.
Office Communication issued in European Patent Application No. 12755126.5, dated Jul. 30, 2014.
Office Communication issued in Canadian Patent Application No. 2,829,322, dated Sep. 29, 2014.

ANDROGEN RECEPTOR ANTAGONISTS AND USES THEREOF

This application is a national phase application under 35 U.S.C. §371 of International Patent Application No. PCT/CN2012/072091, filed Aug. 3, 2012, which claims priority to U.S. Provisional Patent Application Ser. No. 61/451,120 filed Mar. 10, 2011, the entire contents of which are incorporated herein by reference.

FIELD OF THE INVENTION

The present invention relates to novel substituted thioimidazolidinone compounds and pharmaceutical compositions comprising such compounds for treatment of androgen receptor-associated diseases or disorders, such as prostate cancer, benign prostatic hypertrophy, male hair loss, muscle loss, acne and hirsutism.

BACKGROUND OF THE INVENTION

The androgen receptor (AR) is a 110 Kda steroidal nuclear receptor. One of its key functions is androgen-activated gene transcription. The androgen receptor plays an important role in many male hormone related diseases such as prostate cancer, benign prostatic hypertrophy, male hair loss, muscle loss and hirsutism (hypertrichosis). For this reason, selective androgen receptor antagonists may be useful for such conditions and diseases including but not limited to: male contraception; treatment of a variety of male hormone-related conditions such as hypersexuality and sexual deviation; treatment of conditions including benign prostatic hyperplasia, acne vugaris, androgenetic alopecia, and hirsutism; preventing the symptoms associated with reduced testosterone such as hot flashes after castration; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer is one of the most common cancers in men around the world, and is one of the leading causes of cancer death in men in the United States. Current standard treatment for local prostate cancer is surgery and radiation. Unfortunately, the cancer relapses in one-third of the treated patients. Together with patients diagnosed with advanced prostate cancer, they are treated with surgical castration or chemical castration, which is called hormone therapy (HT). Often HT is also combined with drugs acting as androgen receptor antagonists. Hormone therapy is highly effective for controlling cancer cells in most of patients with advanced prostate cancer. However, the prostate cancer cells eventually adapt to the low androgen environment and become resistant to HT. As a result, the cancer will recur in almost all such patients in 2-5 years.

Androgen receptor antagonist drugs, such as flutamide and bicalutamide, were originally designed to avoid the side effects of HT and to overcome resistance in prostate cancer patients. Although these androgen receptor antagonists work well as a co-treatment with HT in naïve advanced prostate cancer patients, their efficacy against refractory prostate cancer, as a single agent, or co-treatment, has been limited. There have been reports that androgen agonism was observed for hydroxyfluamide (the active form of flutamide) and bicalutamide. The residual agonistic effect may be responsible for the drugs' ineffectiveness in overcoming resistance. The therapeutic benefit of these androgen receptor antagonist drugs have also been hampered by significant side effects such as liver toxicities associated with flutamide and bicalutamide. Recent studies have suggested that reactivation of the AR signaling pathway may be the root cause for developing resistance to HT. Mutation and over-expression of AR are two of the common underlying molecular mechanisms for the observed resistance.

Therefore, there is significant medical need for better androgen receptor antagonists that should have potent antagonism but devoid of any agonism when treating castration resistant prostate cancer cells. There is also a need to reduce the observed side effects such as liver toxicity found in existing androgen receptor antagonist drugs.

SUMMARY OF THE INVENTION

The present invention comprises compounds of formulas (Ia), (I), (II), (III) or (IV) below, methods of using such compounds as antagonists of androgen receptors, and pharmaceutical compositions containing such compounds and salts thereof.

In one embodiment, the invention is directed to compounds and pharmaceutical compositions comprising a compound of formula (Ia):

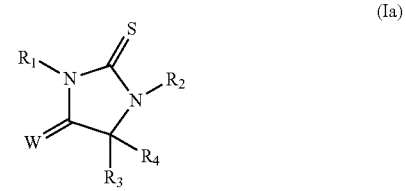

or a pharmaceutically-acceptable salt, solvate, hydrate, prodrug or derivative thereof,
wherein $R_1$ is selected from

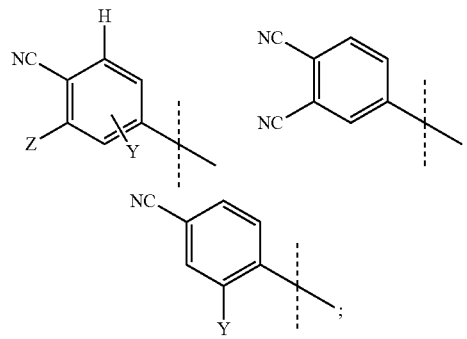

wherein Z is selected from hydrogen, $CF_3$, $C_1$-$C_3$ alkoxy, $CF_3O$, halogen, cyano and $C_1$-$C_4$ alkyl optionally substituted with one or more halogens;
Y is independently selected from one or two halogen, $C_1$-$C_3$ alkoxy, hydroxyl, $CF_3O$ and cyano;
W is selected from oxygen, sulfur and two hydrogens;
$R_3$ and $R_4$ are independently selected from $C_1$-$C_4$ alkyl optionally substituted with one or more fluoro or hydroxyl groups, or $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen; and $R_2$ is a substituted or unsubstituted alkyl, aryl, heteroaryl or heterocyclic group.

In certain embodiments, Y is halogen or cyano. In certain embodiments, Z is halogen, methoxy, cyano, methyl or $CF_3$. In certain embodiments, W is oxygen.

In certain embodiments, $R_2$ is $-A_1-A_2$, wherein $A_1$ is an aryl group or heteoaryl group optionally substituted with one or more $C_1-C_4$ alkyl, cyano, hydroxyl, methoxy, ethoxy, halogen or a 5-6 membered heteroaryl group; and $A_2$ is $(CF_2)_a(CH_2)_mY_1(CH_2)_nQ$ wherein a, m and n are integers independently selected from 0 to 4 and wherein at least one of a or m or n is not zero, or $A_2$ is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1-C_3$ alkoxy, C(S)NR"$R_1"$, C(O)OR", OC(O)NR"$R_1"$, C(O)NR"$R_1"$, optionally substituted 5-6 membered heteroaryl, and an optionally substituted 4-6 membered heterocycle; and $Y_1$ is selected from direct bond, —O—, —S—, and —NR"—; R" and $R_1"$ are independently selected from hydrogen, $C_1-C_6$ alkyl, $C_1-C_6$ cycloalkyl and $C_1-C_6$ alkenyl, or NR"$R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In another embodiment, the invention is directed to compounds and pharmaceutical compositions comprising a compound of formula (I):

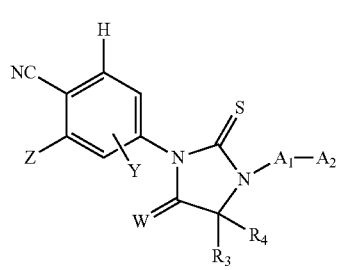

(I)

or a pharmaceutically-acceptable salt, solvate, hydrate, prodrug or derivative thereof, wherein Z is selected from hydrogen, $CF_3$, $C_1-C_3$ alkoxy, $CF_3O$, halogen, cyano and $C_1-C_4$ alkyl optionally substituted with one or more halogens;

Y is selected from halogen, $C_1-C_3$ alkoxy, hydroxyl, $CF_3O$ and cyano;

W is selected from oxygen, sulfur and two hydrogens;

$R_3$ and $R_4$ are independently selected from $C_1-C_4$ alkyl optionally substituted with one or more fluoro or hydroxyl groups, or $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen;

$A_1$ is an aryl group or heteoaryl group optionally substituted with one or more $C_1-C_4$ alkyl, cyano, hydroxyl, methoxy, ethoxyl, halogen or an optionally substituted 5-6 membered heteroaryl group;

$A_2$ is $(CF_2)_a(CH_2)_mY_1(CH_2)_nQ$ wherein a, m and n are integers independently selected from 0 to 4 and wherein at least one of a or m or n is not zero, or $A_2$ is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1-C_3$ alkoxy, C(S)NR"$R_1"$, C(O)OR", OC(O)NR"$R_1"$, C(O)NR"$R_1"$, optionally substituted 5-6 membered heteroaryl, and an optionally substituted 4-6 membered heterocycle; and $Y_1$ is selected from direct bond, —O—, —S—, and —NR"—; R" and $R_1"$ are independently selected from hydrogen, $C_1-C_6$ alkyl, $C_1-C_6$ cycloalkyl and $C_1-C_6$ alkenyl, or NR"$R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of compounds of formula (I), Z is halogen, methoxy, cyano, methyl or $CF_3$. In other embodiments, W is oxygen. In other embodiments, $A_1$ is an phenyl group or pyridyl group optionally substituted with one or more $C_1-C_4$ alkyl, cyano, hydroxyl, methoxy, ethoxy, halogen or an optionally substituted 5-6 membered heteroaryl group. In other embodiments, Q is an optionally substituted 5-6 membered heteroaryl group.

In other embodiments, $A_2$ is $(CH_2)_mY_1(CH_2)_nQ'$ wherein $Y_1$ is a bond, m and n are integers independently selected from 0 to 2 where at least one of m or n is not zero; Q' is selected from C(O)NHR", $C(R_xR_y)C(O)NR"R_1"$, $SO_2R"$, $SO_2NR"R_1"$, cyano, hydroxyl, $C_1-C_3$ alkoxy, C(S)NR"$R_1"$, C(O)OR", OC(O)NR"$R_1"$, C(O)NR"$R_1"$, optionally substituted 5-6 membered heteroaryl, and an optionally substituted 4-6 membered heterocycle; and R" and $R_1"$ are independently selected from hydrogen, $C_1-C_6$ alkyl, $C_1-C_6$ cycloalkyl and $C_1-C_6$ alkenyl or NR"$R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In other embodiments, m+n is 2 or 3.

In other embodiments, Q' is selected from $C(R_xR_y)C(O)NR"R_1"$, OC(O)NR"$R_1"$, an optionally substituted 5-6 membered heteroaryl, and a optionally substituted 4-6 membered heterocycle; and R" and $R_1"$ are independently selected from hydrogen, $C_1-C_6$ alkyl, $C_1-C_6$ cycloalkyl and $C_1-C_6$ alkenyl or NR"$R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In other embodiments, Q' is an optionally substituted 5-6 membered heteroaryl group.

In another embodiment, the invention is directed to compounds and pharmaceutical compositions comprising a compound of formula (II):

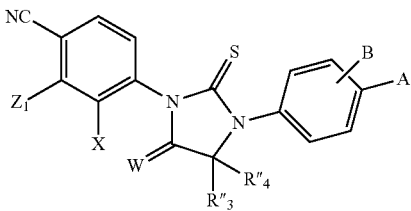

(II)

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, $C_1$-$C_3$ alkoxy, $CF_3O$, hydroxyl and cyano;

W is selected from oxygen, sulfur and two hydrogens;

$R''_3$ and $R''_4$ are methyl, or $R''_3$ and $R''_4$ and the carbon to which they are attached together form a 3-6 membered cycloalkyl ring optionally substituted with one or more fluoro or hydroxyl groups;

B is independently selected from one or more hydrogen, cyano, methyl, $CF_3$ or halogen; and A is $(CF_2)_a(CH_2)_mY_1(CH_2)_nQ$ where a, m and n are integers independently selected from 0 to 4 and wherein at least one of a or m or n is not zero; or A is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, $C(O)OR"$, $OC(O)NR"R_1"$, $C(O)NR"R_1"$, optionally substituted 5-6 membered heteroaryl, and an optionally substituted 4-6 membered heterocycle; and $Y_1$ is selected from direct bond, —O—, —S—, and —NR"—; R" and $R_1"$ are independently selected from hydrogen, $C_1$-$C_6$ alkyl, $C_1$-$C_6$ cycloalkyl and $C_1$-$C_6$ alkenyl or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of compounds of formula (II), $Z_1$ is $CF_3$, methoxy, halogen. In other embodiments, X is fluorine. In other embodiments, $R''_3$ and $R''_4$ are methyl, or $R''_3$ and $R''_4$ and the carbon to which they are attached together form a cyclopropyl or cyclobutyl or cyclopentyl or cyclohexyl ring which may be optionally substituted with one or more fluoro or hydroxyl groups. In other embodiments, Q is selected from $C(R_xR_y)C(O)NR"R_1"$, $OC(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or NR"$R_1$"together form a 3-7 membered heterocyclic ring wherein one or more carbons may be optional substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In other embodiments, Q is a 5-6 membered heteroaryl group.

In other embodiments, A is $(CH_2)_kQ'$ where k is an integer selected from 1 to 5; Q' is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, $C(O)OR"$, $OC(O)NR"R_1"$, $C(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or heterocyclic ring or a 3-5 membered cyclic ring wherein one carbon is replaced with an oxygen or an amine.

In other embodiments, Q' is selected from $C(R_xR_y)C(O)NR"R_1"$, $OC(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In other embodiments, k is 2 or 3. In other embodiments, Q' is a 5-6 membered heteroaryl group. In other embodiments, B is a hydrogen or a fluorine at ortho position of A. In other embodiments, W is oxygen.

In another embodiment, the invention is directed to compounds and pharmaceutical compositions comprising a compound of formula (III):

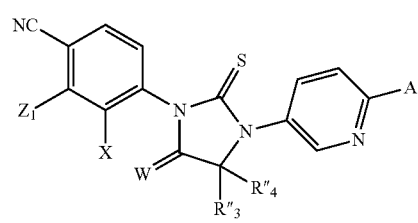

(III)

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, $C_1$-$C_3$ alkoxy, $CF_3O$, hydroxyl and cyano;

W is selected from oxygen, sulfur and two hydrogens;

$R''_3$ and $R''_4$ are methyl, or $R''_3$ and $R''_4$ and the carbon to which they are attached together form a 3-6 membered cycloalkyl ring optionally substituted with one or more fluoro or hydroxyl groups; and A is $(CF_2)_a(CH_2)_mY_1(CH_2)_nQ$ wherein a, m and n are integers independently selected from 0 to 4 and wherein at least one of a or m or n is not zero; or A is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, $C(O)OR"$, $OC(O)NR"R_1"$, $C(O)NR"R_1"$, optionally substituted 5-6 membered heteroaryl, and an optionally substituted 4-6 membered heterocycle; and Y$_1$ is selected from direct bond, —O—, —S—, and —NR"—; R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optionally substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine.

In another embodiment of compounds of formula (III), Z$_1$ is CF$_3$, methoxy, halogen. In another embodiment, X is fluorine. In another embodiment, R"$_3$ and R"$_4$ are methyl, or R"$_3$ and R"$_4$ and the carbon to which they are attached together form a cyclopropyl or cyclobutyl or cyclopentyl or cyclohexyl ring which may be optionally substituted with one or more fluoro or hydroxyl groups. In another embodiment, Q is a 5-6 membered heteroaryl group.

In another embodiment, A is (CH$_2$)$_m$Y$_1$(CH$_2$)$_n$Q' wherein Y$_1$ is a bond, m and n are integers independently selected from 0 to 2 and wherein at least one of m or n is not zero; Q' is selected from C(O)NHR", C(R$_x$R$_y$)C(O)NR"R$_1$", SO$_2$R", SO$_2$NR"R$_1$", cyano, hydroxyl, C$_1$-C$_3$ alkoxy, C(S)NR"R$_1$", C(O)OR", OC(O)NR"R$_1$", C(O)NR"R$_1$", optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optionally substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine.

In another embodiment, A is (CH$_2$)$_k$Q" where k is an integer selected from 1 to 5; Q' is selected from C(O)NHR", C(R$_x$R$_y$)C(O)NR"R$_1$", SO$_2$R", SO$_2$NR"R$_1$", cyano, hydroxyl, C$_1$-C$_3$ alkoxy, C(S)NR"R$_1$", C(O)OR", OC(O)NR"R$_1$", C(O)NR"R$_1$", optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optionally substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or heterocyclic ring or a 3-5 membered cyclic ring wherein one carbon is replaced with an oxygen or an amine. In another embodiment, k is 2 or 3.

In another embodiment, Q' is selected from C(R$_x$R$_y$)C(O)NR"R$_1$", OC(O)NR"R$_1$", a optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optional substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine. In another embodiment, Q' is a 5-6 membered heteroaryl group. In another embodiment, W is oxygen.

In another embodiment, the invention is directed to compounds and pharmaceutical compositions comprising a compound of formula (IV)

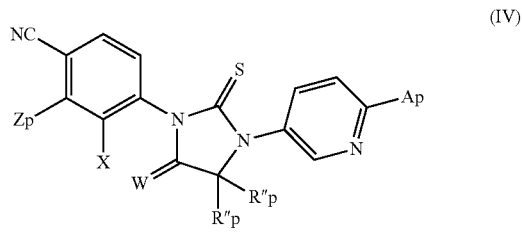

(IV)

or a pharmaceutically-acceptable salt, solvate, hydrate, prodrug or derivative thereof,
wherein Z$_p$ is selected from CF$_3$, methoxy, halogen and cyano;
W is selected from oxygen, sulfur and two hydrogens;
R"$_p$ and R"$_p$ are methyl, or R"$_p$ and R"$_p$ and the carbon to which they are attached together form a 3-6 membered cycloalkyl ring optionally substituted with one or more fluoro or hydroxyl groups; and
A$_p$ is (CH$_2$)$_m$Y$_1$(CH$_2$)$_n$Q where m and n are integers independently selected from 0 to 4 and wherein at least one of a or m or n is not zero; Q is selected from C(O)NHR", C(R$_x$R$_y$)C(O)NR"R$_1$", SO$_2$R", SO$_2$NR"R$_1$", cyano, hydroxyl, C$_1$-C$_3$ alkoxy, C(S)NR"R$_1$", C(O)OR", OC(O)NR"R$_1$", C(O)NR"R$_1$", optionally substituted 5-6 membered heteroaryl, and an optionally substituted 4-6 membered heterocycle; and Y$_1$ is selected from direct bond, —O—, —S—, and —NR"—; R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optional substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine.

In other embodiments, pharmaceutical compositions are provided comprising a compound of any one of the foregoing formulas and a pharmaceutically-acceptable carrier, diluent or excipient. In another embodiment, the invention is directed to a pharmaceutical composition comprising a compound of any one of the foregoing formulas or its pharmaceutically acceptable salt, prodrug or a solution thereof as an active ingredient. In another embodiment, a topical pharmaceutical formulation is provided comprising a compound according to any one of the forgoing formulas, for, in one embodiment, dermal applications.

In other embodiments, methods are provided for preventing, reducing the progression of, treating or regressing a disease or disorder related to androgen receptor activity by administering to a subject at risk for development thereof or afflicted therewith, a compound of any one of the foregoing formulas, or a pharmaceutical composition thereof. In other embodiments, the disease or disorder is selected from hormone sensitive prostate cancer or hormone refractory prostate cancer, benign prostatic hyperplasia, acne, hirsutism, excess sebum and alopecia. In another embodiment, provided are uses of a compound of any one of the foregoing formulas or a pharmaceutical composition thereof for male contraception. In other embodiments, uses are provided of a compound of any one of the foregoing formulas or a pharmaceutical composition thereof for treatment of hypersexuality, sexual deviation, benign prostatic hyperplasia, acne vugaris, androgenetic alopecia or hirsutism. In other embodiments, uses are provided for a compound of any one of the foregoing formulas or a pharmaceutical composition thereof for purposefully preventing or counteracting masculinisation in the case of transsexual women undergoing sex reassignment therapy. In other embodiments, uses are provided for a compound of any one of the foregoing formulas or a pharmaceutical composition thereof as an antineoplastic agent or palliative, adjuvant or neoadjuvant hormonal therapy in prostate cancer. In another embodiment, uses are provided for a compound of any one of the foregoing formulas or a pharmaceutical composition thereof for decreasing the incidence of, halting or causing a regression of prostate cancer.

DEFINITIONS

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds that combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, hetero aromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CH$_2$(CH$_2$)$_{0-6}$CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —C(=O)NHR$_x$; —CH$_2$(CH$_2$)$_{0-6}$C(=O)N(R$_x$)$_2$; —CH$_2$(CH$_2$)$_{0-6}$C(=O)NHR$_x$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzo-fused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$, tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "C$_1$-C$_6$ alkenylidene", as used herein, refers to a substituted or unsubstituted, linear or branched unsaturated divalent radical consisting solely of carbon and hydrogen atoms, having from two to six carbon atoms, having a free valence "—" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

In certain embodiments of the compounds described herein, W is two hydrogens. For example, in formula Ia, when W is two hydrogens, formula Ia is I' a. In formula I, when W is two hydrogens, formula I is I'. In formula II, when W is two hydrogens, formula II is II'. In formula III, when W is two hydrogens, formula III is III'. These are shown below.

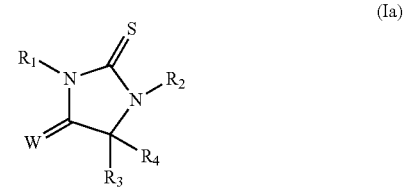

(Ia)

-continued

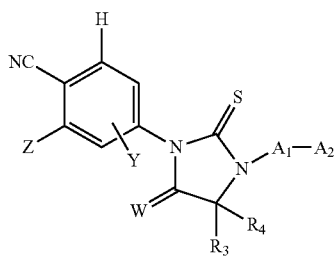
(I)

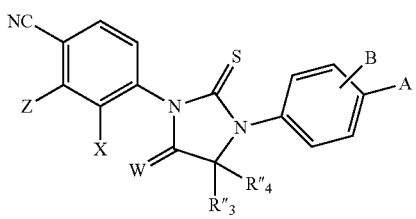
(II)

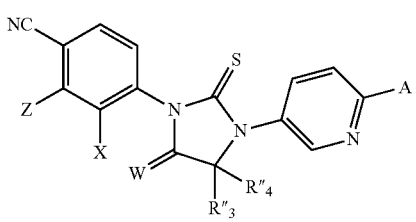
(III)

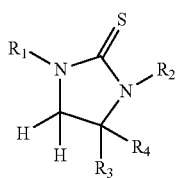
(I'a)

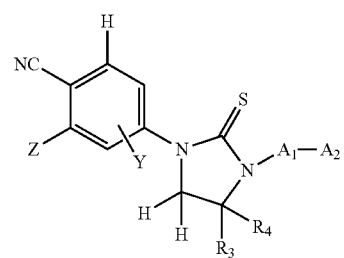
(I')

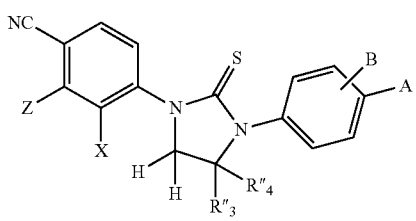
(II')

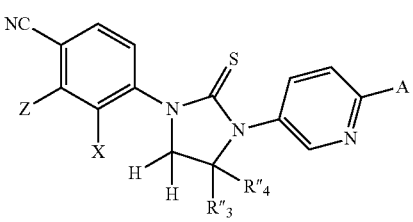
(III')

In other embodiments, one or more hydrogen atoms of a compound described herein can be replaced with a deuterium atom. Such deuterated derivatives are fully embraced by the disclosure herein. In certain embodiments, a hydrogen on a carbon of an aryl group or an heteroaryl group of $R_1$ or $R_2$ (formula Ia) or $A_1$ or $A_2$ (formula I) is replaced with a deuterium. In other embodiment, a hydrogen on a carbon of the alkyl group in Y, Z, R', Y' of formula Ia, I, II or III or the alkoxy group in Y, Y', Z of formula Ia, I, II or III is replaced with a deuterium. In other embodiment, a hydrogen on a carbon of an alkyl group or an alkoxy group if present in A or B of formula II is replaced with a deuterium. In another embodiment, a hydrogen on a carbon of an alkyl group or an alkoxy group in A of formula III is replaced with a deuterium. In other embodiment, a hydrogen on a carbon of the methylene group in $(CH_2)_mY_1(CH_2)_nQ$ of formula II or III wherein A is $(CH_2)_mY_1(CH_2)_nQ$ is replaced with a deuterium. In other embodiment, the hydrogen on a carbon of the methylene group in Q of formula II or III wherein A is $(CH_2)_mY_1(CH_2)_nQ$ is replaced with a deuterium. In other embodiment, the hydrogen on a carbon of the heteroaryl group in Q of formula II or III wherein A is $(CH_2)_mY_1(CH_2)_nQ$ is replaced with a deuterium. In other embodiment, the hydrogen on a carbon of the alkyl group in $R_3/R_4$, $R'_3/R'_4$ of formula Ia, I, II or III is replaced with a deuterium.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others prodrugs. A prodrug (also referred to as pro-drug) is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF THE INVENTION

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

As noted above, prostate cancer is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The present invention addresses the significant medical need for better androgen receptor antagonists that have potent antagonism but devoid of any agonism, and a reduction in the observed side effects such as liver toxicity found in existing androgen receptor antagonist drugs.

The compounds of the present invention are androgen receptor antagonists, which can be used to alleviate any condition associated with inappropriate activation of the androgen receptor. In addition to prostate cancer, other examples of such conditions include acne, hirsutism, seborrhoea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborhhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compounds may also be used topically to decrease seborrhea production and more specifically to alleviate hyperseborrhoea (oily skin), which can be used topically alleviate acne.

1) General Description of Compounds of the Invention

The present invention comprises compounds of formulas (I)-(IV) below, methods of using such compounds as antagonists of androgen receptors, and pharmaceutical compositions containing such compounds and salts thereof.

In certain embodiment, compounds of the invention include compounds of the general formula (Ia):

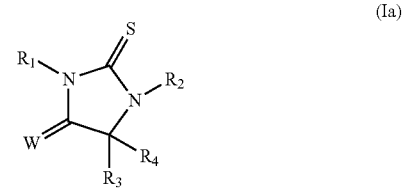

(Ia)

or a pharmaceutically-acceptable salt, solvate, hydrate, prodrug or derivative thereof,
wherein $R_1$ is selected from

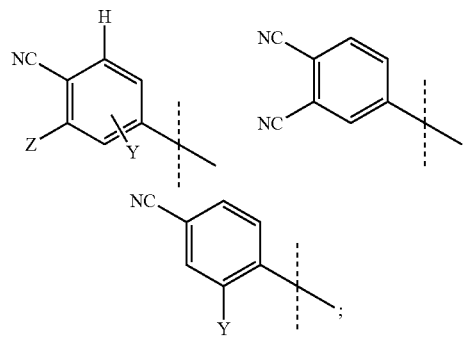

wherein Z is selected from hydrogen, $CF_3$, $C_1$-$C_3$ alkoxy, $CF_3O$, halogen, cyano and $C_1$-$C_4$ alkyl optionally substituted with one or more halogens;
Y is independently selected from one or two halogen, $C_1$-$C_3$ alkoxy, hydroxyl, $CF_3O$ and cyano;
W is selected from oxygen, sulfur and two hydrogens;
$R_3$ and $R_4$ are independently selected from $C_1$-$C_4$ alkyl optionally substituted with one or more fluoro or hydroxyl groups, or $R_3$ and $R_4$ together form a 3-6 membered cycloalkyl ring, wherein one or more carbons may be optional substituted with one or more fluoro or hydroxyl groups, and wherein one of the carbons is optionally an oxygen or nitrogen; and
$R_2$ is a substituted or unsubstituted alkyl, aryl, heteroaryl or heterocyclic group.
In certain embodiments, —$R_2$ is -$A_1$-$A_2$, wherein $A_1$ is an aryl group or heteoaryl group optionally substituted with one or more $C_1$-$C_4$ alkyl, cyano, hydroxyl, methoxy, ethoxy, halogen or a 5-6 membered heteroaryl group; and $A_2$ is $(CF_2)_a(CH_2)_mY_1(CH_2)_nQ$ wherein a, m and n are integers independently selected from 0 to 4 and wherein at least one of a or m or n is not zero, or $A_2$ is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, C(O)OR", OC(O)NR"$R_1$", C(O)NR"$R_1$", optionally substituted 5-6 membered heteroaryl, and an optionally substituted 4-6 membered heterocycle; and $Y_1$ is selected from direct bond, —O—, —S—, and —NR"—; R" and $R_1$" are independently selected from hydrogen, $C_1$-$C_6$ alkyl, $C_1$-$C_6$ cycloalkyl and $C_1$-$C_6$ alkenyl, or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of compounds of formula (Ia), compounds are provided of formula (I):

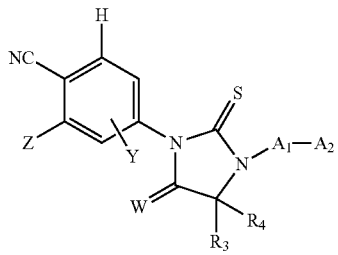

(I)

or a pharmaceutically-acceptable salt, solvate, hydrate, prodrug or derivative thereof, wherein Z is selected from hydrogen, $CF_3$, $C_1$-$C_3$ alkoxy, $CF_3O$, halogen, cyano and $C_1$-$C_4$ alkyl optionally substituted with one or more halogens;

Y is selected from halogen, $C_1$-$C_3$ alkoxy, hydroxyl, $CF_3O$ and cyano;

W is selected from oxygen, sulfur and two hydrogens;

$R_3$ and $R_4$ are independently selected from $C_1$-$C_4$ alkyl optionally substituted with one or more fluoro or hydroxyl groups, or $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen;

$A_1$ is an aryl group or heteoaryl group optionally substituted with one or more $C_1$-$C_4$ alkyl, cyano, hydroxyl, methoxy, ethoxyl, halogen or a 5-6 membered heteroaryl group;

$A_2$ is $(CF_2)_a(CH_2)_mY_1(CH_2)_nQ$ wherein a, m and n are integers independently selected from 0 to 4 and wherein at least one of a or m or n is not zero, or $A_2$ is $(CH_2)_mY_1(CH_2)_nQ$ wherein m and n are integers independently selected from 0 to 4 and wherein at least one of m or n is not zero; Q is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, C(O)OR", OC(O)NR"$R_1$", C(O)NR"$R_1$", optionally substituted 5-6 membered heteroaryl, and an optionally substituted 4-6 membered heterocycle; and $Y_1$ is selected from direct bond, —O—, —S—, and —NR"—; R" and $R_1$" are independently selected from hydrogen, $C_1$-$C_6$ alkyl, $C_1$-$C_6$ cycloalkyl and $C_1$-$C_6$ alkenyl, or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of the compound of formula (I), Y is halogen or cyano. In other embodiments, Z is halogen, methoxy, cyano, methyl or $CF_3$. In other embodiments, W is oxygen. In other embodiments, $A_1$ is an phenyl group or pyridyl group optionally substituted with one or more $C_1$-$C_4$ alkyl, cyano, hydroxyl, methoxy, ethoxyl, halogen or a 5-6 membered heteroaryl group. In certain embodiments, $A_1$ is selected from:

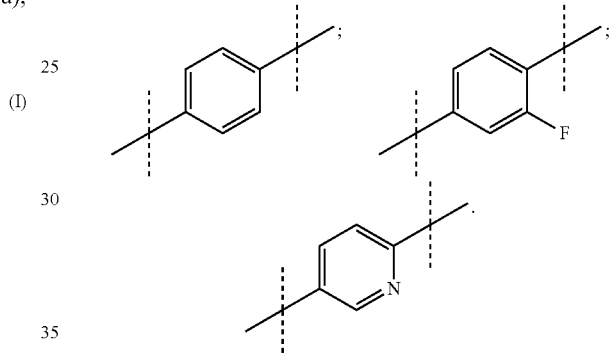

In other embodiments, Q is an optionally substituted 5-6 membered heteroaryl group, such as but not limited to pyridyl, pyrazinyl, pyrimidinyl, pyrrolyl, pyrazolyl, imidazolyl, thienyl, oxazolyl, isooxazolyl, dioxazolyl, thiadiazolyl, oxadiazolyl, tetrazolyl, triazolyl, thiatriazolyl, oxatriazolyl, thiadiazolyl, oxadiazolyl, thiazolyl, isothiazolyl, dithiazolyl. The 5-6 membered heteroaryl group can be substituted with hydroxyl, $C_1$-$C_3$ alkoxy, $C_1$-$C_6$ alkyl, halogen or cyano. In other embodiments, Q is selected from

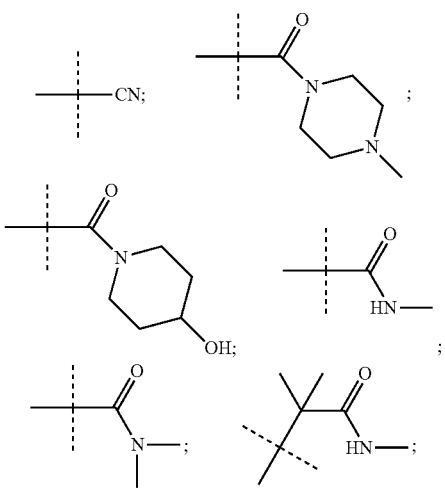

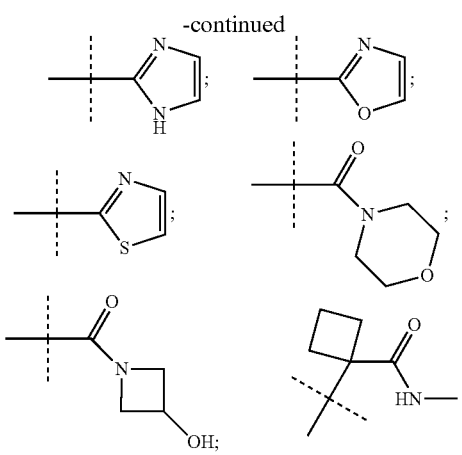

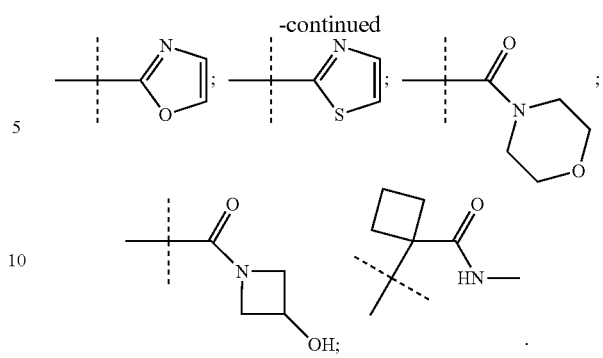

In other embodiments, Q is an optionally substituted 4-6 membered heterocycle, such as but not limited to furanyl, thiofuranyl, pyranyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, dithiazolidinyl, and tetrahydrofuryl. The 4-6 membered heterocycle can be substituted with hydroxyl, $C_1$-$C_3$ alkoxy, $C_1$-$C_6$ alkyl, halogen or cyano.

In other embodiments of the compound of formula (I), $A_2$ is $(CH_2)_m Y_1 (CH_2)_n C'$ wherein $Y_1$ is a bond, m and n are integers independently selected from 0 to 2 where at least one of m or n is not zero; Q' is selected from C(O)NHR", $C(R_xR_y)$ C(O)NR"$R_1$", $SO_2R$", $SO_2NR"R_1$", cyano, hydroxyl, $C_1$-$C_3$ alkoxy, C(S)NR"$R_1$", C(O)OR", OC(O)NR"$R_1$", C(O)NR"$R_1$", optionally substituted 5-6 membered heteroaryl, and an optionally substituted 4-6 membered heterocycle; and R" and $R_1$" are independently selected from hydrogen, $C_1$-$C_6$ alkyl, $C_1$-$C_6$ cycloalkyl and $C_1$-$C_6$ alkenyl or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of the compound of formula (I), Q' is selected from

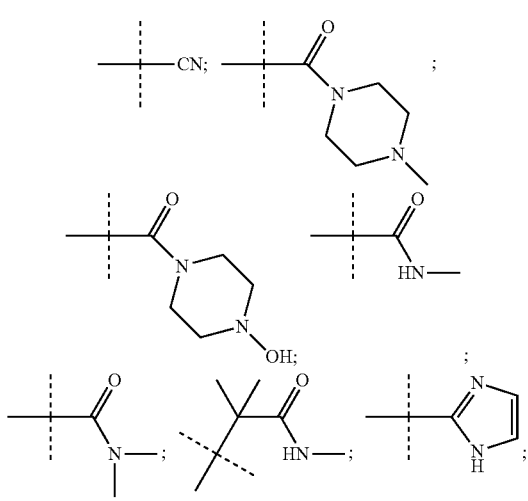

In certain embodiments of the compound of formula (I), m+n is 2 or 3.

In certain embodiments of the compound of formula (I), Q' is selected from $C(R_xR_y)C(O)NR"R_1$", OC(O)NR"$R_1$", optionally substituted 5-6 membered heteroaryl, and an optionally substituted 4-6 membered heterocycle; and R" and $R_1$" are independently selected from hydrogen, $C_1$-$C_6$ alkyl, $C_1$-$C_6$ cycloalkyl and $C_1$-$C_6$ alkenyl or NR"$R_1$" together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In other embodiments, Q' is a 5-6 membered heteroaryl group.

In certain embodiments of compounds of formula (I), NR"$R_1$" together form a 3-7 membered heterocyclic ring wherein one or more carbons may be optionally substituted with one or more hydroxyl, amino, cyano or fluoro groups, such as but not limited to azetidine, azetidin-3-ol, azetidin-3-ylamine, 3-fluoro-azetidine, azetidine-3-carbonitrile, pyrrolidine, pyrrolidin-3-ol, pyrrolidine-3,4-diol, piperidin-4-ol, morpholine, 4-methyl-piperazine, piperazine, or 4,4-difluoro-piperidine.

In certain embodiments, $C(R_xR_y)$ together form an optionally substituted 3-5 membered cyclic alkyl ring. Optional substituents include one or more hydroxyl, amino, cyano or fluoro groups. Non-limiting examples of such NR"$R_1$" include but not limited to cyclopropyl, cyclobutyl, cyclopentyl, or cyclobutan-3-ol.

In certain embodiments, $C(R_xR_y)$ together for a 3-5 membered cyclic ring wherein one carbon is replaced with an oxygen or an amine, such as but not limited to azetidine, N-methyl-azetidine, or oxetane.

A number of important subclasses of the compounds of formula (I) deserve special mention.
1) Z is hydrogen;
2) Z is $C_1$-$C_4$ alkyl such as but not limited to methyl or ethyl, optionally substituted with one or more halogen groups;
3) Z is $CF_3$;
4) Z is $C_1$-$C_3$ alkoxy;
5) Z is $CF_3O$;
6) Z is halogen;
7) Z is cyano;
8) Z is fluoro;
9) Y is halogen;
10) Y is alkoxy such as but not limited to methoxy and ethoxy;
11) Y is hydroxyl;
12) Y is $CF_3O$;
13) Y is cyano;
14) W is oxygen;

15) W is sulfur;
16) W is two hydrogens;
17) $R_3$ and $R_4$ are independently methyl, ethyl, propyl or butyl groups;
18) $R_3$ and $R_4$ and the carbon to which they are attached together form a 3-6 membered cycloalkyl ring optionally substituted with one or more fluoro groups, and in which one of the carbons is optionally an oxygen or nitrogen;
19) $R_3$ and $R_4$ and the carbon to which they are attached together form cyclopropyl;
20) $R_3$ and $R_4$ and the carbon to which they are attached together form cyclobutyl;
21) $R_3$ and $R_4$ and the carbon to which they are attached together form cyclopentyl;
22) $R_3$ and $R_4$ and the carbon to which they are attached together form azetidine, pyrrolidine or piperidine;
23) $R_3$ and $R_4$ and the carbon to which they are attached together form oxetane, tetrahydrofuran or tetrahydropyran.
24) $A_1$ is phenyl or naphthyl;
25) $A_1$ is a substituted aryl group such as but not limited to

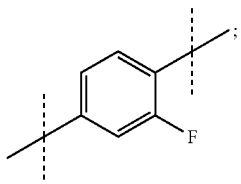

26) $A_1$ is a substituted heteroaryl group such as but not limited to

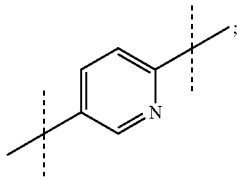

27) $A_1$ is substituted with one or more $C_1$-$C_6$ alkyl;
28) $A_1$ is substituted with one or more cyano;
29) $A_1$ is substituted with one or more hydroxyl;
30) $A_1$ is substituted with one or more alkoxy, such as methoxy and ethyoxy;
31) $A_1$ is substituted with one or more halogen;
32) $A_1$ is substituted with one or more optionally substituted 5-6 membered heteroaryl group such as but not limited to

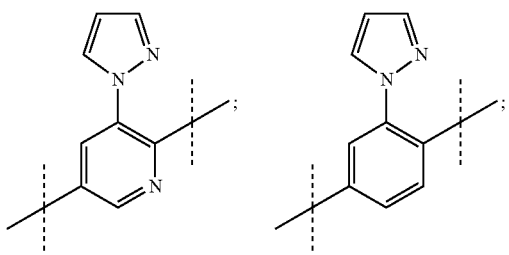

-continued

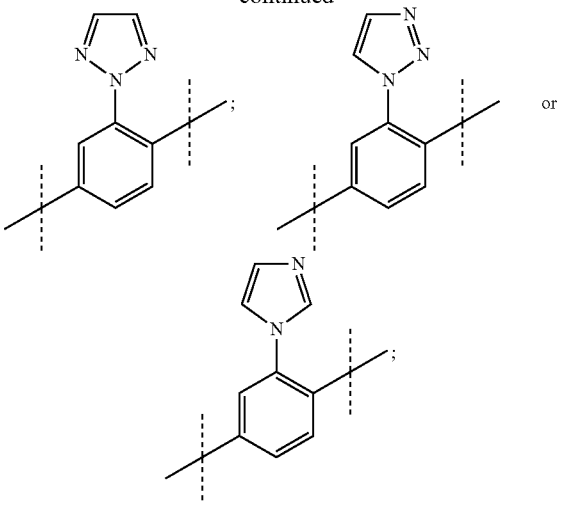

33) $Y_1$ is a direct bond;
34) $Y_1$ is —O—;
35) $Y_1$ is —S—;
36) $Y_1$ is —NR"—; wherein R" is hydrogen, $C_1$-$C_6$ alkyl, $C_1$-$C_6$ cycloalkyl or $C_1$-$C_6$ alkenyl;
37) $A_2$ is $(CH_2)_m Y_1 (CH_2)_n Q'$ wherein $Y_1$ is a bond, m and n are integers independently selected from 0 to 2 where at least one of m or n is not zero; and Q' is selected from $C(R_x R_y)C(O)NR"R_1"$, $OC(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or NR"$R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_x R_y)$ together form an optionally substituted 3-5 membered cyclic alkyl ring or a 3-5 membered cyclic ring wherein one carbon is replaced with an oxygen or an amine;
38) $A_2$ is $(CH_2)_m Y_1 (CH_2)_n Q'$ wherein $Y_1$ is a bond, m and n are integers independently selected from 0 to 2 where at least one of m or n is not zero; and Q' is an optionally substituted 5-6 membered heteroaryl group such as but not limited to

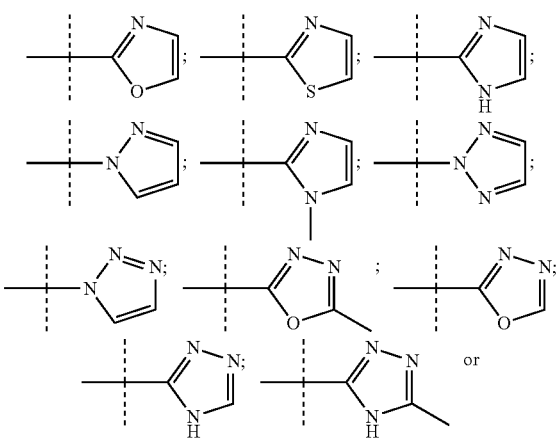

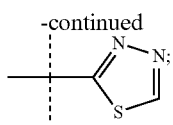

39) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from an optionally substituted 4-6 membered heterocycle such as but not limited to

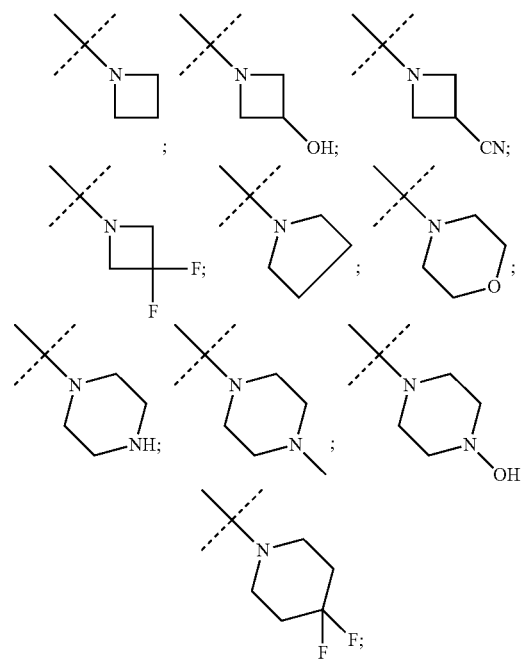

40) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from $C(R_xR_y)C(O)NR''R_1''$ or $OC(O)NR''R_1''$, and $R''$ and $R_1''$ are independently selected from hydrogen, $C_1$-$C_6$ alkyl, $C_1$-$C_6$ cycloalkyl and $C_1$-$C_6$ alkenyl; and $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine;

41) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from $C(R_xR_y)C(O)NR''R_1''$ or $OC(O)NR''R_1''$, and $NR''R_1''$ together form a 3-7 membered heterocyclic ring wherein one or more carbons may be optionally substituted with one or more hydroxyl, amino, cyano or fluoro groups such as

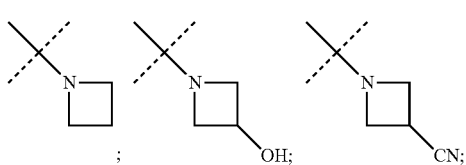

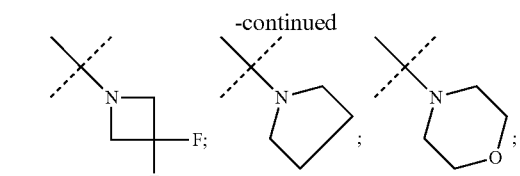

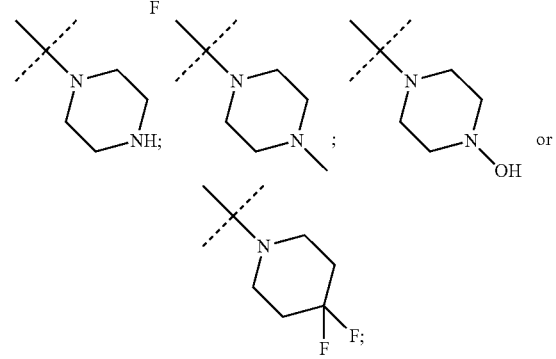

$R_x$ and $R_y$ are independently selected from hydrogen or methyl;

42) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from $C(R_xR_y)C(O)NR''R_1''$, $OC(O)NR''R_1''$, and $NR''R_1''$ together form a 3-7 membered heterocyclic ring wherein one or more carbons may be optionally substituted with one or more hydroxyl, amino, cyano or fluoro groups; and $R_x$ and $R_y$ are independently selected from hydrogen or methyl;

43) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from $C(R_xR_y)C(O)NR''R_1''$, $OC(O)NR''R_1''$; and $R''$ and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optionally substituted with one or more hydroxyl, amino, cyano or fluoro groups; and $C(R_xR_y)$ together form an optionally substituted 3-5 membered cyclic alkyl ring such as

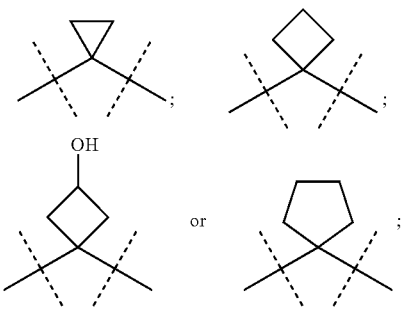

44) $A_2$ is $(CH_2)_m Y_1 (CH_2)_n Q'$ wherein $Y_1$ is a bond, m and n are integers independently selected from 0 to 2 where at least one of m or n is not zero; and $Q'$ is selected from $C(R_xR_y)C(O)NR''R_1''$, $OC(O)NR''R_1''$; and $R''$ and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optionally substituted with one or more hydroxyl, amino, cyano or fluoro groups; and C(R$_x$R$_y$) together form a 3-5 membered cyclic ring wherein one carbon is replaced with an oxygen or an amine, such as

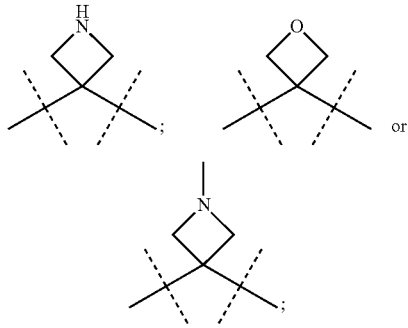

45) Q' is an optionally substituted 5-6 membered heteroaryl such as but not limited to pyridyl, pyrazinyl, pyrimidinyl, furanyl, thiofuranyl, pyranyl, pyrrolyl, pyrazolyl, imidazolyl, thienyl, oxazolyl, isooxazolyl, dioxazolyl, thiadiazolyl, oxadiazolyl, tetrazolyl, triazolyl, thiatriazolyl, oxatriazolyl, thiadiazolyl, oxadiazolyl, thiazolyl, isothiazolyl, dithiazolyl;

46) Q' is a 5-6 membered heteroaryl group substituted with hydroxyl, C$_1$-C$_3$ alkoxy, C$_1$-C$_6$ alkyl, halogen or cyano;

47) Q' is an optionally substituted 4-6 membered heterocycle such as but not limited to pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, dithiazolidinyl, tetrahydrofuryl;

48) Q' is a 4-6 membered heterocycle substituted with hydroxyl, C$_1$-C$_3$ alkoxy, C$_1$-C$_6$ alkyl, halogen or cyano;

49) C(R$_x$R$_y$) together form an 3-5 membered cyclic alkyl ring that is optionally substituted with one or more hydroxyl, amino, cyano or fluoro groups, such as cyclopropyl, 2-hydroxycyclopropyl, cyclobutyl, 3-hydroxycyclobutyl, or cyclopentyl; or 50) C(R$_x$R$_y$) together form a 3-5 membered cyclic ring wherein one carbon is replaced with an oxygen or an amine, such as but not limited to azetidine, oxetane, or N-methyl-azetidine.

Non-limiting examples of compounds of formula (I) include:

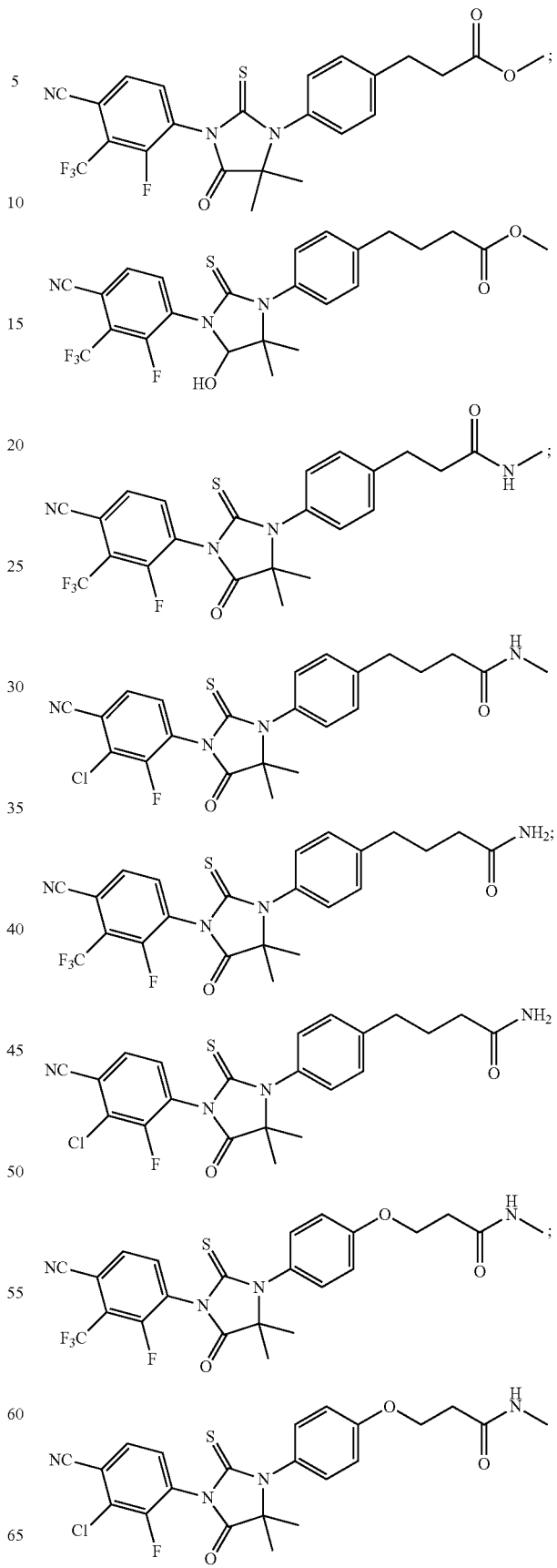

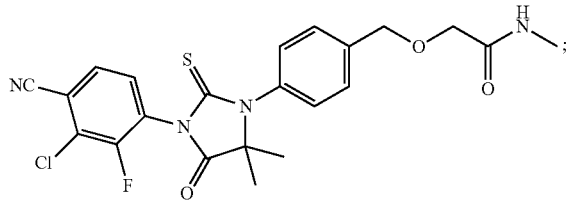
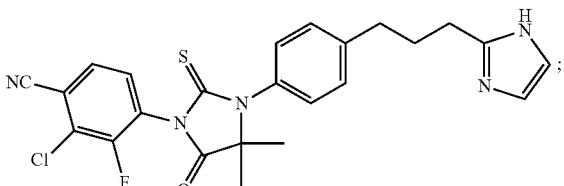
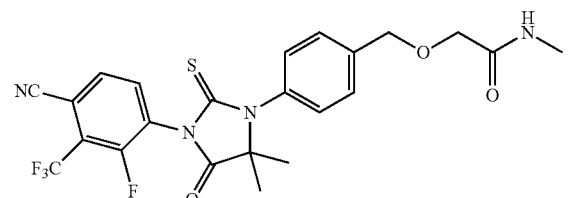
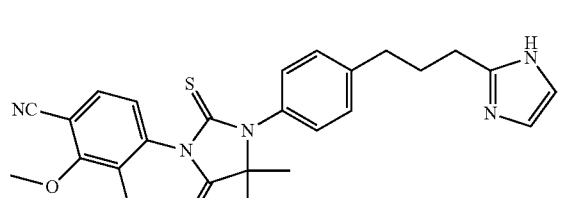
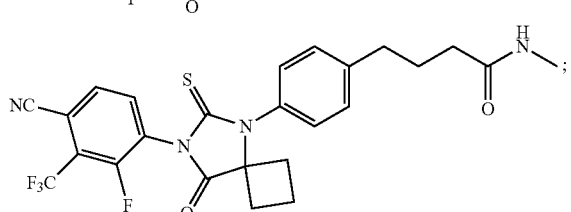
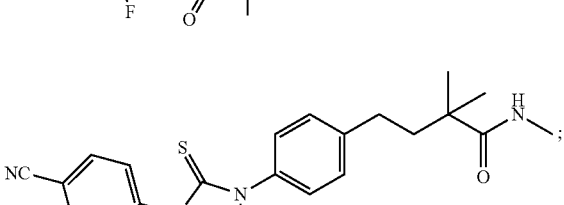
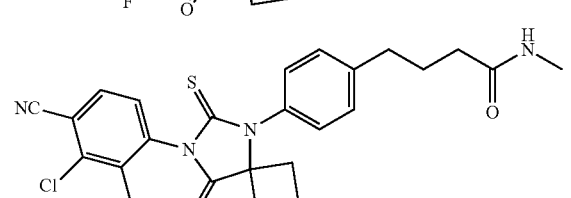
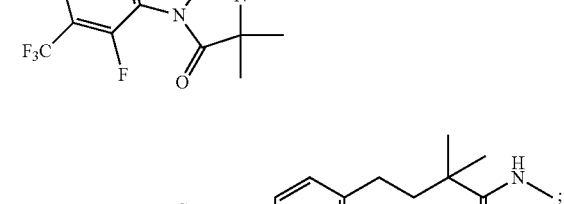
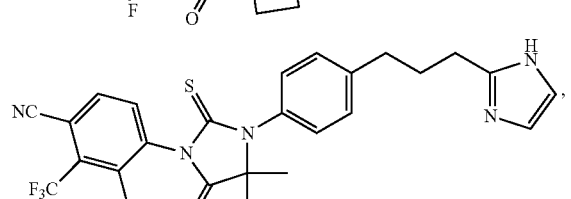
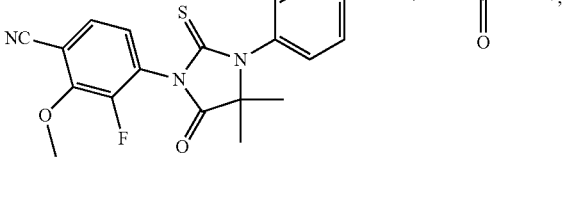
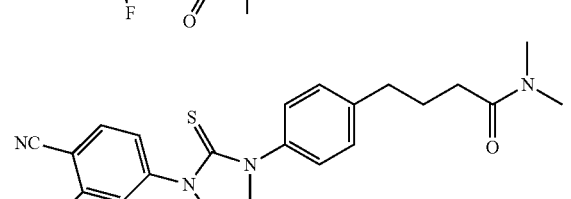
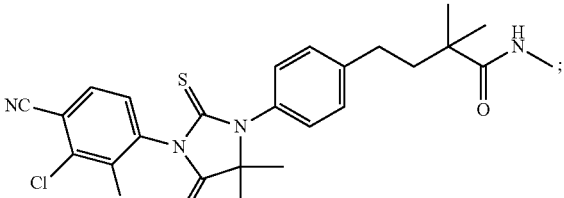
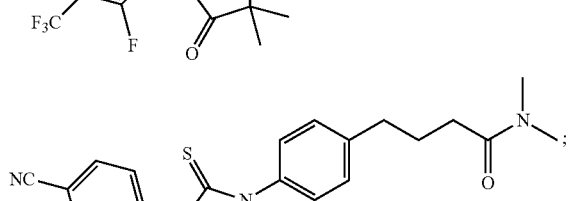
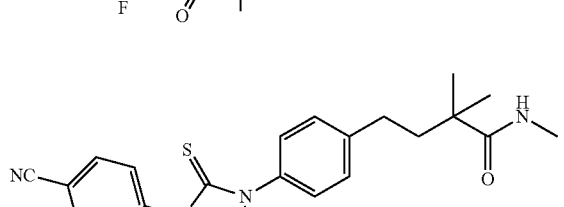
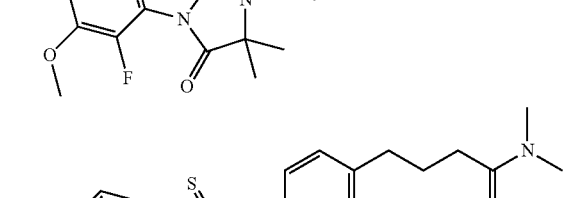
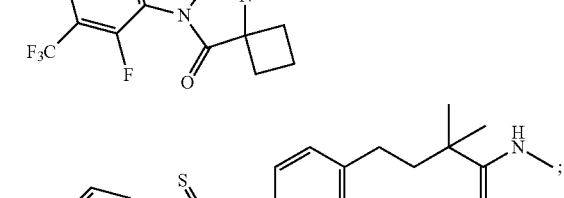
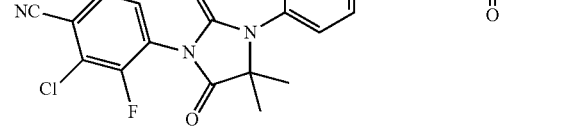
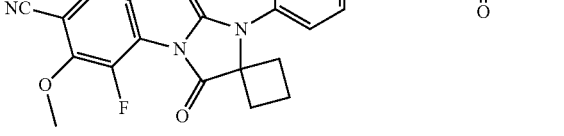

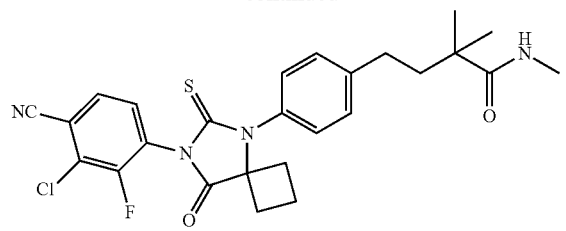
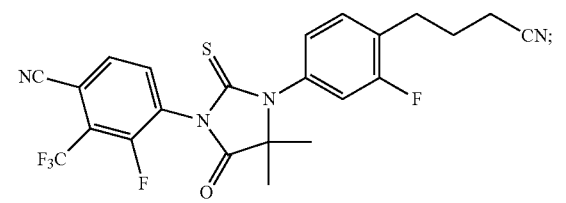
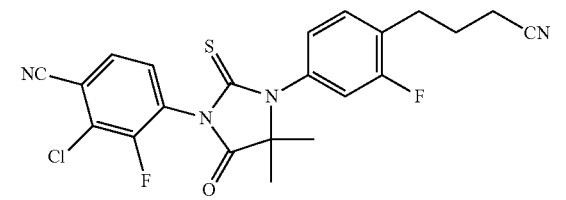
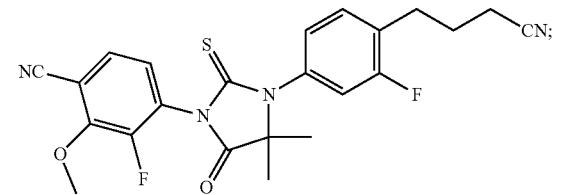
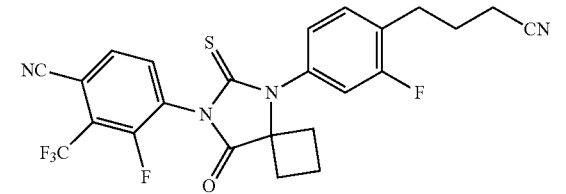
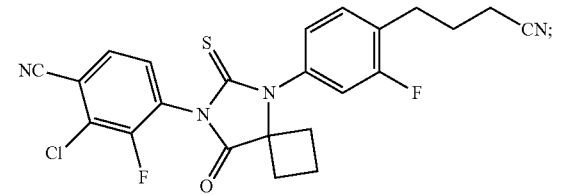
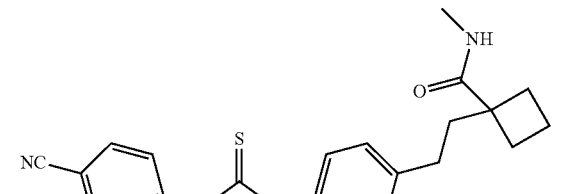
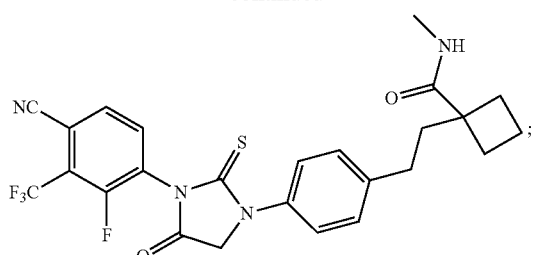
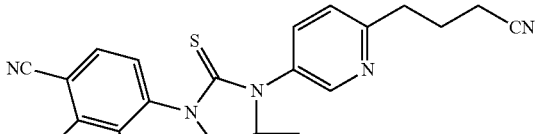
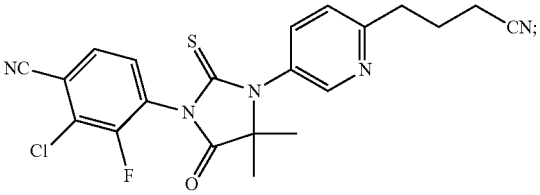
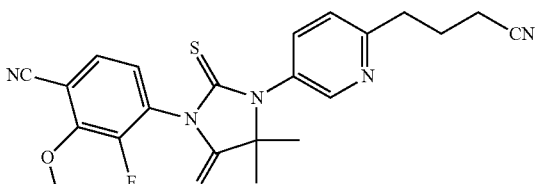
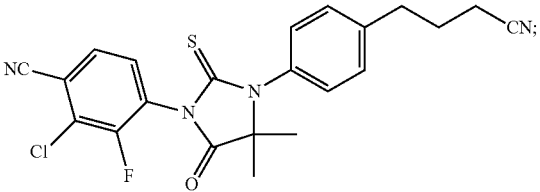
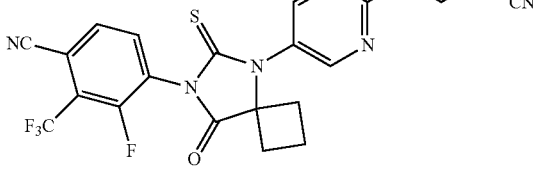
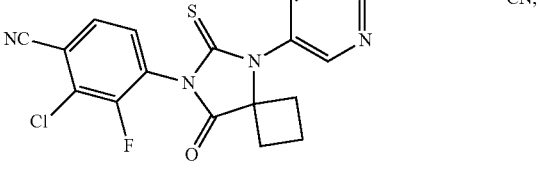
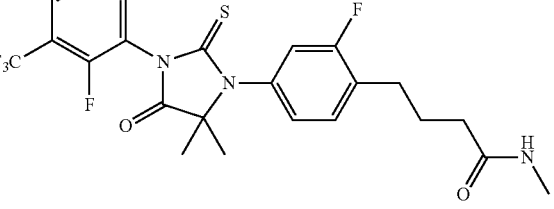

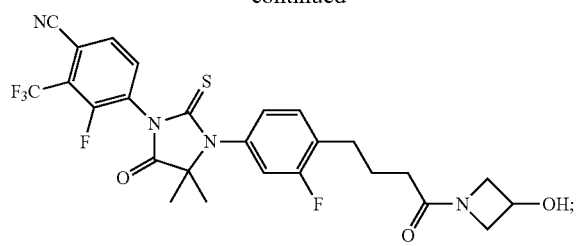
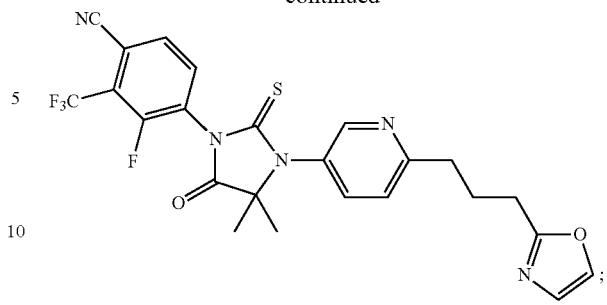
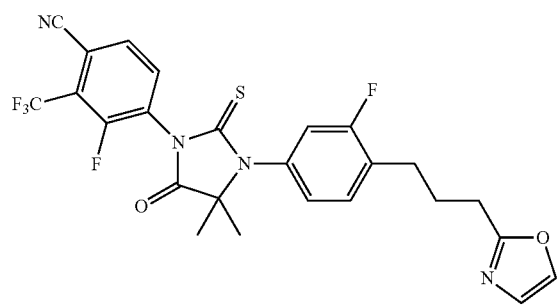
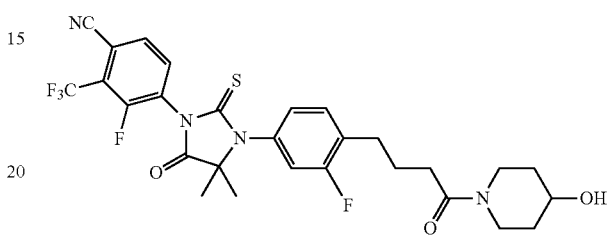
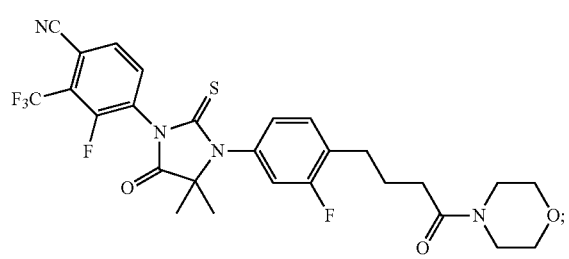
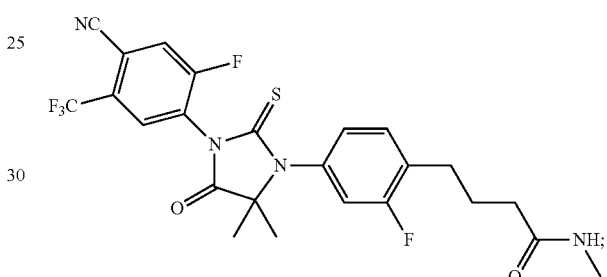
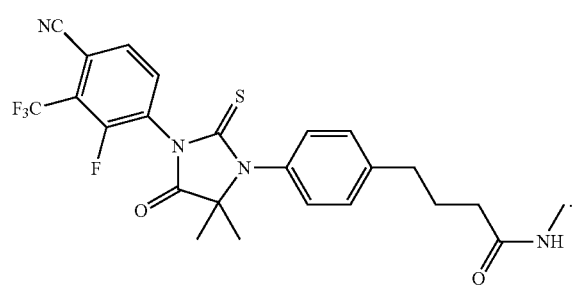
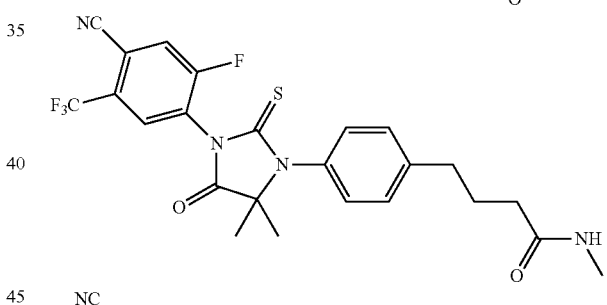
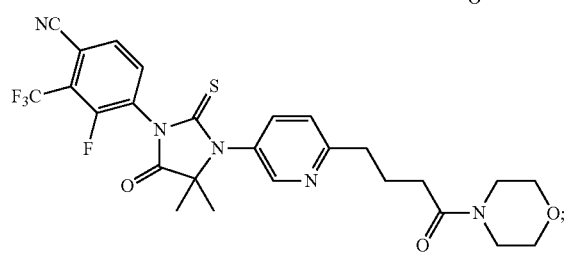
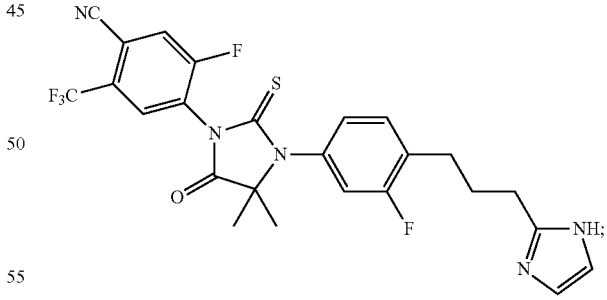
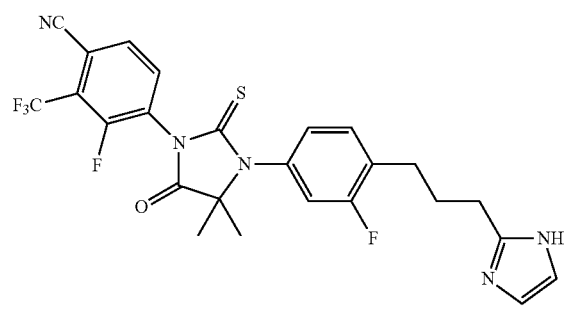
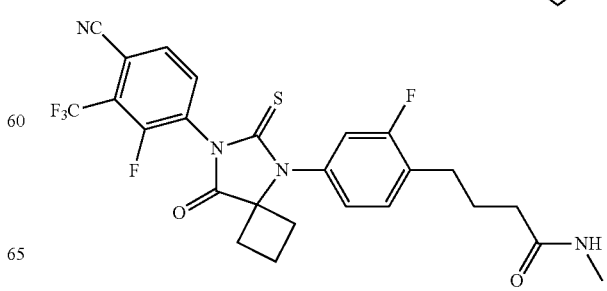

-continued

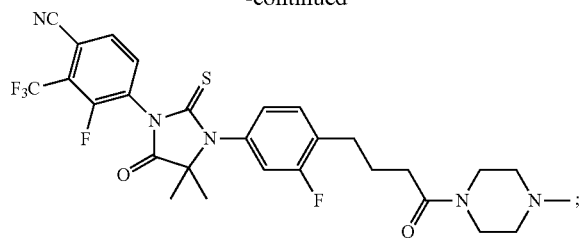

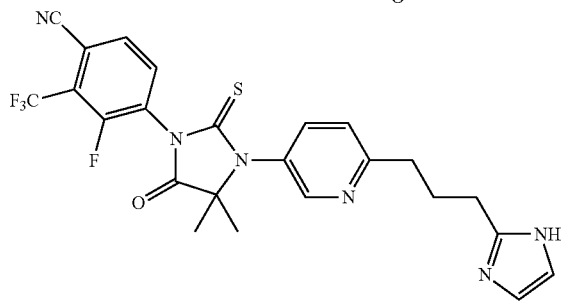

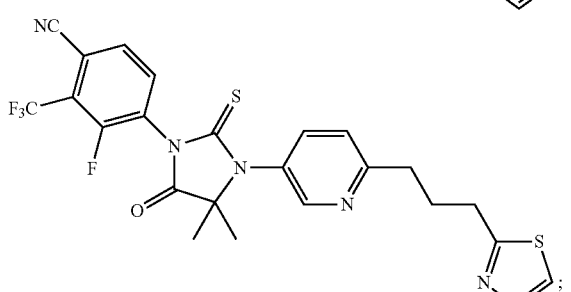

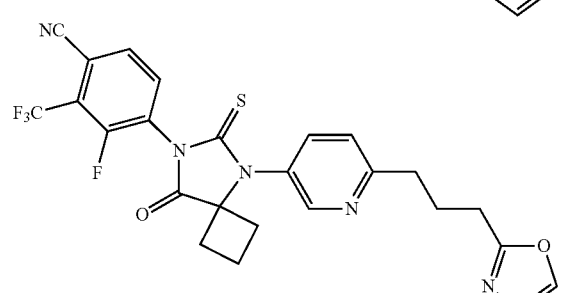

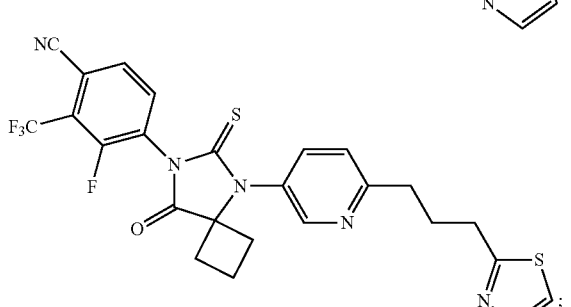

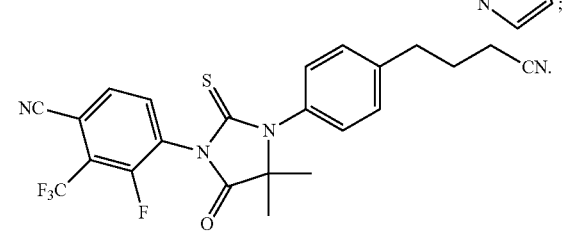

In certain embodiments, the present invention defines particular classes of compounds of special interest, in one aspect, compounds of formula (II):

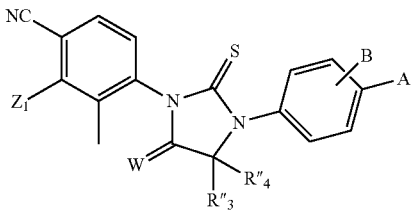

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, $C_1$-$C_3$ alkoxy, $CF_3O$, hydroxyl and cyano;

W is selected from oxygen, sulfur and two hydrogens;

$R''_3$ and $R''_4$ are methyl, or $R''_3$ and $R''_4$ and the carbon to which they are attached together form a 3-6 membered cycloalkyl ring optionally substituted with one or more fluoro or hydroxyl groups;

B is independently selected from one or more hydrogen, cyano, methyl, $CF_3$ or halogen; and A is $(CF_2)_a(CH_2)_mY_1(CH_2)_nQ$ where a, m and n are integers independently selected from 0 to 4 and wherein at least one of a or m or n is not zero; or A is $(CH_2)_mY_1(CH_2)_nQ$ wherein m and n are integers independently selected from 0 to 4 and wherein at least one of m or n is not zero; Q is selected from $C(O)NHR''$, $C(R_xR_y)C(O)NR''R_1''$, $SO_2R''$, $SO_2NR''R_1''$, cyano, hydroxyl, $C_1$-$C_3$ alkoxy, $C(S)NR''R_1''$, $C(O)OR''$, $OC(O)NR''R_1''$, $C(O)NR''R_1''$, optionally substituted 5-6 membered heteroaryl, and an optionally substituted 4-6 membered heterocycle; and $Y_1$ is selected from direct bond, —O—, —S—, and —NR''—; R'' and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine.

In certain embodiments of the compounds of formula (II), $Z_1$ is $CF_3$, methoxy, halogen. In certain embodiments, X is fluorine. In certain embodiments, $R''_3$ and $R''_4$ are methyl, or $R''_3$ and $R''_4$ and the carbon to which they are attached together form a cyclopropyl or cyclobutyl or cyclopentyl or cyclohexyl ring which may be optionally substituted with one or more fluoro or hydroxyl groups.

In certain embodiments of the compounds of formula (II), Q is selected from

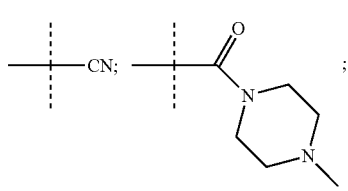

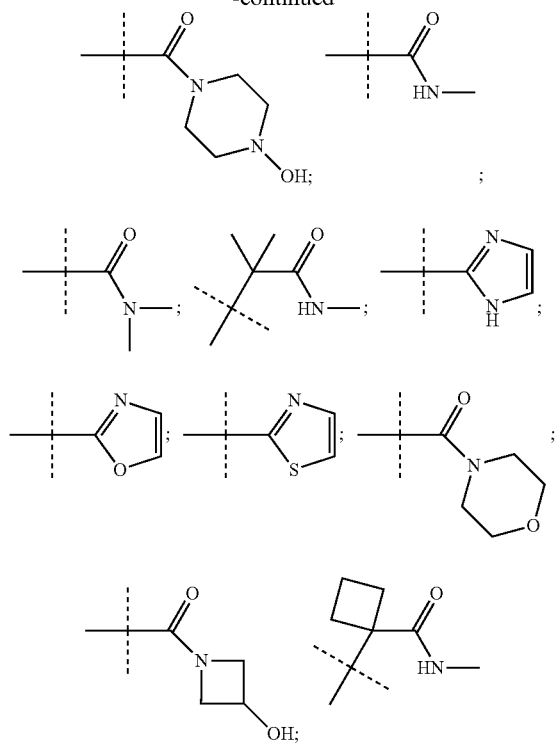

In other embodiments of compounds of formula (II), Q is selected from C(R$_x$R$_y$)C(O)NR"R$_1$", OC(O)NR"R$_1$", optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optional substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine. In certain embodiments, Q is a 5-6 membered heteroaryl group.

In other embodiments of compounds of formula (II), A is (CH$_2$)$_k$Q' where k is an integer selected from 1 to 5; Q' is selected from C(O)NHR", C(R$_x$R$_y$)C(O)NR"R$_1$", SO$_2$R", SO$_2$NR"R$_1$", cyano, hydroxyl, C$_1$-C$_3$ alkoxy, C(S)NR"R$_1$", C(O)OR", OC(O)NR"R$_1$", C(O)NR"R$_1$", optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optionally substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or heterocyclic ring or a 3-5 membered cyclic ring wherein one carbon is replaced with an oxygen or an amine. The 4-5 membered heteroaryl group or 4-6 membered heterocycle can be substituted with hydroxyl, C$_1$-C$_3$ alkoxy, C$_1$-C$_6$ alkyl, halogen or cyano. In certain embodiments, Q' is selected from C(R$_x$R$_y$)C(O)NR"R$_1$", OC(O)NR"R$_1$", optionally substituted 5-6 membered heteroaryl, and an optionally substituted 4-6 membered heterocycle; and R" and R$_1$" are independently selected from hydrogen, C$_1$-C$_6$ alkyl, C$_1$-C$_6$ cycloalkyl and C$_1$-C$_6$ alkenyl or NR"R$_1$" together form a 3-7 membered heterocyclic ring wherein one or more carbons may be optionally substituted with one or more hydroxyl, amino, cyano or fluoro groups; R$_x$ and R$_y$ are independently selected from hydrogen or methyl; or C(R$_x$R$_y$) together form an optionally substituted 3-5 membered cyclic alkyl ring or a 3-5 membered cyclic ring wherein one carbon is replaced with an oxygen or an amine. In certain embodiments, k is 2 or 3.

In certain embodiments, Q' is an optionally substituted 5-6 membered heteroaryl group.

In certain embodiments of the compounds of formula (II), B is a hydrogen or a fluorine at ortho position of A.

In certain embodiments of the compounds of formula (II), W is oxygen.

A number of important subclasses of the compounds of formula (II) deserve special mention.
1) Z is hydrogen;
2) Z is C$_1$-C$_4$ alkyl such as but not limited to methyl or ethyl, optionally substituted with one or more halogen groups;
3) Z is CF$_3$;
4) Z is C$_1$-C$_3$ alkoxy;
5) Z is CF$_3$O;
6) Z is halogen;
7) Z is cyano;
8) Z is fluoro;
9) W is oxygen;
10) W is sulfur;
11) W is two hydrogens;

12) R₃" and R₄" are independently methyl, ethyl, propyl or butyl groups;
13) R₃" and R₄" and the carbon to which they are attached together form a 3-6 membered cycloalkyl ring optionally substituted with one or more fluoro groups, and in which one of the carbons is optionally an oxygen or nitrogen; R₃" and R₄" and the carbon to which they are attached together form cyclopropyl;
14) R₃" and R₄" and the carbon to which they are attached together form cyclobutyl;
15) R₃" and R₄" and the carbon to which they are attached together form cyclopentyl;
16) R₃" and R₄" and the carbon to which they are attached together form azetidine, pyrrolidine or piperidine;
17) R₃" and R₄" and the carbon to which they are attached together form oxetane, tetrahydrofuran or tetrahydropyran.
18) $Y_1$ is a direct bond;
19) $Y_1$ is —O—;
20) $Y_1$ is —S—;
21) $Y_1$ is —NR"—; wherein R" is hydrogen, $C_1$-$C_6$ alkyl, $C_1$-$C_6$ cycloalkyl or $C_1$-$C_6$ alkenyl;
22) B is hydrogen, cyano, methyl, $CF_3$ or halogen;
23) $A_2$ is $(CH_2)_k Q'$ wherein k is an integer between 1 and 5, and Q' is an optionally substituted 5-6 membered heteroaryl, such as but not limited to furanyl, thiofuranyl, pyranyl, pyrrolyl, pyrazolyl, imidazolyl, thienyl, oxazolyl, isooxazolyl, dioxazolyl, thiadiazolyl, oxadiazolyl, tetrazolyl, triazolyl, thiatriazolyl, oxatriazolyl, thiadiazolyl, oxadiazolyl, thiazolyl, isothiazolyl, and dithiazolyl;
24) Q' is a 5-6 membered heteroaryl group substituted with hydroxyl, $C_1$-$C_3$ alkoxy, $C_1$-$C_6$ alkyl, halogen or cyano;
25) $A_2$ is $(CH_2)_k Q'$ wherein k is an integer between 1 and 5, and Q' is a optionally substituted 5-6 membered heterocycle, such as but not limited to pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, dithiazolidinyl, and tetrahydrofuryl;
26) Q' is a 4-6 membered heterocycle substituted with hydroxyl, $C_1$-$C_3$ alkoxy, $C_1$-$C_6$ alkyl, halogen or cyano;

27) Q' is

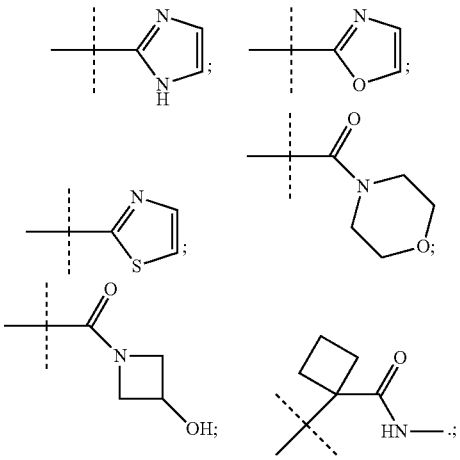

28) Q' is an optionally substituted 4-6 membered heterocycle such as but not limited to

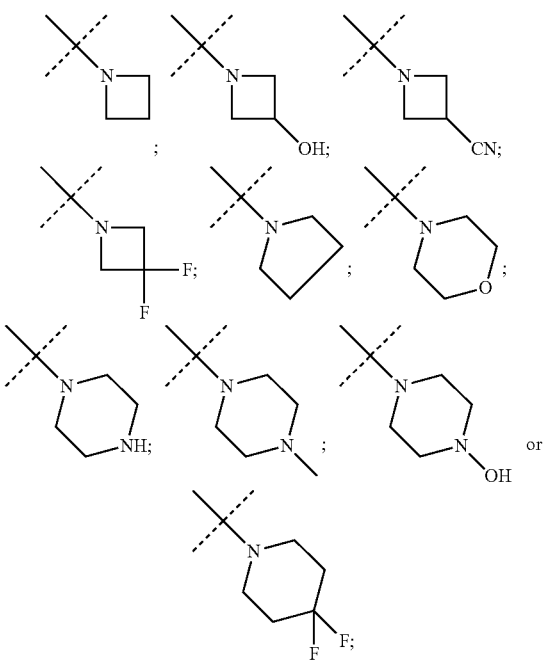

29) Q' is an optionally substituted 5-6 membered heteroaryl group such as but not limited

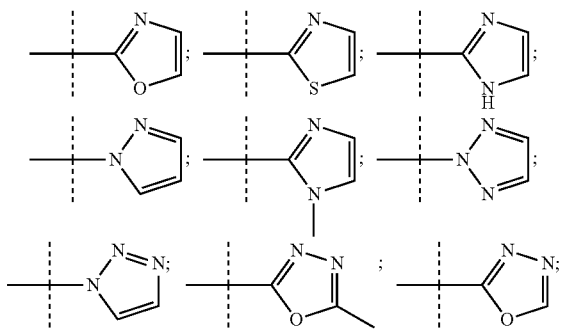

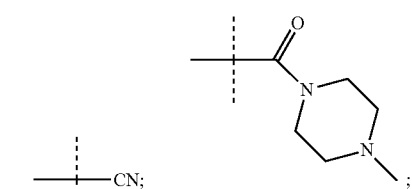

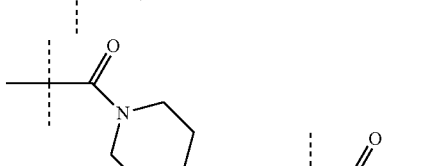

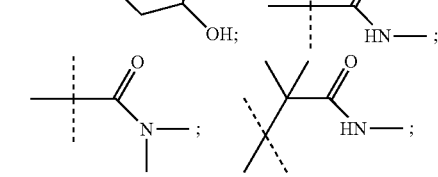

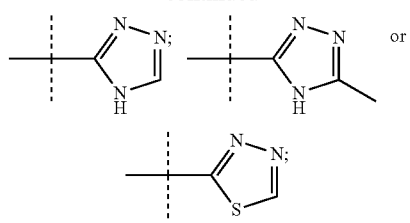

30) $A_2$ is $(CH_2)_k Q'$ wherein k is an integer between 1 and 5, and Q' is $C(R_xR_y)C(O)NR''R_1''$ wherein R'' and $R_1''$ are independently selected from hydrogen, $C_1$-$C_6$ alkyl, $C_1$-$C_6$ cycloalkyl and $C_1$-$C_6$ alkenyl; and $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine;

31) $A_2$ is $(CH_2)_k Q'$ wherein k is an integer between 1 and 5, and Q' is $C(R_xR_y)C(O)NR''R_1''$ wherein $NR''R_1''$ together form a 3-7 membered heterocyclic ring wherein one or more carbons may be optional substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine;

32) $A_2$ is $(CH_2)_k Q'$ wherein k is an integer between 1 and 5, and Q' is selected from $OC(O)NR''R_1''$ wherein R'' and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optional substituted with one or more hydroxyl, amino, cyano or fluoro groups;

33) $NR''R_1''$ together form a 3-7 membered heterocyclic ring wherein one or more carbons may be optional substituted with one or more hydroxyl, amino, cyano or fluoro groups, such as but not limited to such as

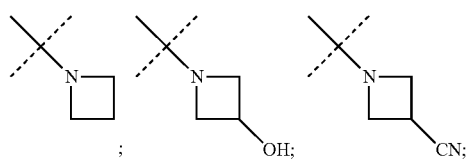

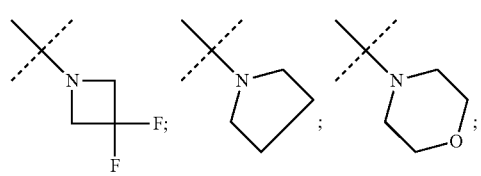

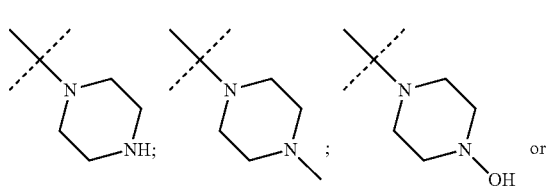

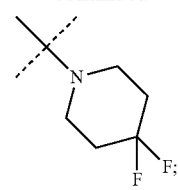

34) $C(R_xR_y)$ together form an 3-5 membered cyclic alkyl ring that is optionally substituted with one or more hydroxyl, amino, cyano or fluoro groups, such as cyclopropyl, 2-hydroxycyclopropyl, cyclobutyl, 2-hydroxycyclobutyl, or cyclopentyl; or 35) $C(R_xR_y)$ together form a 3-5 membered cyclic ring wherein one carbon is replaced with an oxygen or an amine, such as but not limited to azetidine, oxtane or N-methyl-azetidine.

Non-limiting examples of compounds of formula (II) include:

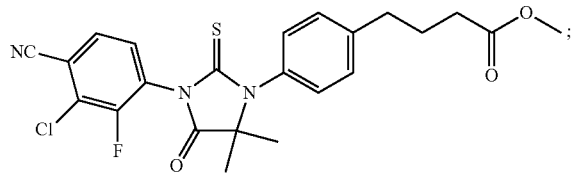

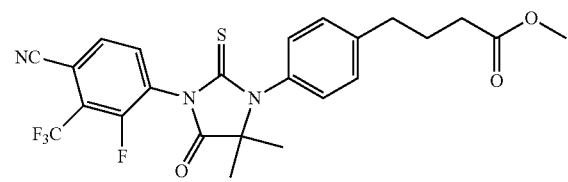

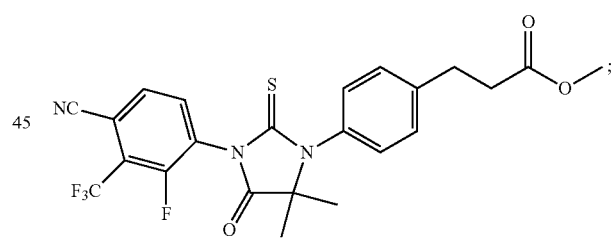

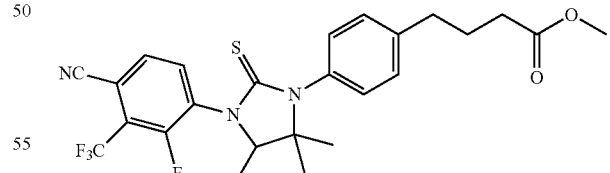

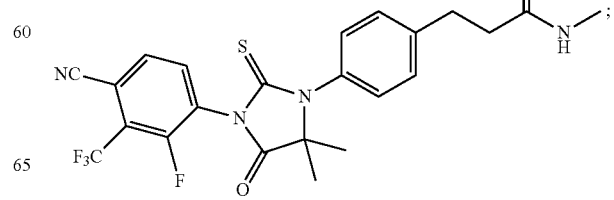

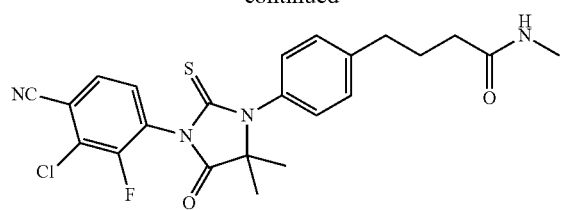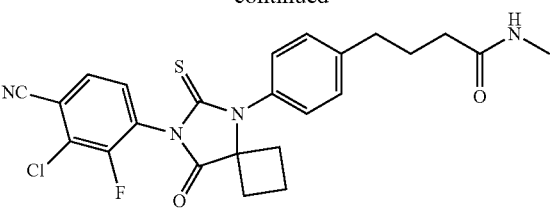

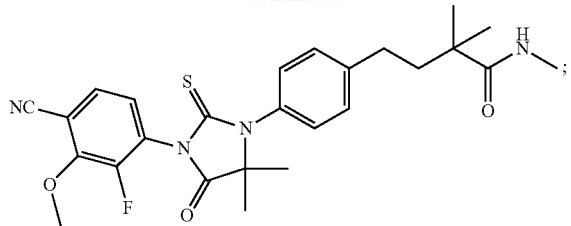
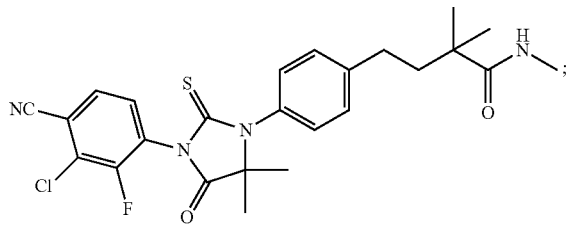
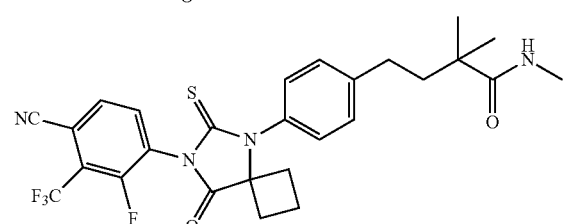
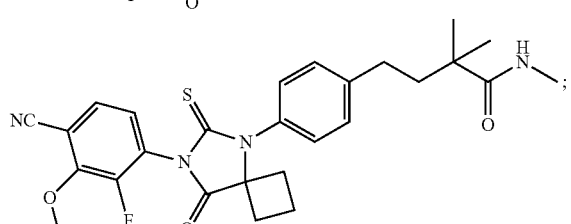
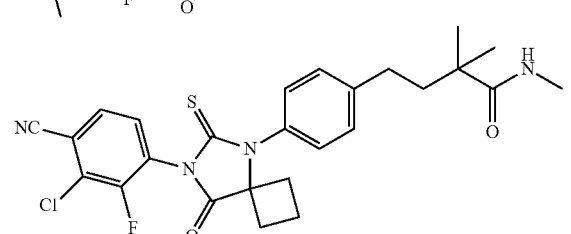
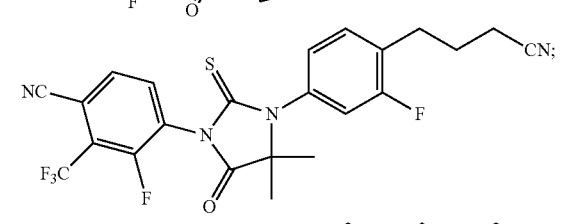
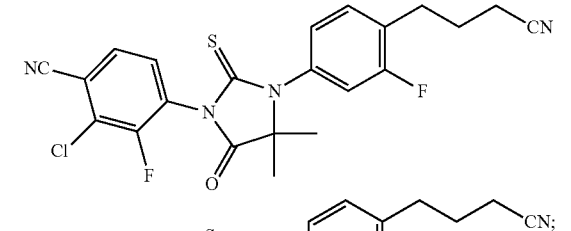
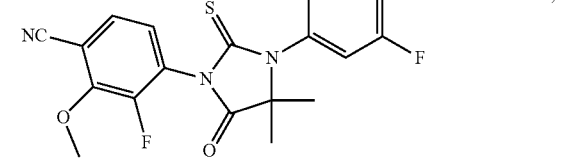
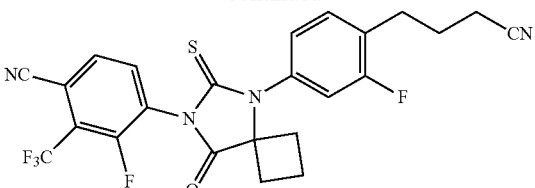
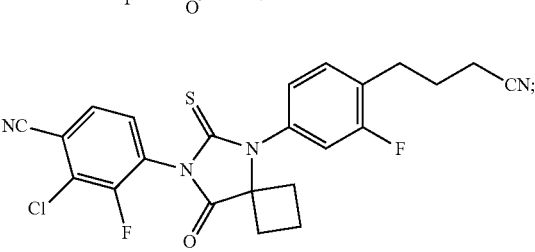
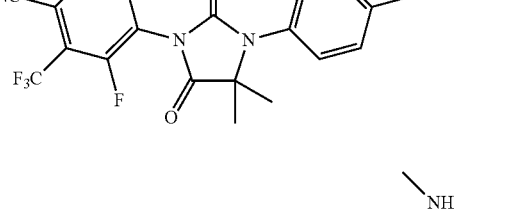
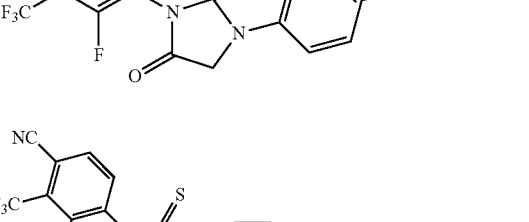
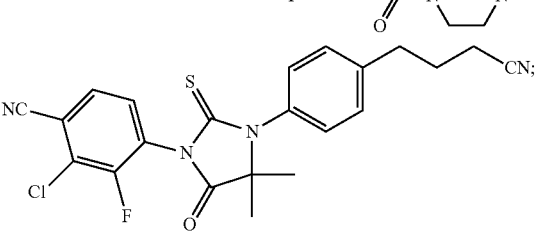
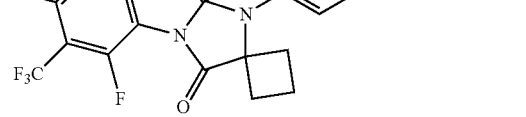

47
-continued
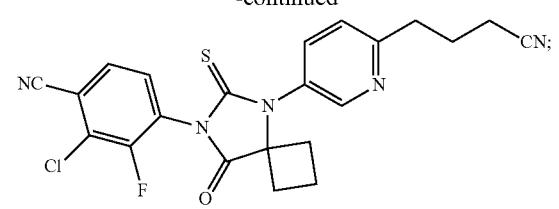
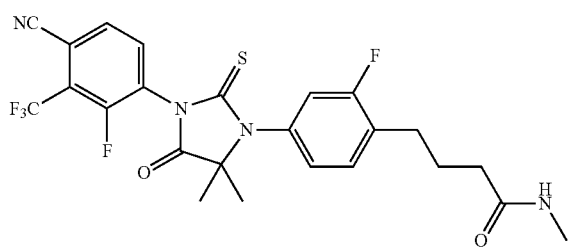
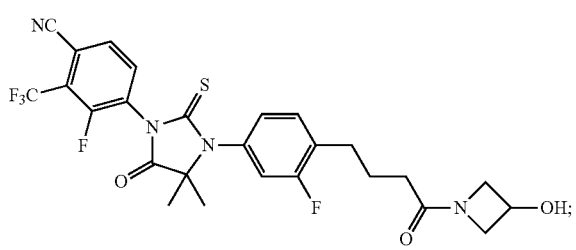
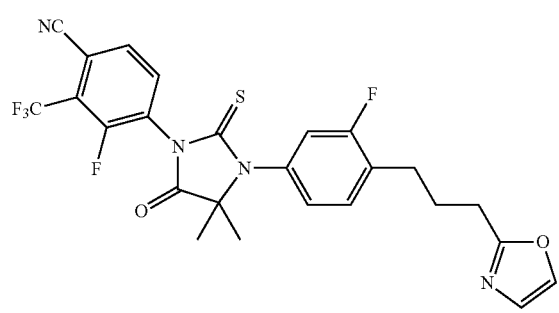
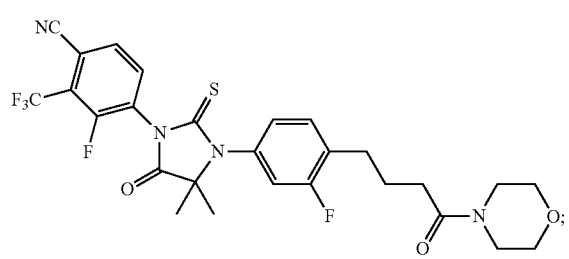
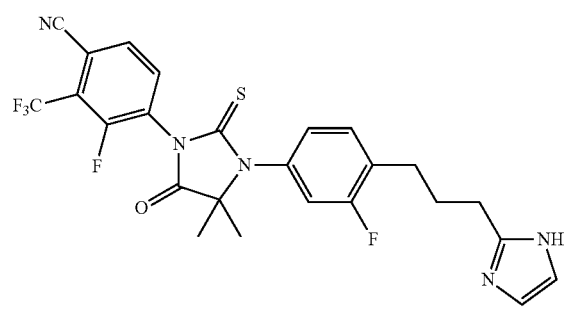
48
-continued
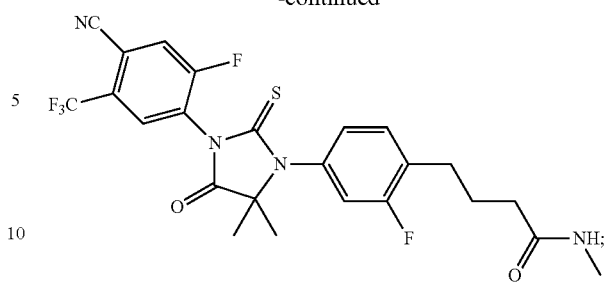
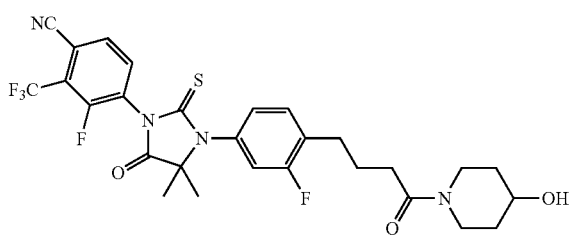
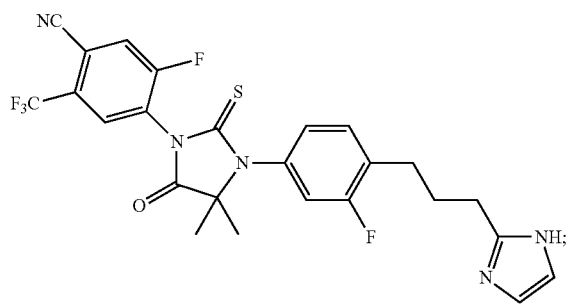
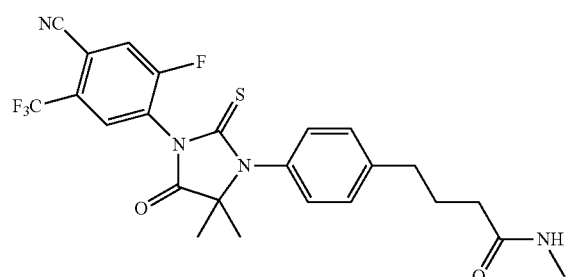
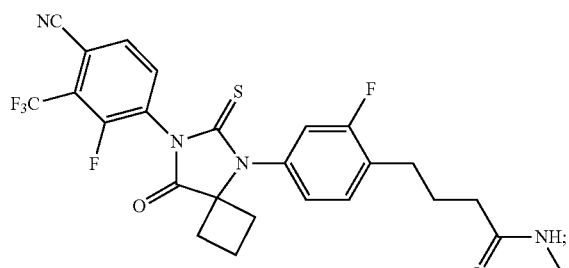
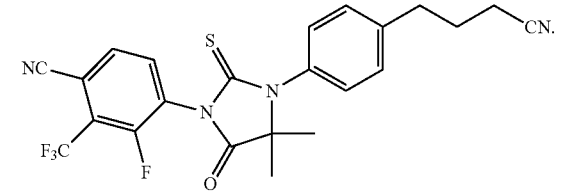 [SMILES: CC1(C)C(=O)N(c2ccc(C#N)c(C(F)(F)F)c2F)C(=S)N1c1ccc(CCCC#N)cc1]

In another embodiment, compounds are provided of formula (III):

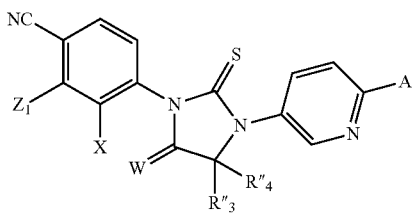

(III)

or a pharmaceutically-acceptable salt, solvate, hydrate, prodrug or derivative thereof,
wherein $Z_1$ is selected from $CF_3O$, methyl, $CH_2F$, $CHF_2$, $CF_3$, methoxy, halogen and cyano;
X is selected from halogen, $C_1$-$C_3$ alkoxy, $CF_3O$, hydroxyl and cyano;
W is selected from oxygen, sulfur and two hydrogens;
R''$_3$ and R''$_4$ are methyl, or R''$_3$ and R''$_4$ and the carbon to which they are attached together form a 3-6 membered cycloalkyl ring optionally substituted with one or more fluoro or hydroxyl groups; and
A is $(CF_2)_a(CH_2)_mY_1(CH_2)_nQ$ wherein a, m and n are integers independently selected from 0 to 4 and wherein at least one of a or m or n is not zero; or A is $(CH_2)_mY_1(CH_2)_nQ$ wherein m and n are integers independently selected from 0 to 4 and wherein at least one of m or n is not zero; Q is selected from C(O)NHR'', C($R_xR_y$)C(O)NR''$R_1$'', $SO_2$R'', $SO_2$NR''$R_1$'', cyano, hydroxyl, $C_1$-$C_3$ alkoxy, C(S)NR''$R_1$'', C(O)OR'', OC(O)NR''$R_1$'', C(O)NR''$R_1$'', optionally substituted 5-6 membered heteroaryl, and an optionally substituted 4-6 membered heterocycle; and $Y_1$ is selected from direct bond, —O—, —S—, and —NR''—; R'' and $R_1$'' are independently selected from hydrogen, $C_1$-$C_6$ alkyl, $C_1$-$C_6$ cycloalkyl and $C_1$-$C_6$ alkenyl or NR''$R_1$'' together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or C($R_xR_y$) together form an optionally substituted 3-5 membered cyclic alkyl ring or a 3-5 membered cyclic ring wherein one carbon is replaced with an oxygen or an amine.

In certain embodiments of compounds of formula (III), $Z_1$ is $CF_3$, methoxy, halogen.

In certain embodiments of compounds of formula (III), X is fluorine.

In certain embodiments of compounds of formula (III), R''$_3$ and R''$_4$ are methyl, or R''$_3$ and R''$_4$ and the carbon to which they are attached together form a cyclopropyl or cyclobutyl or cyclopentyl or cyclohexyl ring which may be optionally substituted with one or more fluoro or hydroxyl groups.

In certain embodiments of compounds of formula (III), Q is selected from

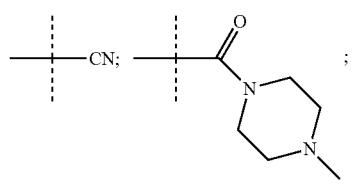

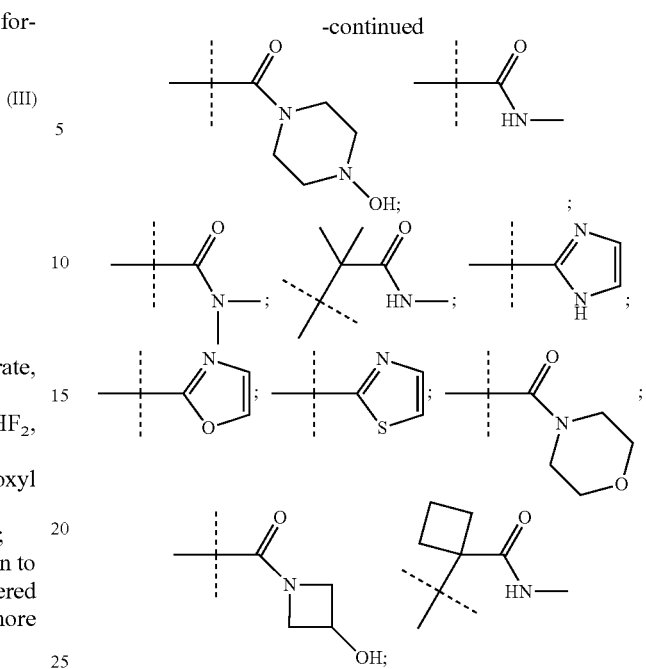

In certain embodiments of compounds of formula (III), Q is an optionally substituted 5-6 membered heteroaryl group or optionally substituted 4-6 membered heterocycle. In certain embodiments, the 5-6 membered heteroaryl group or 4-6 membered heterocycle can be substituted with hydroxyl, $C_1$-$C_3$ alkoxy, $C_1$-$C_6$ alkyl, halogen or cyano.

In certain embodiments of compounds of formula (III), A is $(CH_2)_mY_1(CH_2)_nQ'$ wherein $Y_1$ is a bond, m and n are integers independently selected from 0 to 2 and wherein at least one of m or n is not zero; Q' is selected from C(O)NHR'', C($R_xR_y$)C(O)NR''$R_1$'', $SO_2$R'', $SO_2$NR''$R_1$'', cyano, hydroxyl, $C_1$-$C_3$ alkoxy, C(S)NR''$R_1$'', C(O)OR'', OC(O)NR''$R_1$'', C(O)NR''$R_1$'', optionally substituted 5-6 membered heteroaryl, and an optionally substituted 4-6 membered heterocycle; and R'' and $R_1$'' are independently selected from hydrogen, $C_1$-$C_6$ alkyl, $C_1$-$C_6$ cycloalkyl and $C_1$-$C_6$ alkenyl or NR''$R_1$'' together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or C($R_xR_y$) together form an optionally substituted 3-5 membered cyclic alkyl ring or a 3-5 membered cyclic ring wherein one carbon is replaced with an oxygen or an amine.

In certain embodiments of compounds of formula (III), Q' is an optionally substituted 5-6 membered heteroaryl group or optionally substituted 4-6 membered heterocycle. In certain embodiments, the 5-6 membered heteroaryl group or 4-6 membered heterocycle can be substituted with hydroxyl, $C_1$-$C_3$ alkoxy, $C_1$-$C_6$ alkyl, halogen or cyano.

In certain embodiments of compounds of formula (III), Q' is selected from

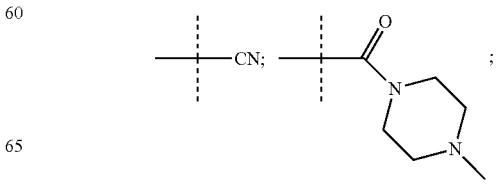

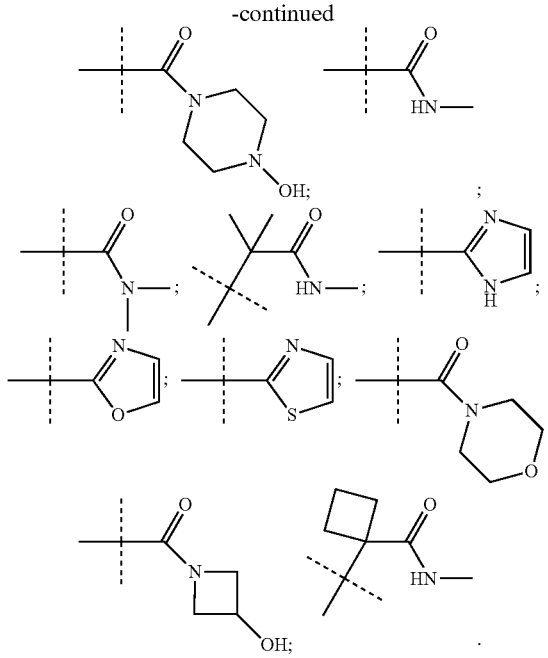

In certain embodiments of compounds of formula (III), A is $(CH_2)_kQ'$ where k is an integer selected from 1 to 5; Q' is selected from C(O)NHR", $C(R_xR_y)C(O)NR"R_1"$, $SO_2R"$, $SO_2NR"R_1"$, cyano, hydroxyl, $C_1$-$C_3$ alkoxy, $C(S)NR"R_1"$, C(O)OR", $OC(O)NR"R_1"$, $C(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or $NR"R_1"$ together form a 3-7 membered heterocyclic ring wherein one or more carbons may be optionally substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or heterocyclic ring or a 3-5 membered cyclic ring wherein one carbon is replaced with an oxygen or an amine. In certain embodiments, k is 2 or 3.

In certain embodiments of compounds of formula (III), Q' is an optionally substituted 5-6 membered heteroaryl group or optionally substituted 4-6 membered heterocycle. In certain embodiments, the 5-6 membered heteroaryl group or 4-6 membered heterocycle can be substituted with hydroxyl, $C_1$-$C_3$ alkoxy, $C_1$-$C_6$ alkyl, halogen or cyano.

In certain embodiments of compounds of formula (III), Q' is selected from $C(R_xR_y)C(O)NR"R_1"$, $OC(O)NR"R_1"$, optionally substituted 5-6 membered heteroaryl, and an optionally substituted 4-6 membered heterocycle; and R" and $R_1"$ are independently selected from hydrogen, $C_1$-$C_6$ alkyl, $C_1$-$C_6$ cycloalkyl and $C_1$-$C_6$ alkenyl or $NR"R_1"$ together form a 3-7 membered heterocyclic ring wherein one or more carbons may be optional substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine. In certain embodiments, Q' is an optionally substituted 5-6 membered heteroaryl group. In certain embodiments, the 5-6 membered heteroaryl group can be substituted with hydroxyl, $C_1$-$C_3$ alkoxy, $C_1$-$C_6$ alkyl, halogen or cyano.

In certain embodiments of compounds of formula (III), W is oxygen.

A number of important subclasses of the compounds of formula (III) deserve special mention:

36) Z is hydrogen;
37) Z is $C_1$-$C_4$ alkyl such as but not limited to methyl or ethyl, optionally substituted with one or more halogen groups;
38) Z is $CF_3$;
39) Z is $C_1$-$C_3$ alkoxy;
40) Z is $CF_3O$;
41) Z is halogen;
42) Z is cyano;
43) Z is fluoro;
44) W is oxygen;
45) W is sulfur;
46) W is two hydrogens;
47) $R_3"$ and $R_4"$ are independently methyl, ethyl, propyl or butyl groups;
48) $R_3"$ and $R_4"$ and the carbon to which they are attached together form a 3-6 membered cycloalkyl ring optionally substituted with one or more fluoro groups, and in which one of the carbons is optionally an oxygen or nitrogen; $R_3"$ and $R_4"$ and the carbon to which they are attached together form cyclopropyl;
49) $R_3"$ and $R_4"$ and the carbon to which they are attached together form cyclobutyl;
50) $R_3"$ and $R_4"$ and the carbon to which they are attached together form cyclopentyl;
51) $R_3"$ and $R_4"$ and the carbon to which they are attached together form azetidine, pyrrolidine or piperidine;
52) $R_3"$ and $R_4"$ and the carbon to which they are attached together form oxetane, tetrahydrofuran or tetrahydropyran.
53) $Y_1$ is a direct bond;
54) $Y_1$ is —O—;
55) $Y_1$ is —S—;
56) $Y_1$ is —NR"—; wherein R" is hydrogen, $C_1$-$C_6$ alkyl, $C_1$-$C_6$ cycloalkyl or $C_1$-$C_6$ alkenyl;
57) B is hydrogen, cyano, methyl, $CF_3$ or halogen;
58) $A_2$ is $(CH_2)_kQ'$ wherein k is an integer between 1 and 5, and Q' is an optionally substituted 5-6 membered heteroaryl, such as but not limited to pyridyl, pyrazinyl, pyrimidinyl, furanyl, thiofuranyl, pyranyl, pyrrolyl, pyrazolyl, imidazolyl, thienyl, oxazolyl, isooxazolyl, dioxazolyl, thiadiazolyl, oxadiazolyl, tetrazolyl, triazolyl, thiatriazolyl, oxatriazolyl, thiadiazolyl, oxadiazolyl, thiazolyl, isothiazolyl, and dithiazolyl;

Q' is a 5-6 membered heteroaryl group substituted with hydroxyl, $C_1$-$C_3$ alkoxy, $C_1$-$C_6$ alkyl, halogen or cyano;

59) $A_2$ is $(CH_2)_kQ'$ wherein k is an integer between 1 and 5, and Q' is an optionally substituted 5-6 membered heterocycle, such as but not limited to pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinylisothiazolidinyl, dithiazolidinyl, and tetrahydrofuryl;

60) Q' is a 4-6 membered heterocycle substituted with hydroxyl, $C_1$-$C_3$ alkoxy, $C_1$-$C_6$ alkyl, halogen or cyano;

61) Q' is

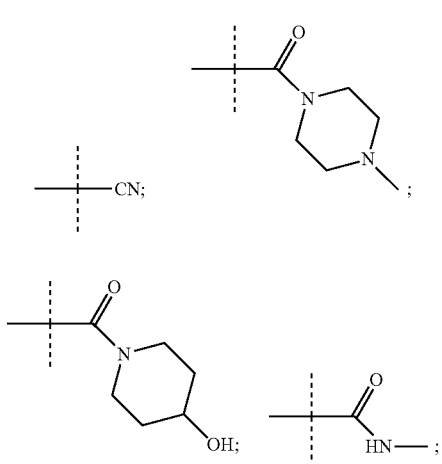

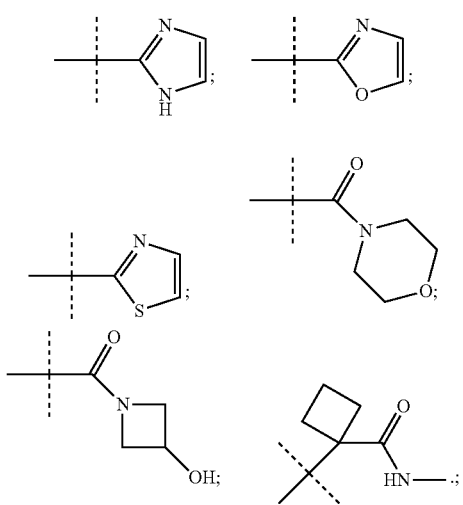

62) Q' is an optionally substituted 4-6 membered heterocycle such as but not limited to

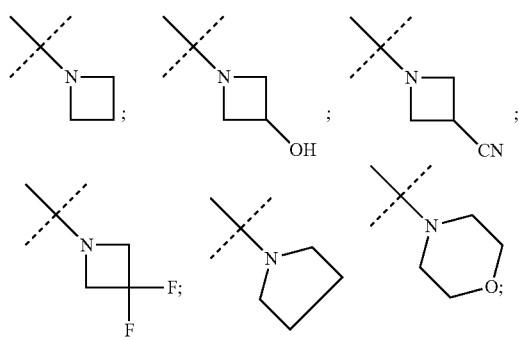

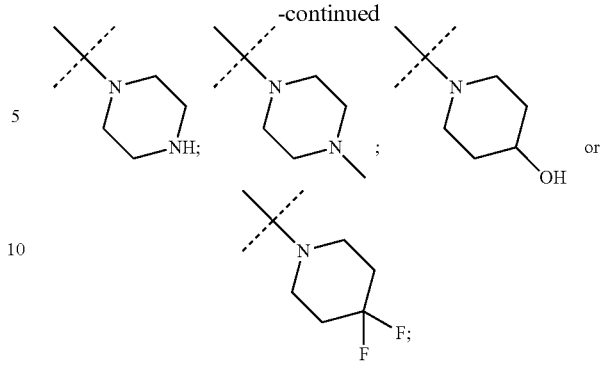

63) Q' is an optionally substituted 5-6 membered heteroaryl group such as but not limited

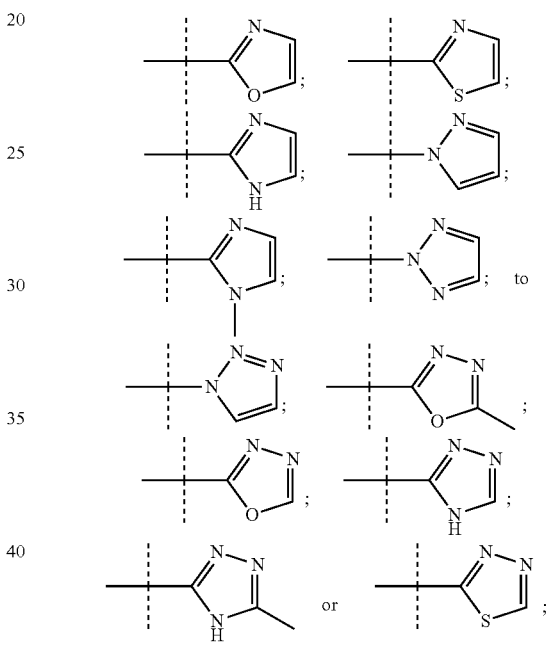

64) $A_2$ is $(CH_2)_k Q'$ wherein k is an integer between 1 and 5, and Q' is $C(R_xR_y)C(O)NR''R_1''$ wherein R'' and $R_1''$ are independently selected from hydrogen, $C_1$-$C_6$ alkyl, $C_1$-$C_6$ cycloalkyl and $C_1$-$C_6$ alkenyl; and $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine;

65) $A_2$ is $(CH_2)_k Q'$ wherein k is an integer between 1 and 5, and Q' is $C(R_xR_y)C(O)NR''R_1''$ wherein $NR''R_1''$ together form a 3-7 membered heterocyclic ring wherein one or more carbons may be optional substituted with one or more hydroxyl, amino, cyano or fluoro groups; $R_x$ and $R_y$ are independently selected from hydrogen or methyl; or $C(R_xR_y)$ together form an optionally substituted 3-5 membered cyclic alkyl ring or a 3-5 membered cyclic ring wherein one carbon is replaced with an oxygen or an amine;

66) $A_2$ is $(CH_2)_k Q'$ wherein k is an integer between 1 and 5, and Q' is selected from $OC(O)NR''R_1''$ wherein R'' and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optional substituted with one or more hydroxyl, amino, cyano or fluoro groups;

67) NR"R₁" together form a 3-7 membered heterocyclic ring wherein one or more carbons may be optional substituted with one or more hydroxyl, amino, cyano or fluoro groups, such as but not limited to such as

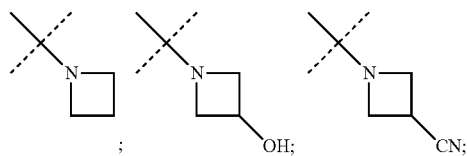

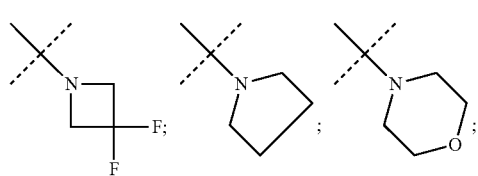

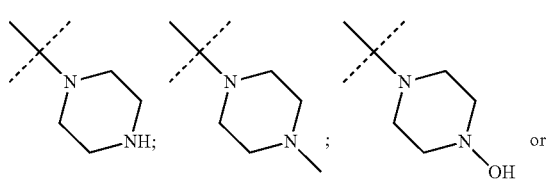

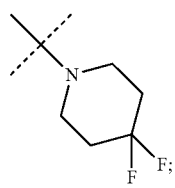

68) C(R$_x$R$_y$) together form an 3-5 membered cyclic alkyl ring that is optionally substituted with one or more hydroxyl, amino, cyano or fluoro groups, such as cyclopropyl, 2-hydroxycyclopropyl, cyclobutyl, 2-hydroxycyclobutyl, or cyclopentyl; or 69) C(R$_x$R$_y$) together form a 3-5 membered cyclic ring wherein one carbon is replaced with an oxygen or an amine, such as but not limited to azetidine, oxetane or N-methyl azetidine.

Non-limiting examples of compounds of formula (III) include:

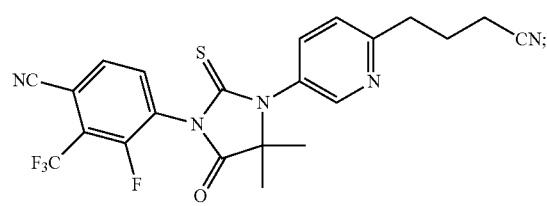

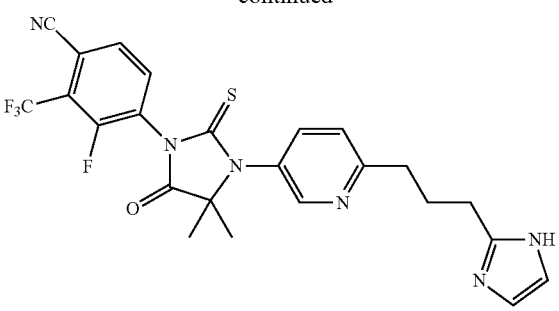

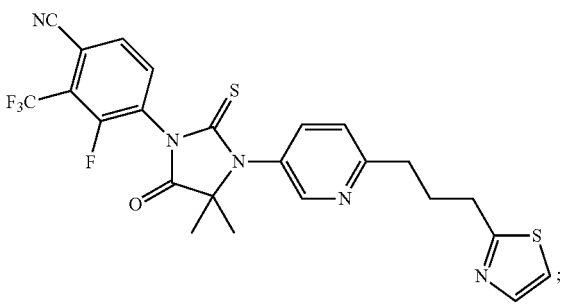

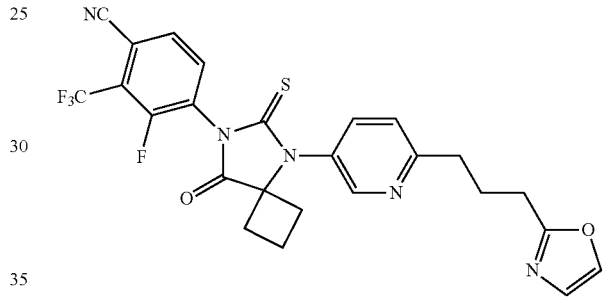

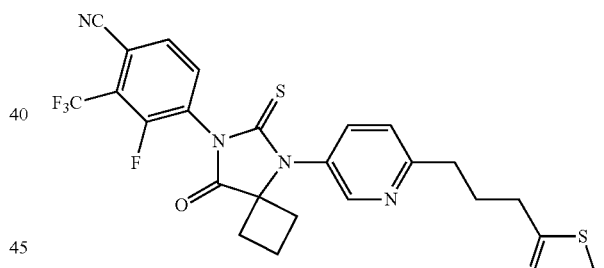

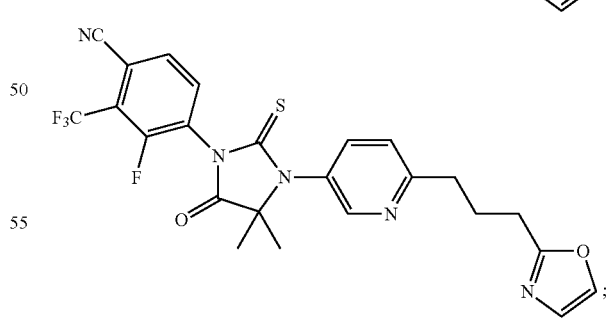

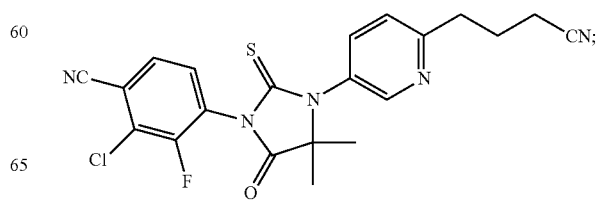

-continued

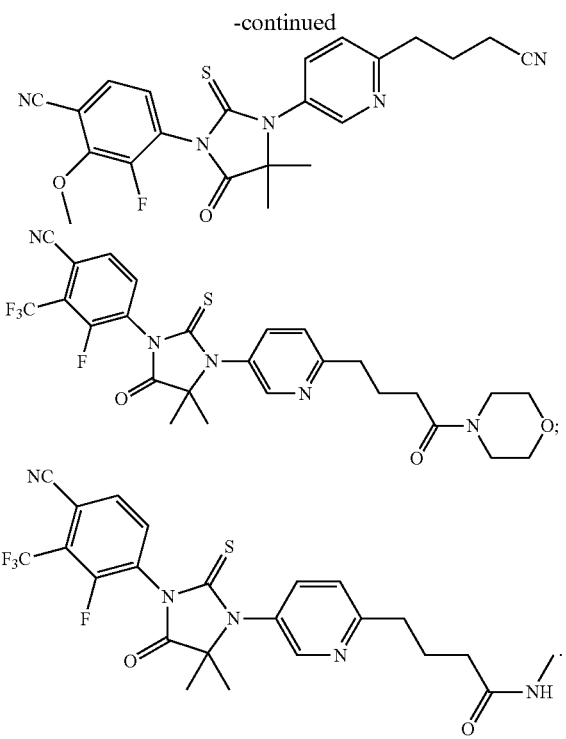

In another embodiment of special interest, compounds of formula (III-a) are

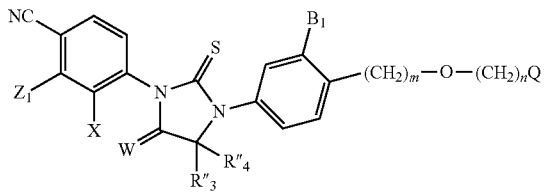

III-a wherein $Z_1$ is selected from $CF_3O$, methyl, $CH_2F$, $CHF_2$, $CF_3$, methoxy, halogen and cyano;
X is selected from halogen, $C_1$-$C_3$ alkoxy, $CF_3O$, hydroxyl and cyano;
W is selected from oxygen, sulfur and two hydrogens;
$R''_3$ and $R''_4$ are methyl, or $R''_3$ and $R''_4$ and the carbon to which they are attached together form a 3-6 membered alkyl ring which may be optionally substituted with one or more fluoro or hydroxyl groups;
B1 is hydrogen, halogen or cyano group;
m is 0, 1, 2, 3 or 4 and n is 0, 1, 2, 3, or 4 with the proviso that at least one of m or n is not zero.
Q is selected from C(O)NHR'', $SO_2R''$, $SO_2NHR''$, cyano, hydroxyl, $C_1$-$C_3$ alkoxy, C(S)NHR'', C(O)OR'', OC(O)NHR'', optionally substituted 5-6 membered heteroaryl, and an optionally substituted 4-6 membered heterocycle; and
R'' is selected from hydrogen, $C_1$-$C_6$ alkyl, $C_1$-$C_6$ cycloalkyl and $C_1$-$C_6$ alkenyl.

A number of important subclasses of the compounds of formula (III-a) deserve special mention, and include compounds comprising one or more selections of the following substituents.

1) $Z_1$ is Cl;
2) $Z_1$ is $CF_3$;
3) $Z_1$ is MeO;
4) X is Cl;
5) X is F;
6) X is Br;
7) W is O;
8) W is S;
9) W is two hydrogens;
10) $R''_3$ and $R''_4$ are methyl groups;
11) $R''_3$ and $R''_4$ and the carbon to which they are attached together form cyclobutyl;
12) $R''_3$ and $R''_4$ and the carbon to which they are attached together form cyclopentyl;
13) $B_1$ is hydrogen;
14) $B_1$ is fluorine;
15) $B_1$ is cyano group;
16) m is 0;
17) m is 1;
18) m is 2;
19) n is 1;
20) n is 2;
21) n is 3;
22) Q is —C(O)NHMe;
23) Q is —C(O)$NH_2$;
24) Q is —OC(O)NHMe;
25) Q is —OC(O)$NH_2$;
26) Q is an optionally substituted 5-6 membered heteroaryl such as but not limited to pyridyl, pyrazinyl, pyrimidinyl, furanyl, thiofuranyl, pyranyl, pyrrolyl, pyrazolyl, imidazolyl, thienyl, oxazolyl, isooxazolyl, dioxazolyl, thiadiazolyl, oxadiazolyl, tetrazolyl, triazolyl, thiatriazolyl, oxatriazolyl, thiadiazolyl, oxadiazolyl, thiazolyl, isothiazolyl, and dithiazolyl;
27) Q is a 5-6 membered heteroaryl group substituted with hydroxyl, $C_1$-$C_3$ alkoxy, $C_1$-$C_6$ alkyl, halogen or cyano;
Q is an optionally substituted 4-6 membered heterocycle such as but not limited to pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, dithiazolidinyl, and tetrahydrofuryl;
Q is a 4-6 membered membered heterocycle substituted with hydroxyl, $C_1$-$C_3$ alkoxy, $C_1$-$C_6$ alkyl, halogen or cyano.
28) Q is 1H-imidazol-2-yl;
29) Q is 1-methyl-1H-imidazol-2-yl;
30) Q is 4,5-dihydro-1H-imidazol-2-yl;
31) Q is hydroxyl group;
32) Q is 1-methyl-1H-imidazol-2-yl when m is 0 and n is 1;
33) Q is 1-methyl-1H-imidazol-2-yl when m is 0 and n is 2;
34) Q is 1-methyl-1H-imidazol-2-yl when m is 1 and n is 1;
35) Q is 1H-imidazol-2-yl when m is 0 and n is 1;
36) Q is 1H-imidazol-2-yl when m is 0 and n is 2;
37) Q is 1H-imidazol-2-yl when m is 1 and n is 1;
38) Q is 1H-imidazol-2-yl when m is 1 and n is 2;
39) Q is 1H-imidazol-2-yl when m is 2 and n is 0;
40) Q is 1H-imidazol-2-yl when m is 2 and n is 1;
41) Q is —C(O)NHMe when m is 0 and n is 1;
42) Q is —C(O)NHMe when m is 0 and n is 2;
43) Q is —C(O)NHMe when m is 0 and n is 3;
44) Q is —C(O)NHMe when m is 1 and n is 1;
45) Q is —C(O)NHMe when m is 1 and n is 0;
46) Q is —C(O)NHMe when m is 1 and n is 2;
47) Q is —C(O)NHMe when m is 2 and n is 1;
48) Q is —C(O)NHMe when m is 2 and n is 0;
49) Q is 4,5-dihydro-1H-imidazol-2-yl when m is 0 and n is 1;
50) Q is 4,5-dihydro-1H-imidazol-2-yl when m is 0 and n is 2;
51) Q is 4,5-dihydro-1H-imidazol-2-yl when m is 1 and n is 1;

52) Q is —C(O)NH$_2$ when m is 0 and n is 1;
53) Q is —C(O)NH$_2$ when m is 0 and n is 2;
54) Q is —C(O)NH$_2$ when m is 1 and n is 1;
55) Q is hydroxyl group when m is 0 and n is 2;
56) Q is hydroxyl group when m is 0 and n is 3;
57) Q is hydroxyl group when m is 1 and n is 2;
58) Q is —OC(O)NHMe when m is o and n is 2;
59) Q is —OC(O)NH$_2$ when m is o and n is 2;
Non-limiting examples of compounds in formula III-a include:
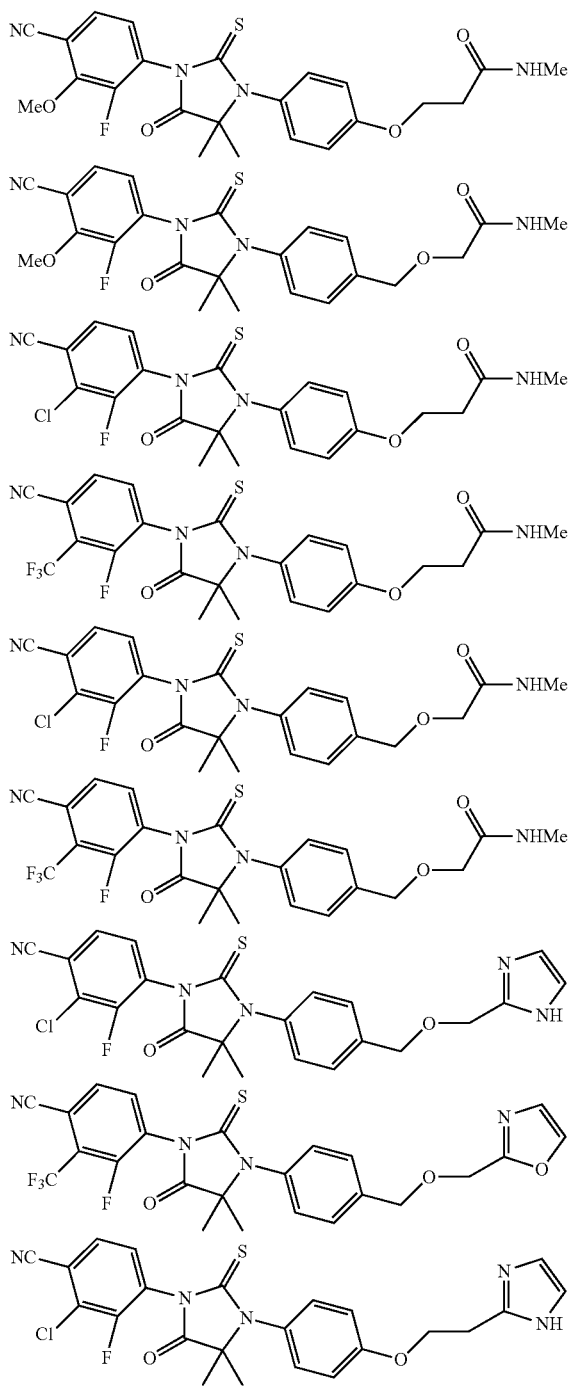
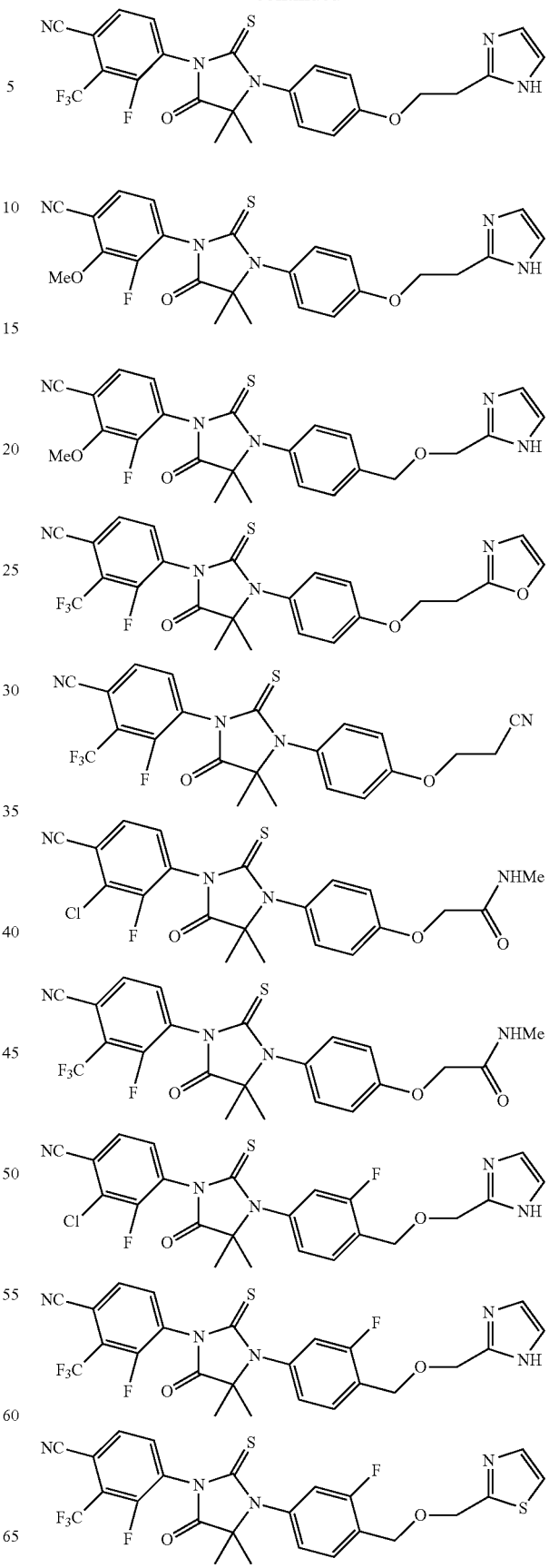

-continued

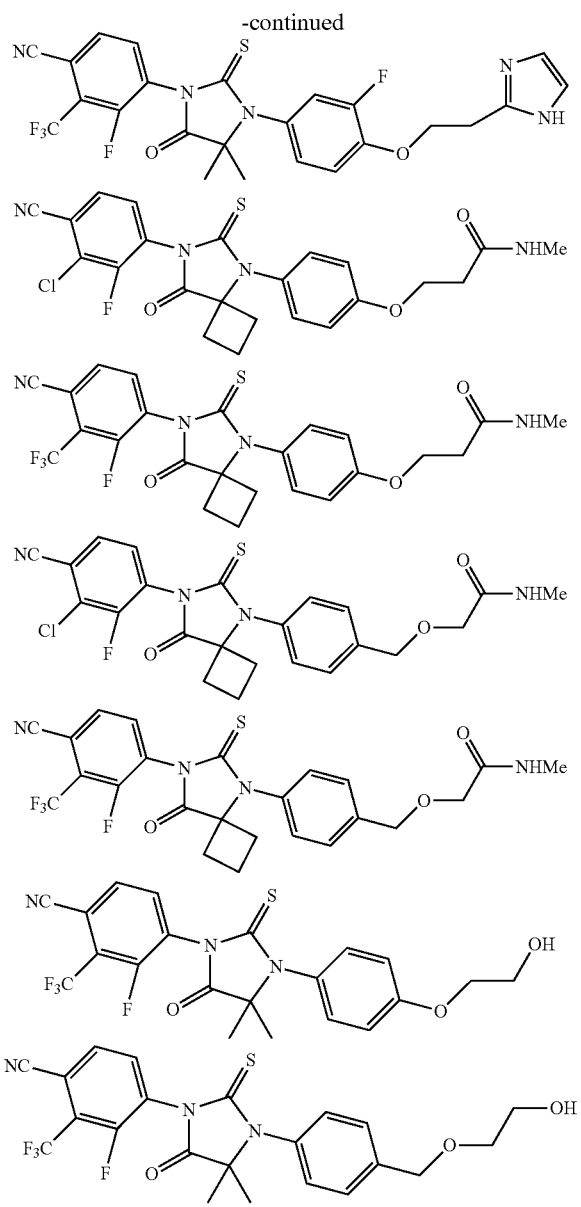

In another embodiment, compounds are provided having a structure of formula (IV)

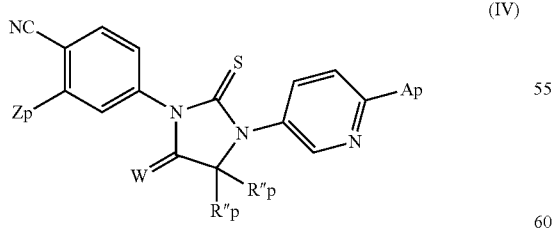

(IV)

or a pharmaceutically-acceptable salt, solvate, hydrate, prodrug or derivative thereof, wherein $Z_p$ is selected from $CF_3$, methoxy, halogen and cyano;

W is selected from oxygen, sulfur and two hydrogens;

$R''_p$ and $R''_p$ are methyl, or $R''_p$ and $R''_p$ and the carbon to which they are attached together form a 3-6 membered cycloalkyl ring optionally substituted with one or more fluoro or hydroxyl groups; and $A_p$ is $(CH_2)_m Y_1 (CH_2)_n Q$ where m and n are integers independently selected from 0 to 4 and wherein at least one of a or m or n is not zero; Q is selected from C(O)NHR'', $C(R_x R_y)C(O)NR''R_1''$, $SO_2R''$, $SO_2NR''R_1''$, cyano, hydroxyl, $C_1$-$C_3$ alkoxy, $C(S)NR''R_1''$, C(O)OR'', $OC(O)NR''R_1''$, $C(O)NR''R_1''$, optionally substituted 5-6 membered heteroaryl, and an optionally substituted 4-6 membered heterocycle; and $Y_1$ is selected from direct bond, —O—, —S—, and —NR''—; R'' and $R_1''$ are independently selected from hydrogen, $C_1$-$C_6$ alkyl, $C_1$-$C_6$ cycloalkyl and $C_1$-$C_6$ alkenyl or $NR''R_1''$ together form a 3-7 membered heterocyclic ring wherein one or more carbons may be optional substituted with one or more hydroxyl, amino, cyano or fluoro groups; $R_x$ and $R_y$ are independently selected from hydrogen or methyl; or $C(R_x R_y)$ together form an optionally substituted 3-5 membered cyclic alkyl ring or a 3-5 membered cyclic ring wherein one carbon is replaced with an oxygen or an amine.

Non-limiting examples of compounds of formula (IV) include:

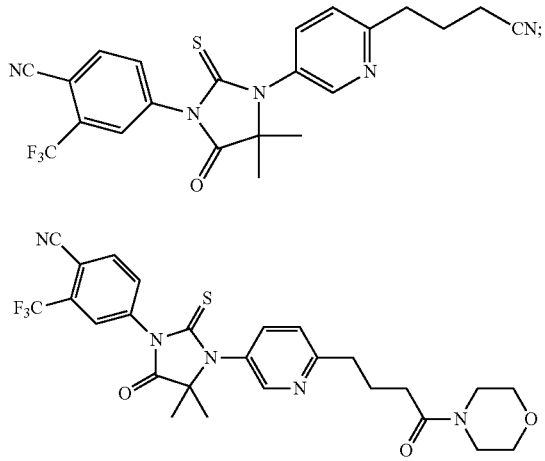

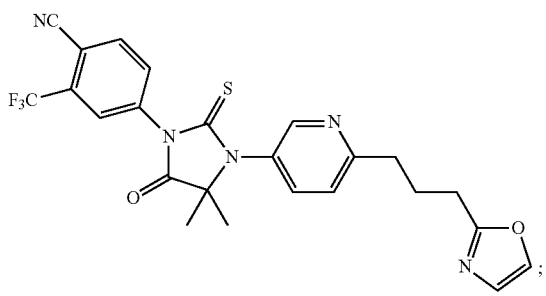

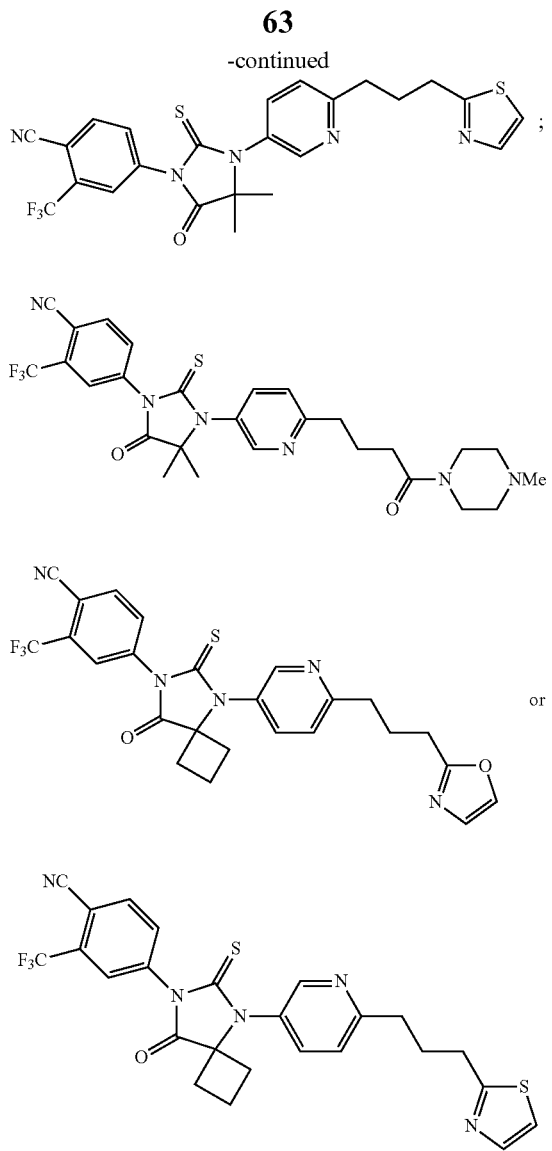

In another embodiment, compounds are provided having following formula

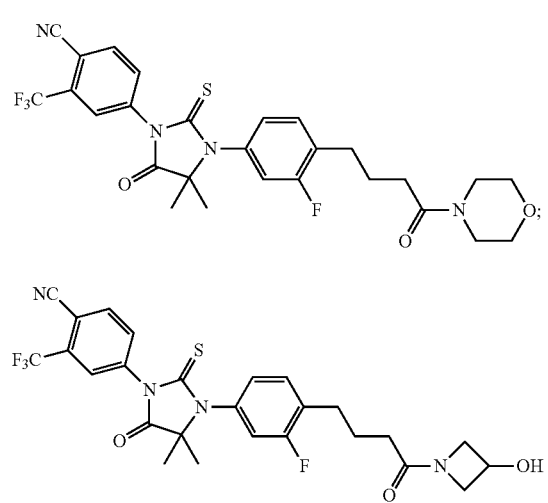

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I), (II), (III) and (IV) under different conditions and may exist as one or a combination of polymorphs of compound of general formula (I), (II), (III) and (IV) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their pharmaceutically acceptable salts their pharmaceutically acceptable solvates and pharmaceutically acceptable compositions containing them.

2) Pharmaceutical Compositions

In another embodiment, the invention is directed to a pharmaceutical composition comprising a compound of formulas (Ia), (I), (II), (III) or (IV) or its pharmaceutically acceptable salt, prodrug or a solution thereof as an active ingredient.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to androgen receptor activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "prodrugs" or "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed herein may achieve a desired effect for the particular disorder, for example, directly increasing hair growth or killing prostate cancer cells; or they may achieve indirect effects that still benefit the particular disorder or the treatment thereof (e.g., reduction of any adverse effects, different dosing schedule, different route of administration). In non-limiting examples, one or more compounds of the invention may be formulated with at least another biological, such as Sipuleucel-T (PROVENGE®), or with at least another small molecule compound. Non-limiting examples of pharmaceutical agents that may be combined therapeutically with compounds of the invention include: HT agents such as LUPRON®, DEGARELIX® and ABIRATERONE®; inhibitors of oncogenic kinases, e.g., VEGF, mTOR, EGFR, SRC and PI3K; cancer chemotherapy agents such as taxanes, etoposide, estramustine phosphate, and doxorubicin; HSP90 inhibitors; agents or natural extracts known to promote hair-growth; agents or natural extracts known to treat acne; or agents or natural extracts known to treat hirsutism.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

3) Methods of Use

As noted above, the present compounds can be used as androgen receptor antagonists. The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; preventing the symptoms associated with reduced testosterone such as hot flashes after castration; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer as noted above is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The present invention addresses the significant medical need for better androgen receptor antagonists that have potent antagonism but devoid of any agonism, and a reduction in the observed side effects such as liver toxicity found in existing androgen receptor antagonist drugs. Compounds of the invention offer a solution to this need.

In addition to prostate cancer, several other conditions and diseases are amenable to treatment with an AR antagonist. The compounds of the present invention are androgen receptor antagonists, which can be used to alleviate any condition associated with inappropriate activation of the androgen receptor. In addition to prostate cancer, other examples of such conditions include acne, hirsutism, seborrhoea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborrhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compounds may also be used topically to decrease seborrhea production and more specifically to alleviate hyperseborrhoea (oily skin), which can be used topically alleviate acne. In further embodiments, the invention comprises a method of administering such compounds of formulas (I)-(IV) or pharmaceutical compositions thereof for treating a disease or disorder related to androgen receptor activity, by way of non-limiting example, treating hormone sensitive prostate cancer or hormone refractory prostate cancer, treating benign hyperplasia of the prostate, treating acne, treating hirsutism, treating excess sebum and treating alopecia due to an androgen receptor disorder.

The compounds of present invention are antagonist of the androgen receptor. Certain compounds have potent antagonistic potent ($IC_{50}<1$ μM) without any significant agonism activity. The compounds of the present invention can be used alone or in combination with one or more other therapeutic agent(s).

As will be seen in the examples below, the biological activity of the compounds embodied herein were tested on hormone sensitive (LNCaP, LAPC4) and hormone refractory prostate cancer cells (LNCaP-AR, LAPC4-AR, LNCaP C4-2, 22RV1, LNCaP-AI and LNCaP-abl) to determine their antagonistic and agonistic activities. Prostate specific antigen (PSA) level can also be used as a marker for androgen receptor antagonistic activity. The MTS (4,5-dimethylthiazol-2-yl)-5-(3-carboxymethoxyphenyl)-2-(4-sulfophenyl)-2H-tetrazolium) assay is also used to evaluate the present compounds for potency of inhibiting cell growth. The selective, potent androgen receptor antagonists with acceptable rodent oral exposure are further evaluated for in vivo efficacy using prostate cancer xenografts. The cell lines can be selected from LNCaP, LAPC4, LAPC9, CWR22, LNCaP-AR, LNCaP C4-2, 22RV1, LNCaP-abl and LNCaP-AI.

As will also be seen in the examples, below, the PSA Assay (Inhibition Test of the Compound of the Present Invention on Prostate-specific Antigen (PSA) Production in Various Prostate Cancer Cells) demonstrated that while bicalutamide inhibited PSA production in LNCaP cells with an $IC_{50}$ of 3.1 micromolar, the preferred compounds showed $IC_{50}$s less than about 0.5 micromolar. Thus, the compounds of the present invention showed a strong PSA production suppressing activity.

In another assay that can be used to assess the biological activity of the compounds embodied herein measuring cell viability, LNCaP and 22RV1 cells can be used to show that compounds of the invention inhibit viability. Typically, an inhibition of 60-90% is expected. Thus, the compounds of the present invention are anticipated to show stronger inhibitory activity against both hormone sensitive and hormone refractory cells, as compared with bicalutamide.

In an in vivo assay for the activity of the compounds embodied herein, a C57BL/6 mouse hair growth model can be used. Solutions containing test compounds at various concentrations can be topically applied to the shaved lower back. The treatment regiment regimen can be twice daily (BID) application for 4 weeks. Local irritation can be recorded before each application and hair growth scores can be recorded every other day. After 4 weeks of treatment, mice can then be further observed for one more week during which hair growth and skin irritation are scored every other day. A scale can be used for scoring hair growth. The results in this model are expected to show that compounds of the invention demonstrate in vivo activity for stimulating hair growth and possess desirable physiochemical properties for dermal delivery, indicating the compounds of the present invention are expected to be excellent therapeutics for promoting hair growth and/or other clinical indication such as reducing oily skin due to their desirable local biological effect against androgen receptor and result in low systemic exposure to avoid unwanted side effects.

As detailed in the exemplification herein, in assays to determine the ability of compounds to inhibit production of PSA by prostate cancer cells, certain inventive compounds exhibited IC50 values ≤5 µM. In certain other embodiments, inventive compounds exhibit IC50 values ≤2.5 µM. In certain embodiments, inventive compounds exhibit IC50 values ≤1 µM. In certain other embodiments, inventive compounds exhibit IC50 values ≤750 nM. In certain other embodiments, inventive compounds exhibit IC50 values ≤500 nM. In certain other embodiments, inventive compounds exhibit IC50 values ≤250 nM. In certain other embodiments, inventive compounds exhibit IC50 values ≤100 nM. In other embodiments, exemplary compounds exhibit IC50 values ≤75 nM. In other embodiments, exemplary compounds exhibit IC50 values ≤50 nM. In other embodiments, exemplary compounds exhibit IC50 values ≤40 nM. In other embodiments, exemplary compounds exhibit IC50 values ≤30 nM. In other embodiments, exemplary compounds exhibit IC50 values ≤20 nM. In other embodiments, exemplary compounds exhibit IC50 values ≤10 nM. In other embodiments, exemplary compounds exhibit IC50 values ≤5 nM.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules, or topical forms. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols. 1-17, John Wiley and Sons, New York, N.Y., 1991; Rodd 1989 "Chemistry of Carbon Compounds", vols. 1-5 and supps., Elsevier Science Publishers, 1989; "Organic Reactions", vols. 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2nd ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

EXAMPLES

Synthetic Examples

Synthesis of Compounds of the Invention

The compounds of formula I-III of the invention can be prepared as shown in the following reaction schemes (using formula I as an example) and description thereof

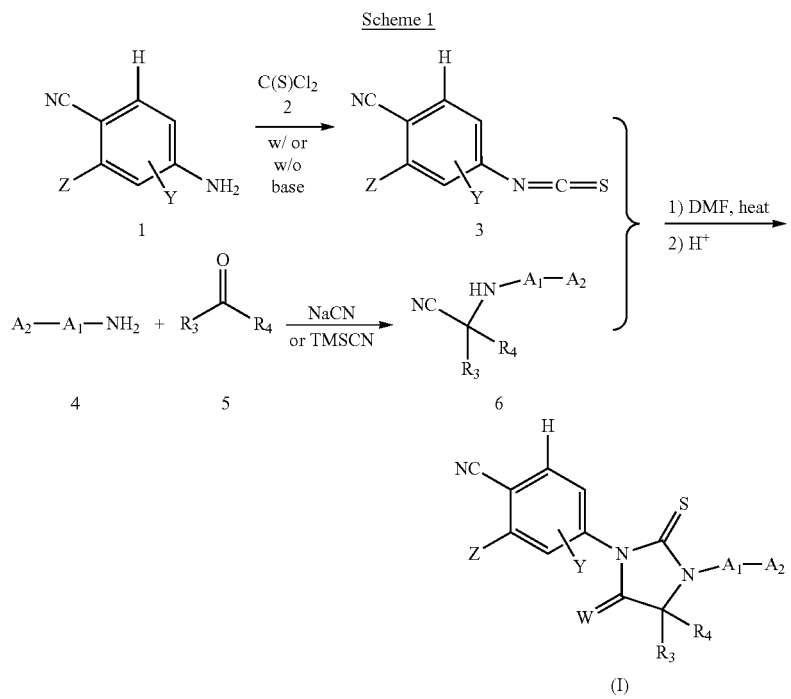

As shown in Scheme 1, isothiocyanate 3 can be prepared from aniline 1 with treatment of thiophosgene. Intermediate 6 can be synthesized by condensing amine or aniline 4 and ketone 5 in the presence of TMSCN or sodium cyanide. The condensation can also be accomplished by reacting the aniline 4 and an appropriate ketone cyanoanhydrin in the presence of $MgSO_4$. The final thioimidazolidinone, compound of formula I, can be prepared from reaction between 3 and 6. Aniline 1 can be obtained commercially, or can be prepared by methods shown below or known in the literature, for example, reduction of nitrobenzenes.

Synthesis of Isothiocyanate 3a

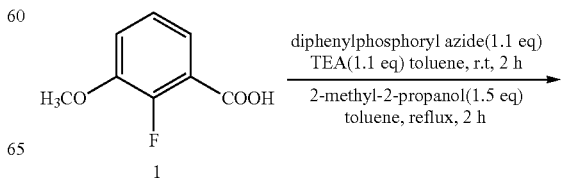

-continued

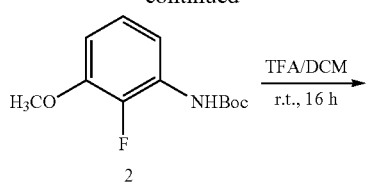
2

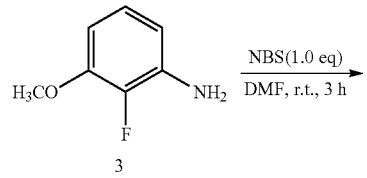
3

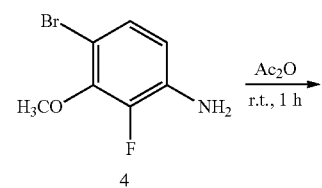
4

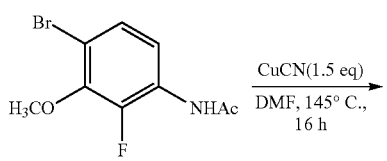
5

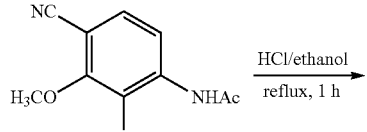
6

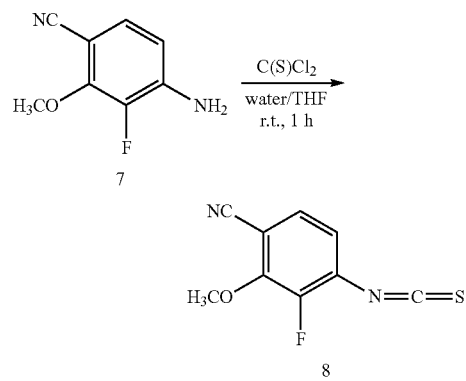
7
8

Preparation of Compound 8

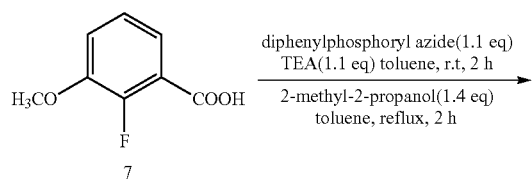
7

-continued

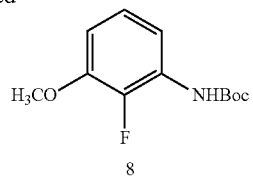
8

To a solution of compound 7 (7.5 g, 44 mmol) in toluene (150 mL), TEA (7 mL, 48 mmol, 1.1 eq) was added, followed by DPPA (10.5 mL, 48.4 mmol, 1.1 eq). The reaction mixture was stirred at room temperature for 2 h. 2-Methyl-2-propanol (6.3 mL, 66 mmol, 1.5 eq) was then added and the resulting mixture was heated at reflux for 2 h. Solvent was removed in vacuo and the residue was diluted with ethyl acetate (200 mL), washed with water (1×50 mL). The organic layer was dried (Na$_2$SO$_4$), filtered, and concentrated to give the title compound 8 as a light yellow solid (8.9 g, 90% yield), which was used directly in the next step without further purification. ESI-MS (M-C$_4$H$_9$)$^+$: 186.

Preparation of Compound 9

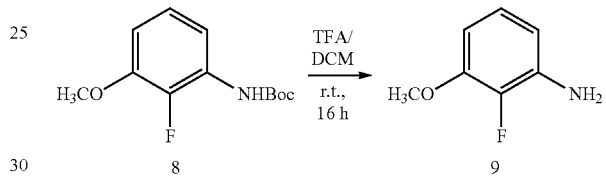
8
9

To a compound 8 (24 g, 100 mmol) solution in dichloromethane (100 mL) was slowly added TFA (40 mL) at 0° C. The reaction mixture was stirred at room temperature overnight, then extracted with H$_2$O (2×300 mL). The aqueous phase was neutralized by addition of saturated NaHCO$_3$ aqueous solution until pH=8, then extracted with ethyl acetate (3×100 mL). The combined organic layers were dried (Na$_2$SO$_4$), filtered, and concentrated to give the title compound 9 as a brown liquid (13 g, 92% yield). ESI-MS (M-C$_4$H$_9$)$^+$: 142

Preparation of Compound 10

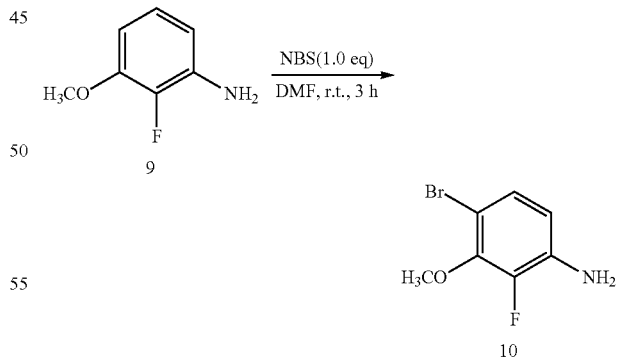
9

10

To a solution of compound 9 (13 g, 92 mmol) in DMF (100 mL) was added a solution of NBS (16.4 g, 92 mmol, 1.0 eq) in DMF (100 mL) drop-wise. The reaction mixture was stirred at room temperature for 3 h, then diluted with ethyl acetate (500 mL) and washed with brine (2×150 mL). The organic phase was dried (Na$_2$SO$_4$), filtered and concentrated to give the title compound 10 as brown oil (23 g, 98% yield). ESI-MS (M+H)$^+$: 219.9.

Preparation of Compound 11

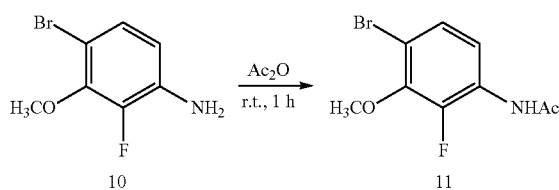 [SMILES: "Ac2O" ; COc1c(Br)ccc(N)c1F ; COc1c(Br)ccc(NC(C)=O)c1F]

Compound 10 (11.2 g, 51 mmol) was dissolved in 10 mL of Ac$_2$O and stirred at room temperature for 1 h. The solution was concentrated in vacuo and the residue was added ice (~10 g) and sodium bicarbonate (until pH=7). The resulted mixture was extracted with ethyl acetate (3×100 mL). The organic layers were combined, dried (Na$_2$SO$_4$), filtered and concentrated to give the title compound 11 as a brown solid (9.8 g, 74% yield). $^1$H NMR (400 MHz, CDCl$_3$) δ 7.94-7.91 (m, 1H), 7.55 (br, 1H), 7.28-7.26 (m, 1H), 3.93 (s, 3H), 2.08 (s, 3H); ESI-MS (M+H)$^+$: 263.9.

Preparation of Compound 12

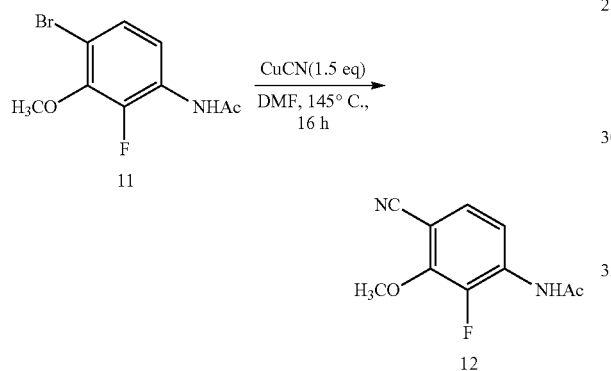

A mixture of compound 11 (5.0 g, 19 mmol) and CuCN (2.5 g, 29 mmol, 1.5 eq) in DMF (20 mL) was heated at 145° C. under nitrogen overnight. The reaction mixture was cooled to room temperature and then poured into ice water (50 mL). Ethyl acetate (100 mL) was added and the insoluble solid was filtered off (washed with ethyl acetate [2×30 mL]). The organic layer was separated, and the aqueous layer was extracted with ethyl acetate (2×50 mL). The combined extracts were washed with saturated aqueous NaHCO$_3$ solution (1×150 mL), brine (3×100 mL), and dried over MgSO$_4$. The resulting material was concentrated and the residue was purified by silica gel chromatography (petroleum ether:ethyl acetate, 10:1) to afford the title compound 12 as a light yellow solid (2.6 g 66% yield). $^1$H NMR (400 MHz, DMSO-d$_6$) δ 10.13 (s, 1H), 7.93 (d, 1H), 7.53 (d, 1H), 4.05 (s, 3H), 2.15 (s, 3H); ESI-MS (M+H)$^+$: 209.

Preparation of Compound 1a

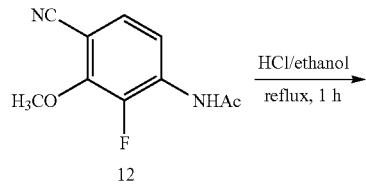

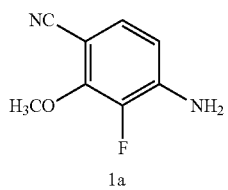

To a solution of compound 12 (4.0 g, 192 mmol) in ethanol (30 mL), was added concentrated HCl solution (12N, 10 mL). The mixture was heated at reflux for 1 h. Solvent was removed in vacuo. The residue was re-dissolved in water (50 mL). The resulting aqueous solution was added saturated NaHCO$_3$ aqueous solution until pH=7~8, then extracted with ethyl acetate (3×150 mL). The combined organic layers were dried with Na$_2$SO$_4$, filtered, and concentrated to provide the title compound 1a as a light yellow solid (3.2 g, 90% yield). $^1$H NMR (400 MHz, DMSO-d$_6$) δ 7.18 (d, 1H), 6.50 (t, 1H), 6.28 (s, 2H), 3.97 (s, 3H); ESI-MS (M+H)$^+$: 167.

Preparation of Compound 3a

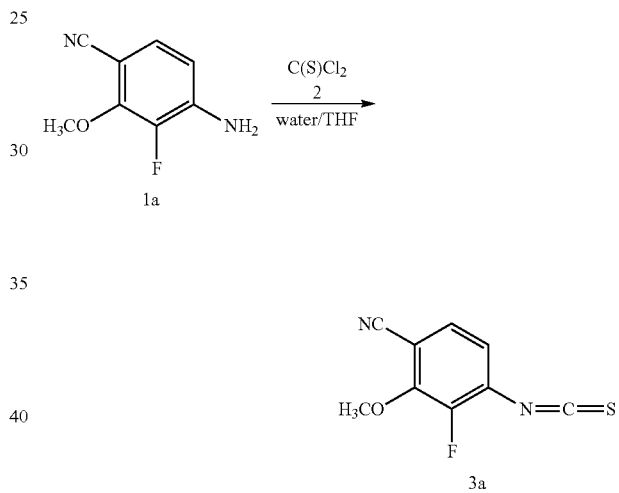

To a solution of 1a (332 mg, 2 mmol) in THF (5 mL), a solution of thiophosgene (2 mL) in water (5 mL) was slowly added at room temperature. The reaction mixture was stirred for 1 h then concentrated. The residue was partitioned between H$_2$O (50 mL) and ethyl acetate (30 mL). The resulted aqueous phase was extracted with ethyl acetate (2×30 mL). The organic extracts were combined, washed with brine (2×50 mL), dried with anhydrous MgSO$_4$, filtered, and concentrated to provide the title compound 3a as a light yellow solid, which was used directly in next step without further purification.

Synthesis of Isothiocyanate 3b

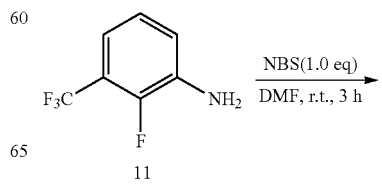

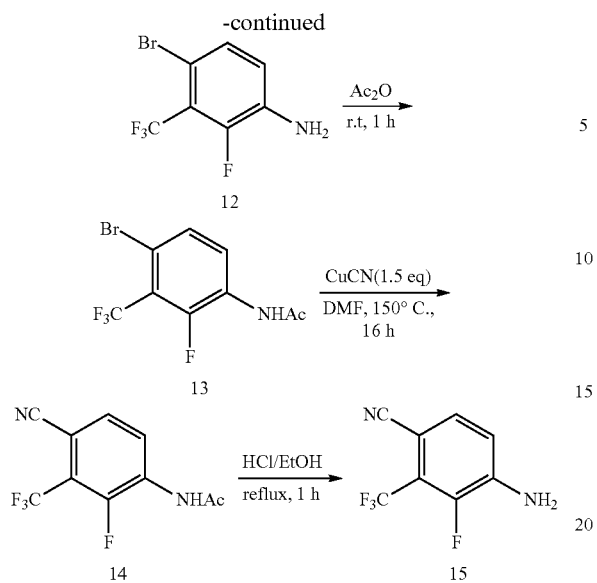

Preparation of Compound 3b
Synthesis of compound 3b from 1b followed a procedure similar to the preparation of 3a. The title compound 3b was obtained in 95% yield.

Synthesis of Isothiocyanate 3c

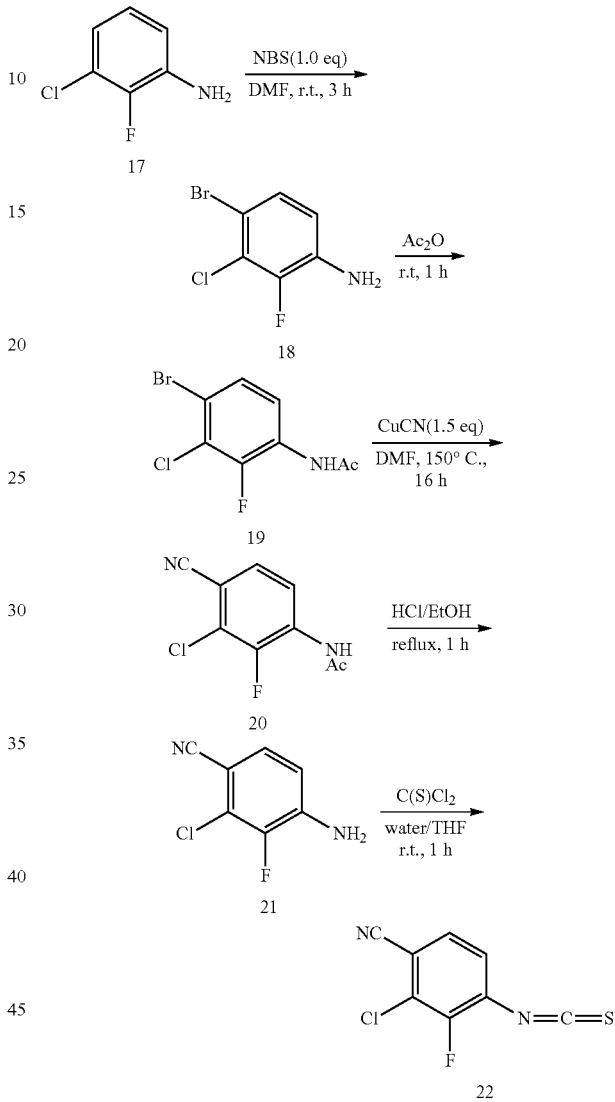

Preparation of Compound 14
To a compound 13 (2.88 g, 16.1 mmol) solution in DMF (30 mL) was added a DMF solution (30 mL) of NBS (2.86 g, 16.1 mmol) drop-wise at room temperature. After 3 h, the reaction mixture is diluted with Et$_2$O (100 mL) and washed with brine (2×100 mL). The separated organic phase was dried (Na$_2$SO$_4$) and concentrated to give the title compound 14 as an oil (3.1 g, 75% yield). $^1$H NMR (400 MHz, DMSO-d$_6$) δ 7.32 (d, 1H), 6.96 (t, 1H), 5.847 (s, 2H); ESI-MS (M+H)$^1$: 259.8.

Preparation of Compound 15
A mixture of compound 14 (2.58 g) and acetic anhydride (5 mL) was stirred at room temperature for 3 h, then concentrated in vacuo. The residue was added ice (~10 g) and sodium bicarbonate (until pH=7). The resulted mixture was extracted with ethyl acetate (3×100 mL). The organic layers were combined, dried (Na$_2$SO$_4$), filtered and concentrated to give the title compound 15. (2.68 g, 85% yield). ESI-MS (M+H)$^+$: 301.8.

Preparation of Compound 16
A mixture of compound 15 (1.5 g, 5 mmol), CuCN (0.72 g, 6 mmol) in DMF (8 mL) was heated at 145° C. under nitrogen overnight. The reaction mixture was cooled to room temperature and then poured into ice water (25 mL). Ethyl acetate (30 mL) was added and the insoluble solid was filtered off [rinsed with ethyl acetate (3×10 mL)]. The organic layer was separated, and the aqueous layer was extracted with ethyl acetate (1×50 mL). The combined extracts were washed with saturated aqueous NaHCO$_3$ (2×50 mL), brine (3×50 mL), dried over MgSO$_4$, filtered and concentrated in vacuo. The residue was purified with silica gel chromatography (10:1/Petroleum ether:ethyl acetate) to afford the title compound 16 as a light yellow solid (1.1 g, 80% yield). ESI-MS (M+H)$^+$: 246.9.

Preparation of Compound 1b
To a solution of compound 16 (1.45 g, 5.89 mmol) in EtOH (10 mL) was added concentrated HCl solution (12N, 10 mL). The mixture was heated at reflux for 1 h, cooled to room temperature, then concentrated in vacuo. The resulting white solid was dissolved in ethyl acetate (25 mL), washed with saturated aqueous NaHCO$_3$ (1×25 mL), dried over MgSO$_4$ and concentrated to give compound 1b (1.0 g, 90% yield) as a white solid. ESI-MS (M+H)$^+$: 205.

Preparation of Compound 18
A solution of compound 17 (5 g, 0.034 mol) in DMF (50 mL) was added a DMF solution (50 mL) of NBS (6.05 g, 0.034 mol) drop-wise at room temperature. After 16 h, the reaction mixture was diluted with ethyl acetate (100 mL) and washed with brine (2×100 mL). The separated organic phase was dried over Na$_2$SO$_4$ and concentrated to give the title compound 18 as an oil (5.0 g, 65% yield). ESI-MS (M+H)$^+$: 223.92.

Preparation of Compound 19
A mixture of compound 18 (5.0 g, 22 mmol), acetic anhydride (5 mL) and pyridine (0.1 mL) was stirred at room temperature for 50 min, then concentrated in vacuo. The residue was added ice (~10 g) and sodium bicarbonate (until pH=7). The resulted mixture was extracted with ethyl acetate (3×50 mL). The organic layers were combined, dried (Na$_2$SO$_4$), filtered and concentrated to give the title compound 19. (4.0 g, 68% yield). ESI-MS (M+H)$^+$: 265.93.

Preparation of Compound 20

A mixture of compound 19 (4.0 g, 15 mmol) and CuCN (1.59 g, 18 mmol) in DMF (40 mL) was heated at 145° C. under nitrogen atmosphere overnight. The reaction mixture was cooled to room temperature, poured into ice water (20 mL). Ethyl acetate (25 mL) was added and the insoluble solid was filtered off [rinsed with ethyl acetate (3×10 mL)]. The organic layer was separated, and the aqueous layer was extracted with ethyl acetate (1×25 mL). The combined extracts were washed with saturated aqueous NaHCO$_3$ solution (2×30 mL), brine (3×40 mL), dried (MgSO$_4$), and concentrated in vacuo. The residue was purified by silica gel chromatography (5:1/Petroleum ether:ethyl acetate) to afford the title compound 20 as a light yellow solid (2.56 g, 80% yield). ESI-MS (M+H)$^+$: 213.02

Preparation of Compound 1c

To a solution of compound 20 (2.56 g, 12 mmol) in EtOH (10 mL) was added concentrated HCl solution (12N, 10 mL). The mixture was heated at reflux for 1 h and then concentrated in vacuo. The resulting white solid was dissolved in ethyl acetate (50 mL). The solution was washed with saturated aqueous NaHCO$_3$ solution (1×50 mL), dried over MgSO$_4$ and concentrated to give the title compound 1c (1.8 g, 88% yield) as a white solid. $^1$H NMR (400 MHz, CDCl$_3$) δ 7.55 (d, J=6.0 Hz, 1H), 7.07-7.04 (m, 1H), 6.82 (br s, 2H). ESI-MS (M+H)$^+$: 171.00.

Preparation of Compound 3c

To a solution of 1c (1.8 g, 11 mmol) in THF (20 mL) was added a solution of thiophosgene (11 mL) in water (11 mL) slowly at room temperature. The reaction mixture was stirred for 1 h, then concentrated in vacuo. The residue was dissolved in H$_2$O (50 mL). The aqueous solution was extracted with ethyl acetate (3×50 mL). The organic extracts were combined and washed with brine (2×50 mL), dried with anhydrous MgSO$_4$, filtered, concentrated to provide compound the title compound 3c as a light yellow solid, which was used directly in next step without further purification.

Synthesis of 5-Fluoro-4-isothiocyanato-2-trifluoromethyl-benzonitrile 3d

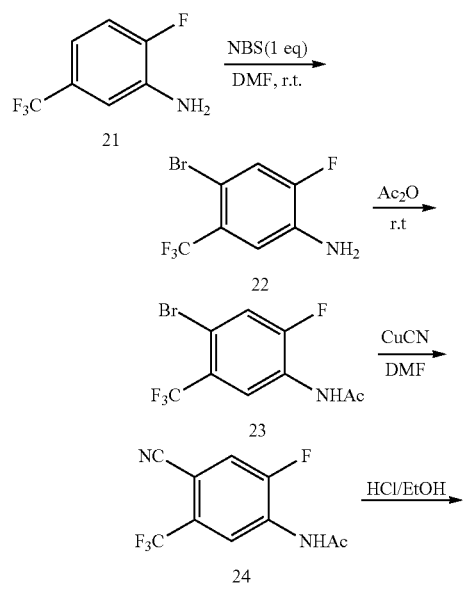

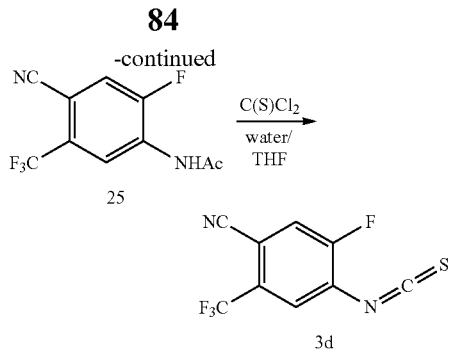

Preparation of 4-bromo-2-fluoro-5-(trifluoromethyl)aniline 22

To a compound 21 (2.2 g, 12.3 mmol) solution in DMF (10 mL) was added dropwise a solution (10 mL) of NBS (2.19 g, 12.3 mmol) at room temperature. After 3 h, the reaction mixture is diluted with EtOAc and washed with brine. The separated organic phase was dried over Na2SO4 and concentrated to give the title compound 22 (3.6 g, 99%) as a yellow oil.

Preparation of N-(4-bromo-2-fluoro-5-(trifluoromethyl)phenyl)acetamide 23

A mixture of compound 22 (3.6 g, 14 mmol), acetic anhydride (8 mL) and pyridine (0.1 mL) was stirred at room temperature for 1 h, then concentrated in vacuo. The residue was added ice and sodium bicarbonate (until pH=7). The resulted mixture was extracted with EtOAc. The organic layers were combined, washed by brine, dried over Na2SO4, filtered and concentrated to give the title compound 23 (3.5 g, 83%). 1H NMR (400 MHz, CDCl3) δ8.79 (d, 1H, J=7.8 Hz), 7.46 (d, 1H, J=10.0 Hz), 7.38 (br s, 1H), 2.24 (s, 3H).

Preparation of N-(4-cyano-2-fluoro-5-(trifluoromethyl)phenyl)acetamide 24

A mixture of compound 23 (300 mg, 1 mmol), CuCN (355 mg, 4 mmol) in DMF (6 mL) was heated at 150° C. under N2 overnight. The reaction mixture was cooled to room temperature and then poured into ice water. EtOAc was added and the insoluble solid was filtered off (rinsed with EtOAc). The organic layer was separated, and the aqueous layer was extracted with EtOAc. The combined organic layers were washed with aq.NaHCO3 and brine, dried over Na2SO4, filtered and concentrated in vacuo. The residue was purified with silica gel chromatography (PE:EtOAc=4:1) to afford the title compound 24 (140 mg, 28%) as a white solid. 1H NMR (400 MHz, CDCl3) δ8.99 (d, 1H, J=7.2 Hz), 7.55 (d, 1H, J=10.0 Hz), 2.92 (s, 3H).

Preparation of 4-amino-5-fluoro-2-(trifluoromethyl)benzonitrile 25

To a solution of compound 24 (800 mg, 3.25 mmol) in EtOH (10 mL) was added concentrated HCl solution (12N, 5 mL). The mixture was heated at reflux for 1 h, cooled to room temperature, concentrated in vacuo. The resulting white solid was dissolved in EtOAc, washed with saturated aqueous NaHCO3, dried over Na2SO4 and concentrated to give compound 25 (660 mg, 99%) as a light yellow solid. 1H NMR (400 MHz, CDCl3) δ7.40 (d, 1H, J=7.2 Hz), 7.09 (d, 1H, J=10.0 Hz), 4.48 (br s, 2H).

Preparation of 5-fluoro-4-isothiocyanato-2-(trifluoromethyl)benzonitrile 3d

To a solution of the compound 25 (660 mg, 3.25 mmol) in THF (6 mL) was added a solution of thiophosgene (1 mL, 13 mmol) in water (1 mL) slowly at room temperature. The reaction mixture was stirred for 1 h, then concentrated in vacuo. The residue was diluted with H2O. The aqueous solution was extracted with ethyl acetate. The organic layers were combined and washed with aq.NaHCO3 and brine, dried over Na2SO4, filtered and concentrated to provide the title compound 3d (700 mg, 88%) as a light yellow solid, which was used directly in next step without further purification. 1H NMR (400 MHz, CDCl3) δ7.63 (d, 1H, J=8.5 Hz), 7.57 (d, 1H, J=6.9 Hz).

Synthesis of cyanoamine 28

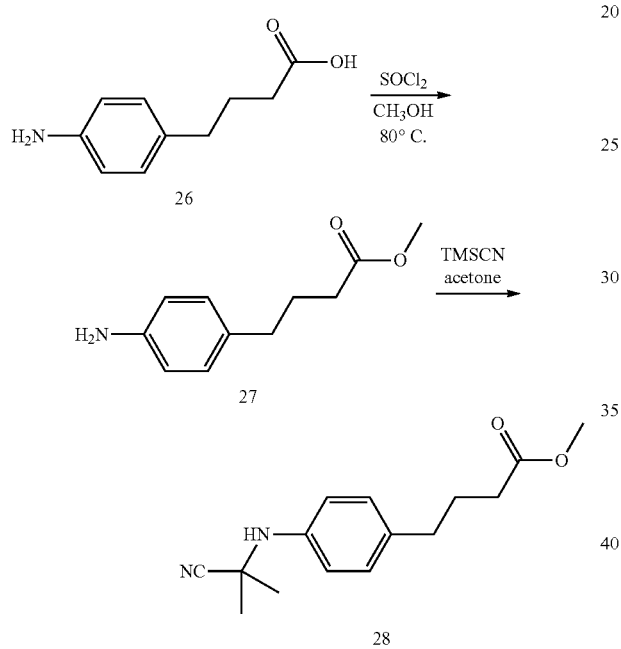

Preparation of methyl 4-(4-aminophenyl)butanoate 27

To a mixture of compound 26 (0.92 g, 5.13 mmol) in CH3OH (20 mL) was added dropwise thionyl chloride (1.9 mL, 25.7 mmol) at 0° C. with stirring. After addition, the reaction mixture was stirred at 80° C. for 16 h, concentrated in vacuo. The residue was diluted with aqNaHCO3, and extracted with ethyl acetate. The combined organic layers were washed with brine, dried over Na2SO4 and concentrated to dryness to give compound 27 (0.7 g, 70%) as a light yellow solid. 1H NMR (400 MHz, CDCl3) δ6.97 (d, 2H, J=8.3 Hz), 6.64 (d, 2H, J=8.3 Hz), 3.68 (br s, 2H), 3.66 (s, 3H), 2.54 (t, 2H, J=7.4 Hz), 2.31 (t, 2H, J=7.4 Hz), 1.85-1.95 (m, 2H).

Preparation of methyl 4-(4-((2-cyanopropan-2-yl)amino)phenyl)butanoate 28

TMSCN (1.44 mL, 10.8 mmol) was added to a mixture of the compound 27 (0.7 g, 3.6 mmol), acetone (1.60 mL, 21.6 mmol) and 12 (50 mg, 0.4 mmol) with stirring. The reaction mixture was stirred at 50° C. for 0.5 h. The reaction was concentrated in vacuo. The residue was diluted with aq Na2SO3 and extracted with ethyl acetate. The combined organic layers were washed with aqNa2SO3 and brine, dried over Na2SO4 and concentrated to dryness to give compound 28 (0.9 g) as a light yellow oil. The crude product was used directly for the next step without purification. 1H NMR (400 MHz, CDCl3) δ7.07 (d, 2H, J=8.3 Hz), 6.87 (d, 2H, J=8.3 Hz), 3.66 (s, 3H), 2.58 (t, 2H, J=7.4 Hz), 2.32 (t, 2H, J=7.4 Hz), 1.85-1.95 (m, 2H), 1.68 (s, 6H).

Synthesis of compound 31

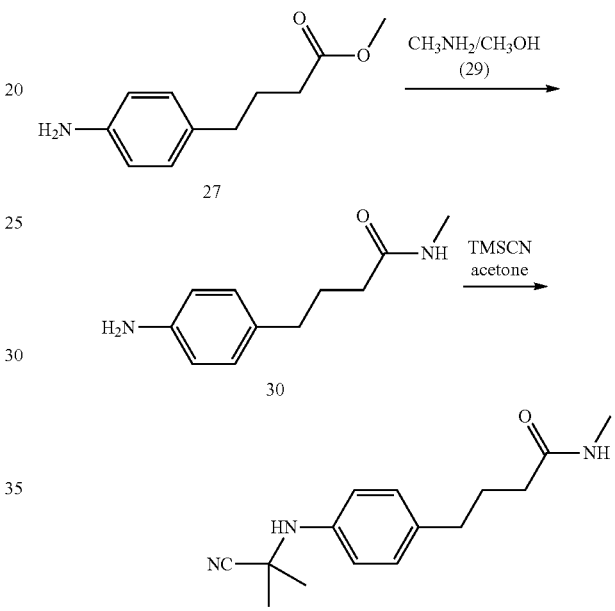

Preparation of 4-(4-aminophenyl)-N-methylbutanamide 30

A solution of compound 27 (450 mg, 2.33 mmol) in CH3NH2/CH3OH (29, 50 mL) was stirred at room temperature for overnight. The reaction mixture was concentrated to dryness to give compound 30 (450 mg, 95%) as a white solid. The crude product was used directly for the next step without purification. 1H NMR (400 MHz, CDCl3) δ6.95 (d, 2H, J=8.3 Hz), 6.61 (d, 2H, J=8.3 Hz), 5.30 (br s, 1H), 3.50 (br s, 2H), 2.78 (d, 3H, J=4.8 Hz), 2.54 (t, 2H, J=7.4 Hz), 2.14 (t, 2H, J=7.4 Hz), 1.85-1.95 (m, 2H).

Preparation of 4-(4-((2-cyanopropan-2-yl)amino)phenyl)-N-methylbutanamide 31

TMSCN (0.1 mL, 0.78 mmol) was added to a mixture of the compound 30 (50 mg, 0.26 mmol), acetone (0.12 mL, 1.56 mmol) and 12 (4 mg, 0.03 mmol) with stirring. The reaction mixture was stirred at 40° C. for 1 h, and concentrated in vacuo. The residue was diluted with aqNa2SO3, and extracted with ethyl acetate. The combined organic layers were washed with aqNa2SO3 and brine, dried over Na2SO4 and concentrated to dryness to give compound 31 as light yellow oil. The crude product was used directly for the next step without purification. 1H NMR (400 MHz, CDCl3) δ7.07 (d, 2H, J=8.4 Hz), 6.88 (d, 2H, J=8.4 Hz), 5.33 (br s, 1H), 2.79 (d, 3H, J=4.8 Hz), 2.59 (t, 2H, J=7.4 Hz), 2.16 (t, 2H, J=7.4 Hz), 1.85-1.95 (m, 2H), 1.68 (s, 6H).

Synthesis of Compound 34

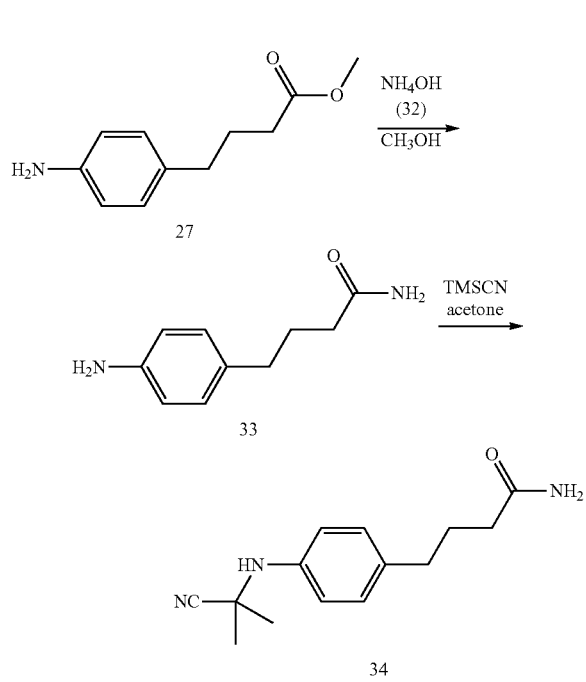

Preparation of 4-(4-aminophenyl)butanamide 33

To a solution of compound 27 (300 mg, 1.55 mmol) in CH3OH (5 mL) was added NH4OH (32) at room temperature with stirring. The reaction mixture was stirred at room temperature for 6 h and concentrated in vacuo. The residue was diluted with water and extracted with DCM/CH3OH (10:1). The combined organic layers were dried over Na2SO4 and concentrated to dryness to give compound 33 (194 mg, 70%) as a white solid. The crude product was used directly for the next step without purification.

1H NMR (400 MHz, CDCl3) δ 6.96 (d, 2H, J=8.1 Hz), 6.61 (d, 2H, J=8.1 Hz), 5.29 (br s, 2H), 3.55 (br s, 2H), 2.57 (t, 2H, J=7.4 Hz), 2.20 (t, 2H, J=7.4 Hz), 1.85-1.95 (m, 2H).

Preparation of 4-(4-((2-cyanopropan-2-yl)amino) phenyl)butanamide 34

TMSCN (0.3 mL, 2.36 mmol) was added to a mixture of the compound 33 (140 mg, 0.79 mmol), acetone (0.35 mL, 1.56 mmol) and 12 (10 mg, 0.08 mmol). The reaction mixture was stirred at 40° C. for 1 h. The reaction was concentrated in vacuo. The residue was diluted with aqNa2SO3, and extracted with ethyl acetate. The combined organic layers were washed with aqNa2SO3 and brine, dried over Na2SO4 and concentrated to dryness to give compound 34 (80 mg) as a light yellow oil. The crude product was used directly for the next step without purification. 1H NMR (400 MHz, CDCl3) δ7.08 (d, 2H, J=8.5 Hz), 6.88 (d, 2H, J=8.5 Hz), 5.29 (br s, 1H), 2.61 (t, 2H, J=7.4 Hz), 2.20 (t, 2H, J=7.4 Hz), 1.87-1.97 (m, 2H), 1.68 (s, 6H).

Synthesis of compound 37

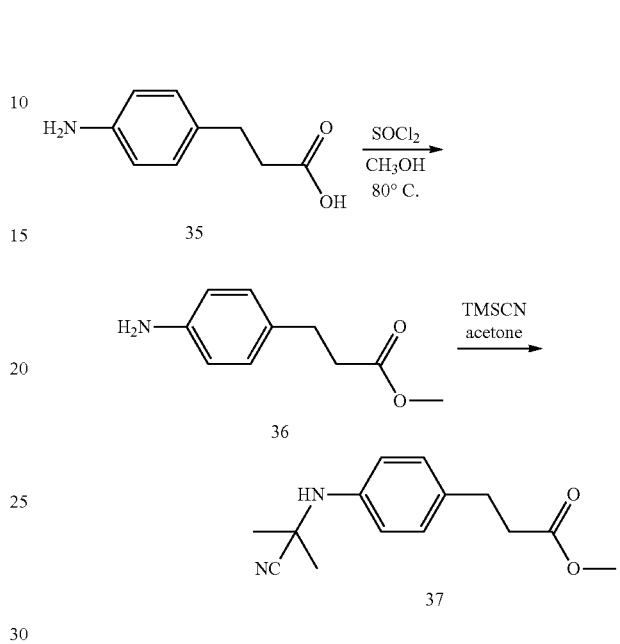

Preparation of methyl 3-(4-aminophenyl) propanoate 36

The procedure and workup were conducted in a similar manner to the synthesis of the compound 27. Compound 36 was obtained in 96% yield as a white solid.

1H NMR (400 MHz, CDCl3) δ6.99 (d, 2H, J=8.2 Hz), 6.62 (d, 2H, J=8.2 Hz), 3.66 (s, 3H), 3.65 (br s, 2H), 2.85 (t, 2H, J=7.6 Hz), 2.57 (t, 2H, J=8.1 Hz).

Preparation of methyl 3-(4-((2-cyanopropan-2-yl) amino)phenyl)propanoate 37

The procedure and workup were conducted in a manner similar to the synthesis of the compound 31. The crude product was carried on to the next step without further purification.

1H NMR (400 MHz, CDCl3) δ7.09 (d, 2H, J=8.2 Hz), 6.87 (d, 2H, J=8.2 Hz), 3.67 (s, 3H), 2.89 (t, 2H, J=7.6 Hz), 2.60 (t, 2H, J=8.1 Hz), 1.68 (s, 3H)

Preparation 3-(4-((2-cyanopropan-2-yl)amino)phenyl)-N-methylpropanamide 38

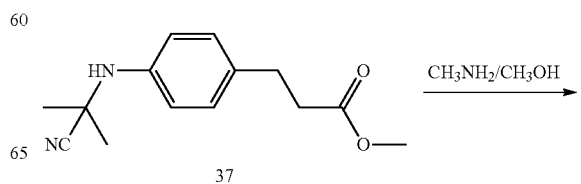

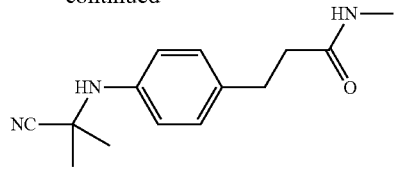

38

To a solution of compound 37 (20 mg, 0.08 mmol) in CH3OH (3 mL) was added dropwise a solution of the CH3NH2 in CH3OH (3 mL) at 0° C. with stirring. The reaction mixture was stirred at 0° C. for 6 h. The ice-water was added into the reaction mixture. The aqueous phase was extracted with DCM. The combined organic layers were washed with brine, dried over Na2SO4 and concentrated to dryness to give compound 38 (25 mg) as a light yellow oil. The crude product was used directly for the next step without purification. 1H NMR (400 MHz, CDCl3) δ7.09 (d, 2H, J=8.2 Hz), 6.86 (d, 2H, J=8.2 Hz), 2.90 (t, 2H, J=7.4 Hz), 2.77 (d, 3H, J=4.8 Hz), 2.43 (t, 2H, J=7.4 Hz), 1.68 (s, 6H).

Synthesis of methyl 4-(4-(3-(3-chloro-4-cyano-2-fluorophenyl)-5,5-dimethyl-4-oxo-2-thioxoimidazolidin-1-yl)phenyl)butanoate Example 1

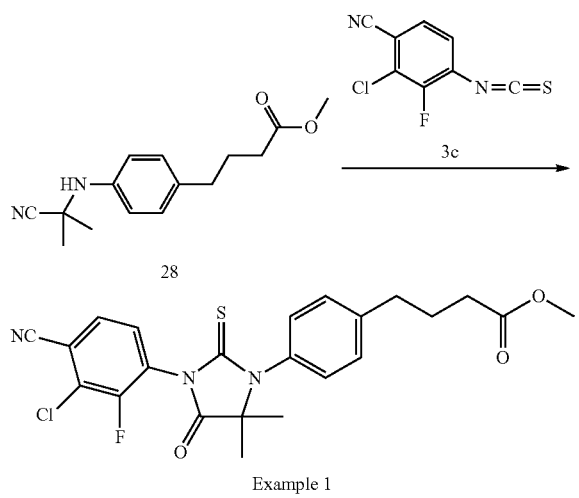

Example 1

A mixture of 3c (66 mg, 0.31 mmol) and 28 (50 mg, 0.19 mmol) in DMF (0.2 mL) was stirred at room temperature for overnight. To this mixture was added CH3OH (10 mL) and aq. 3N HCl (10 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified with silica gel column chromatography using Petroleum ether:Ethyl acetate (3:1) affording the title compound EXAMPLE 1 (5 mg, 5%) as a white solid. 1H NMR (400 MHz, CDCl3) δ7.59-7.64 (m, 1H), 7.48-7.53 (m, 1H), 7.55 (d, 2H, J=8.2 Hz), 7.22 (d, 2H, J=8.2 Hz), 3.69 (s, 3H), 2.73 (t, 2H, J=7.5 Hz), 2.39 (t, 2H, J=7.4 Hz), 1.95-2.05 (m, 2H), 1.57 (d, 6H, J=5.7 Hz).

Synthesis of methyl 4-(4-(3-(4-cyano-2-fluoro-3-(trifluoromethyl)phenyl)-5,5-dimethyl-4-oxo-2-thioxoimidazolidin-1-yl)phenyl)butanoate Example 2

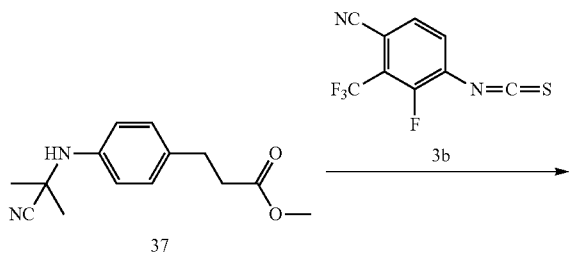

Example 2

A mixture of 28 (800 mg, 3.07 mmol) and 3b (1.1 g, 4.60 mmol) in DMF (0.7 mL) was stirred at room temperature for overnight. To this mixture was added CH3OH (6 mL) and aq. 3N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified with silica gel column chromatography using Petroleum ether:Ethyl acetate (10:1) affording the title compound EXAMPLE 2 (1.1 g, 68%) as a white solid. 1H NMR (400 MHz, CDCl3) δ7.75-7.85 (m, 2H), 7.35 (d, 2H, J=8.3 Hz), 7.22 (d, 2H, J=8.3 Hz), 3.69 (s, 3H), 2.73 (t, 2H, J=7.5 Hz), 2.39 (t, 2H, J=7.4 Hz), 1.98-2.08 (m, 2H), 1.58 (d, 6H, J=4.9 Hz).

Synthesis of methyl 3-(4-(3-(4-cyano-2-fluoro-3-(trifluoromethyl)phenyl)-5,5-dimethyl-4-oxo-2-thioxoimidazolidin-1-yl)phenyl)propanoate Example 3

-continued

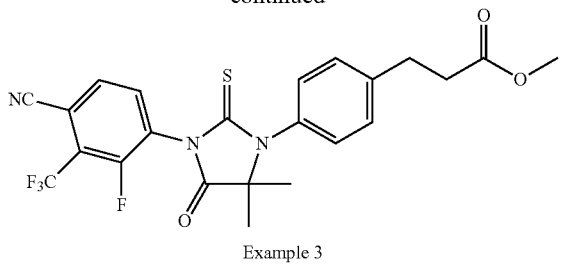

Example 3

A mixture of 37 (600 mg, 2.44 mmol) and 3b (1.08 g, 4.38 mmol) in DMF (1 mL) was stirred at room temperature for overnight. To this mixture was added CH3OH (10 mL) and aq. 3N HCl (10 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified with silica gel column chromatography using Petroleum ether:Ethyl acetate (10:1) affording the title compound EXAMPLE 3 (950 mg, 79%) as a white solid. 1H NMR (400 MHz, CDCl3) δ7.81-7.86 (m, 1H), 7.76-7.81 (m, 1H), 7.37 (d, 2H, J=8.2 Hz), 7.22 (d, 2H, J=8.2 Hz), 3.69 (s, 3H), 3.04 (t, 2H, J=7.6 Hz), 2.69 (t, 2H, J=7.8 Hz), 1.58 (d, 6H, J=4.9 Hz).

Synthesis of 3-(4-(3-(4-cyano-2-fluoro-3-(trifluoromethyl)phenyl)-5,5-dimethyl-4-oxo-2-thioxoimidazolidin-1-yl)phenyl)-N-methylpropanamide Example 4

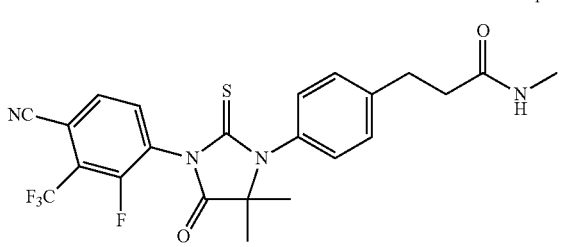

Example 4

EXAMPLE 4 was synthesized via a reaction between 3b and 38 following a manner similar to the synthetic procedure of EXAMPLE 3. EXAMPLE 4 was obtained in 8% yield as a white solid.

1H NMR (400 MHz, CDCl3) δ7.75-7.85 (m, 2H), 7.37 (d, 2H, J=8.2 Hz), 7.22 (d, 2H, J=8.2 Hz), 5.36 (br s, 1H), 3.06 (t, 2H, J=7.4 Hz), 2.81 (d, 3H, J=3.8 Hz), 2.52 (t, 2H, J=7.4 Hz), 1.58 (d, 6H, J=4.9 Hz). LCMS (M+H)+: 493.2.

Synthesis of 4-(4-(3-(4-cyano-2-fluoro-3-(trifluoromethyl)phenyl)-5,5-dimethyl-4-oxo-2-thioxoimidazolidin-1-yl)phenyl)-N-methylbutanamide Example 5

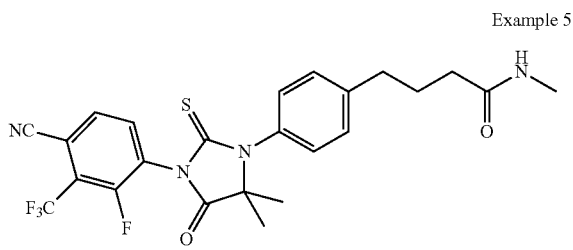 [SMILES: CNC(=O)CCCc1ccc(N2C(=S)N(c3ccc(C#N)c(C(F)(F)F)c3F)C(=O)C2(C)C)cc1]

Example 5

EXAMPLE 5 was synthesized via a reaction between 3b and 31 following a manner similar to the synthetic procedure of EXAMPLE 3. EXAMPLE 5 was obtained in 60% yield as a white solid.

1H NMR (400 MHz, CDCl3) δ7.75-7.85 (m, 2H), 7.35 (d, 2H, J=8.2 Hz), 7.21 (d, 2H, J=8.2 Hz), 5.39 (br s, 1H), 2.82 (d, 3H, J=4.8 Hz), 2.74 (t, 2H, J=7.6 Hz), 2.23 (t, 2H, J=7.3 Hz), 1.98-2.08 (m, 2H), 1.58 (d, 6H, J=4.9 Hz). LCMS (M+H)+: 493.2.

Synthesis of 4-(4-(3-(4-cyano-2-fluoro-5-(trifluoromethyl)phenyl)-5,5-dimethyl-4-oxo-2-thioxoimidazolidin-1-yl)phenyl)-N-methylbutanamide Example 6

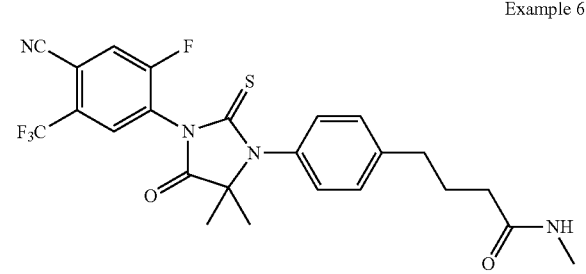 [SMILES: CNC(=O)CCCc1ccc(N2C(=S)N(c3cc(C(F)(F)F)c(C#N)cc3F)C(=O)C2(C)C)cc1]

Example 6

EXAMPLE 6 was synthesized via a reaction between 3d and 31 following a manner similar to the synthetic procedure of EXAMPLE 3. EXAMPLE 6 was obtained in 45% yield as a white solid.

1H NMR (400 MHz, CDCl3) δ7.93 (d, 1H, J=6.4 Hz), 7.73 (d, 1H, J=8.3 Hz), 7.35 (d, 2H, J=8.3 Hz), 7.25 (d, 2H, J=8.3 Hz), 5.38 (br s, 1H), 2.82 (d, 3H, J=4.7 Hz), 2.74 (t, 2H, J=7.5

Hz), 2.23 (t, 2H, J=7.3 Hz), 1.97-2.09 (m, 2H), 1.58 (d, 6H, J=5.7 Hz). LCMS (M+H)+: 507.4.

Synthesis of 4-(4-(3-(3-chloro-4-cyano-2-fluorophenyl)-5,5-dimethyl-4-oxo-2-thioxoimidazolidin-1-yl)phenyl)-N-methylbutanamide Example 7

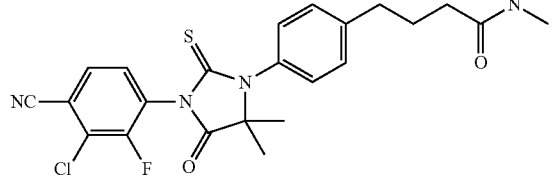

Example 7

EXAMPLE 7 was synthesized via a reaction between 3c and 31 following a manner similar to the synthetic procedure of EXAMPLE 3. EXAMPLE 7 was obtained in 10% yield as a white solid.

1H NMR (400 MHz, CDCl3) δ7.60-7.64 (m, 1H), 7.48-7.52 (m, 1H), 7.35 (d, 2H, J=8.2 Hz), 7.21 (d, 2H, J=8.2 Hz), 5.39 (br s, 1H), 2.82 (d, 3H, J=4.8 Hz), 2.74 (t, 2H, J=7.8 Hz), 2.23 (t, 2H, J=8.3 Hz), 1.98-2.08 (m, 2H), 1.57 (d, 6H, J=5.8 Hz). LCMS (M+H)+: 473.2.

Synthesis of 4-(4-(3-(4-cyano-2-fluoro-3-(trifluoromethyl)phenyl)-5,5-dimethyl-4-oxo-2-thioxoimidazolidin-1-yl)phenyl)butanamide Example 8

Example 8

EXAMPLE 8 was synthesized from a reaction between 3b and 34 following a manner similar to the synthetic procedure of EXAMPLE 3. EXAMPLE 8 was obtained in 10% yield as a white solid.

1H NMR (400 MHz, CDCl3) δ7.75-7.85 (m, 2H), 7.35 (d, 2H, J=8.2 Hz), 7.21 (d, 2H, J=8.2 Hz), 5.39 (br s, 2H), 2.76 (t, 2H, J=7.6 Hz), 2.29 (t, 2H, J=7.3 Hz), 1.98-2.10 (m, 2H), 1.58 (d, 6H, J=4.9 Hz). LCMS (M+H)+: 493.7.

Synthesis of 4-(4-(3-(3-chloro-4-cyano-2-fluorophenyl)-5,5-dimethyl-4-oxo-2-thioxoimidazolidin-1-yl)phenyl)butanamide Example 9

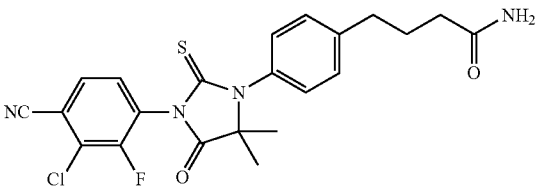

Example 9

EXAMPLE 9 was synthesized from a reaction between 3c and 34 following a manner similar to the synthetic procedure of EXAMPLE 3. EXAMPLE 9 was obtained in 16% yield as a white solid.

1H NMR (400 MHz, CDCl3) δ7.58-7.64 (m, 1H), 7.48-7.52 (m, 1H), 7.35 (d, 2H, J=8.2 Hz), 7.21 (d, 2H, J=8.2 Hz), 5.41 (br s, 2H), 2.76 (t, 2H, J=7.4 Hz), 2.30 (t, 2H, J=7.3 Hz), 1.98-2.08 (m, 2H), 1.57 (d, 6H, J=5.8 Hz). LCMS (M+H)+: 459.2.

Synthesis of Example 10

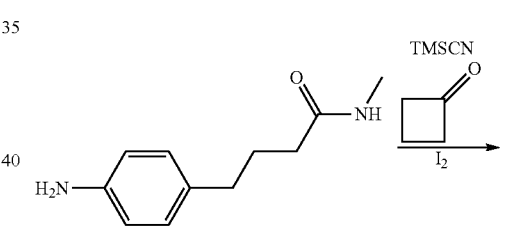

30

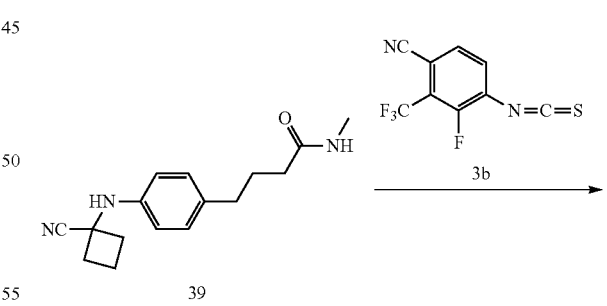

39

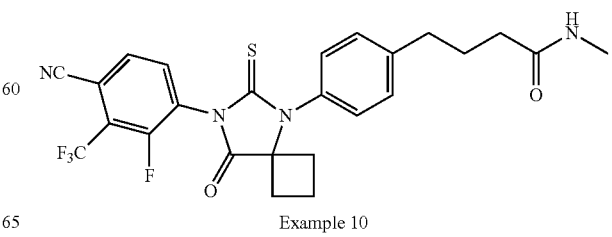

Example 10

Preparation of 4-(4-((1-cyanocyclobutyl)amino)phenyl)-N-methylbutanamide 39

TMSCN (0.09 mL, 0.70 mmol) was added to a mixture of the compound 30 (90 mg, 0.47 mmol), cyclobutanone (0.05 mL, 0.70 mmol) and 12 (6 mg, 0.05 mmol) with stirring. The reaction mixture was stirred at room temperature for 10 min, and concentrated in vacuo. The residue was diluted with aq Na2SO3, and extracted with DCM. The combined organic layers were washed with aq Na2SO3 and brine, dried over Na2SO4 and concentrated. The residue was purified with silica gel column chromatography using Petroleum ether: Ethyl acetate (10:1) affording to compound 39 (85 mg, 67%) as a light yellow oil. 1H NMR (400 MHz, CDCl3) δ6.98 (d, 2H, J=8.4 Hz), 6.56 (d, 2H, J=8.4 Hz), 5.39 (br s, 1H), 2.66-2.76 (m, 5H), 2.50 (t, 2H, J=8.4 Hz), 2.28-2.40 (m, 2H), 2.10-2.22 (m, 2H), 2.08 (t, 2H, J=8.4 Hz), 1.80-1.90 (m, 2H).

Synthesis of 4-(4-(7-(4-cyano-2-fluoro-3-(trifluoromethyl)phenyl)-8-oxo-6-thioxo-5,7-diazaspiro[3.4]octan-5-yl)phenyl)-N-methylbutanamide Example 10

EXAMPLE 10 was synthesized from a reaction between 3b and 39 following a manner similar to the synthetic procedure of EXAMPLE 3. EXAMPLE 10 was obtained in 56% yield as a white solid.

1H NMR (400 MHz, CDCl3) δ7.58-7.64 (m, 1H), 7.48-7.52 (m, 1H), 7.41 (d, 2H, J=8.2 Hz), 7.24 (d, 2H, J=8.2 Hz), 5.51 (br s, 1H), 2.83 (d, 3H, J=3.7 Hz), 2.72-2.80 (m, 2H), 2.62-2.70 (m, 2H), 2.50-2.60 (m, 2H), 2.20-2.30 (m, 3H), 2.00-2.10 (m, 2H), 1.65-1.72 (m, 1H). LCMS (M+H)+: 519.8.

Synthesis of 4-(4-(7-(3-chloro-4-cyano-2-fluorophenyl)-8-oxo-6-thioxo-5,7-diazaspiro[3.4]octan-5-yl)phenyl)-N-methylbutanamide Example 11

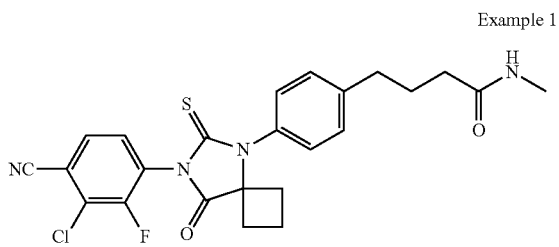

Example 11

EXAMPLE 11 was synthesized from a reaction between 3c and 39 following a manner similar to the synthetic procedure of EXAMPLE 3. EXAMPLE 11 was obtained in 72% yield as a white solid.

1H NMR (400 MHz, CDCl3) δ7.60-7.64 (m, 1H), 7.48-7.54 (m, 1H), 7.41 (d, 2H, J=8.2 Hz), 7.24 (d, 2H, J=8.2 Hz), 5.51 (br s, 1H), 2.83 (d, 3H, J=3.7 Hz), 2.72-2.80 (m, 2H), 2.62-2.70 (m, 2H), 2.50-2.60 (m, 2H), 2.20-2.30 (m, 3H), 2.00-2.10 (m, 2H), 1.65-1.72 (m, 1H). LCMS (M+H)+: 485.4.

Preparation of Compound 40

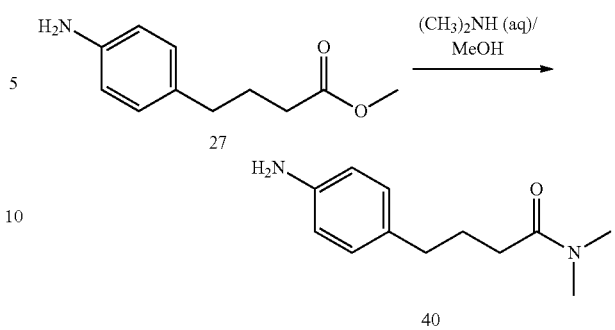

To a solution of compound 27 (500 mg, 2.33 mmol) in (CH3)2NH (aq) (50 mL)/MeOH (50 mL) was stirred at room temperature for 72 h. After removed the most MeOH, the residue was diluted with H2O, and extracted with DCM. The combined organic layers were washed with brine, dried over Na2SO4 and concentrated to give compound 40 (450 mg, 84.3%) as a white solid. The crude product was used directly for the next step without further purification.

1H NMR (400 MHz, CDCl3) δ6.97 (d, J=8.0 Hz, 2H), 6.61 (d, J=8.0 Hz, 2H), 2.93 (s, 6H), 2.58~2.55 (m, 2H), 2.36~2.30 (m, 2H), 1.93~1.89 (m, 2H).

Preparation of Compound 41

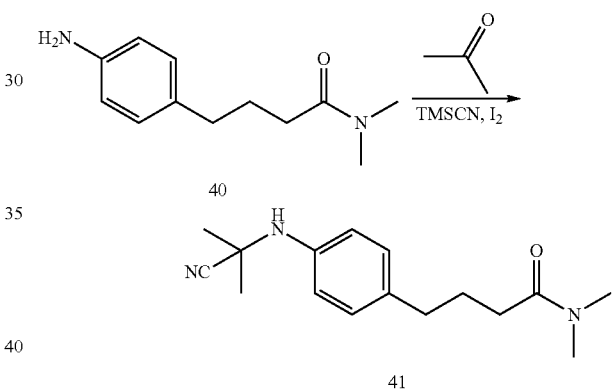

TMSCN (0.6 mL, 4.8 mmol) was added to a mixture of the compound 40 (330 mg, 1.6 mmol), acetone (1.20 mL) and 12 (10 mg) with stirring. The reaction mixture was stirred at RT for 3 h. The mixture was diluted with aqNa2SO3, and extracted with ethyl acetate. The combined organic layers were washed with brine, dried over Na2SO4 and concentrated to give compound 41 (240 mg, 54.6%) as an oil. The crude product was used directly for the next step without purification.

Synthesis of 4-{4-[3-(4-Cyano-2-fluoro-3-trifluoromethyl-phenyl)-5,5-dimethyl-4-oxo-2-thioxo-imidazolidin-1-yl]-phenyl}-N,N-dimethyl-butyramide Example 12

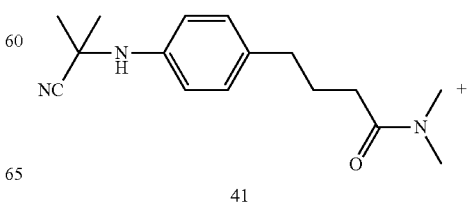

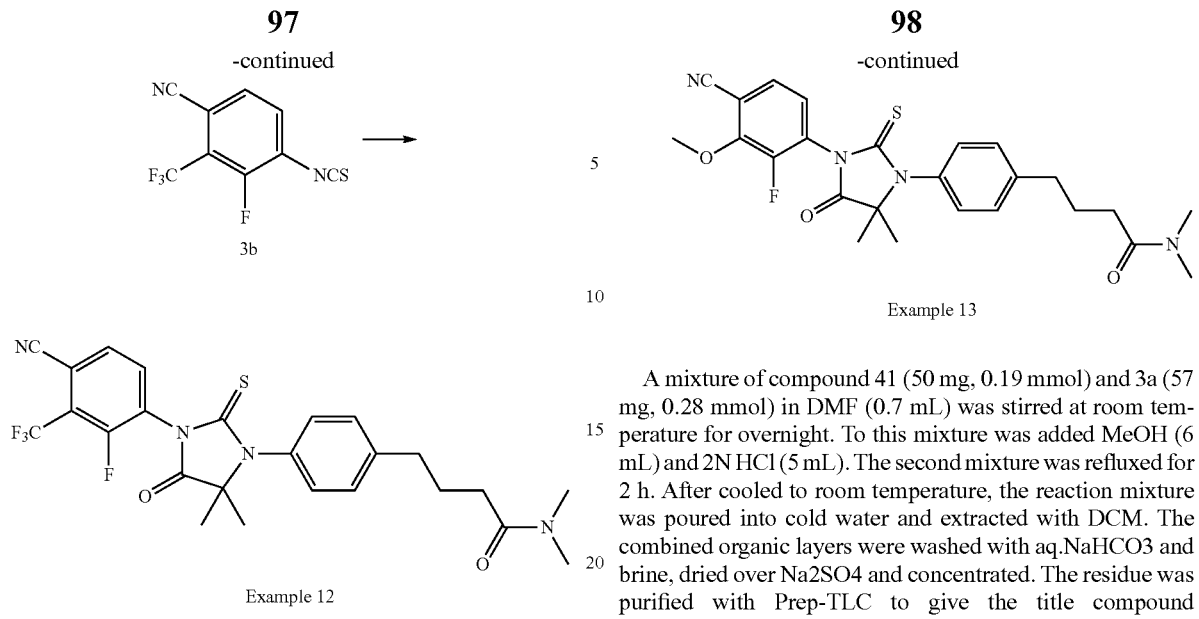

A mixture of compound 41 (50 mg, 0.19 mmol) and 3b (72 mg, 0.29 mmol) in DMF (0.7 mL) was stirred at room temperature for overnight. To this mixture was added MeOH (6 mL) and 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 12 (40 mg, 39.8%) as a white solid.

1H NMR (400 MHz, CDCl3) δ 7.85~7.76 (m, 2H), 7.77 (d, J=8.0 Hz, 2H), 7.21 (d, J=8.0 Hz, 2H), 2.97 (s, 6H), 2.78~2.75 (m, 2H), 2.41~2.37 (m, 2H), 2.05~2.01 (m, 2H), 1.58 (d, J=4.8 Hz, 6H). LCMS (M+H)+: 521.6.

Synthesis of 4-{4-[3-(4-Cyano-2-fluoro-3-methoxy-phenyl)-5,5-dimethyl-4-oxo-2-thioxo-imidazolidin-1-yl]-phenyl}-N,N-dimethyl-butyramide Example 13

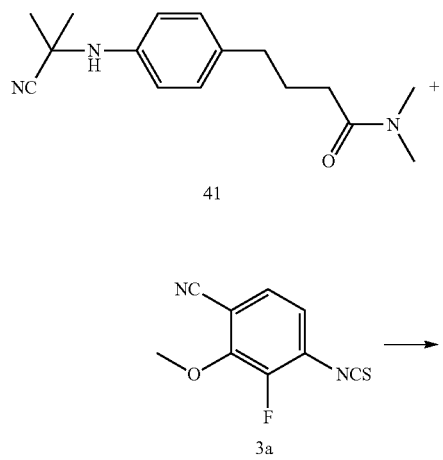

A mixture of compound 41 (50 mg, 0.19 mmol) and 3a (57 mg, 0.28 mmol) in DMF (0.7 mL) was stirred at room temperature for overnight. To this mixture was added MeOH (6 mL) and 2N HCl (5 mL). The second mixture was refluxed for 2 h. After cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 13 (15 mg, 15.9%) as a white solid.

1H NMR (400 MHz, CDCl3) δ7.48~7.46 (m, 1H), 7.36 (d, J=8.0 Hz, 2H), 7.21~7.16 (m, 3H), 4.19 (d, J=2.8 Hz, 3H), 2.96 (d, J=5.6 Hz, 6H), 2.89-2.74 (m, 2H), 2.41~2.37 (m, 2H), 2.05-2.01 (m, 2H), 1.57 (d, J=2.8 Hz, 6H). LCMS (M+H)+: 483.6.

Synthesis of 4-{4-[3-(3-Chloro-4-cyano-2-fluoro-phenyl)-5,5-dimethyl-4-oxo-2-thioxo-imidazolidin-1-yl]-phenyl}-N,N-dimethyl-butyramide Example 14

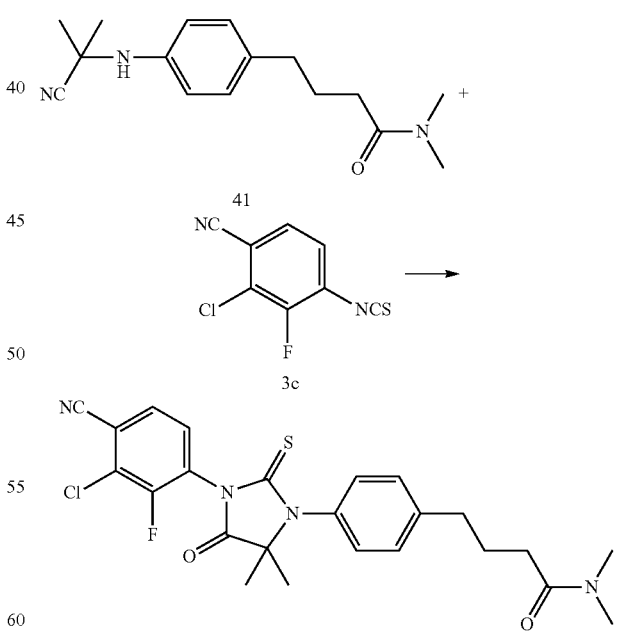

A mixture of compound 41 (50 mg, 0.19 mmol) and 3c (58 mg, 0.28 mmol) in DMF (0.7 mL) was stirred at room temperature for overnight. To this mixture was added MeOH (6 mL) and 2N HCl (5 mL). The second mixture was refluxed for 2 h. After cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound Example 14 (25 mg, 28.1%) as a white solid.

1H NMR (400 MHz, CDCl3) δ7.64~7.62 (m, 1H), 7.53~7.49 (m, 1H), 7.37 (d, J=8.0 Hz, 2H), 7.21 (d, J=8.0 Hz, 2H), 2.96 (d, J=5.6 Hz, 6H), 2.78~2.74 (m, 2H), 2.40~2.36 (m, 2H), 2.05~2.00 (m, 2H), 1.57 (d, J=6.0 Hz, 6H). LCMS (M+H)+: 487.5.

Preparation of 46:

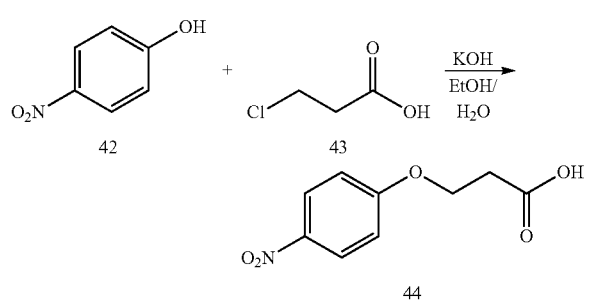

A mixture of 42 (15 g, 107.9 mmol), 43 (35.1 g, 325 mmol) and KOH (27.3 g, 488 mmol) in 150 mL of water and 150 mL of EtOH was refluxed for 3 h. The result mixture was cooled to room temperature and acidified with concentrated HCl to pH=1. The aqueous layer was extracted with ethyl acetate (100 mL×3). The combined organic layers were washed with saturated NaHCO3 solution (100 mL×2). The aqueous NaHCO3 layer was acidified with concentrated HCl and extracted with ethyl acetate (100 mL×3). The combined EA layers were washed with brine (100 mL×2), dried over anhydrous Na2SO4 and concentrated. The residue was crystallized from Et2O and hexane to get the desired product 44 (4.0 g, 17.5%) as a white solid. LCMS (M+1)+: 212.

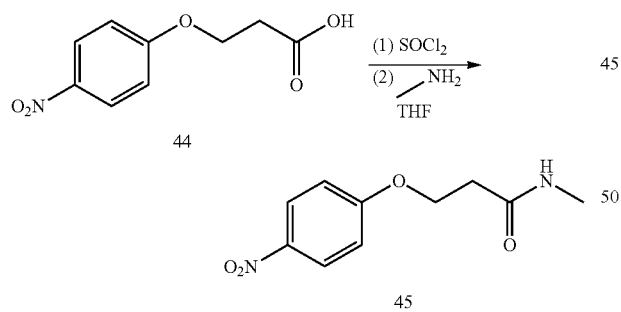

A mixture of 44 (4.0 g, 19.0 mmol) in 50 mL of SOCl was stirred at 40° C. for 1 h. The solvent was removed under reduced pressure. The residue was dissolved in 20 mL of THF and added to the solution of methylamine (33 wt % in ethanol, 40 mL, 326.2 mmol) in 30 mL of THF dropwise at 0° C. The result mixture was stirred at room temperature for another 1 h. The solvent was removed under reduced pressure. 100 mL of water was added and the aqueous layer was extracted with ethyl acetate (200 mL×3). The combined organic layers were washed with brine (100 mL×2), dried over anhydrous Na2SO4 and concentrated. The residue was chromato- graphed on silica gel (PE:EA 3:1) to get the desired product 45 (3.5 g, 82.2%) as a white solid. LCMS (M+1)+: 225.

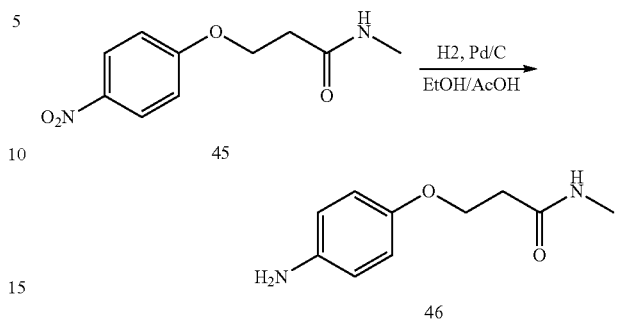

A mixture of 45 (2.0 g, 8.93 mmol), Pd/C (0.35 g) in 12 mL of AcOH and 150 mL of EtOH was stirred under H2 balloon pressure at room temperature for 1.5 hours. The solvent was removed under reduced pressure. 100 mL of saturated NaHCO3 solution was added and the aqueous layer was extracted with ethyl acetate (100 mL×5). The combined organic layers were washed with brine (100 mL×1), dried over anhydrous Na2SO4 and concentrated. The residue was purified with column flash chromatography (silica gel) (PE: MeOH 30:1) to get the desired product 46 (1.6 g, 92.4%) as a pale yellow solid. LCMS (M+1)+: 195.

Synthesis of 3-{4-[3-(4-Cyano-2-fluoro-3-trifluoromethyl-phenyl)-5,5-dimethyl-4-oxo-2-thioxo-imidazolidin-1-yl]-phenoxy}-N-methyl-propionamide Example 15

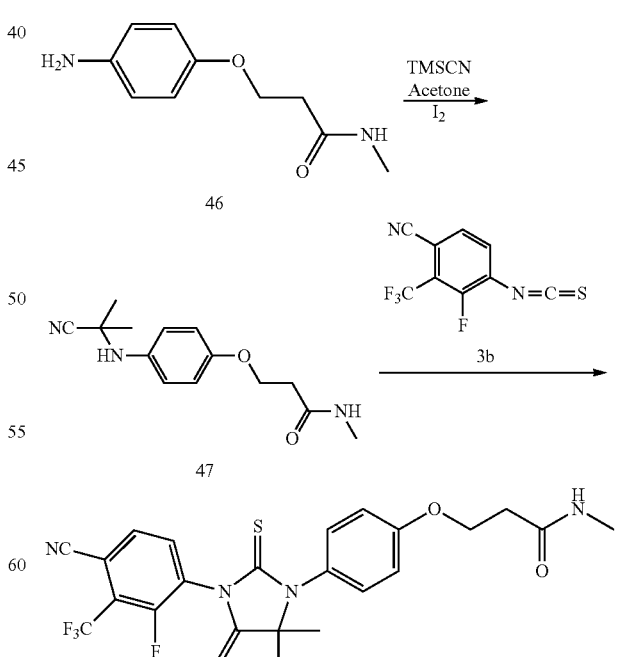

Example 15

Preparation of 3-(4-((2-cyanopropan-2-yl)amino)phenoxy)-N-methylpropanamide 47

TMSCN (0.11 mL, 0.82 mmol) was added to a mixture of compound 46 (53 mg, 0.27 mmol), acetone (0.12 mL, 1.62 mmol) and 12 (4 mg, 0.03 mmol) with stirring at room temperature. The reaction mixture was stirred at 40° C. for 30 min, and concentrated in vacuo. The residue was diluted with aq Na2SO3, and extracted with ethyl acetate. The combined organic layers were washed with aqNa2SO3 and brine, dried over Na2SO4 and concentrated to dryness to give compound 47 (60 mg, 86%) as a light yellow oil. The crude product was used directly for the next step without purification. 1H NMR (400 MHz, CDCl3) δ6.97 (d, 2H, J=8.9 Hz), 6.85 (d, 2H, J=8.9 Hz), 5.85 (br s, 1H), 4.22 (t, 2H, J=6.0 Hz), 2.84 (d, 3H, J=4.8 Hz), 2.64 (t, 2H, J=6.0 Hz), 1.22 (s, 6H).

Synthesis of 3-(4-(3-(4-cyano-2-fluoro-3-(trifluoromethyl)phenyl)-5,5-dimethyl-4-oxo-2-thioxoimidazolidin-1-yl)phenoxy)-N-methylpropanamide

Example 15

A mixture of 47 (60 mg, 0.23 mmol) and 3b (85 mg, 0.35 mmol) in DMF (0.1 mL) was stirred at room temperature for overnight. To this mixture was added CH3OH (1 mL) and aq. 3N HCl (1 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified by TLC DCM:Acetone=7:1) affording the title compound EXAMPLE 15 (50 mg, 43%) as a white solid. 1H NMR (400 MHz, CDCl3) δ7.75-7.85 (m, 2H), 7.22 (d, 2H, J=8.7 Hz), 7.04 (d, 2H, J=8.7 Hz), 5.56 (br s, 1H), 4.32 (t, 2H, J=5.7 Hz), 2.86 (d, 3H), 2.39 (t, 2H, J=5.7 Hz), 1.58 (d, 6H, J=4.8 Hz). LCMS (M+H)+: 509.6.

Synthesis of 3-(4-(3-(3-chloro-4-cyano-2-fluorophenyl)-5,5-dimethyl-4-oxo-2-thioxoimidazolidin-1-yl)phenoxy)-N-methylpropanamide

Example 16

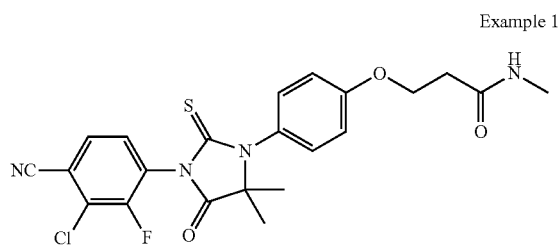

Example 16

EXAMPLE 16 was synthesized from a reaction between 3c and 47 following a manner similar to the synthetic procedure of EXAMPLE 15. EXAMPLE 16 was obtained in 40% yield as a white solid.
1H NMR (400 MHz, CDCl3) δ7.60-7.65 (m, 1H), 7.47-7.53 (m, 1H), 7.22 (d, 2H, J=8.7 Hz), 7.04 (d, 2H, J=8.7 Hz), 5.56 (br s, 1H), 4.32 (t, 2H, J=5.7 Hz), 2.86 (d, 3H), 2.39 (t, 2H, J=5.7 Hz), 1.58 (d, 6H, J=4.8 Hz). LCMS (M+H)+: 475.6.

Preparation of 53:

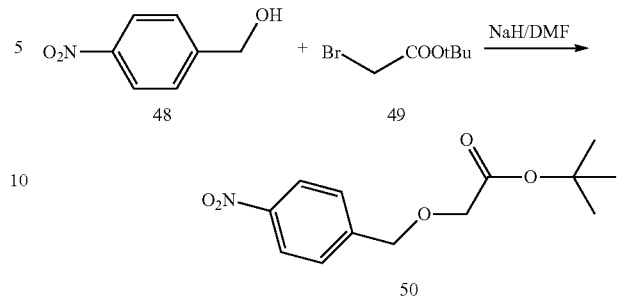

To a mixture of 48 (5 g, 32.7 mmol) and 49 (7 g 75 mmol) in DMF (60 mL) was added NaH (60% 1.45 g 35 mmol) slowly at 0° C. and stirred for 3 h. 50 mL H2O was added slowly and stirred for 10 minutes. The mixture solution was extracted by EA (300 mL×3), The combined organic layers were washed with brine (100 mL×2), dried over anhydrous Na2SO4 and concentrated to get the crude product 50 (6.7 g 71%). LCMS (M+1)+: 268.

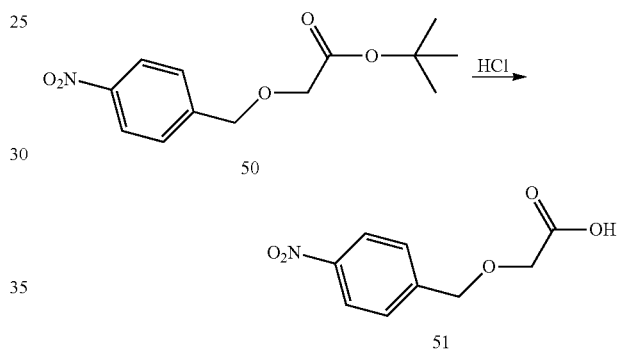

Compound 50 (3 g) was dissolved in THF (20 mL) and 20 mL HCl (36%) and stirred for 2 h at RT. The mixture solution was extracted by EA (200 mL×3), The combined organic layers were washed with brine (100 mL×2), dried over anhydrous Na2SO4 and concentrated to get the crude product 51 (2.25 g 95%). LCMS (M+1)+: 212.

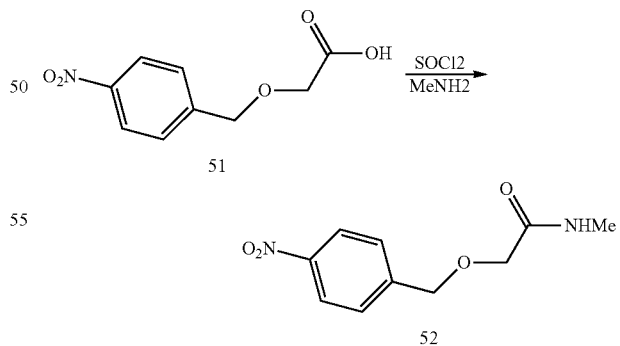

Compound 51 (2.2 g) was dissolved in SOCl (15 mL) and stirred for 2 h at 30° C. The solution was concentrated in vacuo and the residue was dissolved in THF (10 mL) The mixture solution was dropped into THF/NH2Me (5 mL/15 mL) at 0° C. and stirred for 0.5 h. The mixture solution was extracted by EA (200 mL×3), The combined organic layers were washed with brine (100 mL×2), dried over anhydrous Na2SO4 and concentrated to get the crude product 52 (2.2 g 95%). LCMS (M+1)+: 225.

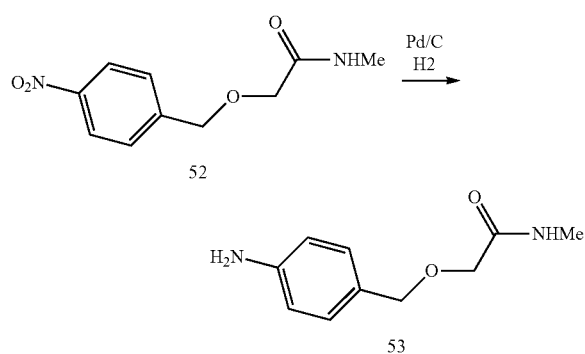

Compound 52 (2.2 g) was dissolved in EtOH/AcOH (20 mL/1 mL). Pd/C (70% 0.5 g) was added and stirred. A big H2 balloon was added and stirred for overnight. The mixture solution was filtered and moved invacuo and extracted by EA (200 mL×3), The combined organic layers were washed with brine (100 mL×2), dried over anhydrous Na2SO4 and concentrated to get the crude product 53 (1.7 g 90%). LCMS (M+23)+: 217.

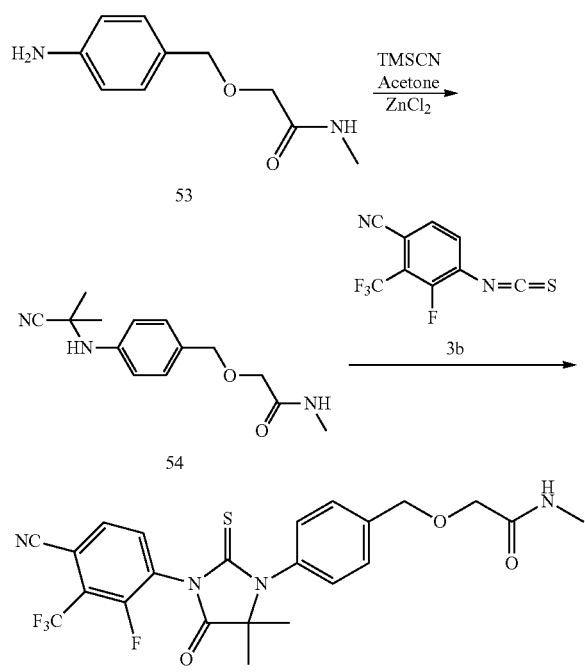

Preparation of 2-((4-((2-cyanopropan-2-yl)amino) benzyl)oxy)-N-methylacetamide 54

TMSCN (0.1 mL, 0.78 mmol) was added to a mixture of the compound 53 (50 mg, 0.26 mmol), acetone (0.2 mL, 2.6 mmol) and ZnCl2 (16 mg, 0.12 mmol) with stirring. The reaction mixture was stirred at room temperature for 1 h and concentrated in vacuo. The residue was diluted with water and extracted with DCM. The combined organic layers were washed with brine, dried over Na2SO4 and concentrated to dryness to give compound 54 (60 mg, 86%) as a light yellow oil. The crude product was used directly for the next step without purification. 1H NMR (400 MHz, CDCl3) δ7.23 (d, 2H, J=8.4 Hz), 6.92 (d, 2H, J=8.4 Hz), 6.51 (br s, 1H), 4.48 (s, 2H), 3.97 (s, 2H), 2.84 (d, 3H, J=5.0 Hz), 1.72 (s, 6H).

Synthesis of 2-((4-(3-(4-cyano-2-fluoro-3-(trifluoromethyl)phenyl)-5,5-dimethyl-4-oxo-2-thioxoimidazolidin-1-yl)benzyl)oxy)-N-methylacetamide Example 17

EXAMPLE 17 was synthesized from a reaction between 3b and 54 following a manner similar to the synthetic procedure of EXAMPLE 15. EXAMPLE 17 was obtained in 59% yield as a white solid.

1H NMR (400 MHz, CDCl3) δ7.75-7.85 (m, 2H), 7.51 (d, 2H, J=8.2 Hz), 7.33 (d, 2H, J=8.2 Hz), 6.55 (br s, 1H), 4.66 (s, 2H), 4.06 (s, 2H), 2.88 (d, 3H, J=4.8 Hz), 1.60 (d, 6H, J=4.0 Hz). LCMS (M+H)+: 509.6.

Synthesis of 2-((4-(3-(3-chloro-4-cyano-2-fluorophenyl)-5,5-dimethyl-4-oxo-2-thioxoimidazolidin-1-yl) benzyl)oxy)-N-methylacetamide Example 18

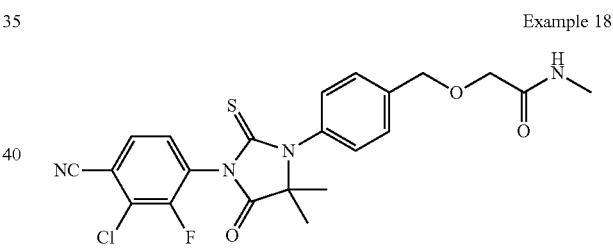

Example 18

EXAMPLE 18 was synthesized from a reaction between 3c and 54 following a manner similar to the synthetic procedure of EXAMPLE 15. EXAMPLE 18 was obtained in 50% yield as a white solid.

1H NMR (400 MHz, CDCl3) δ7.61-7.65 (m, 1H), 7.48-7.53 (m, 3H), 7.33 (d, 2H, J=8.2 Hz), 6.55 (br s, 1H), 4.66 (s, 2H), 4.06 (s, 2H), 2.88 (d, 3H, J=4.8 Hz), 1.60 (d, 6H J=4.9 Hz). LCMS (M+H)+: 475.6.

Synthesis of Example 19

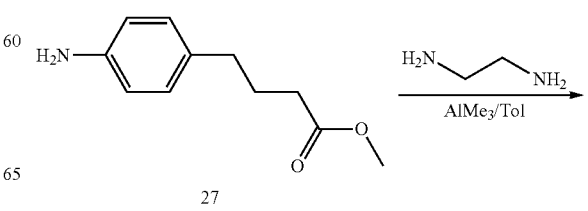

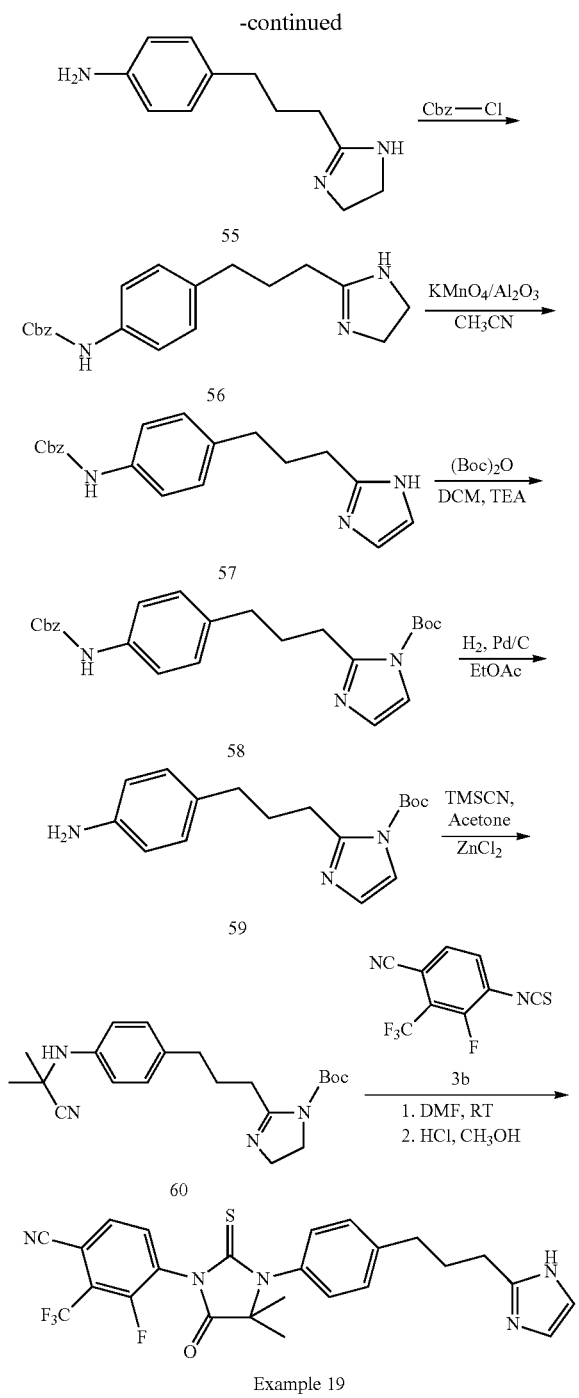

Example 19

Preparation of 4-(3-(4,5-dihydro-1H-imidazol-2-yl)propyl)aniline 55

Ethylenediamine (6.23 mL, 93.1 mmol) was added dropwise to a stirred solution of AlMe3/Tol (58 mL, 2M), so that the temperature did not exceed −20° C. The reaction mixture was stirred at room temperature for 10 min, then to the mixture was added dropwise a solution of the compound 27 (4.5 g, 23.3 mmol) in Toluene (290 mL). The reaction mixture was stirred at 120° C. for overnight. After cooling, the solution was treated dropwise with water, diluted DCM and CH3OH and filtered with over MgSO4. The filtrate was concentrated and purified with silica gel column chromatography (EtOAc:CH3OH:TEA=3:1:0.2) to give the compound 55 (4.5 g, 96%) as a light yellow oil. 1H NMR (400 MHz, CDCl3) δ6.96 (d, 2H, J=8.3 Hz), 6.62 (d, 2H, J=8.3 Hz), 3.56 (s, 4H), 2.55 (t, 2H, J=7.4 Hz), 2.23 (d, 2H, J=7.4 Hz), 1.84-1.94 (m, 2H).

Preparation of benzyl(4-(3-(4,5-dihydro-1H-imidazol-2-yl)propyl)phenyl)carbamate 56

To a solution of compound 55 (318 mg, 1.56 mmol) in DMF (1 mL) was added dropwise CbzCl (0.29 mL, 2.03 mmol) at 0° C. with stirring. The reaction mixture was stirred at room temperature for 3 h. The DMF was removed by vacuum. The residue was purified with silica gel column chromatography (EtOAc:CH3OH:TEA=3:1:0.2) to give compound 56 (400 mg, 76%) as a light yellow oil. 1H NMR (400 MHz, CDCl3) δ7.70 (s, 1H), 7.30-7.40 (m, 5H), 7.25 (d, 2H, J=8.3 Hz), 6.98 (d, 2H, J=8.3 Hz), 5.15 (s, 2H), 3.65 (s, 4H), 2.50 (t, 2H, J=7.4 Hz), 2.43 (d, 2H, J=7.4 Hz), 1.85-1.97 (m, 2H).

Preparation of benzyl(4-(3-(1H-imidazol-2-yl)propyl)phenyl)carbamate 57

Compound 56 (274 mg, 0.81 mmol) was first dissolved in acetonitrile (10 mL), with potassium permanganate (192 mg, 1.22 mol) and alumina (567 mg, 0.3 mol) added into the solution in batch. After stirring the resulting mixture at room temperature for 40 min, CH3OH (1 mL) was added to reduce excess oxidant. The mixture was filtered and the solid material was washed with DCM:CH3OH=10:1. The filtrate was evaporated and the resulting crude material was purified with silica gel column chromatography (PE:EtOAc:TEA=3:1:0.2) to give compound 57 (110 mg, 41%) as a light yellow oil. 1H NMR (400 MHz, CDCl3) δ7.32-7.43 (m, 6H), 7.28 (d, 2H, J=8.3 Hz), 7.09 (d, 2H, J=8.3 Hz), 6.90-9.95 (m, 2H), 6.70 (br s, 1H), 5.19 (s, 2H), 2.65 (t, 2H, J=7.4 Hz), 2.62 (d, 2H, J=7.4 Hz), 1.98-2.07 (m, 2H).

Preparation of tert-butyl 2-(3-(4-(((benzyloxy)carbonyl)amino)phenyl)propyl)-1H-imidazole-1-carboxylate 58

To a solution of compound 57 (500 mg, 1.5 mmol) in DCM (25 mL) was added dropwise TEA (0.3 mL, 2.3 mmol) and (Boc)2O (0.42 mL, 1.8 mmol) at 0° C. with stirring. The reaction mixture was stirred at room temperature for overnight, concentrated and purified with silica gel column chromatography (PE:EtOAc=3:1) to give compound 58 (415 mg, 51%) as a light yellow oil. 1H NMR (400 MHz, CDCl3) δ7.32-7.43 (m, 8H), 7.28 (d, 2H, J=8.3 Hz), 7.14 (d, 2H, J=8.3 Hz), 6.65 (br s, 1H), 5.19 (s, 2H), 2.95-3.08 (m, 2H), 2.65-2.73 (m, 2H), 2.00-2.15 (m, 2H), 1.61 (s, 9H)

Preparation of tert-butyl 2-(3-(4-aminophenyl)propyl)-1H-imidazole-1-carboxylate 59

A solution of compound 58 (80 mg, 0.18 mmol) in EtOAc (5 mL) was added Pd/C (10 mg, 10%) under N2. The suspension was degassed under vacuum and purged with H2 several times. The mixture was stirred under H2 balloon at room temperature for 2 h. The suspension was filtered and the solid was washed by EtOAc. The filtrates were concentrated to dryness to give compound 59 (38 mg, 70%) as a light yellow oil. The crude product was used directly for the next step without purification. 1H NMR (400 MHz, CDCl3) δ7.32-

7.43 (m, 1H), 6.96-7.02 (m, 3H), 6.93 (d, 2H, J=8.3 Hz), 3.17 (t, 2H, J=7.4 Hz), 2.66 (t, 2H, J=7.4 Hz), 2.05-2.13 (m, 2H), 1.62 (s, 9H).

Preparation of tert-butyl 2-(3-(4-((2-cyanopropan-2-yl)amino)phenyl)propyl)-1H-imidazole-1-carboxylate 60

Compound 60 was synthesized from 59 in a manner similar to the synthesis of 54. It was obtained in 94% yield as a light yellow oil.

1H NMR (400 MHz, CDCl3) δ7.30-7.40 (m, 1H), 7.11 (d, 2H, J=8.3 Hz), 6.85-7.02 (m, 1H), 6.86 (d, 2H, J=8.3 Hz), 3.00-3.20 (m, 2H), 2.52-2.54 (m, 2H), 2.00-2.02 (m, 2H), 1.67 (s, 6H), 1.62 (s, 9H).

Synthesis of 4-(3-(4-(3-(1H-imidazol-2-yl)propyl) phenyl)-4,4-dimethyl-5-oxo-2-thioxoimidazolidin-1-yl)-3-fluoro-2-(trifluoromethyl)benzonitrile Example 19

EXAMPLE 19 was synthesized from a reaction between 3b and 60 following a manner similar to the synthetic procedure of EXAMPLE 15. EXAMPLE 19 was obtained in 50% yield as a white solid.

1H NMR (400 MHz, CDCl3) δ7.75-7.88 (m, 2H), 7.36 (d, 2H, J=8.2 Hz), 7.19 (d, 2H, J=8.2 Hz), 7.07 (br s, 2H), 3.00-3.20 (m, 2H), 2.73-2.81 (m, 2H), 2.20-2.34 (m, 2H), 1.58 (d, 6H, J=4.9 Hz). LCMS (M+H)+: 516.2.

Synthesis of 2-Chloro-3-fluoro-4-(3-{4-[3-(1H-imidazol-2-yl)-propyl]-phenyl}-4,4-dimethyl-5-oxo-2-thioxo-imidazolidin-1-yl)-benzonitrile Example 20

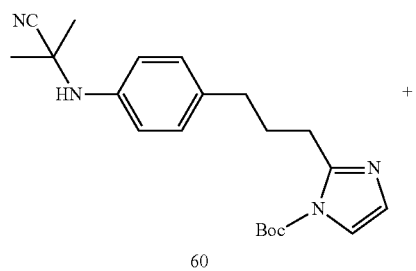

60

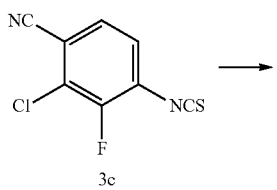

3c

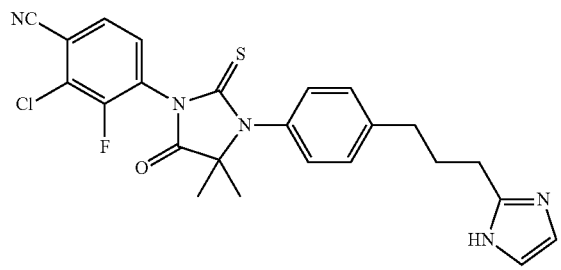

Example 20

A mixture of compound 60 (50 mg, 0.14 mmol) and 3c (43 mg, 0.21 mmol) in DMF (0.7 mL) was stirred at room temperature for overnight. To this mixture was added MeOH (6 mL) and 2N HCl (5 mL). The second mixture was refluxed for 2 h. After cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 20 (25 mg, 38.3%) as a white solid.

1H NMR (400 MHz, CDCl3) δ10.46~10.44 (br s, 1H), 7.64~7.62 (m, 1H), 7.54~7.50 (m, 1H), 7.29~7.27 (m, 1H), 7.18~7.10 (m, 4H), 6.86~6.80 (m, 1H), 3.07~2.83 (m, 2H), 2.69~2.64 (m, 2H), 2.03~1.79 (m, 2H), 1.55 (d, J=4.8 Hz, 6H). LCMS (M+H)+: 483.5.

Synthesis of 3-Fluoro-4-(3-{4-[3-(1H-imidazol-2-yl)-propyl]-phenyl}-4,4-dimethyl-5-oxo-2-thioxo-imidazolidin-1-yl)-2-methoxy-benzonitrile Example 21

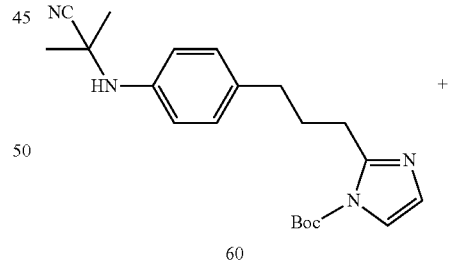

60

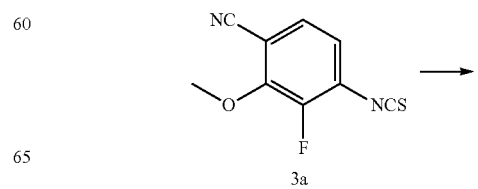

3a

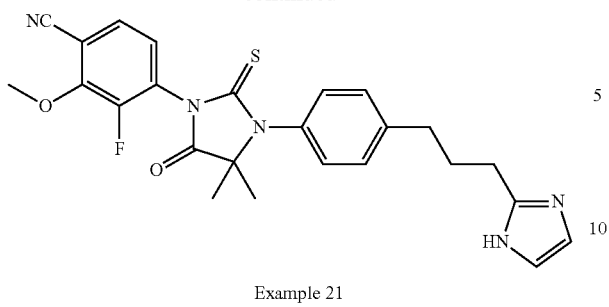

Example 21

A mixture of compound 60 (50 mg, 0.14 mmol) and 3a (42 mg, 0.21 mmol) in DMF (0.7 mL) was stirred at room temperature for overnight. To this mixture was added MeOH (6 mL) and 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 21 (15 mg, 23.9%) as a white solid.

1H NMR (400 MHz, CDCl3) M0.85~10.80 (br s, 1H), 7.48~7.46 (m, 1H), 7.20~7.16 (m, 4H), 7.08~7.01 (m, 2H), 6.85~6.82 (m, 1H), 4.19 (d, J=3.2 Hz, 3H), 3.03~3.00 (m, 2H), 2.69~2.67 (m, 2H), 2.15~2.12 (m, 2H), 1.54 (d, J=5.2 Hz, 6H). LCMS (M+H)+: 478.1.

Synthesis of compound 61

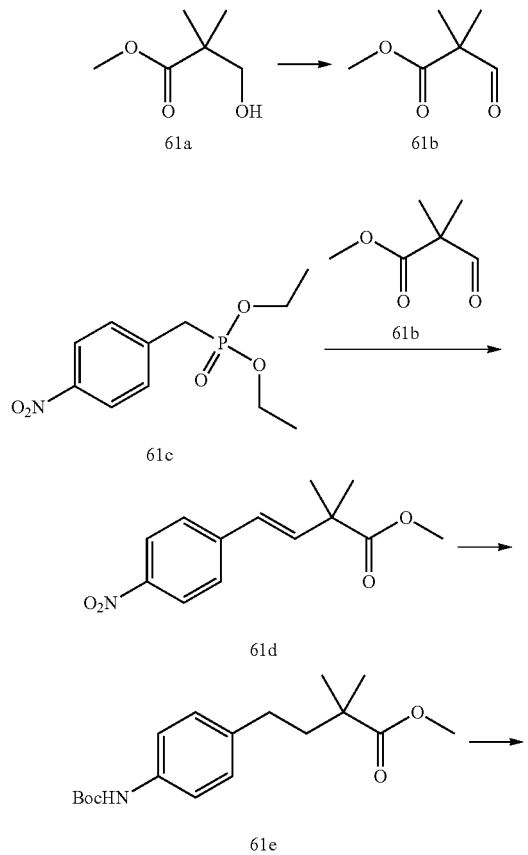

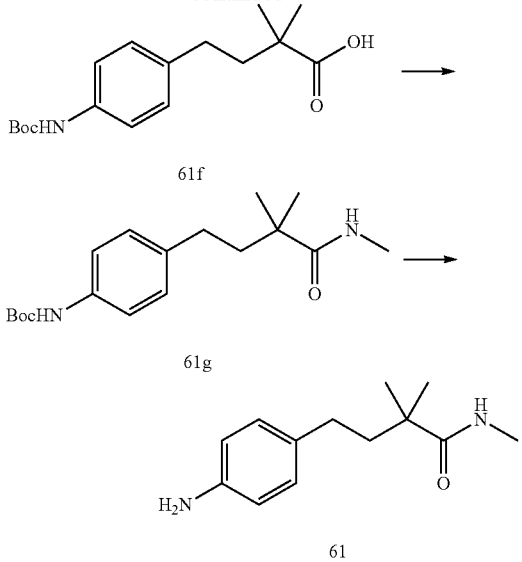

Preparation of Compound 61b

A mixture of oxalyl dichloride (11.5 g, 87 mmol) in CH2Cl2 (180 mL) was cooled down to −78° C., then DMSO (8.9 g, 113 mmol) in CH2Cl2 (40 mL) was added dropwise over 10 minutes, followed by adding a solution of alcohol 61a (10 g) in 40 mL of CH2Cl2. After addition, the mixture was stirred for 15 minutes at −78° C. Et3N (52 mL, 378 mmol) was added dropwise and warmed to r.t. The reaction was quenched with water (200 mL) and extracted with EA (100 mL×2). Dried and removed the solvent to afford the pure product 61b (8.8 g, 88%) as an oil.

Preparation of Compound 61d

A mixture of diethyl 4-nitrobenzylphosphonate (2.5 g, 9.16 mmol) in THF (50 mL) was cooled down to 0° C., then NaH (0.5 g, 11.2 mmol) was added carefully and the mixture was stirred for 10 minutes. Compound 61b (1.6 g, 11.2 mmol) in THF (10 mL) was added dropwise. After addition, the mixture was allowed to warm to r.t and stirred for 1 hour at r.t The reaction was quenched with 1N HCl (40 mL). The mixture was extracted with EA (100 mL×2). Dried and removed the EA to get crude product. The crude material was purified by flash chromatography (silica gel, PE:EA=8:1) to give 61d (1.6 g, 70%) as a white solid.

Preparation of Compound 61e

A mixture of compound 61d (1.6 g, 6.42 mol), (Boc)2O (2.1 g, 9.6 mol) and Pd/C (0.32 g) in MeOH (65 mL) at pressure of gas H2 (1 atm) was stirred over night. The mixture was filtered thought celatom and washed with MeOH. Removed the solvent to obtain product 61e (1.9 g, 90%) as a white solid.

Preparation of Compound 61f

To a mixture of compound 61e (1.9 g, 5.9 mmol) in THF/MeOH (20 mL/20 mL) added NaOH aquoues (20 mL, 20% M/M), then the mixture was stirred over night at r.t. The solvent was removed and 100 mL of water was added, the mixture was extracted with ether (100 mL), The PH of water layer was acidified with 1N HCl then extracted with EA (100 mL×2). Dried and removed the solvent to get pure product 61f (1.6 g, 89%) as white solid.

Preparation of Compound 61 g

To a mixture of compound 61f (1.6 g, 5.2 mmol), Et3N (2.2 mL, 7.8 mmol) and methanamine hydrochloride (0.52 g, 7.8 mmol) in $CH_2Cl_2$ (50 mL) added HATU (2.9 g, 7.8 mmol), then the mixture was stirred for 2 hours. The mixture was quenched with 1N HCl (50 mL). Separated and the water layer was extracted $CH_2Cl_2$ (50 mL). The organics were washed by 1N HCl (30 mL), water (50 mL), dried and removed the solvent to get crude product 61 g (1.6 g, 85%).

Preparation of Compound 61

A suspension of compound 61 g (1.6 g, 5 mmol) in HCl/EA (20 mL) was stirred for 3 hours at r.t. Filtered and washed EA (10 mL) to get product. The solid was stirred at saturated NaHCO3 aqueous and extracted with EA (100 mL×2). Dried and removed the solvent to crude product. The crude material was purified by flash chromatography (silica gel, PE:EA=8:1) to give compound 61 (0.9 g, 75%) as an oil.

Preparation of Compound 62

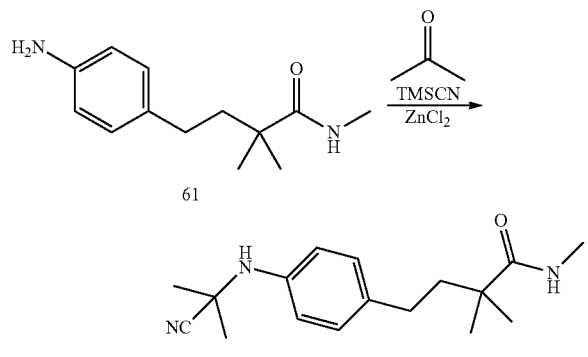

TMSCN (0.34 mL, 2.7 mmol) was added to a mixture of compound 61 (200 mg, 0.9 mmol), acetone (0.5 mL, 5.4 mmol) and ZnCl2 (10 mg) with stirring. The reaction mixture was stirred at RT for 3 h. The mixture was diluted with H2O, and extracted with ethyl acetate. The combined organic layers were washed with brine, dried over Na2SO4 and concentrated to give compound 62 (240 mg, 91.8%) as an oil. The crude product was used directly for the next step without purification.

Synthesis of 4-{4-[3-(4-Cyano-2-fluoro-3-trifluoromethyl-phenyl)-5,5-dimethyl-4-oxo-2-thioxo-imidazolidin-1-yl]-phenyl}-2,2,N-trimethyl-butyramide Example 22

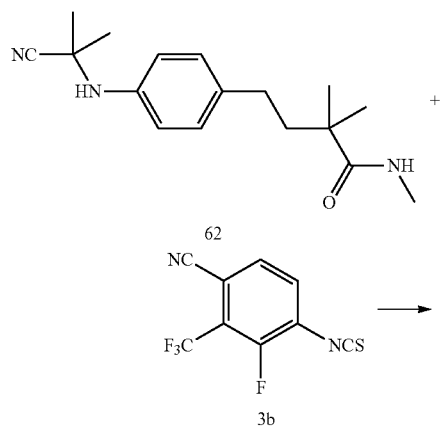

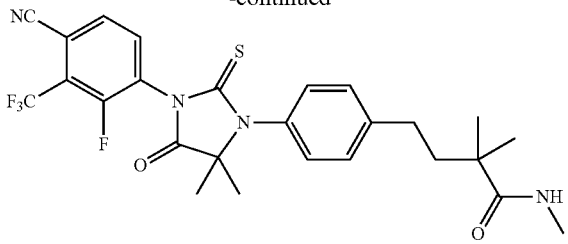

Example 22

A mixture of compound 62 (50 mg, 0.17 mmol) and 3b (64 mg, 0.26 mmol) in DMF (0.7 mL) was stirred at room temperature for overnight. To this mixture was added MeOH (6 mL) and 2N HCl (5 mL). The second mixture was refluxed for 2 h. After cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 22 (49 mg, 52.8%) as a white solid.

1H NMR (400 MHz, CDCl3) δ 7.84~7.76 (m, 2H), 7.34 (d, J=8.0 Hz, 2H), 7.19 (d, J=8.0 Hz, 2H), 5.68-5.65 (br s, 1H), 2.84 (d, J=4.4 Hz, 3H), 2.63~2.59 (m, 2H), 1.89~1.85 (m, 2H), 1.57 (d, J=4.8 Hz, 6H), 1.26 (s, 6H). LCMS (M+H)+: 535.0.

Synthesis of 4-{4-[3-(4-Cyano-2-fluoro-3-methoxy-phenyl)-5,5-dimethyl-4-oxo-2-thioxo-imidazolidin-1-yl]-phenyl}-2,2,N-trimethyl-butyramide Example 23

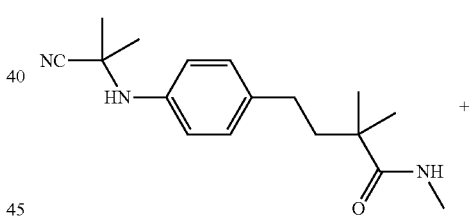

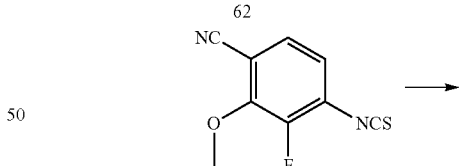

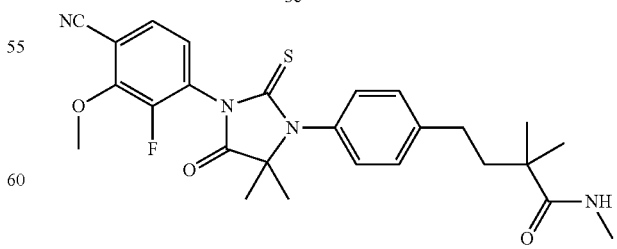

Example 23

A mixture of compound 62 (50 mg, 0.19 mmol) and 3a (54 mg, 0.28 mmol) in DMF (0.7 mL) was stirred at room temperature for overnight. To this mixture was added MeOH (6 mL) and 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 23 (40 mg, 46.3%) as a white solid.

1H NMR (400 MHz, CDCl3) δ 7.45 (d, J=8.0 Hz, 2H), 7.33 (d, J=8.0 Hz, 2H) 7.21-7.16 (m, 2H), 5.69-5.64 (br s, 1H), 4.19 (d, J=2.4 Hz, 3H), 2.84 (d, J=4.4 Hz, 3H), 2.63-2.59 (m, 2H), 1.90-1.85 (m, 2H), 1.55 (d, J=2.8 Hz, 6H), 1.26 (s, 6H). LCMS (M+H)+: 497.6.

Synthesis of 4-{4-[3-(3-Chloro-4-cyano-2-fluoro-phenyl)-5,5-dimethyl-4-oxo-2-thioxo-imidazolidin-1-yl]-phenyl}-2,2,N-trimethyl-butyramide Example 24

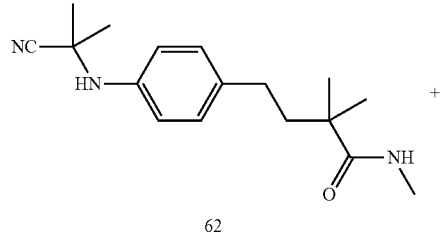

62

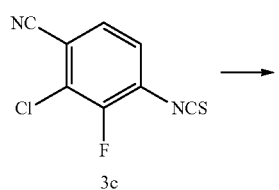

3c

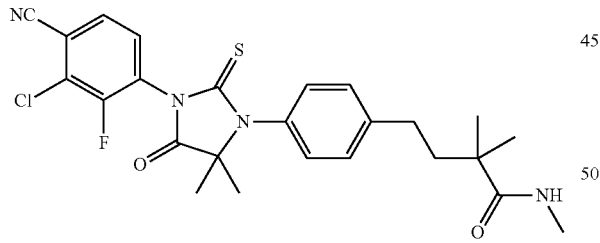

Example 24

A mixture of compound 62 (50 mg, 0.19 mmol) and 3c (55 mg, 0.28 mmol) in DMF (0.7 mL) was stirred at room temperature for overnight. To this mixture was added MeOH (6 mL) and 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 24 (45 mg, 51.6%) as a white solid.

1H NMR (400 MHz, CDCl3) δ 7.62 (d, J=8.4 Hz, 1H), 7.53~7.49 (m, 1H), 7.34 (d, J=8.0 Hz, 2H), 7.19 (d, J=8.0 Hz, 2H), 5.69~5.64 (br s, 1H), 2.84 (d, J=4.4 Hz, 3H), 2.63~2.59 (m, 2H), 1.90~1.85 (m, 2H), 1.56 (d, J=2.8 Hz, 6H), 1.26 (s, 6H). LCMS (M+H)+: 501.5.

Preparation of Compound 63

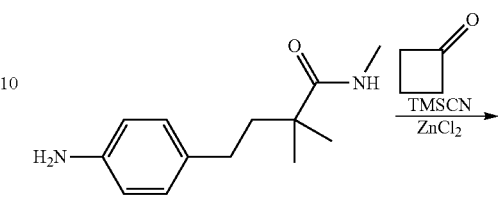

61

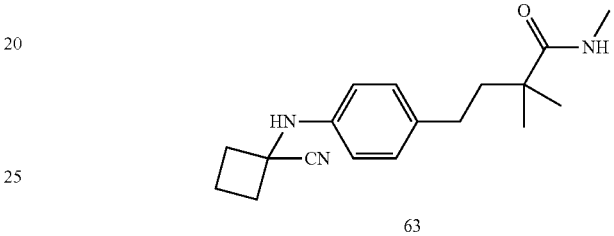

63

TMSCN (0.34 mL, 2.7 mmol) was added to a mixture of compound 61 (200 mg, 0.9 mmol), cyclobutanone (0.4 mL, 5.4 mmol) and ZnCl2 (10 mg) in 1,4-dioxane (2 mL) with stirring. The reaction mixture was stirred at RT for 3 h. The mixture was diluted with H2O, and extracted with ethyl acetate. The combined organic layers were washed with brine, dried over Na2SO4 and concentrated to give compound 63 (230 mg, 84.8%) as a yellow oil. The crude product was used directly for the next step without purification.

Synthesis of 4-{4-[7-(4-Cyano-2-fluoro-3-trifluoromethyl-phenyl)-8-oxo-6-thioxo-5,7-diaza-spiro[3.4]oct-5-yl]-phenyl}-2,2,N-trimethyl-butyramide Example 25

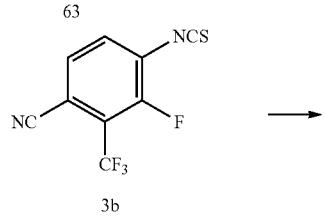

3b

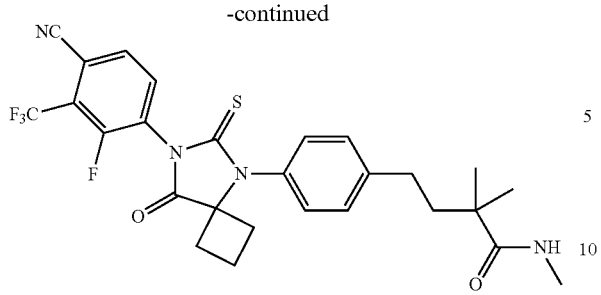

Example 25

A mixture of compound 63 (60 mg, 0.20 mmol) and 3b (74 mg, 0.30 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 25 (65 mg, 59.4%) as a white solid.

1H NMR (400 MHz, CDCl3) δ 7.84~7.75 (m, 2H), 7.39 (d, J=8.0 Hz, 2H), 7.21 (d, J=8.0 Hz, 2H), 5.72~5.70 (br s, 1H), 2.85 (d, J=3.6 Hz, 3H), 2.66~2.62 (m, 4H), 2.56~2.51 (m, 2H), 2.25~2.18 (m, 1H), 1.93~1.88 (m, 2H), 1.67~1.66 (m, 1H), 1.28 (s, 6H). LCMS (M+H)+: 547.5.

Synthesis of 4-{4-[7-(4-Cyano-2-fluoro-3-methoxyphenyl)-8-oxo-6-thioxo-5,7-diaza-spiro[3.4]oct-5-yl]-phenyl}-2,2,N-trimethyl-butyramide Example 26

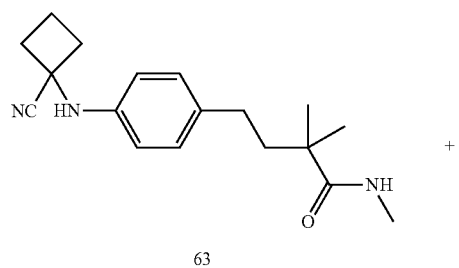

63

+

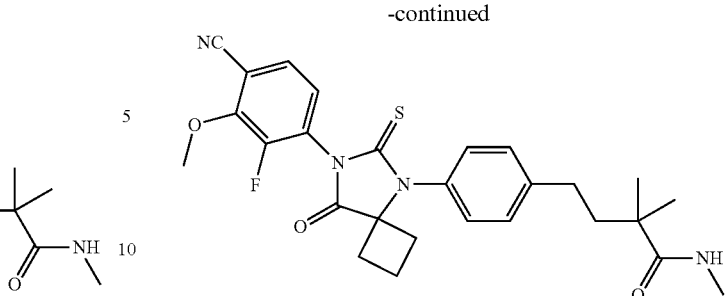

Example 26

A mixture of compound 63 (60 mg, 0.20 mmol) and 3a (64 mg, 0.30 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and. The residue was purified with Prep-TLC to give the title compound EXAMPLE 26 (35 mg, 34.3%) as a white solid.

1H NMR (400 MHz, CDCl3) δ 7.46 (d, J=8.0 Hz, 1H), 7.38 (d, J=8.0 Hz, 2H) 7.23~7.21 (m, 2H), 7.18~7.16 (m, 1H), 5.68~5.64 (br s, 1H), 4.19 (d, J=2.4 Hz, 3H), 2.84 (d, J=4.4 Hz, 3H), 2.66~2.61 (m, 4H), 2.58~2.49 (m, 2H), 2.25~2.18 (m, 1H), 1.92~1.88 (m, 2H), 1.62~2.60 (m, 1H), 1.26 (s, 6H). LCMS (M+H)+: 510.7.

Synthesis of 4-{4-[7-(3-Chloro-4-cyano-2-fluorophenyl)-8-oxo-6-thioxo-5,7-diaza-spiro[3.4]oct-5-yl]-phenyl}-2,2,N-trimethyl-butyramide Example 27

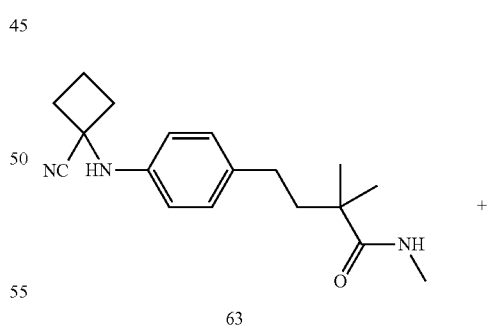

63

+

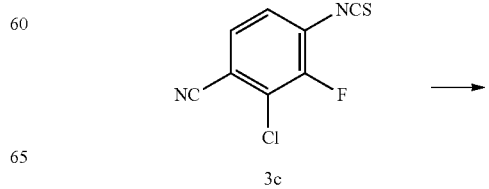

3c

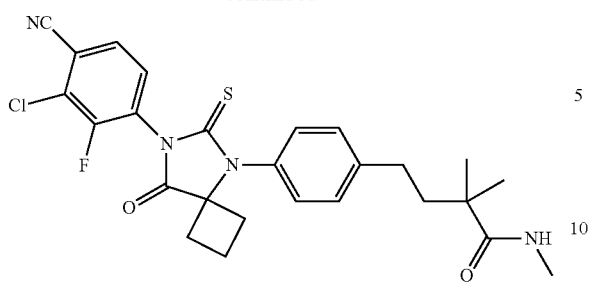

Example 27

A mixture of compound 63 (60 mg, 0.20 mmol) and 3c (64 mg, 0.30 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 27 (40 mg, 38.9%) as a white solid.

1H NMR (400 MHz, CDCl3) δ 7.61 (d, J=8.4 Hz, 1H), 7.52~7.48 (m, 1H), 7.39 (d, J=8.0 Hz, 2H), 7.22 (d, J=8.0 Hz, 2H), 5.69~5.64 (br s, 1H), 2.84 (d, J=4.0 Hz, 3H), 2.68~2.65 (m, 4H), 2.60~2.58 (m, 2H), 2.25~2.17 (m, 1H), 1.92~1.88 (m, 2H), 1.66~1.63 (m, 1H), 1.27 (s, 6H). LCMS (M+H)+: 513.5.

Synthesis of Example 28

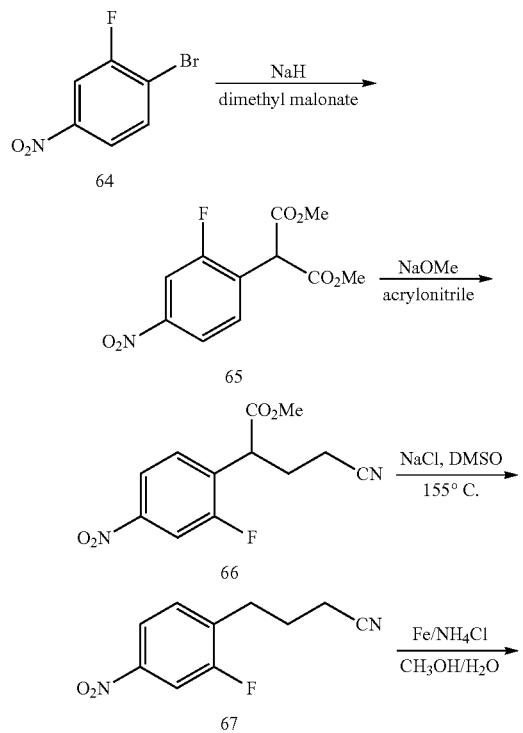

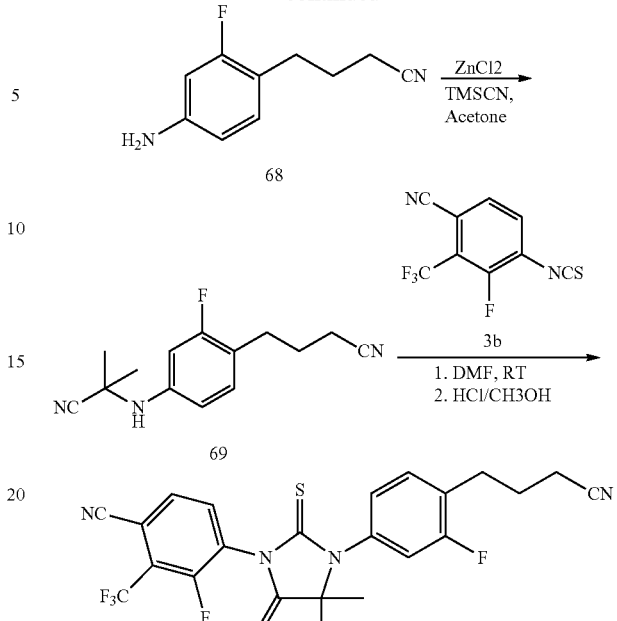

Example 28

Preparation of dimethyl 2-(2-fluoro-4-nitrophenyl)malonate 65

To a suspension of NaH (3.8 g, 95 mmol, 60%) in dry DMF (50 mL) was added dropwise dimethyl malonate (9.9 mL, 86 mmol) at 0° C. with stirring. The mixture was stirred at 0° C. for 30 min, then to the mixture was added dropwise a solution of the compound 64 in DMF (100 mL) under N2. The mixture was stirred at 70° C. for overnight and then allowed to cool to room temperature. The reaction mixture was quenched with saturated NH4Cl and the resulting solid was collected by filtration to give compound 65 (7.8 g, 67%) as a white solid. 1H NMR (400 MHz, CDCl3) δ8.07 (dd, 1H, J=8.6, 2.2 Hz), 7.98 (dd, 1H, J=9.3, 2.2 Hz), 7.74 (dd, 1H, J=8.6, 7.1 Hz), 5.08 (s, 1H), 3.81 (s, 6H).

Preparation of methyl 4-cyano-2-(2-fluoro-4-nitrophenyl)butanoate 66

To a solution of compound 65 (3 g, 11 mmol) and acrylonitrile (3.2 mL, 51 mmol) in absolute CH3OH (50 mL) was added a catalytic amount of CH3ONa (71 mg, 1.32 mmol) at room temperature with stirring under N2. The mixture was stirred at room temperature for overnight under N2. The mixture was diluted with aqNaHCO3 and extracted with DCM. The combined organic layers were washed with brine, dried over Na2SO4, concentrated and purified with silica gel column chromatography (PE:EtOAc=5:1) to give compound 66 (1.9 g, 64%) as a light yellow solid.

Preparation of 4-(2-fluoro-4-nitrophenyl)butanenitrile 67

A mixture of compound 66 (1.2 g, 4.5 mmol), NaCl (0.8 g, 13.5 mmol) and water (1.4 mL) in DMSO (30 mL) was stirred at 160° C. for 24 h under N2. After cooling, the mixture was diluted with water and extracted with EtOAc. The combined organic layers were washed with brine, dried over Na2SO4, concentrated and purified with silica gel column chromatography (PE:EtOAc=5:1) to give the compound 67 (1.6 g, 43%) as a yellow oil. 1H NMR (400 MHz, CDCl3) δ7.99-8.04 (m, 1H), 7.91-7.96 (m, 1H), 7.38-7.44 (m, 1H), 2.93 (t, 2H, J=7.5 Hz), 2.41 (t, 2H, J=7.0 Hz), 1.98-2.07 (m, 2H).

Preparation of 4-(4-amino-2-fluorophenyl)butanenitrile 68

A mixture of compound 67 (1.32 g, 6.3 mmol), NH4Cl (5.08 g, 95 mmol) and iron powder (3.52 g, 63 mmol) in water (30 mL) and CH3OH (50 mL) was stirred at 90° C. for 1 h. After cooling, the reaction mixture was filtered and the solid was washed by DCM. The filtrates were separated, the organic layer was washed with brine, dried over Na2SO4 and concentrated to dryness to give compound 68 (1.07 g, 96%) as a light yellow oil. 1H NMR (400 MHz, CDCl3) δ6.88-6.97 (m, 1H), 6.30-6.44 (m, 1H), 3.65 (br s, 2H), 2.67 (t, 2H, J=7.3 Hz), 2.31 (t, 2H, J=7.2 Hz), 1.86-1.96 (m, 2H).

Preparation of 4-(4-((2-cyanopropan-2-yl)amino)-2-fluorophenyl)butanenitrile 69

TMSCN (0.37 mL, 2.78 mmol) was added to a mixture of compound 68 (165 mg, 0.93 mmol), acetone (0.41 mL, 5.58 mmol) and ZnCl2 (12 mg, 0.09 mmol) with stirring. The reaction mixture was stirred at room temperature for 1 h, and concentrated in vacuo. The residue was diluted with water and extracted with DCM. The combined organic layers were washed with brine, dried over Na2SO4 and concentrated to dryness to give compound 69 (220 mg, 96%) as a light yellow oil. The crude product was used directly for the next step without purification. 1H NMR (400 MHz, CDCl3) δ7.02-7.10 (m, 1H), 6.58-6.65 (m, 2H), 2.72 (t, 2H, J=7.3 Hz), 2.34 (t, 2H, J=7.1 Hz), 1.90-2.00 (m, 2H), 1.71 (s, 6H).

Synthesis of 4-(3-(4-(3-cyanopropyl)-3-fluorophenyl)-4,4-dimethyl-5-oxo-2-thioxoimidazolidin-1-yl)-3-fluoro-2-(trifluoromethyl)benzonitrile Example 28

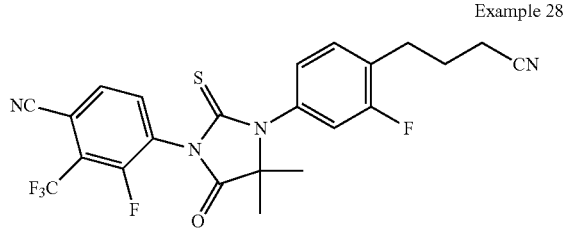 [SMILES: CC1(C)C(=O)N(c2ccc(C#N)c(Cl)c2F)C(=S)N1c1ccc(CCCC#N)c(F)c1]

Example 28

EXAMPLE 28 was synthesized via a reaction between 3b and 69 following a manner similar to the synthetic procedure of EXAMPLE 15. EXAMPLE 28 was obtained in 31% yield as a white solid.

1H NMR (400 MHz, CDCl3) δ7.75-7.85 (m, 2H), 7.36-7.42 (m, 1H), 7.02-7.11 (m, 2H), 2.90 (t, 2H, J=7.6 Hz), 2.43 (t, 2H, J=7.4 Hz), 2.00-2.10 (m, 2H), 1.60 (d, 6H, J=3.9 Hz). LCMS (M+H)+: 493.4.

Synthesis of 2-chloro-4-(3-(4-(3-cyanopropyl)-3-fluorophenyl)-4,4-dimethyl-5-oxo-2-thioxoimidazolidin-1-yl)-3-fluorobenzonitrile Example 29

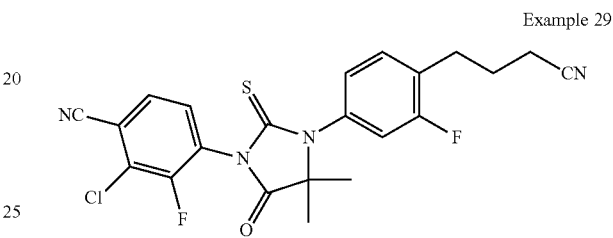

Example 29

EXAMPLE 29 was synthesized via a reaction between 3c and 69 following a manner similar to the synthetic procedure of EXAMPLE 15. EXAMPLE 29 was obtained in 27% yield as a white solid.

1H NMR (400 MHz, CDCl3) δ7.60-7.65 (m, 1H), 67.47-7.53 (m, 1H), 7.36-7.42 (m, 1H), 7.02-7.11 (m, 2H), 2.90 (t, 2H, J=7.6 Hz), 2.43 (t, 2H, J=7.0 Hz), 2.00-2.10 (m, 2H), 1.60 (d, 6H, J=5.1 Hz). LCMS (M+H)+: 459.4.

Synthesis of 4-(3-(4-(3-cyanopropyl)-3-fluorophenyl)-4,4-dimethyl-5-oxo-2-thioxoimidazolidin-1-yl)-3-fluoro-2-methoxybenzonitrile Example 30

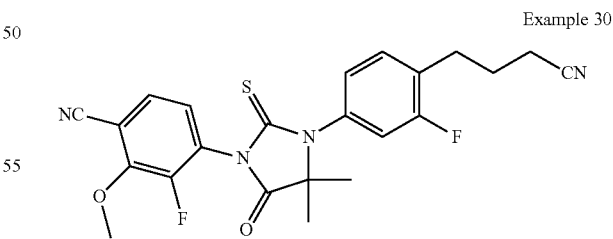

Example 30

EXAMPLE 30 was synthesized via a reaction between 3a and 69 following a manner similar to the synthetic procedure of EXAMPLE 15. EXAMPLE 30 was obtained in 55% yield as a white solid.

1H NMR (400 MHz, CDCl3) δ7.45-7.50 (m, 1H), 67.35-7.40 (m, 1H), 7.14-7.20 (m, 1H), 7.02-7.11 (m, 2H), 4.20 (s,

3H), 2.90 (t, 2H, J=7.5 Hz), 2.43 (t, 2H, J=7.0 Hz), 2.00-2.10 (m, 2H), 1.60 (d, 6H, J=4.3 Hz). LCMS (M+H)+: 455.5.

Synthesis of Example 31

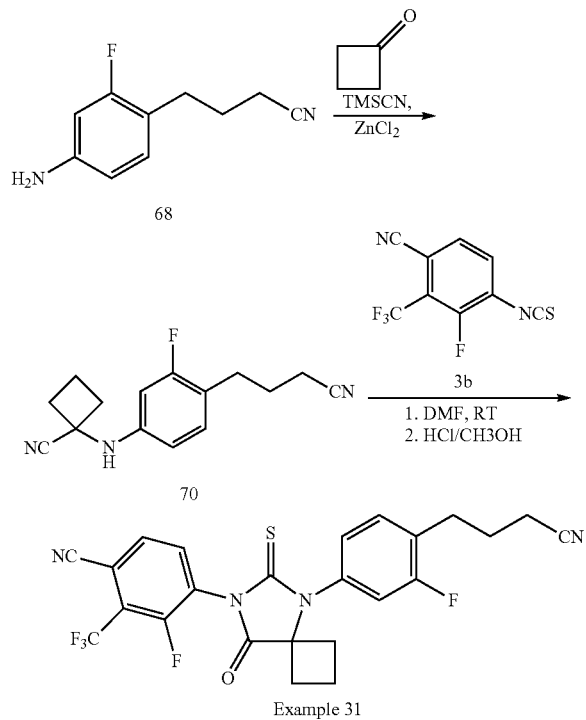

Preparation of 4-(4-((2-cyanopropan-2-yl)amino)-2-fluorophenyl)butanenitrile 70

TMSCN (0.14 mL, 1.01 mmol) was added to a mixture of the compound 68 (60 mg, 0.34 mmol), cyclobutanone (0.15 mL, 2.04 mmol) and ZnCl2 (4 mg, 0.04 mmol) in dioxane (1 mL) with stirring. The reaction mixture was stirred at room temperature for 1 h, and concentrated in vacuo. The residue was diluted with water, and extracted with DCM. The combined organic layers were washed with brine, dried over Na2SO4 and concentrated to dryness to give compound 70 (80 mg, 91%) as a light yellow oil. The crude product was used directly for the next step without purification.

Synthesis of 4-(5-(4-(3-cyanopropyl)-3-fluorophenyl)-8-oxo-6-thioxo-5,7-diazaspiro[3.4]octan-7-yl)-3-fluoro-2-(trifluoromethyl)benzonitrile Example 31

EXAMPLE 31 was synthesized via a reaction between 3b and 70 following a manner similar to the synthetic procedure of EXAMPLE 15. EXAMPLE 31 was obtained in 44% yield as a white solid.

1H NMR (400 MHz, CDCl3) δ7.75-7.85 (m, 2H), 7.40-7.46 (m, 1H), 7.05-7.14 (m, 2H), 2.90 (t, 2H, J=7.5 Hz), 2.62-2.72 (m, 2H), 2.50-2.62 (m, 2H), 2.43 (t, 2H, J=7.0 Hz), 2.20-2.30 (m, 1H), 2.00-2.10 (m, 2H), 1.65-1.75 (m, 1H). LCMS (M+H)+: 505.5.

Synthesis of 4-(5-(4-(3-cyanopropyl)-3-fluorophenyl)-8-oxo-6-thioxo-5,7-diazaspiro[3.4]octan-7-yl)-3-fluoro-2-methoxybenzonitrile Example 32

EXAMPLE 32 was synthesized via a reaction between 3a and 70 following a manner similar to the synthetic procedure of EXAMPLE 15. EXAMPLE 32 was obtained in 28% yield as a white solid.

1H NMR (400 MHz, CDCl3) δ7.40-7.50 (m, 2H), 7.14-7.20 (m, 1H), 7.06-7.13 (m, 2H), 4.20 (d, 3H, J=2.3 Hz), 2.90 (t, 2H, J=7.5 Hz), 2.62-2.72 (m, 2H), 2.50-2.62 (m, 2H), 2.43 (t, 2H, J=7.0 Hz), 2.20-2.30 (m, 1H), 2.00-2.10 (m, 2H), 1.65-1.75 (m, 1H). LCMS (M+H)+: 467.5.

Synthesis of 2-chloro-4-(5-(4-(3-cyanopropyl)-3-fluorophenyl)-8-oxo-6-thioxo-5,7-diazaspiro[3.4]octan-7-yl)-3-fluorobenzonitrile Example 33

EXAMPLE 33 was synthesized via a reaction between 3c and 70 following a manner similar to the synthetic procedure of EXAMPLE 15. EXAMPLE 33 was obtained in 45% yield as a white solid.

1H NMR (400 MHz, CDCl3) δ7.60-7.65 (m, 1H), 67.47-7.53 (m, 1H), 7.40-7.46 (m, 1H), 7.05-7.14 (m, 2H), 2.92 (t, 2H, J=7.5 Hz), 2.62-2.72 (m, 2H), 2.50-2.62 (m, 2H), 2.43 (t, 2H, J=7.0 Hz), 2.20-2.30 (m, 1H), 2.00-2.10 (m, 2H), 1.65-1.75 (m, 1H). LCMS (M+H)+: 471.3.

Synthesis of compound 71

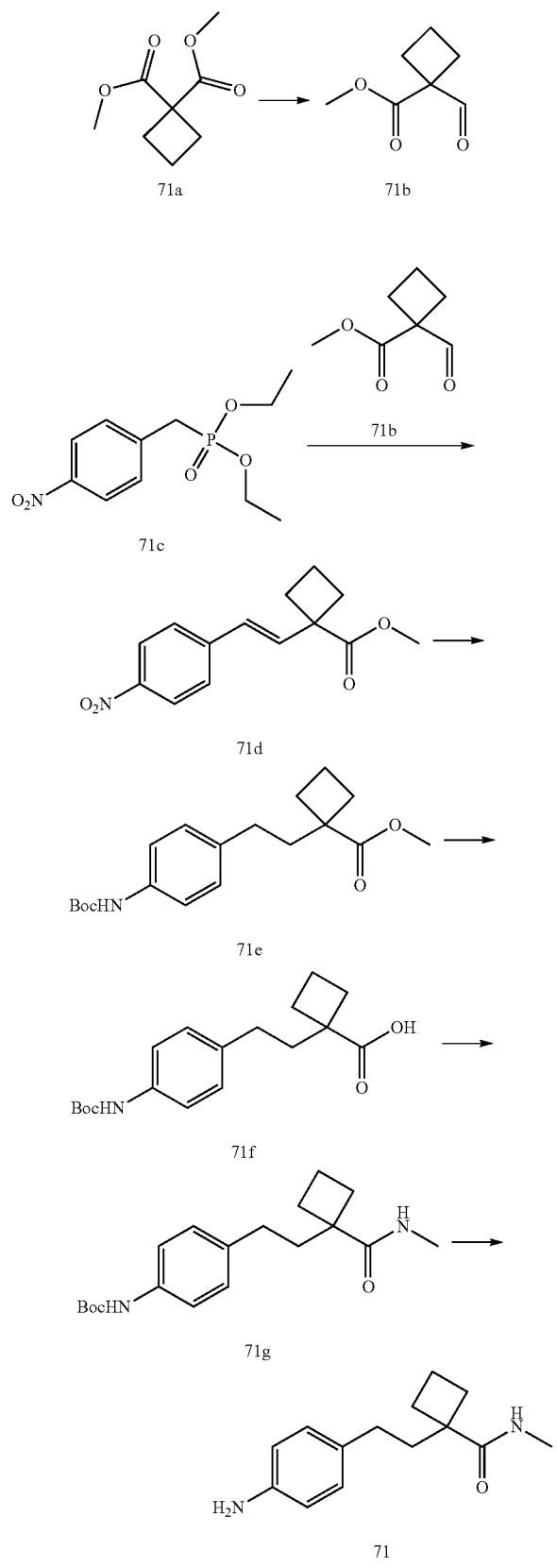

Preparation of Compound 71b

A mixture of dimethyl cyclobutane-1,1-dicarboxylate (5 g, 29 mmol) in $CH_2Cl_2$ (120 mL) was cooled down to −78° C. under protection of N2, then DIBALH (58 mL, 1M, 58 mmol) was added dropwise keeping the temperature below −65° C. After addition, the mixture was stirred for 2 hours. The reaction was quenched with 1N HCl (50 mL). Separated and dried, removed the solvent to obtain the crude product 71b (3 g, yield 50%) for the next steps without purification.

Synthesis of Compound 71d

The mixture of diethyl 4-nitrobenzylphosphonate (2.5 g, 9.16 mmol) in THF (50 mL) was cooled down to 0° C., then NaH (0.73 g, 18.3 mmol) was added carefully and the mixture was stirred for 10 minutes. Compound 71b (3 g, 21 mmol) in THF (10 mL) was added dropwise. After addition, the mixture was allowed to warm to r.t and stirred for 1 hour at r.t The reaction was quenched with 1N HCl (40 mL). The mixture was extracted with EA (100 mL×2). Dried and removed the EA to get crude product. The crude material was purified by flash chromatography (silica gel, PE:EA=8:1) to give 71d (1.6 g, yield 70%) as a white solid.

Preparation of Compound 71e

Compound 71e was prepared from 71d in a manner similar to the synthesis of compound 61e.

Preparation of Compound 71f

Compound 71f was prepared from 71e in a manner similar to the synthesis of compound 61f.

Preparation of Compound 71g

Compound 71g was prepared from 71f in a manner similar to the synthesis of compound 61g.

Preparation of Compound 71

Compound 71 was prepared from 71g in a manner similar to the synthesis of compound 61.

Preparation of Compound 72

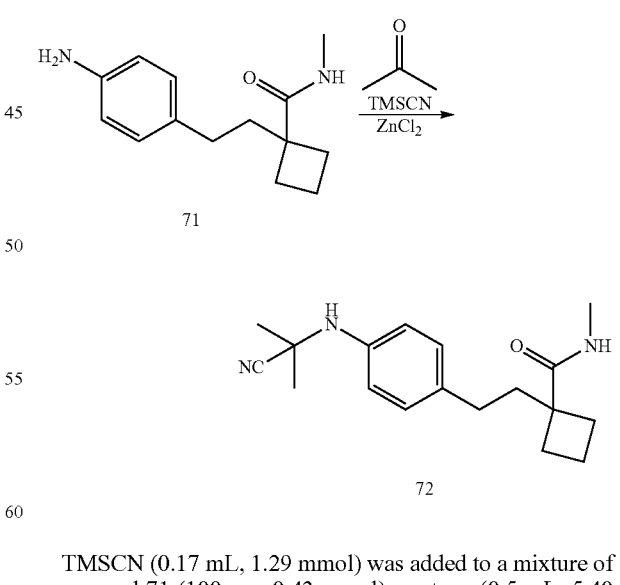

TMSCN (0.17 mL, 1.29 mmol) was added to a mixture of compound 71 (100 mg, 0.43 mmol), acetone (0.5 mL, 5.40 mmol) and ZnCl2 (10 mg) with stirring. The reaction mixture was stirred at RT for 3 h. The mixture was diluted with H2O, and extracted with ethyl acetate. The combined organic layers were washed with brine, dried over Na2SO4 and concentrated to give compound 72 (120 mg, 93.1%). The crude product was used directly for the next step without purification.

Synthesis of 1-(2-{4-[3-(4-Cyano-2-fluoro-3-trifluoromethyl-phenyl)-5,5-dimethyl-4-oxo-2-thioxo-imidazolidin-1-yl]-phenyl}-ethyl)-cyclobutanecarboxylic acid methylamide Example 34

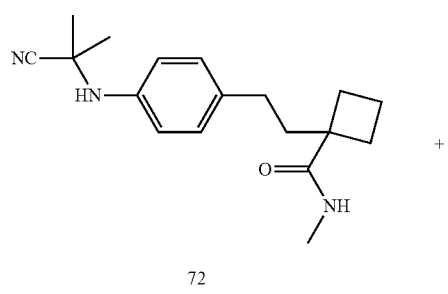

72

+

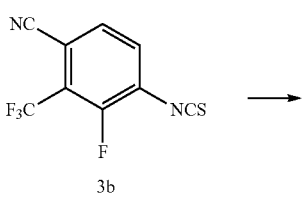

3b

→

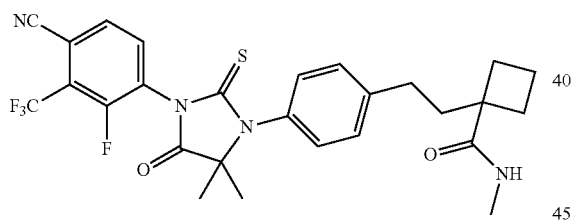

Example 34

A mixture of compound 72 (50 mg, 0.17 mmol) and 3b (61 mg, 0.25 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 34 (25 mg, 27.4%) as a white solid.

1H NMR (400 MHz, CDCl3) δ 7.82~7.76 (m, 2H), 7.35 (d, J=8.0 Hz, 2H), 7.21 (d, J=8.0 Hz, 2H), 5.49~5.00 (br s, 1H), 3.49 (s, 3H), 2.86~2.85 (m, 2H), 2.62~2.57 (m, 2H), 2.40~2.36 (m, 2H), 2.13~2.08 (m, 3H), 1.99~1.86 (m, 1H), 1.59 (d, J=8.0 Hz, 6H). LCMS (M+H)+: 547.8.

Preparation of Compound 73

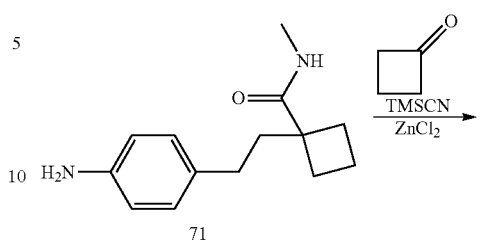

71

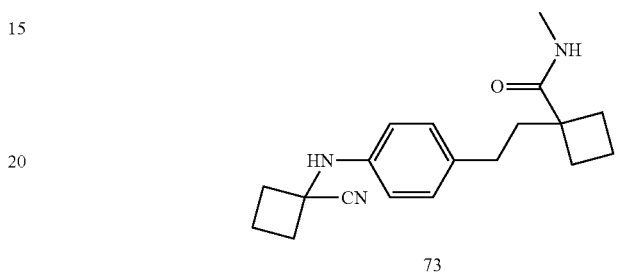

73

TMSCN (0.16 mL, 1.29 mmol) was added to a mixture of compound 71 (100 mg, 0.43 mmol), cyclobutanone (0.2 mL, 2.58 mmol) and ZnCl2 (20 mg) in 1,4-dioxane (2 mL) with stirring. The reaction mixture was stirred at RT for 3 h. The mixture was diluted with H2O, and extracted with ethyl acetate. The combined organic layers were washed with brine, dried over Na2SO4 and concentrated to give compound 73 (120 mg, 89.5%). The crude product was used directly for the next step without purification.

Synthesis of 1-(2-{4-[7-(4-Cyano-2-fluoro-3-trifluoromethyl-phenyl)-8-oxo-6-thioxo-5,7-diaza-spiro[3.4]oct-5-yl]-phenyl}-ethyl)-cyclobutanecarboxylic acid methylamide Example 35

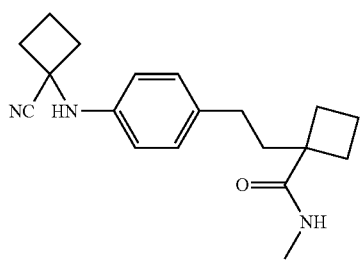

73

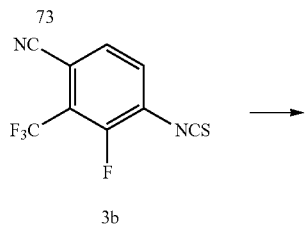

3b

→

-continued

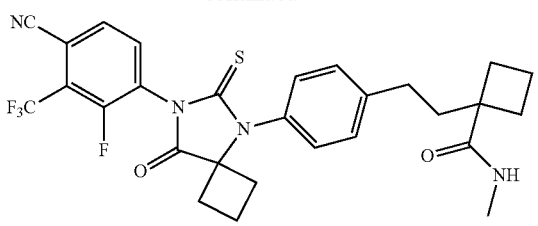

Example 35

A mixture of compound 73 (50 mg, 0.16 mmol) and 3b (60 mg, 0.24 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 35 (39 mg, 39.0%) as a white solid.

1H NMR (400 MHz, CDCl3) δ 7.84~7.75 (m, 2H), 7.39 (d, J=8.0 Hz, 2H), 7.23 (d, J=8.0 Hz, 2H), 5.51~5.49 (br s, 1H), 2.86 (d, J=4.8 Hz, 3H), 2.65~2.61 (m, 6H), 2.40~2.39 (m, 2H), 2.26~2.11 (m, 3H), 1.89~1.86 (m, 4H), 1.67~1.63 (m, 1H).

Synthesis of Example 36

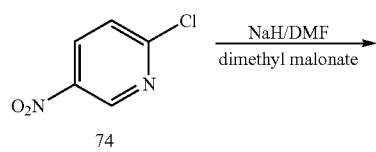

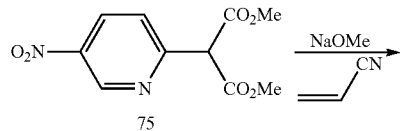

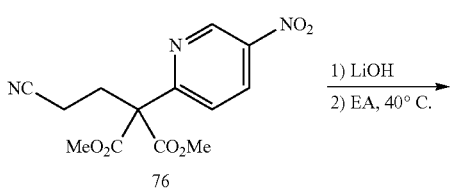

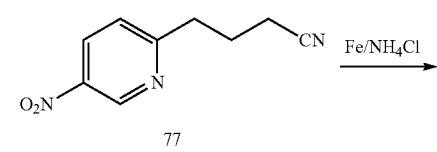

-continued

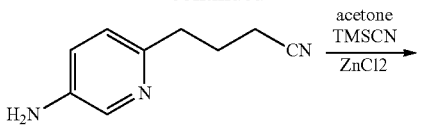

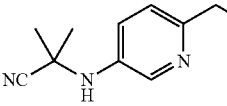

Example 36

Preparation of dimethyl 2-(5-nitropyridin-2-yl)malonate 75

To a suspension of NaH (5.2 g, 129 mmol, 60%) in dry DMF (50 mL) was added dropwise dimethyl malonate (14 mL, 122 mmol) at 0° C. with stirring. The mixture was stirred at 0° C. for 30 min, then to the mixture was added dropwise a solution of compound 74 (9.6 g, 61 mmol) in DMF (100 mL) under N2. The mixture was stirred at 70° C. for overnight and then allowed to cool to room temperature. The reaction mixture was quenched with saturated NH4Cl and the resulting solid was collected by filtration to give compound 75 (10.5 g, 68%) as a white solid.

Preparation of dimethyl 2-(2-cyanoethyl)-2-(5-nitropyridin-2-yl)malonate 76

To a solution of compound 75 (10.5 g, 41 mmol) and acrylonitrile (17.4 g, 328 mmol) in absolute CH3OH (100 mL) was added a catalytic amount of CH3ONa (216 mg, 4 mmol) at room temperature with stirring under N2. The mixture was stirred at room temperature for 10 h under N2. The mixture was diluted with aqNaHCO3 and extracted with DCM. The combined organic layers were washed with brine, dried over Na2SO4, concentrated and purified with silica gel column chromatography (PE:EtOAc=5:1) to give compound 76 (3.3 g, 20%) as a light yellow oil.

Preparation of 4-(5-nitropyridin-2-yl)butanenitrile 77

To a solution of compound 76 (3.3 g, 10.7 mmol) in CH3OH (100 mL) was added a solution of LiOH (15.4 g, 64.2 mmol) in H2O (100 mL) at room temperature with stirring. The mixture was stirred at room temperature for 2 h. Methanol was removed in vacuo and the residual aqueous solution was washed with EtOAc (two times), then was acidified to pH=2 with 1N HCl. The aqueous phase was extracted with EtOAc. The combined organic extract was dried over Na2SO4, then was stirred at 50° C. for overnight. The solution was concentrated to afford compound 77 (1.9 g, 95%) as a yellow oil.

Preparation of 4-(5-aminopyridin-2-yl)butanenitrile 78

A mixture of compound 77 (158 mg, 0.83 mmol), NH4Cl (666 mg, 12 mmol) and Iron Powder (463 mg, 8.3 mmol) in water (5 mL) and CH3OH (5 mL) was stirred at 90° C. for 1 h. After cooling, the reaction mixture was filtered and the solid was washed by DCM. The filtrates were separated, the organic layer was washed with brine, dried over Na2SO4 and concentrated to dryness to give compound 78 (100 mg, 75%) as a light yellow oil. 1H NMR (400 MHz, CDCl3) δ8.04 (s, 1H), 6.90-7.00 (m, 2H), 3.53 (br s, 2H), 2.83 (t, 2H, J=7.1 Hz), 2.36 (t, 2H, J=7.1 Hz), 2.02-2.12 (m, 2H).

Preparation of 4-(5-((2-cyanopropan-2-yl)amino)pyridin-2-yl)butanenitrile 79

TMSCN (0.24 mL, 1.8 mmol) was added to a mixture of compound 78 (100 mg, 0.6 mmol), acetone (0.27 mL, 3.6 mmol) and ZnCl2 (10 mg, 0.08 mmol) with stirring. The reaction mixture was stirred at room temperature for 1 h and concentrated in vacuo. The residue was diluted with water and extracted with DCM. The combined organic layers were washed with brine, dried over Na2SO4 and concentrated to dryness to give compound 79 (140 mg, 98%) as a light yellow oil. The crude product was used directly for the next step without purification. 1H NMR (400 MHz, CDCl3) δ8.12 (s, 1H), 7.20-7.25 (m, 1H), 7.00-7.06 (m, 1H), 2.81 (t, 2H, J=7.1 Hz). 2.32 (t, 2H, J=7.1 Hz), 1.98-2.12 (m, 2H), 1.69 (s, 6H).

Synthesis of 4-(3-(6-(3-cyanopropyl)pyridin-3-yl)-4,4-dimethyl-5-oxo-2-thioxoimidazolidin-1-yl)-3-fluoro-2-(trifluoromethyl)benzonitrile Example 36

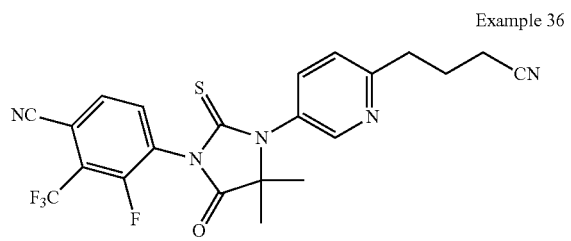

Example 36

EXAMPLE 36 was synthesized via a reaction between 3b and 79 following a manner similar to the synthetic procedure of EXAMPLE 15. EXAMPLE 36 was obtained in 35% yield as a white solid.

1H NMR (400 MHz, CDCl3) δ8.49-8.55 (m, 1H), 7.77-7.86 (m, 2H), 7.62-7.68 (m, 1H), 7.38-7.44 (m, 1H), 3.09 (t, 2H, J=7.1 Hz), 2.50 (t, 2H, J=5.8 Hz), 2.18-2.27 (m, 2H), 1.61 (s, 6H). LCMS (M+H)+: 476.0.

Synthesis of 2-chloro-4-(3-(6-(3-cyanopropyl)pyridin-3-yl)-4,4-dimethyl-5-oxo-2-thioxoimidazolidin-1-yl)-3-fluorobenzonitrile Example 37

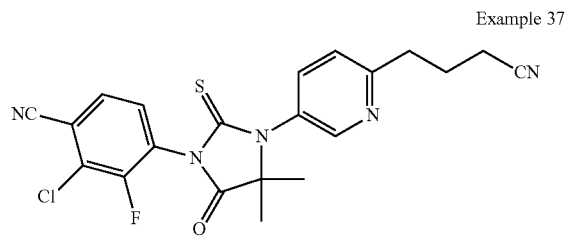 [SMILES: CC1(C)C(=O)N(c2ccc(C#N)c(Cl)c2F)C(=S)N1c1ccc(CCCC#N)nc1]

Example 37

EXAMPLE 37 was synthesized via a reaction between 3c and 79 following a manner similar to the synthetic procedure of EXAMPLE 15. EXAMPLE 37 was obtained in 38% yield as a white solid.

1H NMR (400 MHz, CDCl3) δ8.49-8.55 (m, 1H), 7.62-7.72 (m, 2H), 7.48-7.54 (m, 1H), 7.40-7.45 (m, 1H), 3.09 (t, 2H, J=7.1 Hz), 2.50 (t, 2H, J=6.7 Hz), 2.18-2.27 (m, 2H), 1.61 (s, 6H). LCMS (M+H)+: 442.6.

Preparation of 3e

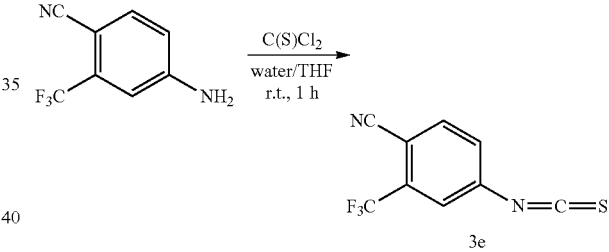

Compound 3e was prepared from commercially available 4-amino-2-trifluoromethyl-benzonitrile in a manner similar to synthesis of 3b.

Synthesis of 4-(3-(6-(3-cyanopropyl)pyridin-3-yl)-4,4-dimethyl-5-oxo-2-thioxoimidazolidin-1-yl)-2-(trifluoromethyl)benzonitrile Example 38

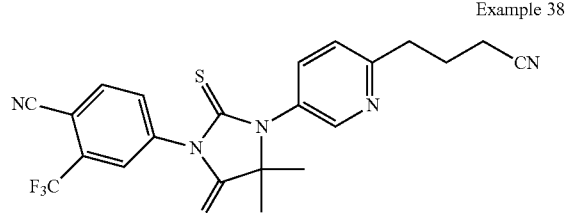

Example 38

EXAMPLE 38 was synthesized via a reaction between 3e and 79 following a manner similar to the synthetic procedure of EXAMPLE 15. EXAMPLE 38 was obtained in 34% yield as a white solid.

1H NMR (400 MHz, CDCl3) δ8.49-8.55 (m, 1H), 7.94-8.02 (m, 2H), 7.80-7.86 (m, 1H), 7.62-7.72 (m, 1H), 7.48-7.54 (m, 1H), 3.12 (t, 2H, J=7.1 Hz), 2.52 (t, 2H, J=6.7 Hz), 2.18-2.27 (m, 2H), 1.60 (s, 6H). LCMS (M+H)+: 458.5.

Synthesis of 4-(3-(6-(3-cyanopropyl)pyridin-3-yl)-4,4-dimethyl-5-oxo-2-thioxoimidazolidin-1-yl)-3-fluoro-2-methoxybenzonitrile Example 39

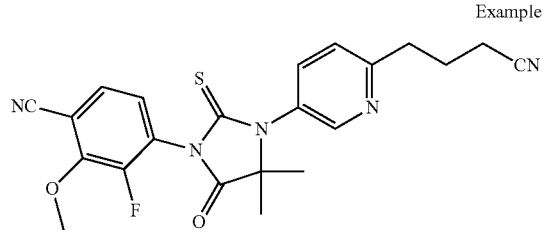

Example 39

EXAMPLE 39 was synthesized via a reaction between 3a and 79 following a manner similar to the synthetic procedure of EXAMPLE 15. EXAMPLE 39 was obtained in 30% yield as a white solid.

1H NMR (400 MHz, CDCl3) δ8.49-8.55 (m, 1H), 7.62-7.72 (m, 1H), 7.48-7.54 (m, 1H), 7.38-7.45 (m, 1H), 7.15-7.20 (m, 1H), 4.20 (d, 3H, J=2.9 Hz), 3.09 (t, 2H, J=7.1 Hz), 2.50 (t, 2H, J=6.9 Hz), 2.18-2.27 (m, 2H), 1.60 (d, 6H, J=6.9 Hz). LCMS (M+H)+: 438.1.

Synthesis of Example 40

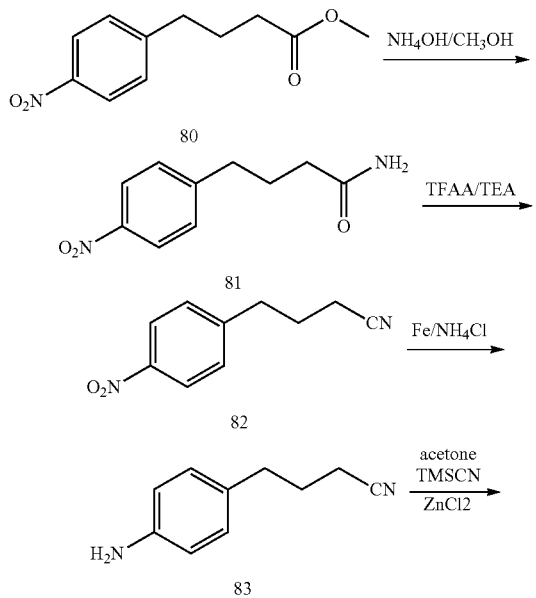

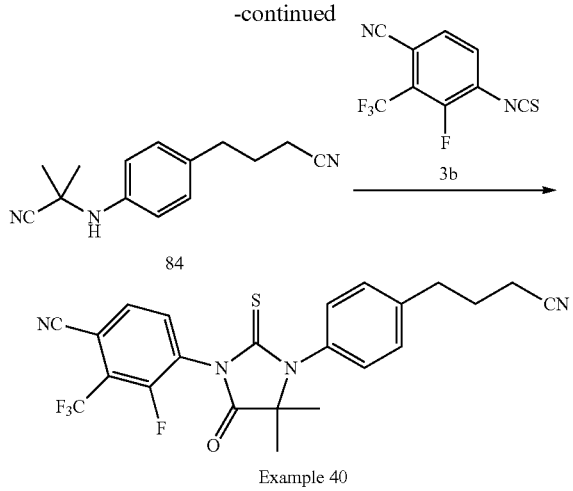

Example 40

Preparation of 4-(4-nitrophenyl)butanamide 81

To a solution of compound 80 (5 g, 22.4 mmol) in CH3OH (200 mL) was added NH4OH (300 mL) at room temperature with stirring. The reaction mixture was stirred at room temperature for 24 h and concentrated in vacuo. The residue was extracted with DCM/CH3OH (10:1). The combined organic layers were dried over Na2SO4 and concentrated to dryness to give compound 81 (3.1 g, 66%) as a white solid. 1H NMR (400 MHz, CDCl3) δ 8.16 (d, 2H, J=8.1 Hz), 7.35 (d, 2H, J=8.1 Hz), 5.40 (br s, 2H), 2.80 (t, 2H, J=7.7 Hz), 2.25 (t, 2H, J=7.3 Hz), 1.97-2.07 (m, 2H).

Preparation of 4-(4-nitrophenyl)butanenitrile 82

To a solution of compound 81 (3.2 g, 22.4 mmol) in DCM (60 mL) was added TEA (10 mL, 77 mmol) at room temperature with stirring. Then to the mixture was added dropwise TFAA (4 mL, 30.8 mmol) at 0° C. The reaction mixture was stirred at room temperature for 4 h. Then the mixture was diluted with DCM, washed by water and brine, dried over Na2SO4 and concentrated to dryness to give compound 82 (2.7 g, 93%) as a yellow oil. 1H NMR (400 MHz, CDCl3) 8.12 (d, 2H, J=8.1 Hz), 7.30 (d, 2H, J=8.1 Hz), 2.85 (t, 2H, J=7.5 Hz), 2.31 (t, 2H, J=7.3 Hz), 1.92-2.05 (m, 2H).

Preparation of 4-(4-aminophenyl)butanenitrile 83

A mixture of compound 82 (2.67 g, 14 mmol), NH4Cl (11.2 g, 210 mmol) and Iron Powder (7.8 g, 140 mmol) in water (90 mL) and CH3OH (90 mL) was stirred at 90° C. for 1 h. After cooling, the reaction mixture was filtered and the solid was washed by DCM. The filtrates were separated, and the organic layer was washed with brine, dried over Na2SO4 and concentrated to dryness to give compound 83 (1.85 g, 83%) as a light yellow oil. 1H NMR (400 MHz, CDCl3) δ 6.90 (d, 2H, J=8.1 Hz), 6.58 (d, 2H, J=8.1 Hz), 3.30 (br s, 2H), 2.59 (t, 2H, J=7.4 Hz), 2.22 (t, 2H, J=7.4 Hz), 1.80-1.90 (m, 2H).

Preparation of 4-(4-((2-cyanopropan-2-yl)amino)phenyl)butanenitrile 84

TMSCN (0.3 mL, 2.25 mmol) was added to a mixture of compound 83 (120 mg, 0.75 mmol), acetone (0.33 mL, 4.5 mmol) and ZnCl2 (10 mg, 0.08 mmol) with stirring. The reaction mixture was stirred at room temperature for 1 h, and concentrated in vacuo. The residue was diluted with water, and extracted with DCM. The combined organic layers were washed with brine, dried over Na2SO4 and concentrated to dryness to give compound 84 (170 mg, 99%) as a light yellow oil. The crude product was used directly for the next step without purification. 1H NMR (400 MHz, CDCl3) δ7.08 (d, 2H, J=8.1 Hz), 6.88 (d, 2H, J=8.1 Hz), 2.72 (t, 2H, J=7.4 Hz), 2.32 (t, 2H, J=7.4 Hz), 1.90-2.00 (m, 2H), 1.69 (s, 6H).

Synthesis of 4-(3-(4-(3-cyanopropyl)phenyl)-4,4-dimethyl-5-oxo-2-thioxoimidazolidin-1-yl)-3-fluoro-2-(trifluoromethyl)benzonitrile Example 40

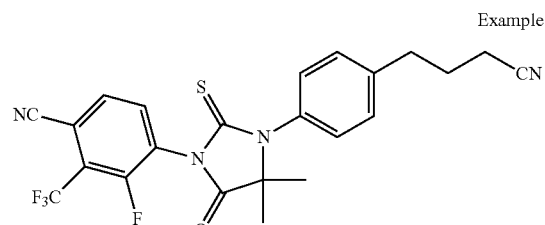

Example 40

EXAMPLE 40 was synthesized via a reaction between 3b and 84 following a manner similar to the synthetic procedure of EXAMPLE 15. EXAMPLE 40 was obtained in 16% yield as a white solid.

1H NMR (400 MHz, CDCl3) δ7.75-7.85 (m, 2H), 7.37 (d, 2H, J=8.2 Hz), 7.26 (d, 2H, J=8.2 Hz), 2.87 (t, 2H, J=7.5 Hz), 2.40 (t, 2H, J=7.0 Hz), 2.00-2.08 (m, 2H), 1.58 (d, 6H, J=4.2 Hz). LCMS (M+H)+: 475.8.

Synthesis of 2-chloro-4-(3-(4-(3-cyanopropyl)phenyl)-4,4-dimethyl-5-oxo-2-thioxoimidazolidin-1-yl)-3-fluorobenzonitrile Example 41

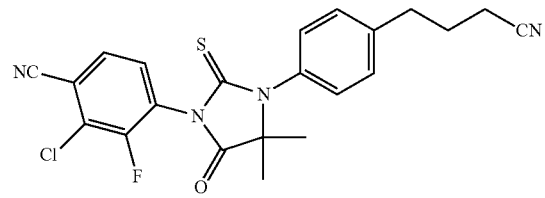

Example 41

EXAMPLE 41 was synthesized via a reaction between 3c and 84 following a manner similar to the synthetic procedure of EXAMPLE 15. EXAMPLE 41 was obtained in 43% yield as a white solid.

1H NMR (400 MHz, CDCl3) δ7.62-7.65 (m, 1H), 7.48-7.54 (m, 1H), 7.37 (d, 2H, J=8.2 Hz), 7.26 (d, 2H, J=8.2 Hz), 2.87 (t, 2H, J=7.5 Hz), 2.40 (t, 2H, J=7.0 Hz), 2.00-2.08 (m, 2H), 1.58 (d, 6H, J=5.2 Hz). LCMS (M+H)+: 441.2.

Synthesis of Example 42

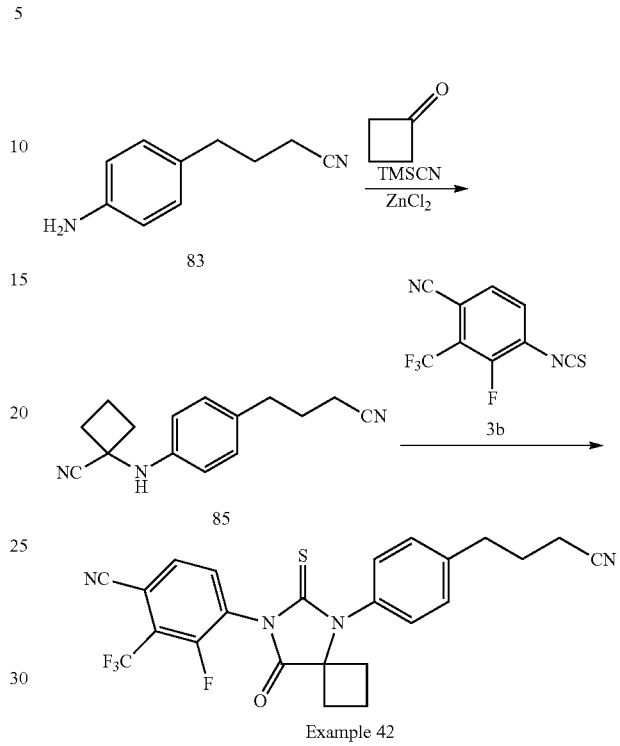

Example 42

Preparation of 1-((4-(3-cyanopropyl)phenyl)amino)cyclobutanecarbonitrile 85

Compound 85 was prepared from compound 83 in a manner similar to synthesis of 84.

1H NMR (400 MHz, CDCl3) δ7.06 (d, 2H, J=8.1 Hz), 6.61 (d, 2H, J=8.1 Hz), 3.09 (t, 2H, J=7.4 Hz), 2.75-2.85 (m, 2H), 2.65-2.73 (m, 2H), 2.42 (t, 2H, J=7.0 Hz), 2.20-2.30 (m, 1H), 2.00-2.10 (m, 2H), 1.65-1.72 (m, 1H).

Synthesis of 4-(5-(4-(3-cyanopropyl)phenyl)-8-oxo-6-thioxo-5,7-diazaspiro[3.4]octan-7-yl)-3-fluoro-2-(trifluoromethyl)benzonitrile Example 42

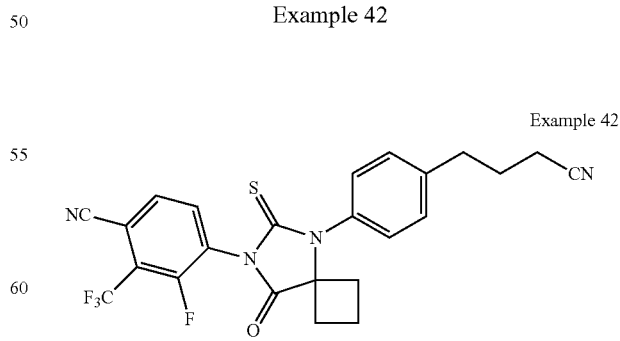

Example 42

EXAMPLE 42 was synthesized via a reaction between 3b and 85 following a manner similar to the synthetic procedure of EXAMPLE 15. EXAMPLE 42 was obtained in 21% yield as a white solid.

1H NMR (400 MHz, CDCl3) δ7.75-7.85 (m, 2H), 7.42 (d, 2H, J=8.2 Hz), 7.28 (d, 2H, J=8.2 Hz), 2.90 (t, 2H, J=7.4 Hz), 2.62-2.70 (m, 2H), 2.50-2.60 (m, 2H), 2.42 (t, 2H, J=7.0 Hz), 2.20-2.30 (m, 1H), 2.00-2.10 (m, 2H), 1.65-1.72 (m, 1H). LCMS (M+H)+: 488.4

Synthesis of 2-chloro-4-(5-(4-(3-cyanopropyl)phenyl)-8-oxo-6-thioxo-5,7-diazaspiro[3.4]octan-7-yl)-3-fluorobenzonitrile Example 43

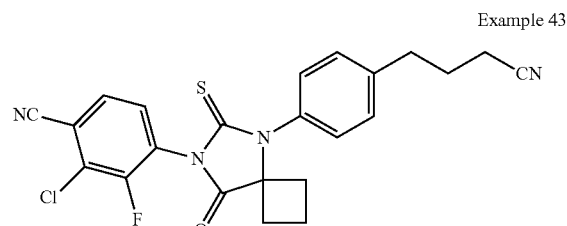

Example 43

EXAMPLE 43 was synthesized via a reaction between 3c and 85 following a manner similar to the synthetic procedure of EXAMPLE 15. EXAMPLE 43 was obtained in 35% yield as a white solid.

1H NMR (400 MHz, CDCl3) δ7.62-7.65 (m, 1H), 7.48-7.54 (m, 1H), 7.42 (d, 2H, J=8.2 Hz), 7.28 (d, 2H, J=8.2 Hz), 2.90 (t, 2H, J=7.4 Hz), 2.62-2.70 (m, 2H), 2.50-2.60 (m, 2H). 2.42 (t, 2H, J=7.0 Hz), 2.20-2.30 (m, 1H), 2.00-2.10 (m, 2H), 1.65-1.72 (m, 1H). LCMS (M+H)+: 452.3.

Synthesis of Example 44, Example 46

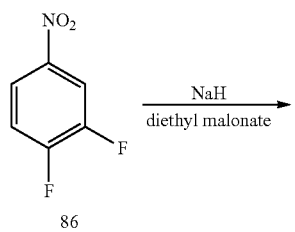

86

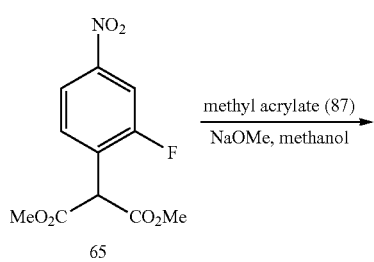

65

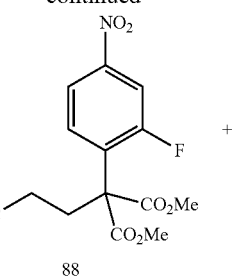

88

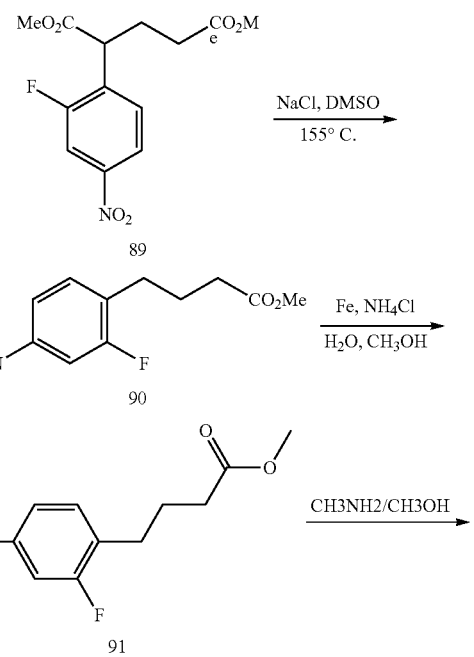

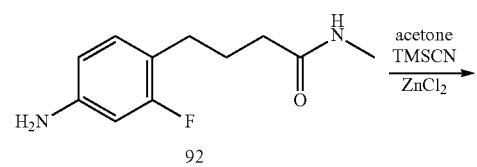

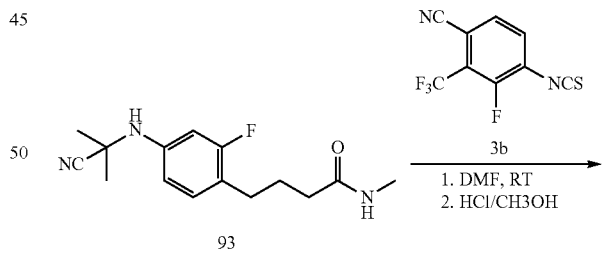

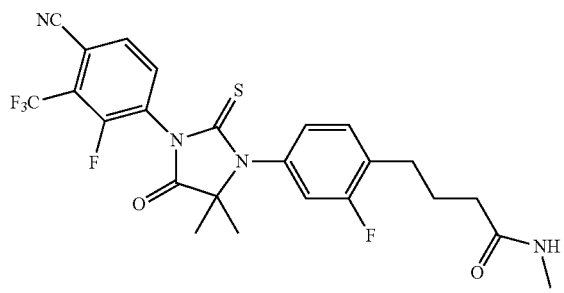

Example 44

137

-continued

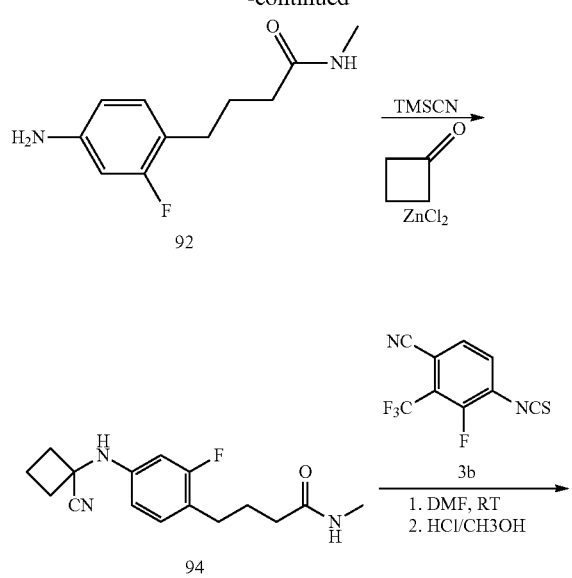

Example 45

Preparation of Compound 65

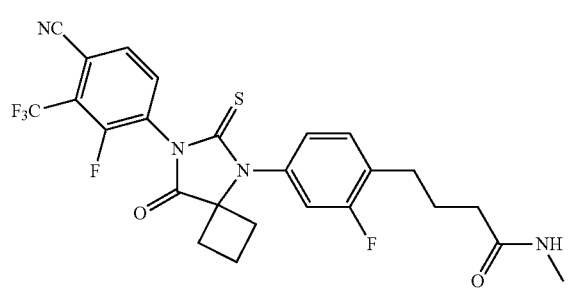

To a suspension of NaH (3.8 g, 95 mmol, 60%) in dry DMF (50 mL) was added dropwise dimethyl malonate (87, 9.9 mL, 86 mmol) at 0° C. with stirring. The mixture was stirred at 0° C. for 30 min, and then to the mixture was added drop wise a solution of compound 86 in DMF (100 mL) under N2. The mixture was stirred at 70° C. for overnight and then allowed to cool to RT. The reaction mixture was quenched with saturated NH4Cl and the resulting solid was collected by filtration to give compound 65 (7.8 g, 67%) as a white solid.

1H NMR (400 MHz, CDCl3) δ 8.07 (dd, J=8.6, 2.2 Hz, 1H), 7.98 (dd, J=9.3, 2.2 Hz, 1H), 7.74 (dd, J=8.6, 7.2 Hz, 1H), 5.08 (s, 1H), 3.81 (s, 6H).

138

Preparation of Compound 88 and 89

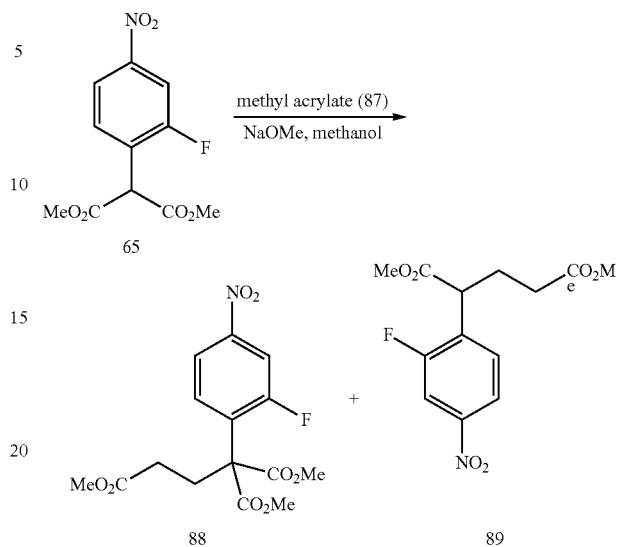

To a solution of compound 65 (4.84 g, 17.8 mmol) and methyl acrylate (13.4 mL, 147.6 mmol) in absolute CH3OH (60 mL) was added a catalytic amount of CH3ONa (149 mg, 2.76 mmol) at RT with stirring under N2. The mixture was stirred at RT for overnight under N2. The mixture was diluted with aqNaHCO3, and extracted with DCM. The combined organic layers were washed with brine, dried over Na2SO4, and concentrated to give the mixture of compound 88 and compound 89 (4.75 g). The crude product was used directly for the next step without further purification.

Preparation of Compound 90

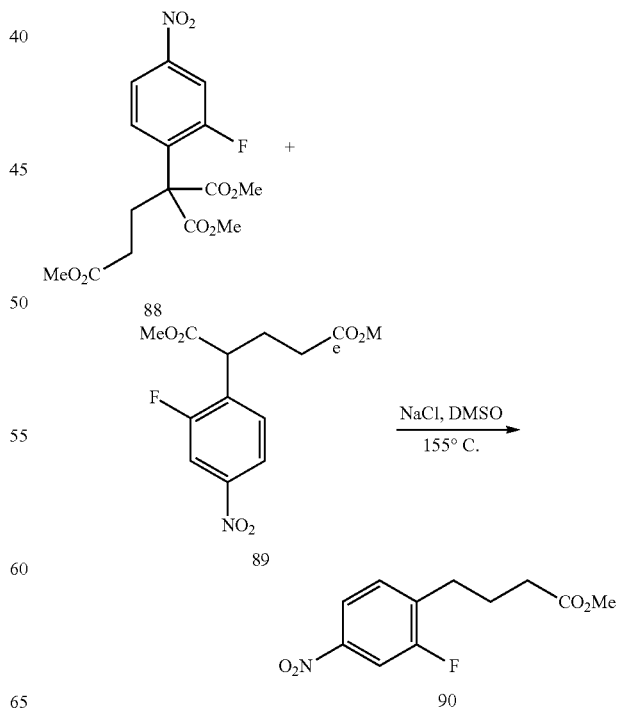

A mixture of compound 88 and compound 89 (4.75 g), NaCl (2.73 g, 47.1 mmol) and water (3.7 mL) in DMSO (70 mL) was stirred at 155° C. for 24 h under N2. After cooling, the mixture was diluted with water, and extracted with EtOAc. The combined organic layers were washed with brine, dried over Na2SO4, concentrated and purified with silica gel column chromatography (PE:EA=5:1) to give the title compound 90 (2.1 g, 65.6%) as a yellow oil.

1H NMR (400 MHz, CDCl3) δ 7.98~7.95 (m, 1H), 7.90~7.87 (m, 1H), 7.39~7.35 (m, 1H), 3.67 (s, 3H), 2.80~2.75 (m, 2H), 2.38~2.34 (m, 2H), 2.02~1.95 (m, 2H).

Preparation of Compound 91

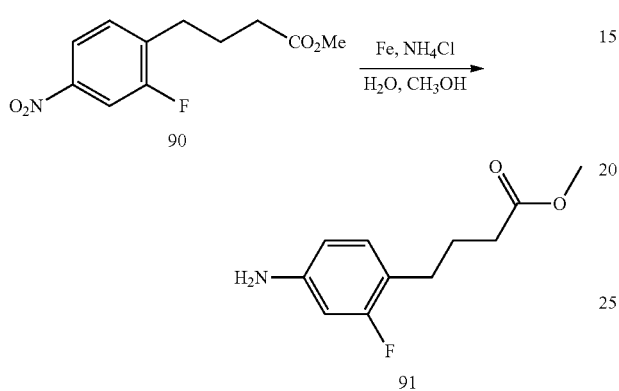

A mixture of compound 90 (1.7 g, 7.0 mmol), NH4Cl (6.3 g, 118 mmol) and Fe (4.22 g, 75 mmol) in water (40 mL) and CH3OH (50 mL) was stirred at 90° C. for 1 h. After cooling, the reaction mixture was filtered and the solid was washed by DCM. The filtrates were separated, the organic layer was washed with brine, dried over Na2SO4 and concentrated to give compound 91 (1.21 g, 81.2%) as a light yellow oil.

1H NMR (400 MHz, CDCl3) δ 6.96~6.92 (m, 1H), 6.41~6.35 (m, 2H), 3.68 (s, 3H), 2.60~2.56 (m, 2H), 2.36~2.32 (m, 2H), 1.93~1.89 (m, 2H)

Preparation of Compound 92

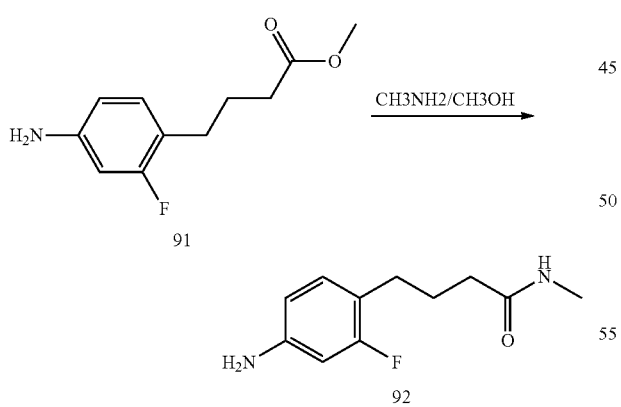

To a solution of compound 91 (812 mg, 3.84 mmol) in CH3NH2/MeOH (70 mL) was stirred at room temperature for 72 h. After removed the most MeOH, the residue was diluted with H2O, and extracted with DCM. The combined organic layers were washed with brine, dried over Na2SO4 and concentrated to give compound 92 (700 mg, 87.3%) as a white solid. The crude product was used directly for the next step without further purification.

1H NMR (400 MHz, CDCl3) δ 6.95~6.93 (m, 1H), 6.42~6.35 (m, 2H), 2.81 (d, J=4.8 Hz, 3H), 2.60~2.56 (m, 2H), 2.20~2.16 (m, 2H), 2.00~1.90 (m, 2H).

Preparation of Compound 93

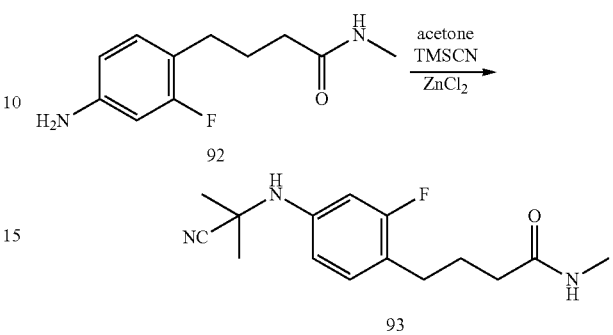

TMSCN (0.15 mL, 1.14 mmol) was added to a mixture of compound 92 (80 mg, 0.38 mmol), acetone (0.50 mL) and ZnCl2 (10 mg) with stirring. The reaction mixture was stirred at RT for 3 h. The mixture was diluted with H2O, and extracted with ethyl acetate. The combined organic layers were washed with brine, dried over Na2SO4 and concentrated to give compound 93 (100 mg, 97.6%) as an oil. The crude product was used directly for the next step without purification.

Synthesis of 4-{4-[3-(4-Cyano-2-fluoro-3-trifluoromethyl-phenyl)-5,5-dimethyl-4-oxo-2-thioxo-imidazolidin-1-yl]-2-fluoro-phenyl}-N-methyl-butyramide Example 44

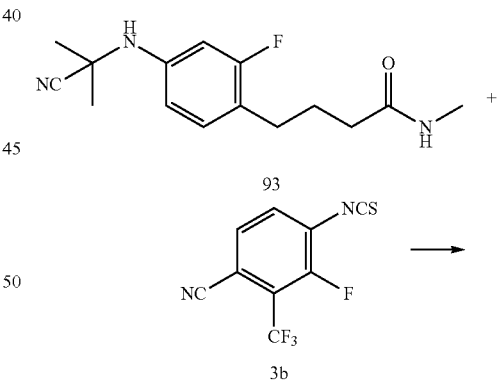

A mixture of compound 93 (50 mg, 0.18 mmol) and 3b (67 mg, 0.27 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 44 (20 mg, 21.8%) as a white solid.

1H NMR (400 MHz, CDCl3) δ 7.84~7.77 (m, 2H), 7.40~7.36 (m, 1H), 7.05~6.99 (m, 2H), 2.82 (d, J=4.4 Hz, 3H), 2.76~2.74 (m, 2H), 2.27~2.23 (m, 2H), 2.05~1.98 (m, 2H), 1.60 (d, J=4.4 Hz, 6H). LCMS (M+H)+: 525.2.

Synthesis of 4-(4-(3-(4-cyano-2-fluoro-5-(trifluoromethyl)phenyl)-5,5-dimethyl-4-oxo-2-thioxoimidazolidin-1-yl)-2-fluorophenyl)-N-methylbutanamide Example 45

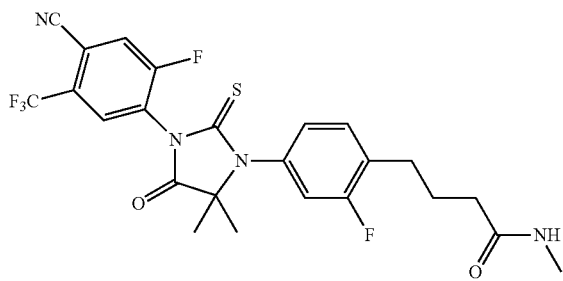

Example 45

EXAMPLE 45 was synthesized via a reaction between 3d and 93 following a manner similar to the synthetic procedure of EXAMPLE 15. EXAMPLE 45 was obtained in 20% yield as a white solid.

1H NMR (400 MHz, CDCl3) δ7.93 (d, 1H, J=6.4 Hz), 7.73 (d, 1H, J=8.3 Hz), 7.35-7.42 (m, 1H), 6.98-7.08 (m, 2H), 5.39 (br s, 1H), 2.82 (d, 3H, J=4.3 Hz), 2.76 (t, 2H, J=7.3 Hz), 2.25 (t, 2H, J=7.3 Hz), 1.97-2.09 (m, 2H), 1.59 (d, 6H, J=5.3 Hz). LCMS (M+H)+: 525.4

Preparation of Compound 94

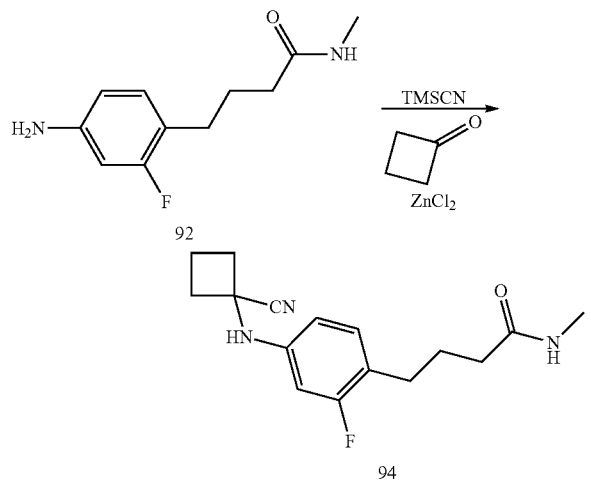

TMSCN (0.27 mL, 2.14 mmol) was added to a mixture of compound 92 (150 mg, 0.71 mmol), cyclobutanone (0.32 mL, 4.28 mmol) and ZnCl2 (20 mg) in 1,4-dioxane (2 mL) with stirring. The reaction mixture was stirred at RT for 3 h. The mixture was diluted with aqNa2SO3, and extracted with ethyl acetate. The combined organic layers were washed with brine, dried over Na2SO4 and concentrated to give compound 94 (200 mg, 96.8%) as an oil. The crude product was used directly for the next step without purification.

Synthesis of 4-{4-[7-(4-Cyano-2-fluoro-3-trifluoromethyl-phenyl)-8-oxo-6-thioxo-5,7-diaza-spiro[3.4]oct-5-yl]-2-fluoro-phenyl}-N-methyl-butyramide Example 46

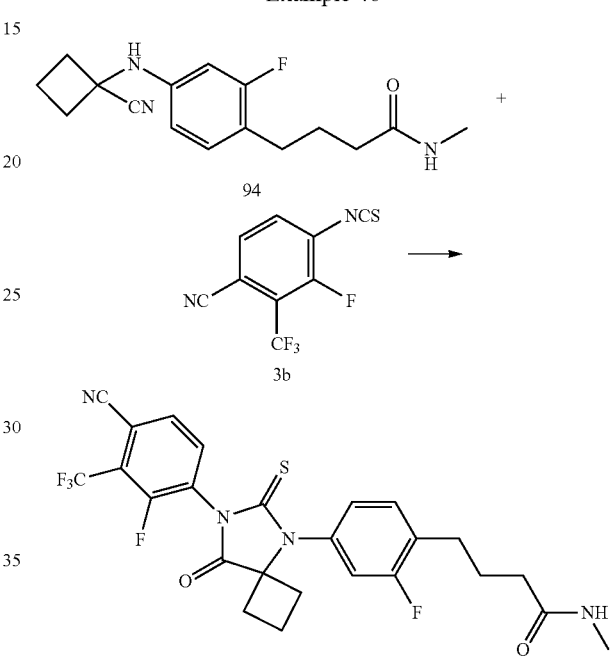

Example 46

A mixture of compound 94 (100 mg, 0.35 mmol) and 3b (127 mg, 0.52 mmol) in DMF (1.0 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 46 (20 mg, 11.8%) as a white solid.

1H NMR (400 MHz, CDCl3) δ 7.83~7.76 (m, 2H), 7.45~7.41 (m, 1H), 7.07~7.02 (m, 2H), 5.45~5.42 (br s, 1H), 2.83 (d, J=3.6 Hz, 3H), 2.80~2.76 (m, 2H), 2.67~2.65 (m, 2H), 2.58~2.50 (m, 2H), 2.28~2.23 (m, 3H), 2.06~2.02 (m, 2H), 1.73~1.69 (m, 1H).

Synthesis of Examples 47-48

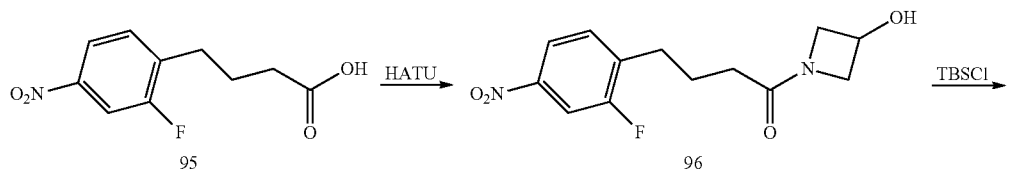

-continued

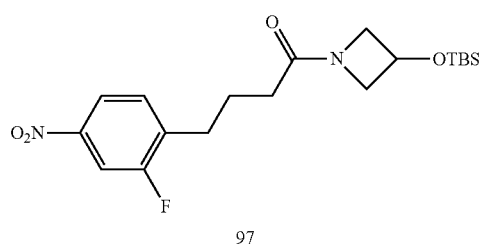
97

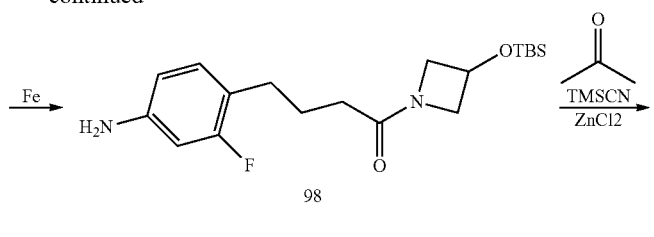
98

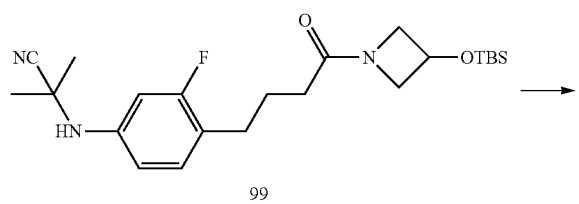
99

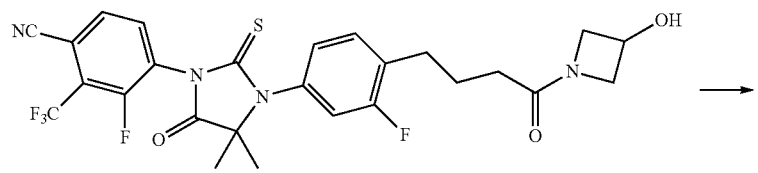
Example 47

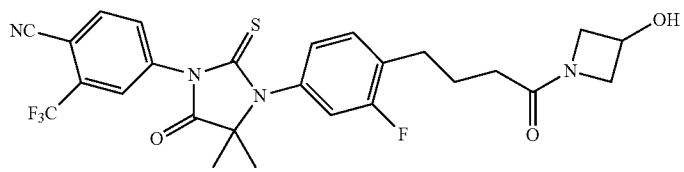
Example 48

Preparation of 4-(2-fluoro-4-nitrophenyl)butanoic acid 95

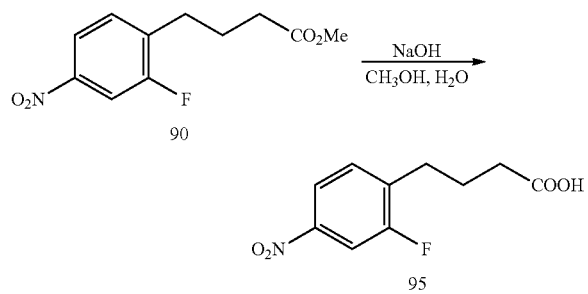

To a solution of compound 90 (511 mg, 2.12 mmol) in MeOH (13 mL) was added a solution of NaOH (2.1 g, 52.5 mmol) in H2O (35 mL). The reaction mixture was stirred at room temperature for 5 h. Methanol was removed in vacuo and the residual aqueous solution was washed with EtOAc (two times), then was acidified to pH=2 with 1N HCl. The aqueous phase was extracted with DCM. The combined organic extract was dried over Na2SO4 and concentrated to afford compound 95 (436 mg, 91%) as a light yellow solid.

Preparation of Compound 96

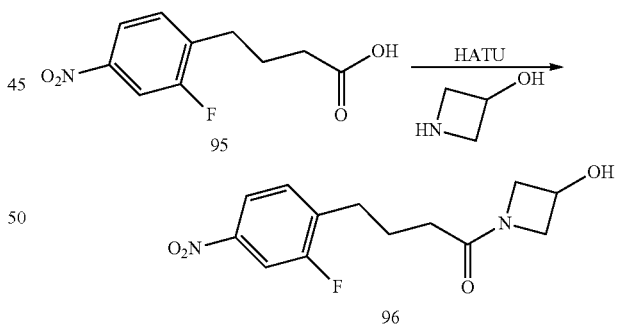

A mixture of compound 95 (350 mg, 1.54 mmol, prepared from 90 through basic hydrolysis) and HATU (878 mg, 2.31 mmol) in DCM (10 mL) was added Et3N (1 mL) at room temperature. After 10 mins, azetidin-3-ol (170 mg, 2.31 mmol) was added. The mixture was stirred at RT for 2 h, diluted with H2O, and extracted with DCM. The combined organic layers were washed with brine, dried over Na2SO4 and concentrated. The residue was purified with silica gel column chromatography to give the title compound 96 (360 mg, 82.6%).

1H NMR (400 MHz, CDCl3) δ 7.98~7.96 (m, 1H), 7.90~7.87 (m, 1H), 7.42~7.38 (m, 1H), 4.69~4.64 (m, 1H), 4.26~4.25 (m, 2H), 3.92~3.87 (m, 2H), 2.78~2.76 (m, 2H), 2.16~2.12 (m, 2H), 2.00~1.93 (m, 2H).

Preparation of Compound 97

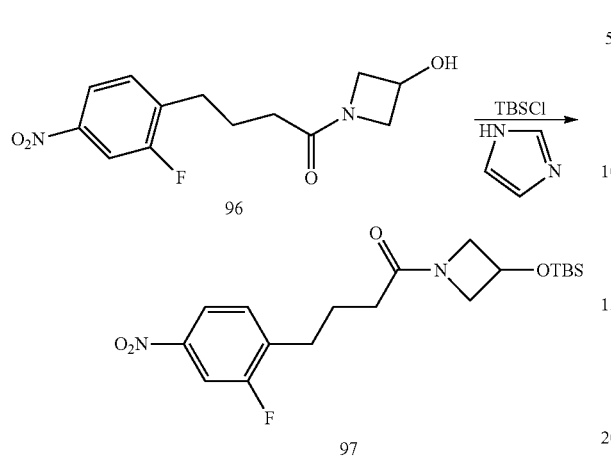

To a stirred solution of compound 96 (100 mg, 0.35 mmol) in DCM (5 mL) was added imidazole (48 mg, 0.70 mmol) and TBSCl (80 mg, 0.51 mmol) at 0° C. After stirred overnight at room temperature, the reaction mixture was washed with water, brine and concentrated in vacuo, the residue 97 (180 mg) was used directly for the next step without further purification.

1H NMR (400 MHz, CDCl3) δ 7.92~7.90 (m, 1H), 7.84~7.81 (m, 1H), 7.36~7.20 (m, 1H), 4.55~4.53 (m, 1H), 4.16~4.12 (m, 2H), 3.80~3.78 (m, 2H), 2.74~2.70 (m, 2H), 2.08~2.04 (m, 2H), 1.94~1.89 (m, 2H), 0.83 (s, 9H), 0.00 (s, 6H).

Preparation of Compound 98

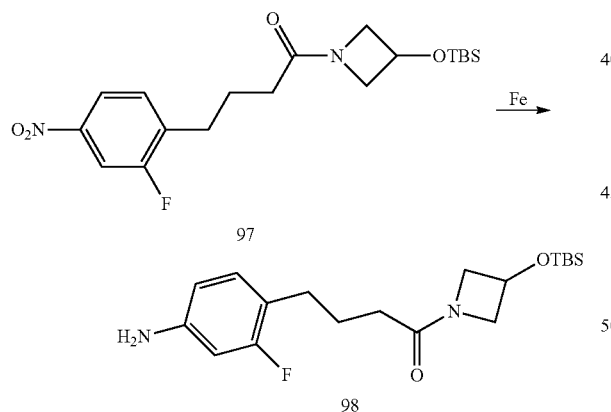

A mixture of compound 97 (180 mg, 0.46 mmol), NH4Cl (437 mg, 8.17 mmol) and Fe (228 mg, 4.09 mmol) in water (8 mL) and CH3OH (10 mL) was stirred at 90° C. for 2 h. After cooling, the reaction mixture was filtered and the solid was washed by DCM. The filtrates were separated, the organic layer was washed with brine, dried over Na2SO4 and concentrated to dryness to give compound 98 (150 mg, 90.1%) as a light yellow oil.

1H NMR (400 MHz, CDCl3) δ 6.90~6.86 (m, 1H), 6.36~6.30 (m, 2H), 4.53~4.50 (m, 1H), 4.16~4.09 (m, 2H), 3.83~3.72 (m, 2H), 2.52~2.48 (m, 2H), 2.03~1.98 (m, 2H), 1.85~1.80 (m, 2H), 0.83 (s, 9H), 0.00 (s, 6H).

Preparation of Compound 99

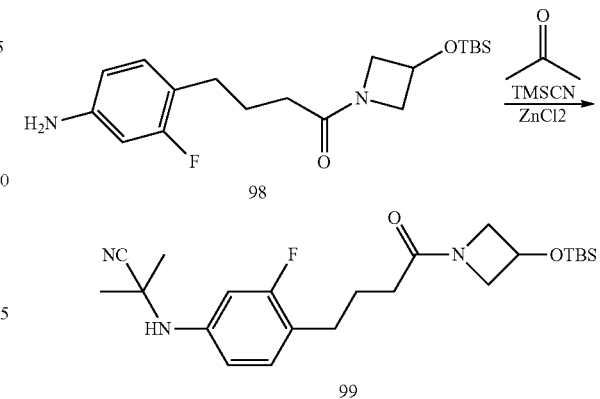

TMSCN (0.15 mL, 1.2 mmol) was added to a mixture of compound 98 (150 mg, 0.4 mmol), acetone (0.20 mL, 2.4 mmol) and ZnCl2 (20 mg) with stirring. The reaction mixture was stirred at RT for 3 h. The mixture was diluted with H2O, and extracted with ethyl acetate. The combined organic layers were washed with brine, dried over Na2SO4 and concentrated to give compound 99 (160 mg, 84.6%). The crude product was used directly for the next step without purification.

Synthesis of 3-Fluoro-4-(3-{3-fluoro-4-[4-(3-hydroxy-azetidin-1-yl)-4-oxo-butyl]-phenyl}-4,4-dimethyl-5-oxo-2-thioxo-imidazolidin-1-yl)-2-trifluoromethyl-benzonitrile Example 47

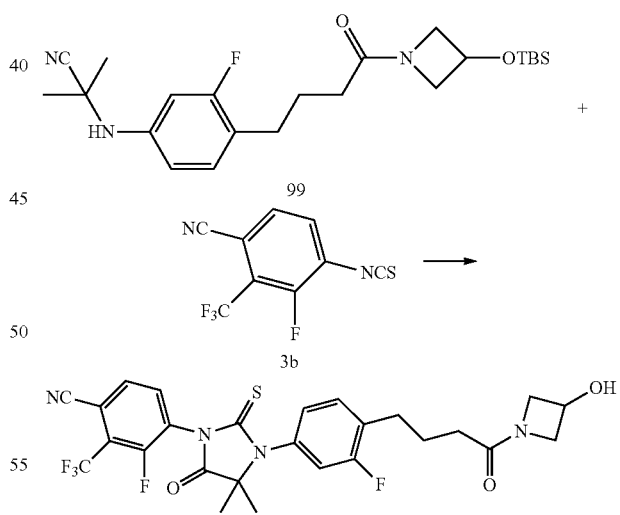

Example 47

A mixture of compound 99 (80 mg, 0.18 mmol) and 3b (68 mg, 0.27 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 47 (18 mg, 17.2%) as a white solid.

1H NMR (400 MHz, CDCl3) δ7.96~7.85 (m, 2H), 7.44~7.36 (m, 1H), 7.05~6.99 (m, 2H), 4.68~4.65 (m, 1H), 4.29~4.24 (m, 2H), 3.91~3.88 (m, 2H), 2.78~2.74 (m, 2H), 2.18~2.15 (m, 2H), 2.04~1.98 (m, 2H), 1.60 (d, J=4.8 Hz, 6H). LCMS (M+H)+: 567.2.

Synthesis of 4-(3-{3-Fluoro-4-[4-(3-hydroxy-azetidin-1-yl)-4-oxo-butyl]-phenyl}-4,4-dimethyl-5-oxo-2-thioxo-imidazolidin-1-yl)-2-trifluoromethyl-benzonitrile Example 48

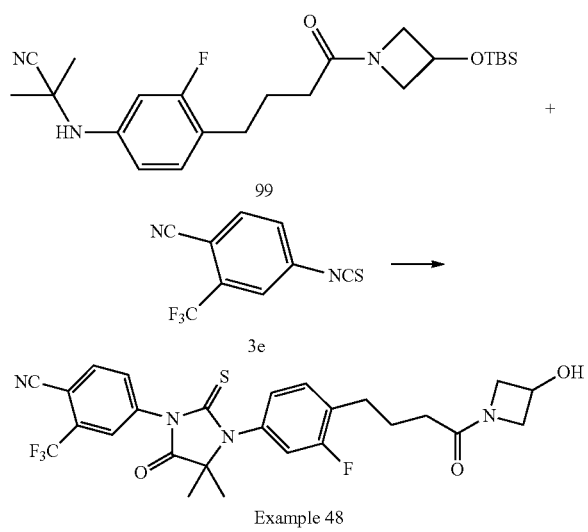

Example 48

A mixture of compound 99 (80 mg, 0.18 mmol) and 3e (63 mg, 0.27 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 48 (18 mg, 17.7%) as a white solid.

1H NMR (400 MHz, CDCl3) δ7.98~~7.95 (m, 2H), 7.84~7.83 (m, 1H), 7.43~7.41 (m, 1H), 7.04~6.98 (m, 2H), 4.67~4.66 (m, 1H), 4.29~4.25 (m, 2H), 3.91~3.88 (m, 2H), 2.78~2.75 (m, 2H), 2.19~2.15 (m, 2H), 2.05~1.98 (m, 2H), 1.60 (d, J=7.6 Hz, 6H).

Synthesis of Example 49, Example 50

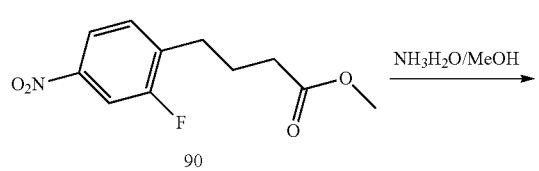

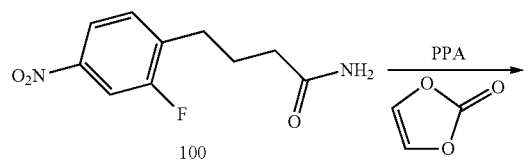

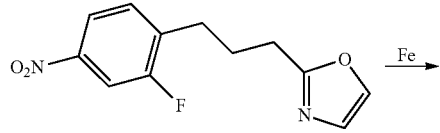

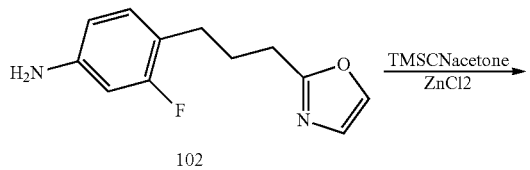

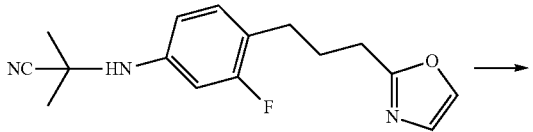

Example 49

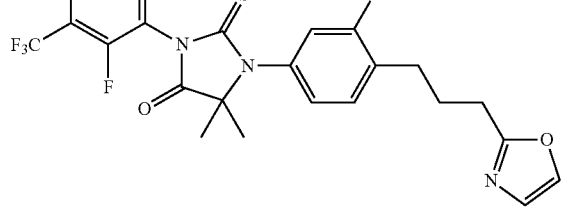

Example 50

Preparation of Compound 100

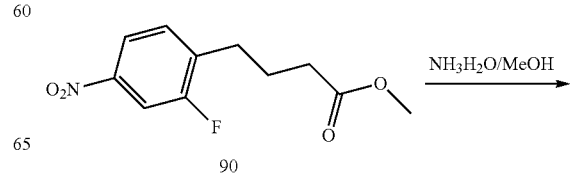

-continued

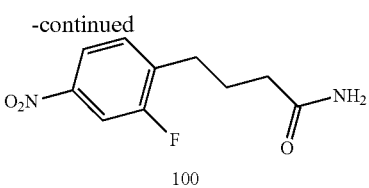

100

To a solution of compound 90 (500 mg, 2.07 mmol) in NH3H2O (20 mL)/MeOH (20 mL) was stirred at room temperature for 48 h. After removed the most MeOH, the residue was diluted with H2O, and extracted with DCM. The combined organic layers were washed with brine, dried over Na2SO4 and concentrated to give compound 100 (400 mg, 83.3%) as a white solid. The crude product was used directly for the next step without further purification.

Preparation of Compound 101

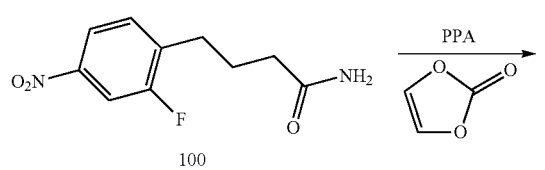

101

A mixture of compound 100 (500 mg, 2.20 mmol) and vinylene carbonate (50 mg, 2.85 mmol) in polyphosphoric acid (5 g) was heated at 160 deg. C. for 3 h. The residue was added to water and extracted with ethyl acetate. The combined organic extracts were washed with water and brine, dried and evaporated. The residue was purified by column chromatography using petroleum ether:ethyl acetate (4:1) to give the title compound 101 (100 mg, 18.1%).

1H NMR (400 MHz, CDCl3) δ 7.98~7.96 (m, 1H), 7.91~7.88 (m, 1H), 7.57 (d, J=0.8 Hz, 1H), 7.41~7.37 (m, 1H), 7.02 (s, 1H), 2.86~2.81 (m, 4H), 2.16~2.12 (m, 2H).

Preparation of Compound 102

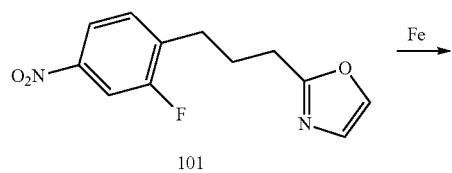

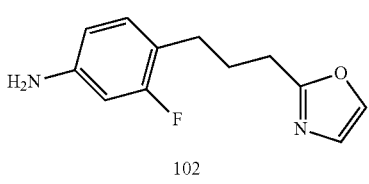

102

A mixture of compound 101 (100 mg, 0.40 mmol), NH4Cl (213 mg, 4.0 mmol) and Fe (133 mg, 2.4 mmol) in water (8 mL) and CH3OH (10 mL) was stirred at 90° C. for 2 h. After cooling, the reaction mixture was filtered and the solid was washed by DCM. The filtrates were separated, the organic layer was washed with brine, dried over Na2SO4 and concentrated to dryness to give compound 102 (150 mg, 90.1%) as a light yellow oil.

Preparation of Compound 103

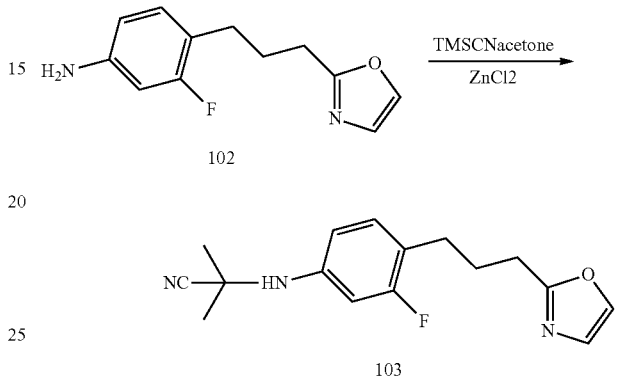

TMSCN (0.15 mL, 1.23 mmol) was added to a mixture of compound 102 (90 mg, 0.41 mmol), acetone (0.5 mL) and ZnCl2 (10 mg) with stirring. The reaction mixture was stirred at RT for 3 h. The mixture was diluted with H2O, and extracted with ethyl acetate. The combined organic layers were washed with brine, dried over Na2SO4 and concentrated to give compound 103 (90 mg, 76.6%) as a yellow oil. The crude product was used directly for the next step without purification.

Synthesis of 3-Fluoro-4-{3-[3-fluoro-4-(3-oxazol-2-yl-propyl)-phenyl]-4,4-dimethyl-5-oxo-2-thioxo-imidazolidin-1-yl}-2-trifluoromethyl-benzonitrile Example 49

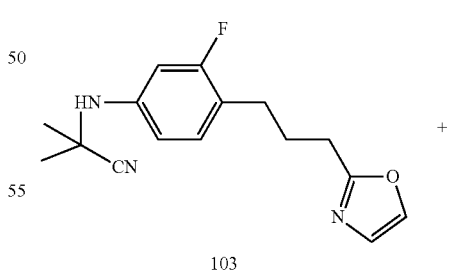

103

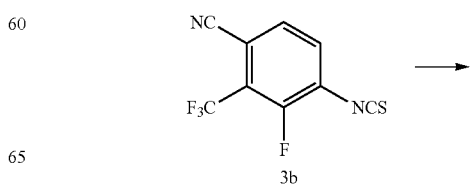

3b

-continued

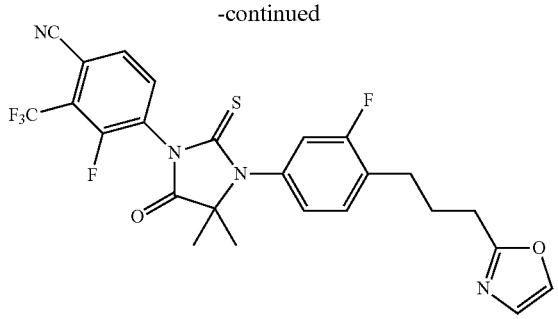

Example 49

A mixture of compound 103 (60 mg, 0.20 mmol) and 3b (77 mg, 0.30 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 49 (30 mg, 26.9%) as a white solid.

1H NMR (400 MHz, CDCl3) δ 7.83~7.76 (m, 2H), 7.58 (s, 1H), 7.40~7.25 (m, 1H), 7.05~7.00 (m, 3H), 2.90~2.86 (m, 2H), 2.86~2.79 (m, 2H), 2.21~2.13 (m, 2H), 1.59 (d, J=4.8 Hz, 6H). MS (M+H)+: 536.4

Synthesis of 4-{3-[3-Fluoro-4-(3-oxazol-2-yl-propyl)-phenyl]-4,4-dimethyl-5-oxo-2-thioxo-imidazolidin-1-yl}-2-trifluoromethyl-benzonitrile Example 50

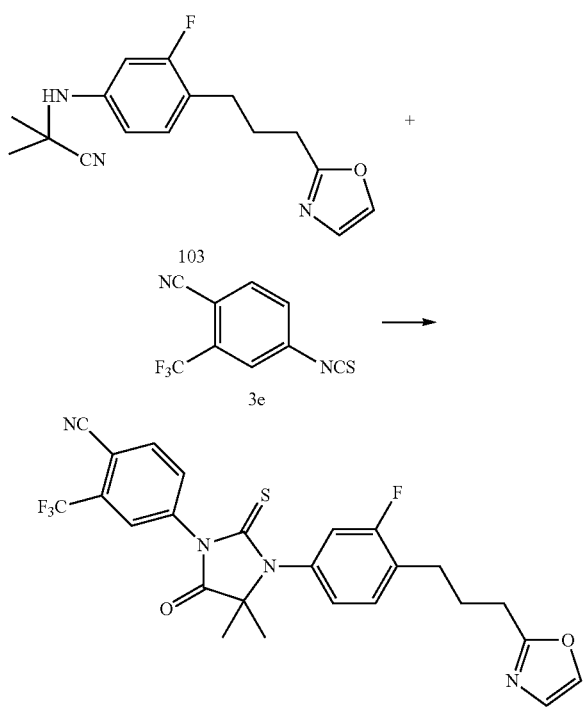

Example 50

A mixture of compound 103 (40 mg, 0.14 mmol) and 3e (47 mg, 0.20 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 50 (10 mg, 13.9%) as a white solid.

1H NMR (400 MHz, CDCl3) δ 7.98~7.95 (m, 2H), 7.84~7.81 (m, 1H), 7.60 (s, 1H), 7.41~7.37 (m, 1H), 7.08~6.99 (m, 3H), 2.95~2.91 (m, 2H), 2.84~2.78 (m, 2H), 2.21~2.16 (m, 2H), 1.59 (d, J=4.8 Hz, 6H). LCMS (M+H)+: 516.8.

Synthesis of Example 51 and Example 52

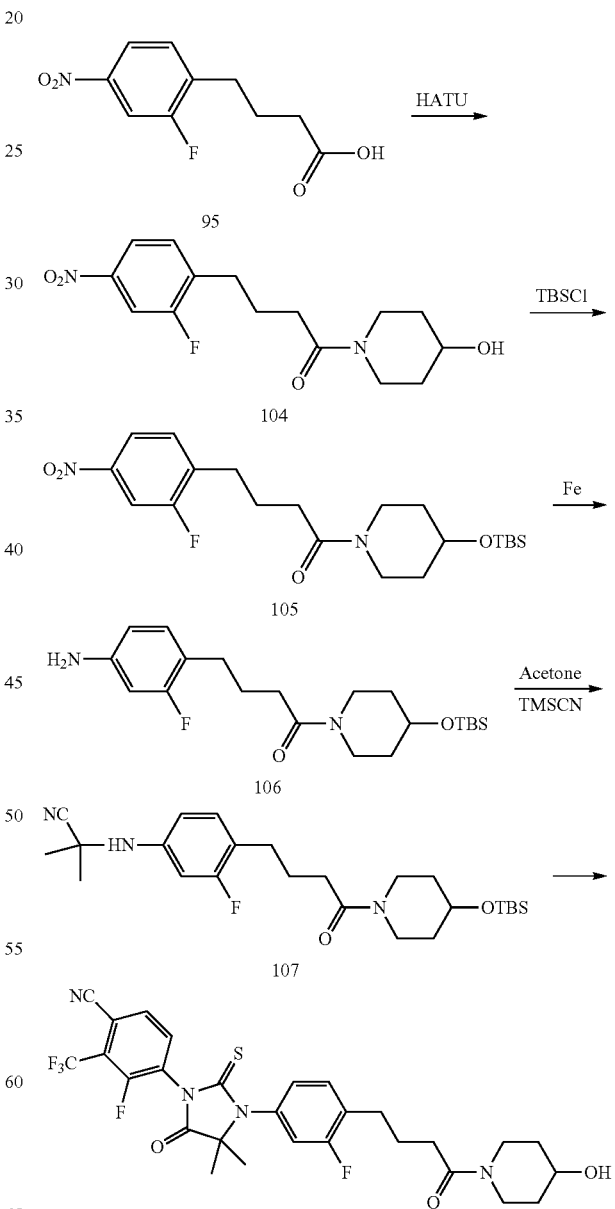

Example 51

Example 52

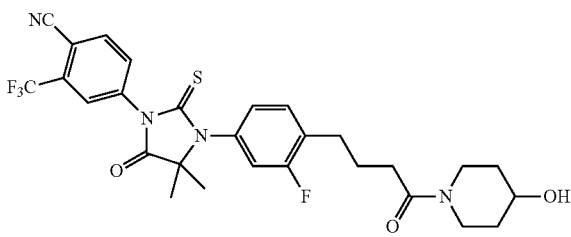

Preparation of Compound 104

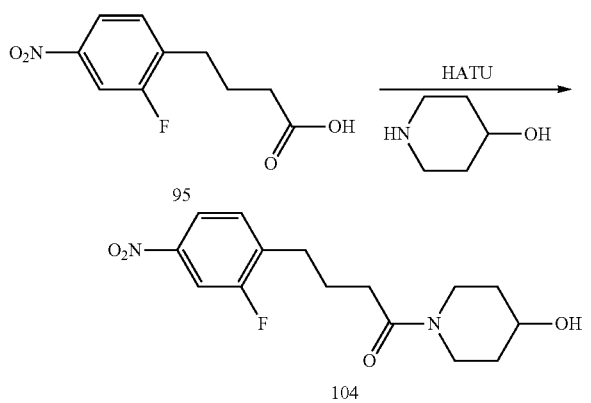

A mixture of compound 95 (150 mg, 0.66 mmol, prepared from 90 through basic hydrolysis) and HATU (376 mg, 0.99 mmol) in DCM (10 mL) was added Et3N (0.5 mL) at room temperature. After 10 mins, piperidin-4-ol (100 mg, 0.99 mmol) was added. The mixture was stirred at RT for 2 h, diluted with H2O, and extracted with DCM. The combined organic layers were washed with brine, dried over Na2SO4 and concentrated. The residue was purified with silica gel column chromatography to give the title compound 104 (200 mg, 97.6%).

1H NMR (400 MHz, CDCl3) δ 7.99~7.96 (m, 1H), 7.90~7.88 (m, 1H), 7.43~7.39 (m, 1H), 3.97~3.93 (m, 2H), 3.70~3.68 (m, 1H), 3.25~3.20 (m, 2H), 2.85~2.79 (m, 2H), 2.41~2.38 (m, 2H), 2.07~1.95 (m, 2H), 1.91~1.85 (m, 2H), 1.53~1.49 (m, 2H).

Preparation of Compound 105

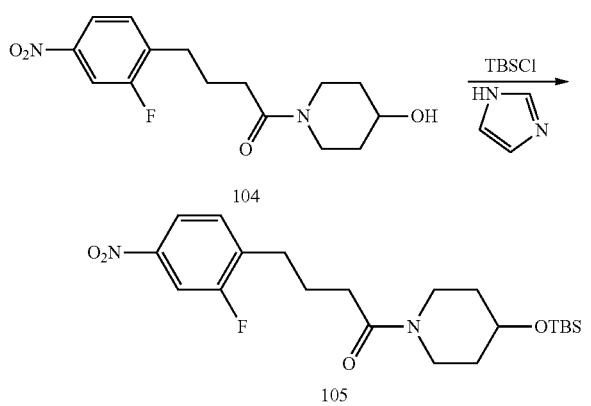

To a stirred solution of compound 104 (200 mg, 0.64 mmol) in DCM (5 mL) was added imidazole (88 mg, 1.29 mmol) and TBSCl (145 mg, 0.97 mmol) at 0° C. After stirred overnight at room temperature, the reaction mixture was washed with water, brine and concentrated in vacuo, the residue (105, 200 mg, 73.1%) was used directly for the next step without further purification.

1H NMR (400 MHz, CDCl3) δ 7.92~7.89 (m, 1H), 7.84~7.81 (m, 1H), 7.37~7.33 (m, 1H), 3.92~3.87 (m, 1H), 3.64~3.59 (m, 1H), 3.55~3.49 (m, 2H), 3.24~3.18 (m, 1H), 2.76~2.72 (m, 2H), 2.32~2.28 (m, 2H), 1.97~1.89 (m, 2H), 1.67~1.60 (m, 2H), 1.48~1.43 (m, 2H), 0.83 (s, 9H), 0.00 (s, 6H).

Preparation of Compound 106

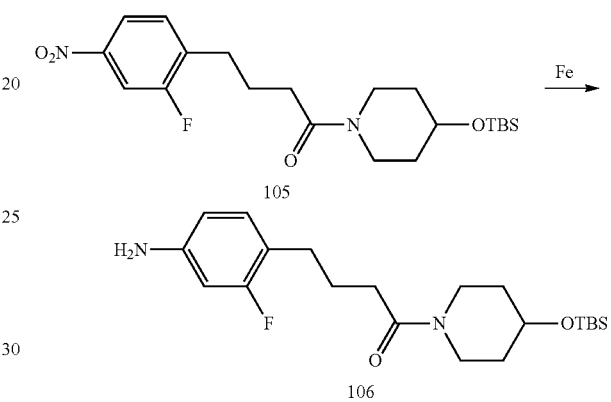

A mixture of the compound 105 (200 mg, 0.81 mmol), NH4Cl (270 mg, 5.04 mmol) and Fe (169 mg, 3.02 mmol) in water (8 mL) and CH3OH (10 mL) was stirred at 90° C. for 2 h. After cooling, the reaction mixture was filtered and the solid was washed by DCM. The filtrates were separated, the organic layer was washed with brine, dried over Na2SO4 and concentrated to dryness to give compound 106 (180 mg, 99.1%) as a light yellow oil.

Preparation of Compound 107

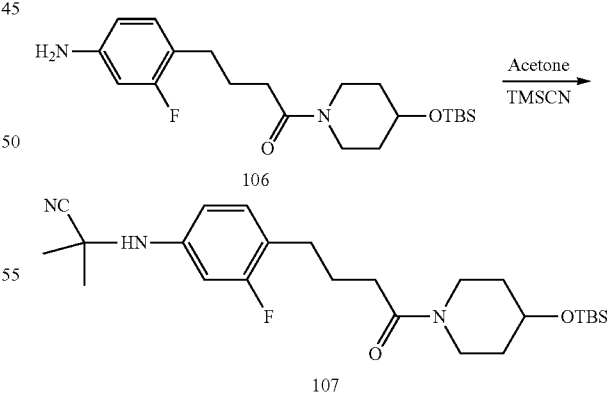

TMSCN (0.17 mL, 1.4 mmol) was added to a mixture of the compound 106 (180 mg, 0.45 mmol), acetone (0.20 mL, 2.8 mmol) and ZnCl2 (20 mg) with stirring. The reaction mixture was stirred at RT for 3 h. The mixture was diluted with H2O, and extracted with ethyl acetate. The combined organic layers were washed with brine, dried over Na2SO4 and concentrated to give compound 107 (200 mg, 95.6%). The crude product was used directly for the next step without purification.

Synthesis of 3-Fluoro-4-(3-{3-fluoro-4-[4-(4-hydroxy-piperidin-1-yl)-4-oxo-butyl]-phenyl}-4,4-dimethyl-5-oxo-2-thioxo-imidazolidin-1-yl)-2-trifluoromethyl-benzonitrile Example 51

Synthesis of 4-(3-{3-Fluoro-4-[4-(4-hydroxy-piperidin-1-yl)-4-oxo-butyl]-phenyl}-4,4-dimethyl-5-oxo-2-thioxo-imidazolidin-1-yl)-2-trifluoromethyl-benzonitrile Example 52

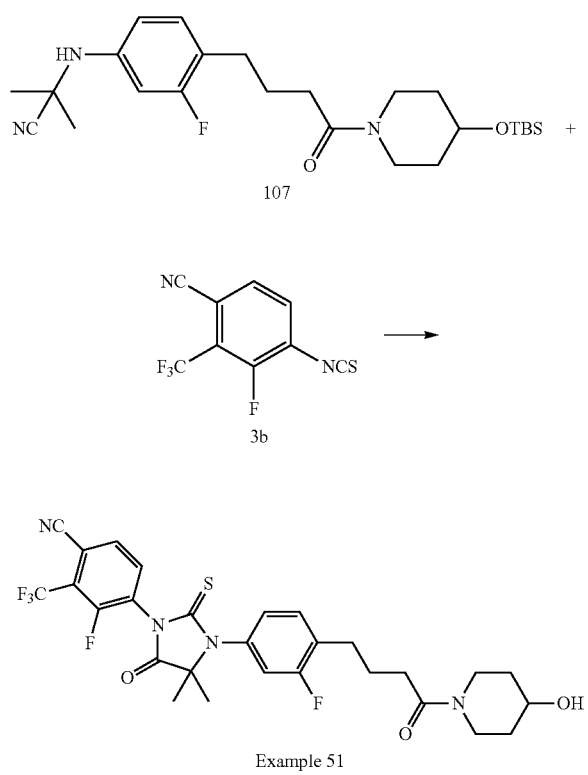

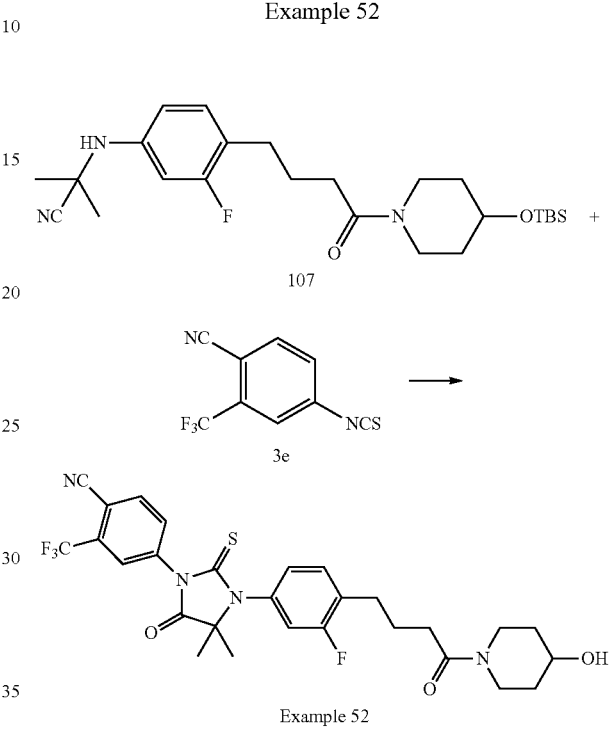

A mixture of compound 107 (100 mg, 0.22 mmol) and 3b (79 mg, 0.33 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo. The residue was purified with Prep-TLC to give the title compound EXAMPLE 51 (30 mg, 23.2%) as a white solid.

1H NMR (400 MHz, CDCl3) δ 7.82~7.75 (m, 2H), 7.41~7.37 (m, 1H), 7.05~6.99 (m, 2H), 3.95~3.90 (m, 1H), 3.24~3.17 (m, 2H), 2.80~2.76 (m, 2H), 2.43~2.39 (m, 2H), 2.03~1.99 (m, 2H), 1.90~1.86 (m, 2H), 1.60 (d, J=4.8 Hz, 6H), 1.56~1.53 (m, 2H), 1.49~1.46 (m, 2H). LCMS (M+H)+: 595.3.

A mixture of compound 107 (100 mg, 0.22 mmol) and 3e (74 mg, 0.33 mol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo. The residue was purified with Prep-TLC to give the title compound EXAMPLE 52 (30 mg, 24.0%) as a white solid.

1H NMR (400 MHz, CDCl3) δ7.97~7.95 (m, 2H), 7.83~7.81 (m, 1H), 7.42~7.37 (m, 1H), 7.04~6.98 (m, 2H), 3.97~3.91 (m, 1H), 3.24~3.19 (m, 2H), 2.80~2.77 (m, 2H), 2.43~2.40 (m, 2H), 2.05~2.00 (m, 2H), 1.91~1.86 (m, 2H), 1.59 (s, 6H), 1.53~1.49 (m, 2H), 1.49~1.46 (m, 2H). LCMS (M+H)+: 577.3.

Synthesis of Examples 53-54

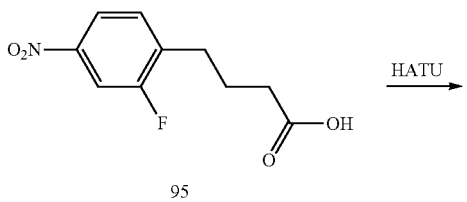

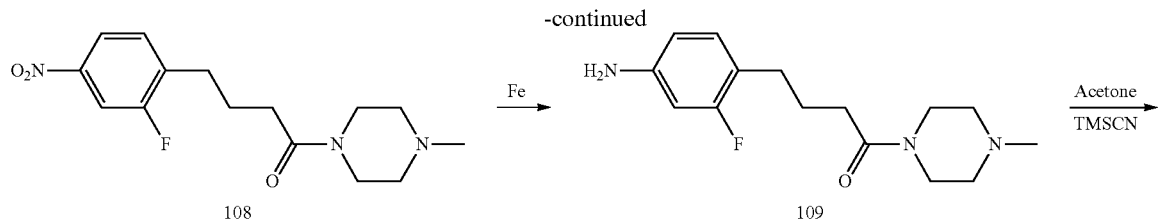

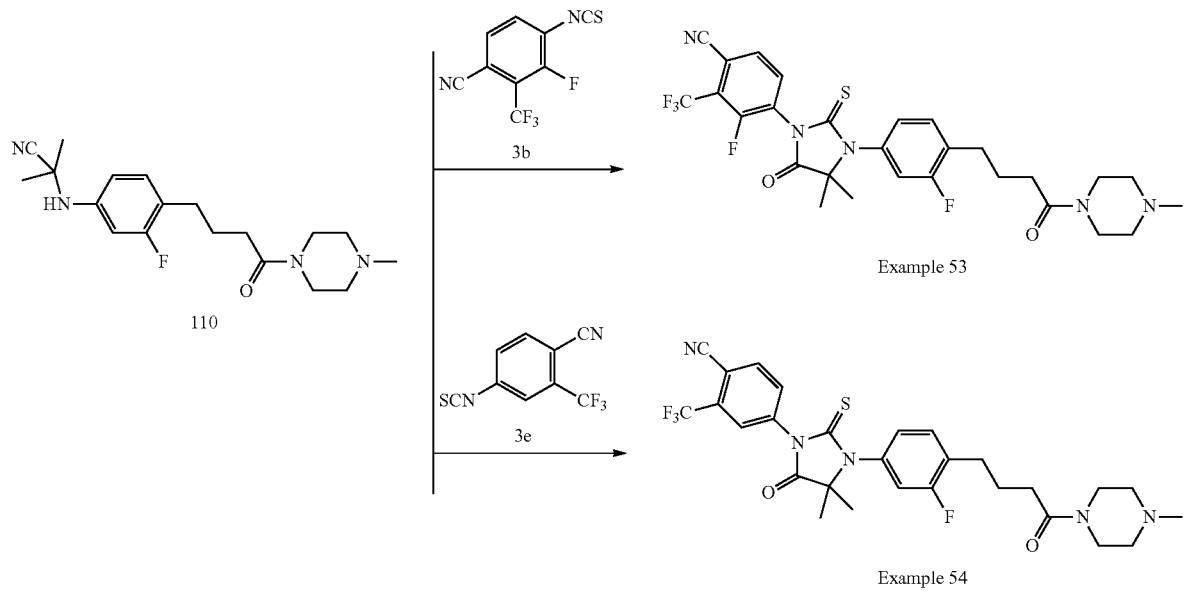

Preparation of Compound 108

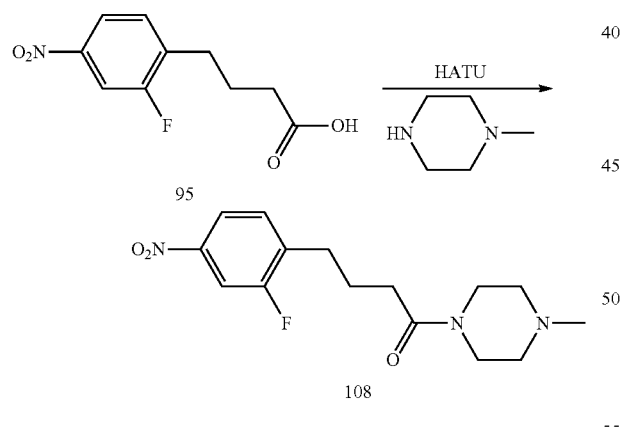

A mixture of compound 95 (250 mg, 1.10 mmol, prepared from 90 through basic hydrolysis) and HATU (327 mg, 1.65 mmol) in DCM (10 mL) was added Et3N (0.5 mL) at room temperature. After 10 min, 1-methylpiperazine (165 mg, 1.65 mmol) was added. The mixture was stirred at RT for 2 h, diluted with H2O, and extracted with DCM. The combined organic layers were washed with brine, dried over Na2SO4 and concentrated. The residue was purified with silica gel column chromatography to give the title compound 108 (250 mg, 73.4%).

1H NMR (400 MHz, CDCl3) δ 7.98~7.96 (m, 1H), 7.90~7.88 (m, 1H), 7.43~7.39 (m, 1H), 3.65~3.63 (m, 2H), 3.46~3.43 (m, 2H), 2.83~2.79 (m, 2H), 2.38~2.32 (m, 6H), 2.31~12.19 (m, 3H), 2.01~1.93 (m, 2H).

Preparation of Compound 109

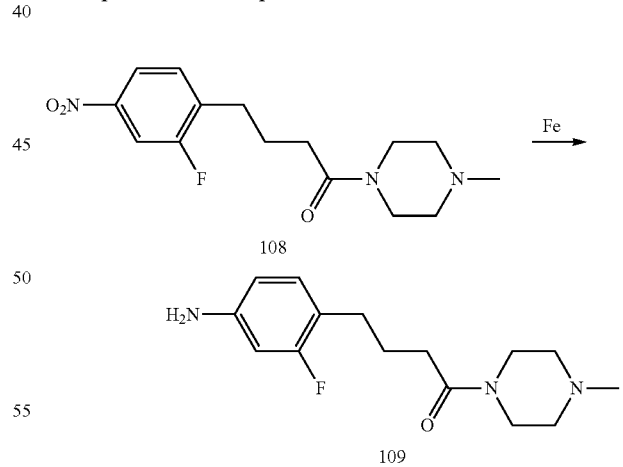

A mixture of compound 108 (250 mg, 0.84 mmol), NH4Cl (207 mg, 3.88 mmol) and Fe (270 mg, 4.85 mmol) in water (15 mL) and CH3OH (20 mL) was stirred at 90° C. for 2 h. After cooling, the reaction mixture was filtered and the solid was washed by DCM. The filtrates were separated, the organic layer was washed with brine, dried over Na2SO4 and concentrated to dryness to give compound 109 (150 mg, 66.1%) as a light yellow oil.

Preparation of Compound 110

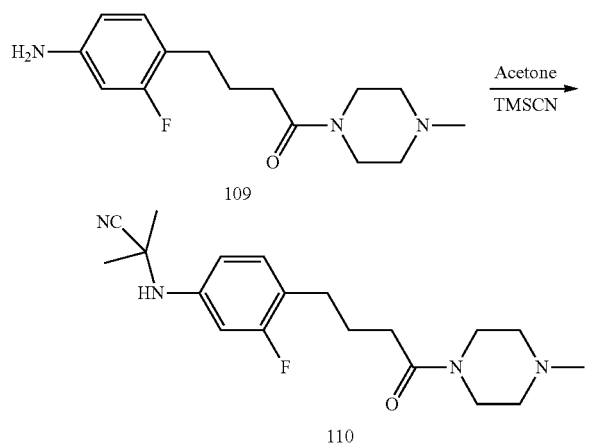

TMSCN (0.21 mL, 1.61 mmol) was added to a mixture of compound 109 (150 mg, 0.54 mmol), acetone (0.24 mL, 3.22 mmol) and ZnCl2 (20 mg) with stirring. The reaction mixture was stirred at RT for 3 h. The mixture was diluted with H2O, and extracted with ethyl acetate. The combined organic layers were washed with brine, dried over Na2SO4 and concentrated to give compound 110 (150 mg, 80.6%). The crude product was used directly for the next step without purification.

Synthesis of 3-Fluoro-4-(3-{3-fluoro-4-[4-(4-methyl-piperazin-1-yl)-4-oxo-butyl]-phenyl}-4,4-dimethyl-5-oxo-2-thioxo-imidazolidin-1-yl)-2-trifluoromethyl-benzonitrile Example 53

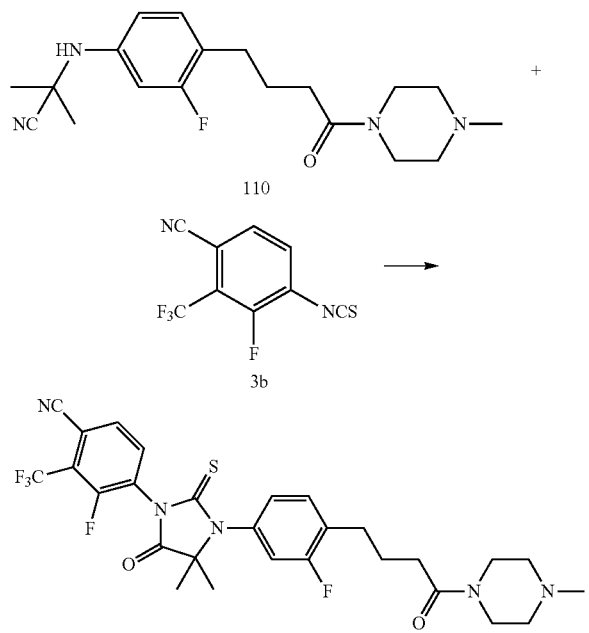

A mixture of compound 110 (100 mg, 0.29 mmol) and 3b (106 mg, 0.43 mmol) in DMF (1.0 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo. The residue was purified with Prep-TLC to give the title compound EXAMPLE 53 (14 mg, 8.2%) as a white solid.

1H NMR (400 MHz, CDCl3) δ7.80~7.78 (m, 2H), 7.41~7.25 (m, 1H), 7.06~6.99 (m, 2H), 3.71~3.68 (m, 2H), 3.54~3.52 (m, 2H), 2.79~2.75 (m, 2H), 2.49~2.41 (m, 4H), 2.39~2.37 (m, 2H), 2.36~2.31 (m, 3H), 2.03~1.99 (m, 2H), 1.60 (d, J=4.8 Hz, 6H). LCMS (M+H)+: 594.3.

Synthesis of 4-(3-{3-Fluoro-4-[4-(4-methyl-piperazin-1-yl)-4-oxo-butyl]-phenyl}-4,4-dimethyl-5-oxo-2-thioxo-imidazolidin-1-yl)-2-trifluoromethyl-benzonitrile Example 54

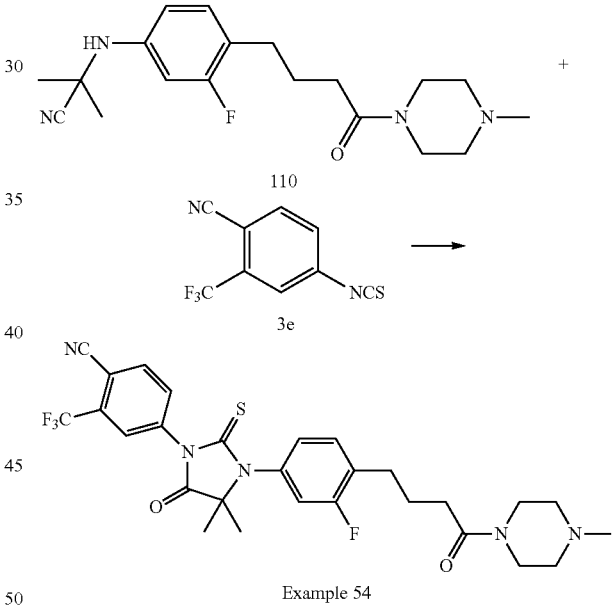

A mixture of compound 110 (40 mg, 0.11 mmol) and 3e (40 mg, 0.17 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo. The residue was purified with Prep-TLC to give the title compound EXAMPLE 54 (7 mg, 10.5%) as a white solid.

1H NMR (400 MHz, CDCl3) δ7.98~7.96 (m, 2H), 7.84~7.81 (m, 1H), 7.41~7.37 (m, 1H), 7.04~6.99 (m, 2H), 3.67 (s, 2H), 3.49 (s, 2H), 2.79~2.76 (m, 2H), 2.43~2.38 (m, 6H), 2.33 (s, 3H), 2.16~2.01 (m, 2H), 1.59 (d, J=4.8 Hz, 6H). LCMS (M+H)+: 576.3.

Synthesis of Example 55
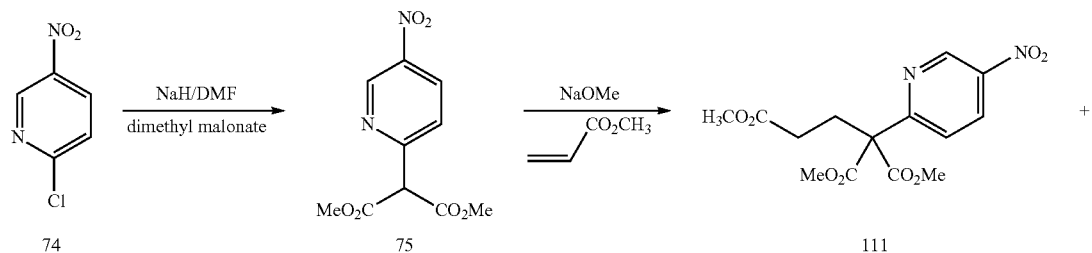
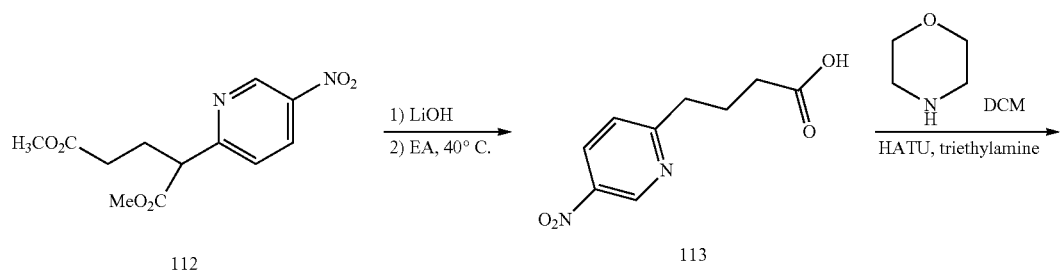
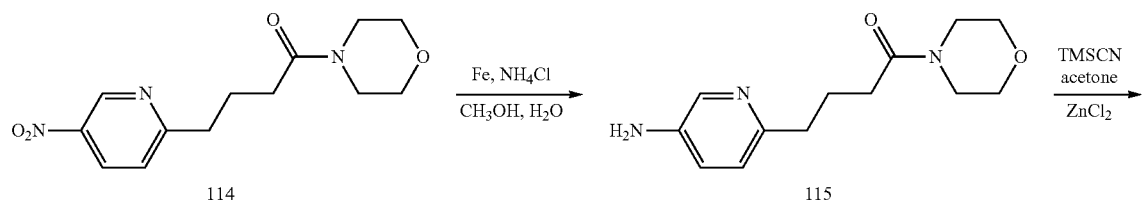
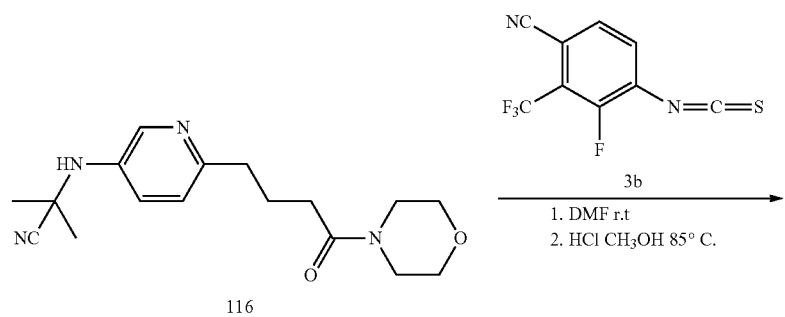
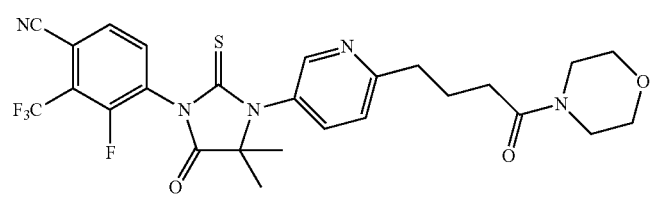
Example 55

Preparation of Compound 111

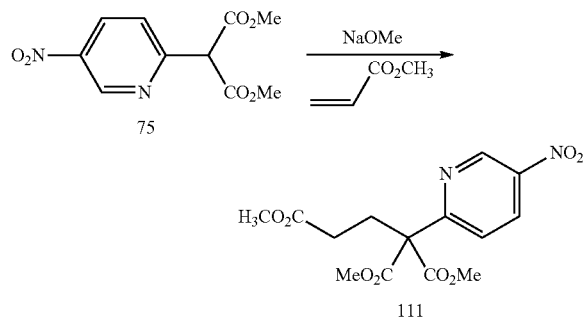

To a solution of compound 75 (20.0 g, 78.7 mmol) and methyl acrylate (68.0 mL, 629.6 mmol) in absolute CH3OH (200 mL) was added a catalytic amount of CH3ONa (850 mg, 15.7 mmol) at RT with stirring under N2. The mixture was stirred at RT for overnight under N2. The mixture was diluted with aqNH4Cl, and extracted with DCM. The combined organic layers were washed with brine, dried over Na2SO4, concentrated to give a mixture of compound 111 and compound 112 (24.3 g). The crude product was used directly for the next step without further purification.

Preparation of Compound 113

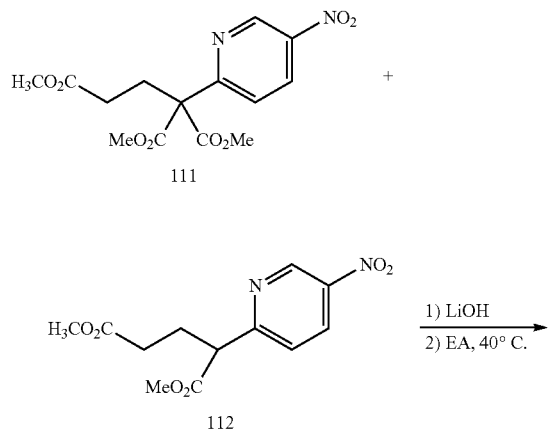

A mixture of compound 111 and compound 112 (24.3 g) was dissolved in MeOH (300 mL) and H2O (100 mL), and then LiOH (10.2 g, 0.41 mol) was added. The mixture was stirred at RT for 2 h. After concentrated, the residue was dissolved in H2O, 1 N HCl was added until pH reached 3, and the mixture was extracted with EA. The organic layer was washed with brine, dried over Na2SO4 and concentrated to provide the crude product. The solution of crude product in EA was stirred at 40° C. for overnight and removed the EA to give the compound 113 (16 g). It was used for the next step without further purification.

1H NMR (400 MHz, CDCl3) δ 9.38 (d, J=6.8 Hz, 1H), 8.45-8.42 (m, 1H), 7.40 (d, J=8.4 Hz, 1H), 3.04 (t, J=7.6 Hz, 2H), 2.47 (t, J=7.2 Hz, 2H), 2.20-2.12 (m, 2H).

Preparation of 114

To a mixture of compound 113 (525 mg, 2.50 mmol), morpholine (325 mg, 2.75 mmol) and triethylamine (1.05 mL) in DCM (30 mL) was added HATU (1.41 g, 3.75 mmol) at room temperature. The reaction mixture was stirred at room temperature for 5 h. Then the mixture was diluted with DCM, washed with 2N HCl, H2O, 5% NaHCO3, and then H2O. The organic layer was dried over Na2SO4, filtered, and concentrated in vacuo to give compound 114 (660 mg, 94.6%) as an oil.

Preparation of 115

A mixture of the compound 114 (660 mg, 2.36 mmol), NH4Cl (1.26 g, 14.2 mmol) and Iron Powder (791 mg, 23.6 mmol) in water (10 mL) and CH3OH (10 mL) was stirred at 90° C. for 1 h. After cooling, the reaction mixture was filtered and the solid was washed by DCM. The filtrates were separated, the organic layer was washed with brine, dried over Na2SO4 and concentrated to dryness to give compound 115 (435 mg, 73.8%) as a light yellow oil.

Preparation of 116

Compound 116 was prepared from 115 in a manner similar to the synthesis of compound 110. The crude product was carried on to the next step without further purification.

Synthesis of 4-{4,4-Dimethyl-3-[6-(4-morpholin-4-yl-4-oxo-butyl)-pyridin-3-yl]-5-oxo-2-thioxo-imidazolidin-1-yl}-3-fluoro-2-trifluoromethyl-benzonitrile Example 55

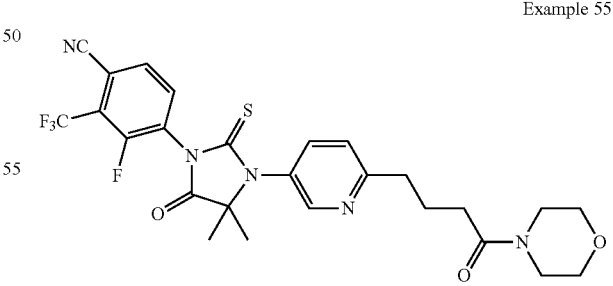

Example 55

EXAMPLE 55 was synthesized via a reaction between 3b and 116 following a manner similar to the synthetic procedure of EXAMPLE 15. EXAMPLE 55 was obtained in 27.4% yield as a white solid.

1H NMR (400 MHz, CDCl3) δ 8.52~8.50 (br s, 1H), 7.83~7.77 (m, 2H), 7.66~7.64 (m, 1H), 7.46~7.43 (br s, 1H), 3.72~3.67 (m, 6H), 3.48~3.45 (m, 2H), 3.04~2.96 (m, 2H), 2.45~2.43 (m, 2H), 2.18~2.12 (m, 2H), 1.61 (d, J=2.8 Hz, 6H).

Synthesis of 4-{4,4-Dimethyl-3-[6-(4-morpholin-4-yl-4-oxo-butyl)-pyridin-3-yl]-5-oxo-2-thioxo-imidazolidin-1-yl}-2-trifluoromethyl-benzonitrile Example 56

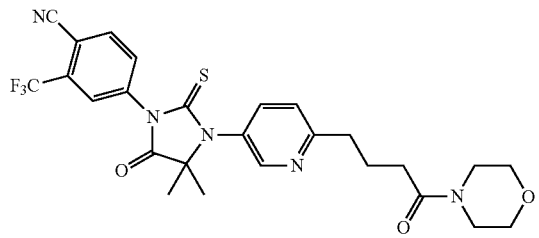

Example 56

EXAMPLE 56 was synthesized via a reaction between 3e and 116 following a manner similar to the synthetic procedure of EXAMPLE 15. EXAMPLE 56 was obtained in 14.9% yield as a white solid.

1H NMR (400 MHz, CDCl3) δ 8.54~8.48 (br s, 1H), 7.99~7.96 (m, 2H), 7.85~7.82 (m, 1H), 7.62~7.60 (m, 1H), 7.50~7.38 (br s, 1H), 3.67~3.62 (m, 6H), 3.48~3.40 (m, 2H), 2.99~2.96 (m, 2H), 2.46~2.43 (m, 2H), 2.18~2.12 (m, 2H), 1.60 (s, 6H).

Synthesis of 4-{5-[3-(4-Cyano-2-fluoro-3-trifluoromethyl-phenyl)-5,5-dimethyl-4-oxo-2-thioxo-imidazolidin-1-yl]-pyridin-2-yl}-N-methyl-butyramide Example 57

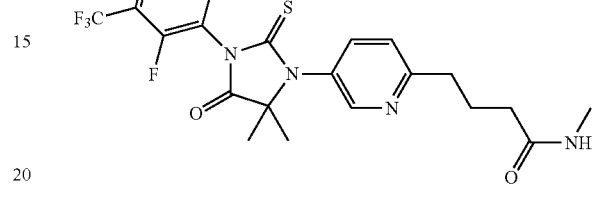

Example 57

EXAMPLE 57 was synthesized through a route similar to the synthetic route to EXAMPLE 55. In the reaction step converting 113 to 114, methylamine instead of morpholine was used.

1H NMR (400 MHz, CDCl3) δ 8.53~8.51 (br s, 1H), 7.83~7.79 (m, 2H), 7.68~7.66 (m, 1H), 7.46~7.44 (m, 1H), 5.57~5.55 (br s, 1H), 3.01~2.97 (m, 2H), 2.82~2.81 (m, 2H), 2.32~2.29 (m, 2H), 2.16 (s, 3H), 1.61 (d, J=2.4 Hz, 6H).

Synthesis of Example 58

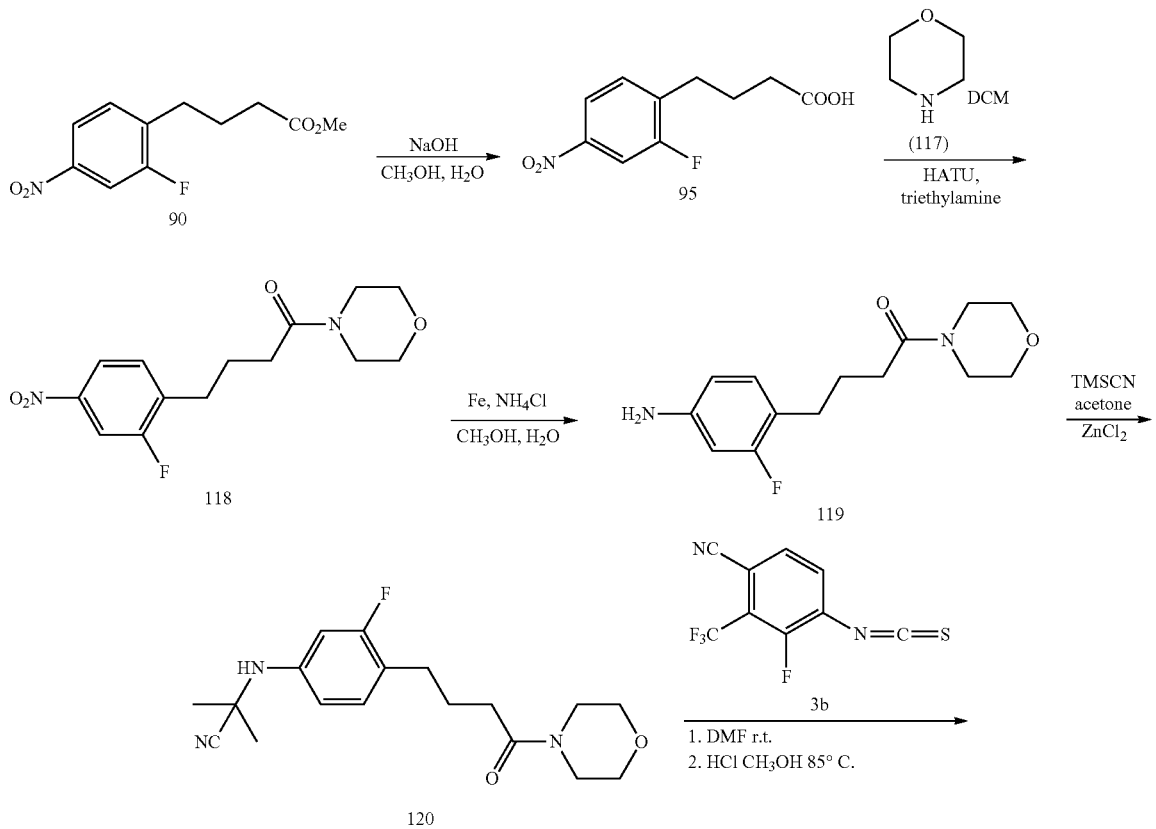

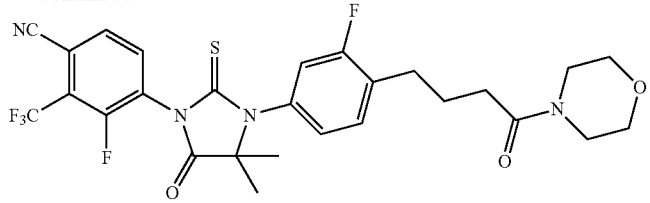

Example 58

Preparation of Compound 118.

To a mixture of compound 95 (436 mg, 1.92 mmol), morpholine (117, 250 mg, 2.88 mmol) and triethylamine (568 mg, 5.76 mmol) in DCM (20 mL) was added HATU (1.6 g, 2.88 mmol) at room temperature. The reaction mixture was stirred at room temperature for 5 h. Then the mixture was diluted with DCM, washed with 2N HCl, H2O, 5% NaHCO3, and then H2O. The organic layer was dried over Na2SO4, filtered, and concentrated in vacuo to give compound 118 (560 mg, 99%) as an oil.

Preparation of Compound 119.

A mixture of compound 118 (550 mg, 1.86 mmol), NH4Cl (1.48 g, 27.7 mmol) and Iron Powder (1.01 g, 18.0 mmol) in water (20 mL) and CH3OH (20 mL) was stirred at 90° C. for 1 h. After cooling, the reaction mixture was filtered and the solid was washed by DCM. The filtrates were separated, the organic layer was washed with brine, dried over Na2SO4 and concentrated to dryness to give compound 119 (480 mg, 97%) as a light yellow oil.

Preparation of 120

Compound 120 was prepared from 119 in a manner similar to the synthesis of compound 110. The crude product was carried on to the next step without further purification.

Synthesis of 3-fluoro-4-(3-(3-fluoro-4-(4-morpholino-4-oxobutyl)phenyl)-4,4-dimethyl-5-oxo-2-thioxoimidazolidin-1-yl)-2-(trifluoromethyl)benzonitrile Example 58

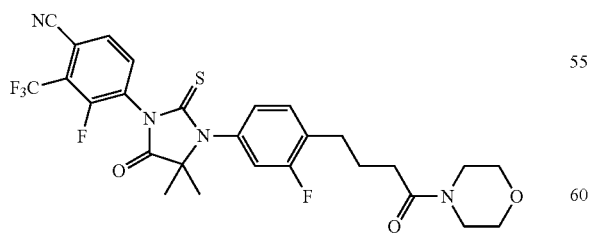

EXAMPLE 58 was synthesized via a reaction between 3b and 120 following a manner similar to the synthetic procedure of EXAMPLE 3. EXAMPLE 58 was obtained in 15% yield as a white solid.

1H NMR (400 MHz, CDCl3) δ 7.78-7.86 (m, 2H), 7.39-7.45 (m, 1H), 77.01-7.10 (m, 2H), 3.62-3.72 (m, 6H), 3.44-3.48 (m, 2H), 2.81 (t, 2H, J=7.6 Hz), 2.42 (t, 2H, J=7.4 Hz), 2.00~2.10 (m, 2H), 1.61 (d, 6H, J=4.8 Hz). LCMS (M+H)+: 581.2.

Synthesis of Example 59

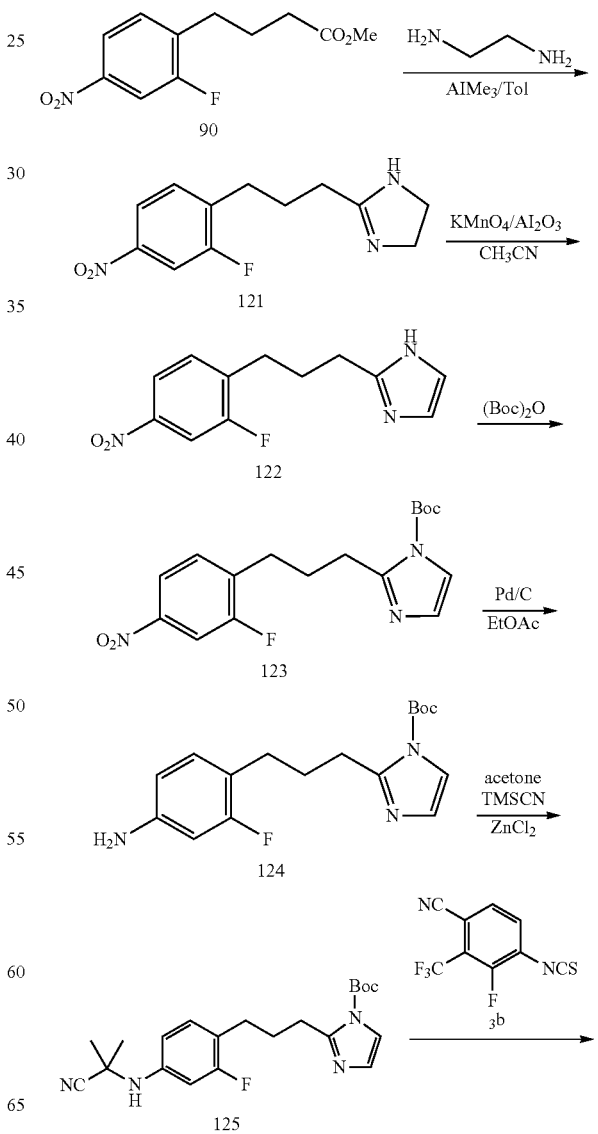

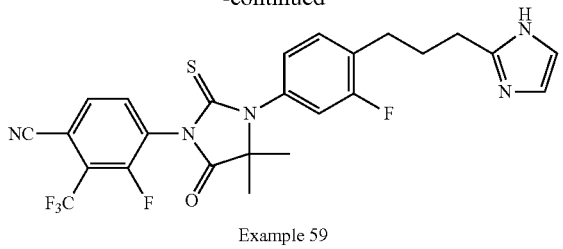

Example 59

Preparation of 2-(3-(2-fluoro-4-nitrophenyl)propyl)-4,5-dihydro-1H-imidazole 121

Ethylenediamine (2.07 mL, 41.5 mmol) was added dropwise to a stirred solution of AlMe3/Tol (32 mL, 2M), so that the temperature did not exceed −20° C. The reaction mixture was stirred at room temperature for 10 min, then to the mixture was added dropwise a solution of the compound 90 (1.5 g, 8.29 mmol) in Tol (50 mL). The reaction mixture was stirred at 100° C. for 20 min. After cooling, the solution was treated dropwise with CH3OH at 0° C., diluted DCM, filtered with over MgSO4. The filtrate was concentrated, and purified with silica gel column chromatography (EtOAc:TEA=1:0.1) to give the compound 121 (938 mg, 45%) as a light yellow solid. 1H NMR (400 MHz, CDCl3) δ7.94-8.00 (m, 1H), 7.86-7.92 (m, 1H), 7.36-7.44 (m, 1H), 3.59 (s, 4H), 2.82 (t, 2H, J=7.6 Hz), 2.28 (d, 2H, J=7.6 Hz), 1.95-2.05 (m, 2H).

Preparation of 2-(3-(2-fluoro-4-nitrophenyl)propyl)-1H-imidazole 122

Compound 121 (888 mg, 3.53 mmol) was first dissolved in acetonitrile (100 mL), with potassium permanganate (1.12 g, 7.07 mmol) and alumina (4.9 g) added into the solution in batch. After stirring the resulting mixture at room temperature for 40 min, CH3OH (1 mL) was added to reduce excess oxidant. The mixture was then filtered and the solid material was washed with DCM:CH3OH=10:1. The filtrate was evaporated to dryness to give the compound 122 (600 mg, 68%) as a light yellow oil. The crude product was used directly for the next step without purification. 1H NMR (400 MHz, CDCl3) δ7.94-7.99 (m, 1H), 7.85-7.91 (m, 1H), 7.35-7.41 (m, 1H), 6.96 (br s, 2H), 2.75-2.85 (m, 4H), 2.06-2.19 (m, 2H).

Preparation of tert-butyl 2-(3-(2-fluoro-4-nitrophenyl)propyl)-1H-imidazole-1-carboxylate 123

To a solution of compound 122 (615 mg, 2.85 mmol) in DCM (20 mL) was added dropwise TEA (1.05 mL, 7.53 mmol) and (Boc)2O (675 mg, 3.01 mmol) at 0° C. with stirring. The reaction mixture was stirred at room temperature for overnight, concentrated and purified with silica gel column chromatography (PE:EtOAc=5:1) to give the compound 123 (718 mg, 82%) as a white solid. 1H NMR (400 MHz, CDCl3) δ7.94-7.99 (m, 1H), 7.85-7.91 (m, 1H), 7.35-7.41 (m, 1H), 7.29-7.31 (m, 1H), 6.85-6.87 (m, 1H), 3.08 (t, 2H, J=7.5 Hz), 2.86 (t, 2H, J=7.7 Hz), 2.10-2.19 (m, 2H), 1.61 (s, 9H).

Preparation of tert-butyl 2-(3-(4-amino-2-fluorophenyl)propyl)-1H-imidazole-1-carboxylate 124

A solution of compound 123 (150 mg, 0.43 mmol) in EtOAc (10 mL) was added Pd/C (25 mg, 10%) under N2. The suspension was degassed under vacuum and purged with H2 several times. The mixture was stirred under H2 balloon at room temperature for 2 h. The suspension was filtered and the solid was washed by EtOAc. The filtrates were concentrated to dryness to give compound 124 (100 mg, 64%) as a light yellow oil. 1H NMR (400 MHz, CDCl3) δ7.28-7.32 (m, 1H), 6.93-6.98 (m, 1H), 6.82-6.86 (m, 1H), 6.30-6.40 (m, 2H), 3.02 (t, 2H, J=7.6 Hz), 2.63 (t, 2H, J=7.6 Hz), 1.97-2.09 (m, 2H), 1.62 (s, 9H).

Preparation of tert-butyl 2-(3-(4-((2-cyanopropan-2-yl)amino)-2-fluorophenyl)propyl)-1H-imidazole-1-carboxylate 125

Compound 125 was synthesized from 124 in a manner similar to the synthesis of compound 120. It was obtained in 96% yield as a yellow oil.

1H NMR (400 MHz, CDCl3) δ7.28-7.32 (m, 1H), 7.05-7.10 (m, 1H), 6.82-6.86 (m, 1H), 6.58-6.62 (m, 2H), 3.64 (br s, 1H), 3.02 (t, 2H, J=7.6 Hz), 2.68 (t, 2H, J=7.6 Hz), 1.97-2.09 (m, 2H), 1.69 (s, 6H), 1.62 (s, 9H).

Synthesis of 2-chloro-4-(3-(4-(3-cyanopropyl)phenyl)-4,4-dimethyl-5-oxo-2-thioxoimidazolidin-1-yl)-3-fluorobenzonitrile Example 59

EXAMPLE 59 was synthesized via a reaction between 3b and 125 following a manner similar to the synthetic procedure of EXAMPLE 15. EXAMPLE 59 was obtained in 45% yield as a light yellow solid.

1H NMR (400 MHz, CDCl3) δ7.75-7.85 (m, 2H), 7.30-7.38 (m, 1H), 6.95-7.08 (m, 4H), 2.91 (t, 2H, J=7.6 Hz), 2.76 (t, 2H, J=7.6 Hz), 2.05-2.20 (m, 2H), 1.58 (d, 6H, J=3.5 Hz). LCMS (M+H)+: 534.7.

Synthesis of 4-(3-(4-(3-(1H-imidazol-2-yl)propyl)-3-fluorophenyl)-4,4-dimethyl-5-oxo-2-thioxoimidazolidin-1-yl)-5-fluoro-2-(trifluoromethyl)benzonitrile Example 60

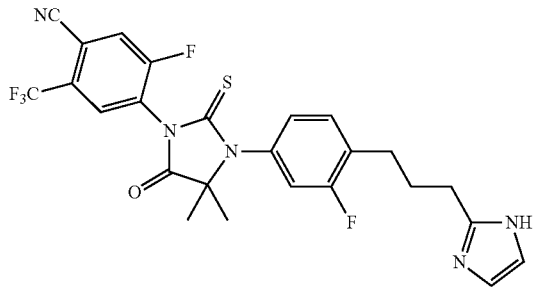

Example 60

EXAMPLE 60 was synthesized via a reaction between 3d and 125 following a manner similar to the synthetic procedure of EXAMPLE 15. EXAMPLE 60 was obtained in 35% yield as a light yellow solid.

1H NMR (400 MHz, CDCl3) δ7.93 (d, 1H, J=6.4 Hz), 7.73 (d, 1H, J=8.3 Hz), 7.31-7.39 (m, 1H), 6.98-7.08 (m, 4H), 2.88 (t, 2H, J=7.6 Hz), 2.77 (t, 2H, J=7.6 Hz), 2.09-2.20 (m, 2H), 1.59 (d, 6H, J=5.6 Hz). LCMS (M+H)+: 534.3.

Synthesis of Examples 61-62

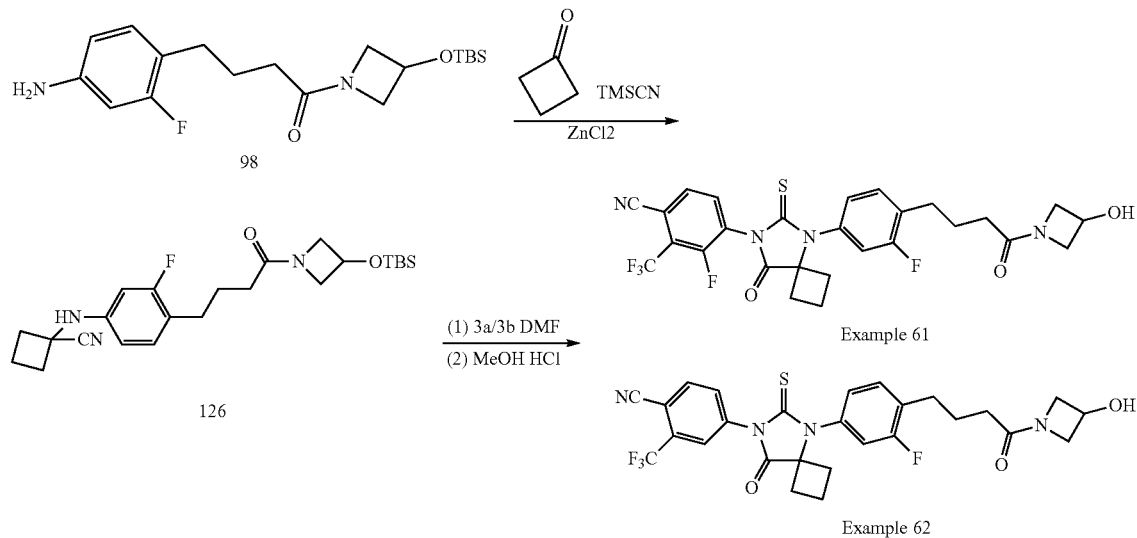

Example 61

Example 62

Preparation of Compound 126

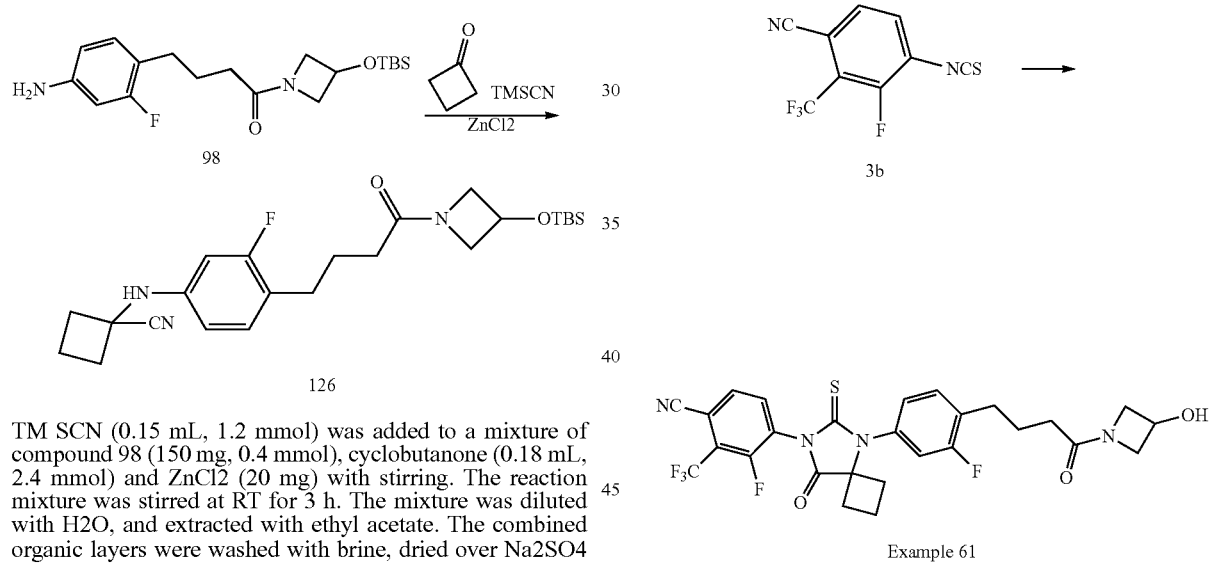

TM SCN (0.15 mL, 1.2 mmol) was added to a mixture of compound 98 (150 mg, 0.4 mmol), cyclobutanone (0.18 mL, 2.4 mmol) and ZnCl2 (20 mg) with stirring. The reaction mixture was stirred at RT for 3 h. The mixture was diluted with H2O, and extracted with ethyl acetate. The combined organic layers were washed with brine, dried over Na2SO4 and concentrated to give compound 126 (200 mg). The crude product was used directly for the next step without purification.

Synthesis of 3-Fluoro-4-(5-{3-fluoro-4-[4-(3-hydroxy-azetidin-1-yl)-4-oxo-butyl]-phenyl}-8-hydroxy-6-thioxo-5,7-diaza-spiro[3.4]oct-7-yl)-2-trifluoromethyl-benzonitrile

Example 61

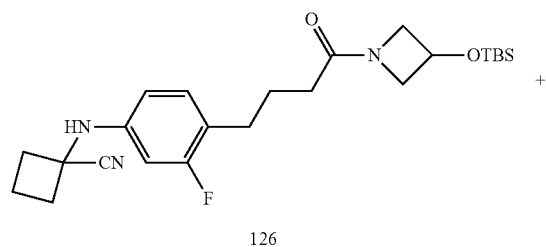

A mixture of compound 126 (100 mg, 0.22 mmol) and 3b (83 mg, 0.33 mmol) in DMF (1.0 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 61 (25 mg, 19.2%) as a white solid.

1H NMR (400 MHz, CDCl3) δ7.83~7.79 (m, 2H), 7.45~7.42 (m, 1H), 7.08~7.05 (m, 2H), 4.69~4.66 (m, 1H), 4.31~4.25 (m, 2H), 3.96~3.85 (m, 2H), 2.81~2.76 (m, 2H), 2.68~2.64 (m, 2H), 2.60~2.55 (m, 2H), 2.23~2.16 (m, 2H), 2.05~2.00 (m, 2H), 1.73~1.69 (m, 2H).

Synthesis of 4-(5-{3-Fluoro-4-[4-(3-hydroxy-azetidin-1-yl)-4-oxo-butyl]-phenyl}-8-oxo-6-thioxo-5,7-diaza-spiro[3.4]oct-7-yl)-2-trifluoromethyl-benzonitrile

Example 62

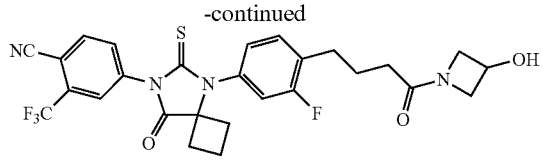

Example 62

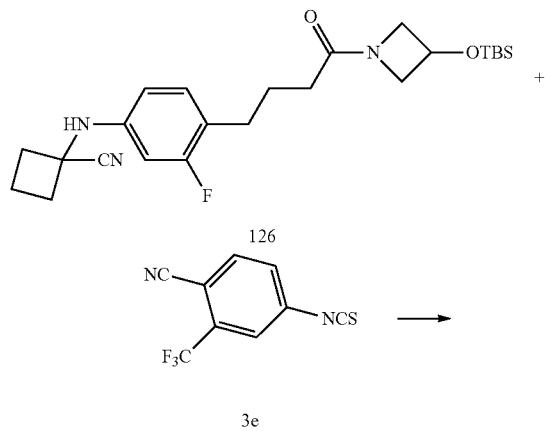

A mixture of compound 126 (100 mg, 0.22 mmol) and 3e (77 mg, 0.33 mmol) in DMF (1.0 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated. The residue was purified with Prep-TLC to give the title compound EXAMPLE 62 (25 mg, 19.9%) as a white solid.

1H NMR (400 MHz, CDCl3) δ7.98~7.96 (m, 2H), 7.85~7.83 (m, 1H), 7.46~7.42 (m, 1H), 7.07~6.99 (m, 2H), 4.70~4.66 (m, 1H), 4.32~4.24 (m, 2H), 3.97~3.85 (m, 2H), 2.81~2.77 (m, 2H), 2.67~2.65 (m, 2H), 2.58~2.55 (m, 2H), 2.25~2.19 (m, 2H), 2.04~2.01 (m, 2H), 1.73~1.67 (m, 2H).

Synthesis of Examples 63-64

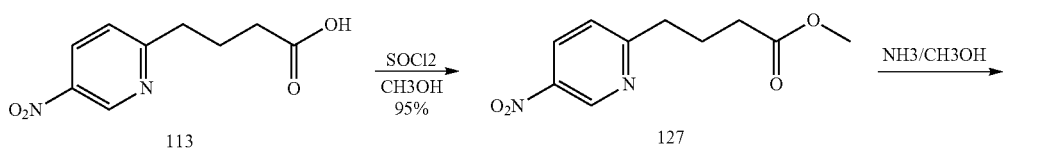

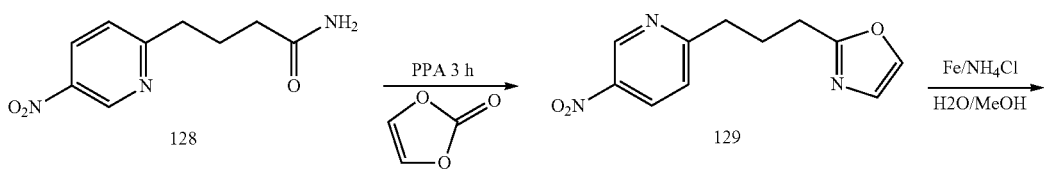

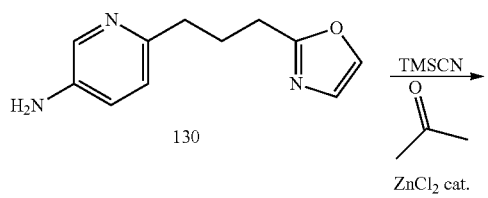

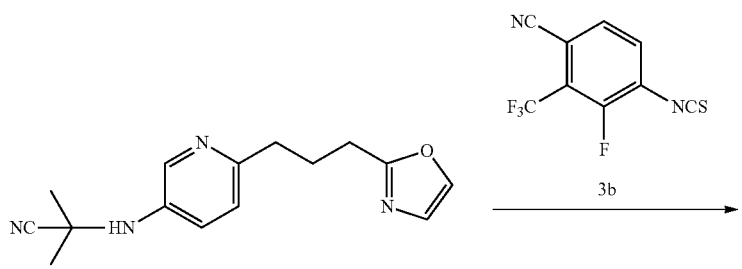

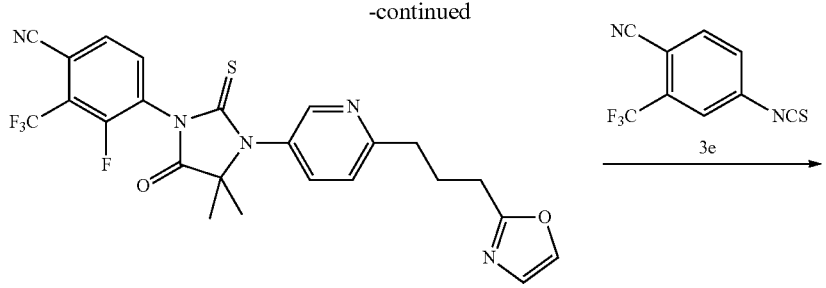

Example 63

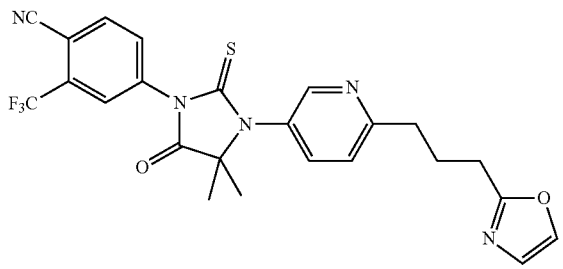

Example 64

Preparation of Compound 127

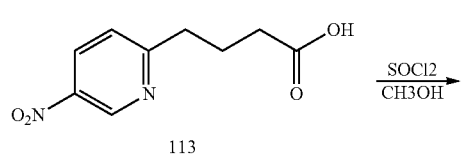

To a solution of compound 113 (5.0 g, 23.8 mmol) in CH3OH (50 mL) was added dropwise thionyl chloride (12.5 mL, 142.7 mmol) at 0° C. with stirring. After addition, the reaction mixture was stirred at 80° C. for 2 h, and then concentrated in vacuo. The residue was diluted with aqNaHCO3, and extracted with ethyl acetate. The combined organic layers were washed with brine, dried over Na2SO4 and concentrated to dryness to give compound 127 (2.9 g, 54.3%).

1H NMR (400 MHz, CDCl3) δ 9.38 (d, J=6.8 Hz, 1H), 8.41~8.38 (m, 1H), 7.38~7.35 (m, 1H), 3.71 (s, 3H), 3.00 (t, J=6.8 Hz, 2H), 2.40 (t, J=7.2 Hz, 2H), 2.20~2.12 (m, 2H).

Preparation of Compound 128

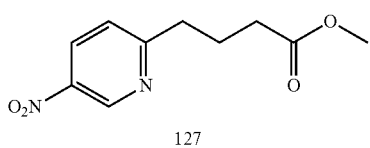

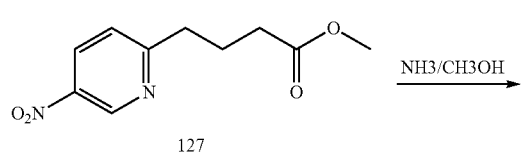

To a solution of compound 127 (500 mg, 2.07 mmol) in NH3H2O (20 mL)/MeOH (20 mL) was stirred at room temperature for 48 h. After removed the most MeOH, the residue was diluted with H2O, and extracted with DCM. The combined organic layers were washed with brine, dried over Na2SO4 and concentrated to give compound 128 (670 mg, 71.8%) as a white solid. The crude product was used directly for the next step without further purification.

1H NMR (400 MHz, CDCl3) δ 9.34 (d, J=2.8 Hz, 1H), 8.40~8.37 (m, 1H), 7.39~7.35 (m, 1H), 6.20~5.52 (br s, 2H), 3.00 (t, J=7.2 Hz, 2H), 2.30 (t, J=7.2 Hz, 2H), 2.15~2.12 (m, 2H).

Preparation of Compound 129

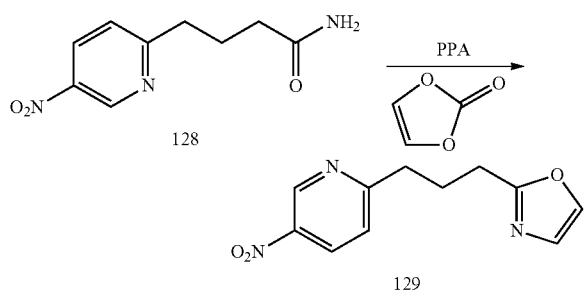

A mixture of compound 128 (570 mg, 2.72 mmol) and vinylene carbonate (281 mg, 3.27 mmol) in polyphosphoric acid (6 g) was heated at 160 deg. C. for 3 h. The residue was added to water and extracted with ethyl acetate. The combined organic extracts were washed with water and brine, dried and evaporated. The residue was purified by column chromatography using petroleum ether:ethyl acetate (4:1) to give the title compound 129 (130 mg, 20.1%).

1H NMR (400 MHz, CDCl3) δ 9.35 (s, 1H), 8.39~8.36 (m, 1H), 7.56 (s, 1H), 7.36 (d, J=8.0 Hz, 1H), 7.01 (s, 1H), 3.01 (t, J=6.8 Hz, 2H), 2.87 (t, J=7.2 Hz, 2H), 2.30~2.26 (m, 2H).

Preparation of Compound 130

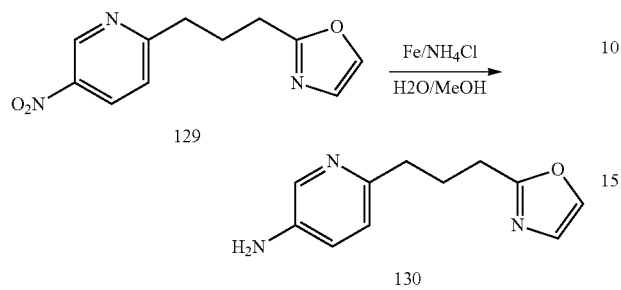

A mixture of compound 129 (200 mg, 0.86 mmol), NH4Cl (458 mg, 8.58 mmol) and Fe (287 mg, 5.15 mmol) in water (10 mL) and CH3OH (15 mL) was stirred at 90° C. for 2 h. After cooling, the reaction mixture was filtered and the solid was washed by DCM. The filtrates were separated, the organic layer was washed with brine, dried over Na2SO4 and concentrated to dryness to give compound 130 (150 mg, 86.1%) as a light yellow oil.

Preparation of Compound 131

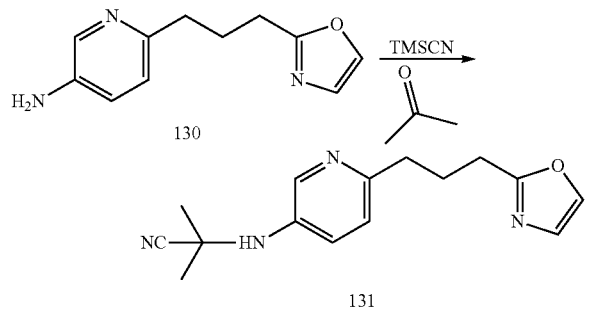

TMSCN (0.24 mL, 1.92 mmol) was added to a mixture of compound 130 (130 mg, 0.64 mmol), acetone (0.50 mL) and ZnCl2 (20 mg) with stirring. The reaction mixture was stirred at RT for 3 h. The mixture was diluted with H2O, and extracted with ethyl acetate. The combined organic layers were washed with brine, dried over Na2SO4 and concentrated to give compound 131 (130 mg, 75.2%) as an oil. The crude product was used directly for the next step without purification.

Synthesis of 4-{4,4-Dimethyl-3-[6-(3-oxazol-2-yl-propyl)-pyridin-3-yl]-5-oxo-2-thioxo-imidazolidin-1-yl}-3-fluoro-2-trifluoromethyl-benzonitrile Example 63

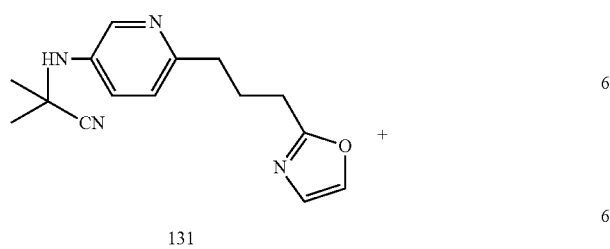

-continued

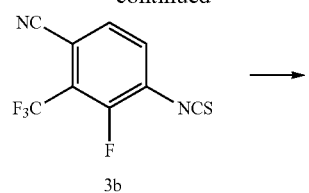

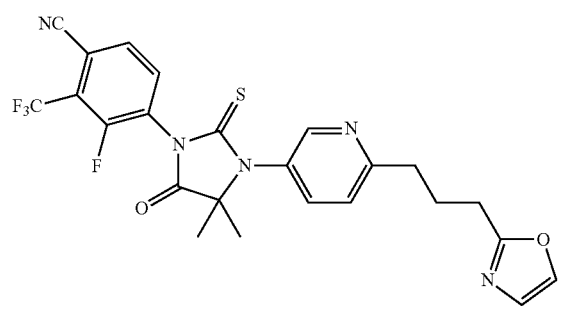

Example 63

A mixture of compound 131 (100 mg, 0.37 mmol) and 3b (136 mg, 0.55 mmol) in DMF (1.0 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo. The residue was purified with Prep-TLC to give the title compound EXAMPLE 63 (30 mg, 15.7%) as a white solid.

1H NMR (400 MHz, CDCl3) δ 8.30 (s, 1H), 7.83~7.76 (m, 2H), 7.61~7.56 (m, 2H), 7.38~7.36 (m, 1H), 7.02 (s, 1H), 3.01~2.98 (m, 2H), 2.92~2.87 (m, 2H), 2.35~2.27 (m, 2H), 1.62 (d, J=3.2 Hz, 6H). LCMS (M+H)+: 518.6.

Synthesis of 4-{4,4-Dimethyl-3-[6-(3-oxazol-2-yl-propyl)-pyridin-3-yl]-5-oxo-2-thioxo-imidazolidin-1-yl}-2-trifluoromethyl-benzonitrile Example 64

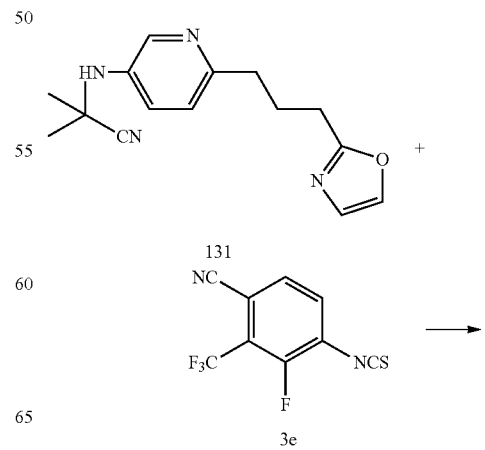

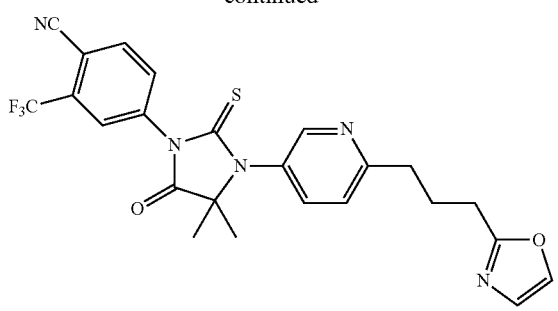

Example 64

A mixture of compound 131 (30 mg, 0.11 mmol) and 3e (38 mg, 0.16 mmol) in DMF (0.7 mL) was stirred at room temperature for overnight. To this mixture was added MeOH (6 mL) and aq. 2N HCl (5 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified with Prep-TLC to give the title compound EXAMPLE 64 (5 mg, 9.1%) as a white solid.

1H NMR (400 MHz, CDCl3) δ 8.51 (s, 1H), 7.98~7.96 (m, 2H), 7.84~7.82 (m, 1H), 7.58~7.57 (m, 2H), 7.38~7.37 (m, 1H), 7.04 (s, 1H), 3.01~2.98 (m, 2H), 2.92~2.88 (m, 2H), 2.33~2.29 (m, 2H), 1.32 (s, 6H). LCMS (M+H)+: 501.5.

Synthesis of 3-Fluoro-4-{5-[6-(3-oxazol-2-yl-propyl)-pyridin-3-yl]-8-oxo-6-thioxo-5,7-diaza-spiro[3.4]oct-7-yl}-2-trifluoromethyl-benzonitrile Example 65

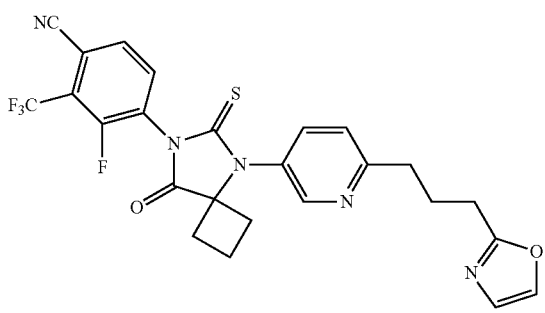

Example 65

EXAMPLE 65 was synthesized through a route similar to the synthesis of Example 63. In the reaction step converting 130 to 131, cyclobutanone instead of acetone was used.

1H NMR (400 MHz, CDCl3) δ 8.52 (d, J=2.4 Hz, 1H), 7.83~7.75 (m, 2H), 7.62~7.57 (m, 2H), 7.42~7.39 (m, 1H), 7.01 (s, 1H), 3.03~2.98 (m, 2H), 2.94~2.91 (m, 2H), 2.73~2.67 (m, 2H), 2.51~2.46 (m, 2H), 2.37~2.29 (m, 2H), 1.73~1.64 (m, 2H). LCMS (M+H)+: 530.2.

Synthesis of Example 66

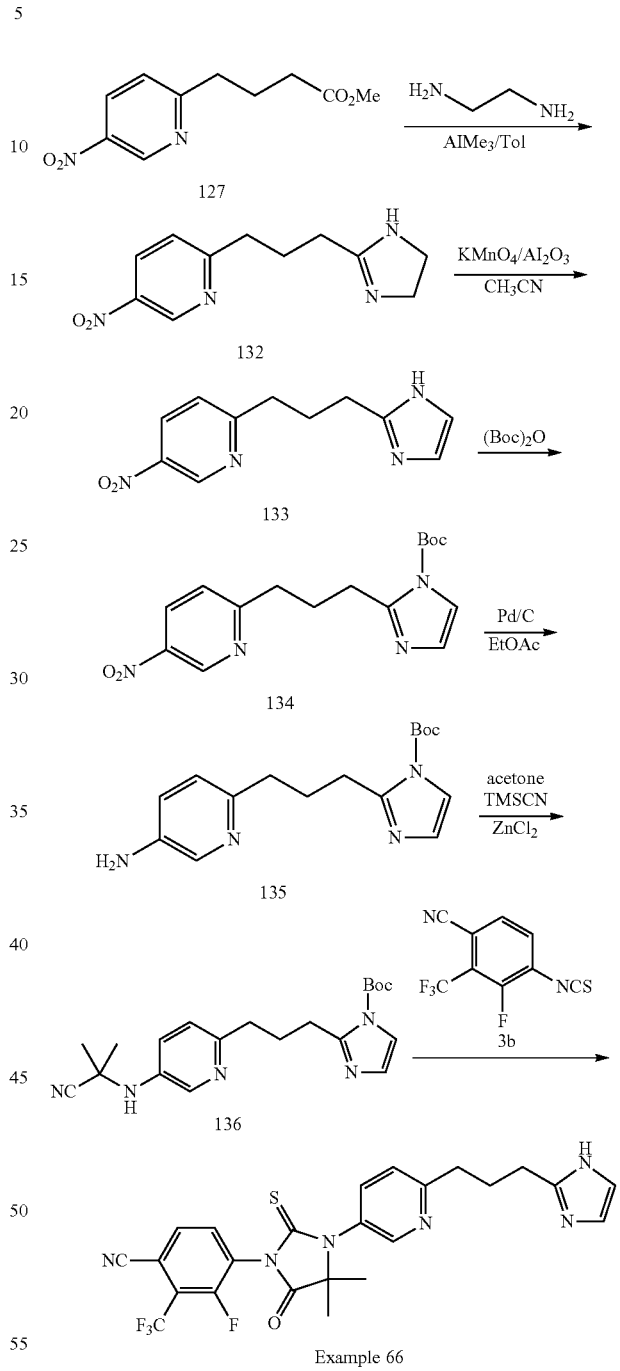

Preparation of 2-(3-(4,5-dihydro-1H-imidazol-2-yl)propyl)-5-nitropyridine 132

Ethylenediamine (1.04 mL, 15.6 mmol) was added dropwise to a stirred solution of AlMe3/Tol (11 mL, 2M), so that the temperature did not exceed –20° C. The reaction mixture was stirred at room temperature for 10 min, then to the mixture was added dropwise a solution of the compound 127 (1 g, 4.5 mmol) in Tol (15 mL). The reaction mixture was stirred at 60° C. for 3 h. After cooling, the solution was treated dropwise with CH3OH at 0° C., diluted DCM, filtered with over MgSO4. The filtrate was concentrated and purified with silica gel column chromatography (EtOAc:CH3OH:TEA=6:1:0.1) to give compound 132 (400 mg, 38%) as a black solid. 1H NMR (400 MHz, CDCl3) δ9.29-9.32 (m, 1H), 8.40-8.45 (m, 1H), 7.50-7.55 (m, 1H), 3.96 (br s, 4H), 3.04 (t, 2H, J=7.6 Hz), 2.83 (d, 2H, J=7.6 Hz), 2.25-2.35 (m, 2H).

Preparation of 2-(3-(1H-imidazol-2-yl)propyl)-5-nitropyridine 133

Compound 132 (400 mg, 1.71 mmol) was first dissolved in acetonitrile (20 mL), with potassium permanganate (952 mg, 5.13 mmol) and alumina (1.2 g) added into the solution in batch. After stirring the resulting mixture at room temperature for 40 min, CH3OH (1 mL) was added to reduce excess oxidant. The mixture was then filtered and the solid material was washed with DCM:CH3OH=10:1. The filtrate was concentrated, and purified with silica gel column chromatography (EtOAc:TEA=1:0.1) to give compound 133 (110 mg, 30%) as a yellow solid. 1H NMR (400 MHz, CDCl3) δ9.32-9.37 (m, 1H), 8.37-8.42 (m, 1H), 7.35-7.41 (m, 1H), 6.97 (br s, 2H), 2.98 (t, 2H, J=7.2 Hz), 2.78 (d, 2H, J=7.2 Hz), 2.17-2.26 (m, 2H).

Preparation of tert-butyl 2-(3-(5-nitropyridin-2-yl)propyl)-1H-imidazole-1-carboxylate 134

To a solution of compound 133 (110 mg, 0.47 mmol) in DCM (10 mL) was added dropwise TEA (0.26 mL, 1.88 mmol) and (Boc)2O (300 mg, 1.37 mmol) at 0° C. with stirring. The reaction mixture was stirred at room temperature for overnight, concentrated and purified with silica gel column chromatography (PE:EtOAc=5:1) to give the compound 134 (110 mg, 71%) as a light yellow oil. 1H NMR (400 MHz, CDCl3) δ9.32-9.37 (m, 1H), 8.37-8.42 (m, 1H), 7.35-7.41 (m, 1H), 7.27-7.31 (m, 1H), 6.85-6.87 (m, 1H), 3.11 (t, 2H, J=7.2 Hz), 3.05 (t, 2H, J=7.6 Hz), 2.23-2.33 (m, 2H), 1.61 (s, 9H).

Preparation of tert-butyl 2-(3-(5-aminopyridin-2-yl)propyl)-1H-imidazole-1-carboxylate 135

A solution of the compound 134 (50 mg, 0.15 mmol) in EtOAc (10 mL) was added Pd/C (10 mg, 10%) under N2. The suspension was degassed under vacuum and purged with H2 several times. The mixture was stirred under H2 balloon at room temperature for 2 h. The suspension was filtered and the solid was washed by EtOAc. The filtrates were concentrated to dryness to give compound 135 (45 mg, 99%) as a light yellow oil. 1H NMR (400 MHz, CDCl3) δ8.02-8.05 (m, 1H), 7.28-7.31 (m, 1H), 6.92-7.02 (m, 2H), 6.82-6.86 (m, 1H), 3.05 (t, 2H, J=7.6 Hz), 2.81 (t, 2H, J=7.6 Hz), 2.10-2.20 (m, 2H), 1.62 (s, 9H).

Preparation of tert-butyl 2-(3-(5-((2-cyanopropan-2-yl)amino)pyridin-2-yl)propyl)-1H-imidazole-1-carboxylate 136

Compound 136 was synthesized from 135 in a manner similar to the synthesis of 131. It was obtained in 98% yield as a yellow oil.

Synthesis of 4-(3-(6-(3-(1H-imidazol-2-yl)propyl)pyridin-3-yl)-4,4-dimethyl-5-oxo-2-thioxoimidazolidin-1-yl)-3-fluoro-2-(trifluoromethyl)benzonitrile Example 66

EXAMPLE 66 was synthesized via a reaction between 3b and 136 following a manner similar to the synthetic procedure of EXAMPLE 15. EXAMPLE 66 was obtained in 36% yield as a light yellow solid.

1H NMR (400 MHz, CDCl3) δ8.50-8.55 (m, 1H), 7.75-7.85 (m, 2H), 7.60-7.65 (m, 1H), 7.38-7.44 (m, 1H), 7.03 (br s, 2H), 2.96 (t, 2H, J=6.8 Hz), 2.88 (t, 2H, J=6.8 Hz), 2.18-2.28 (m, 2H), 1.69 (d, 6H, J=2.0 Hz). LCMS (M+H)+: 517.2.

Synthesis of Example 67

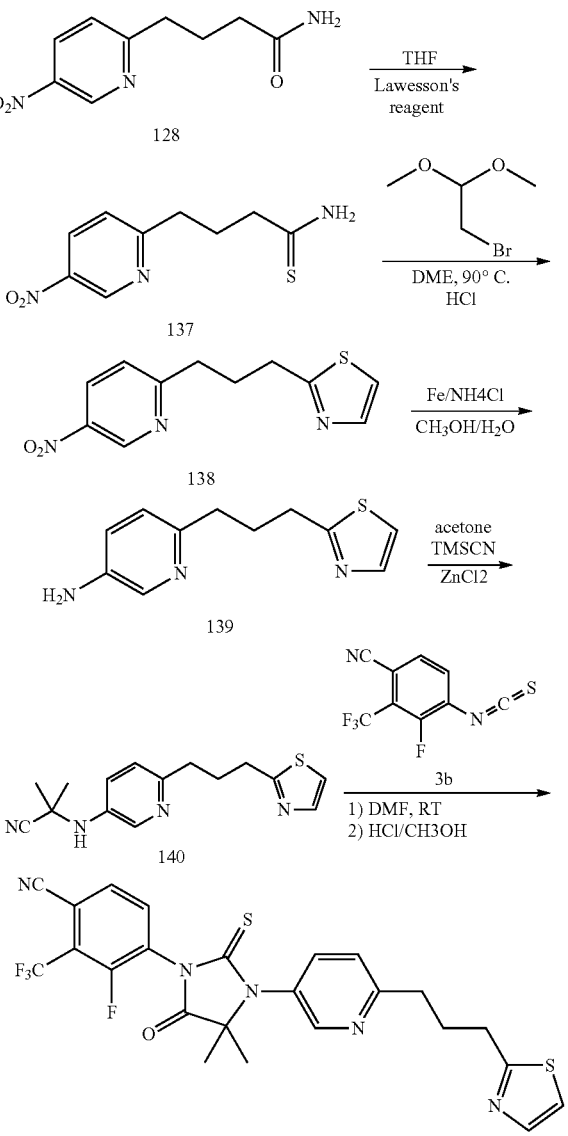

Example 67

Preparation of 4-(5-nitropyridin-2-yl)butanethioamide 137

A solution of compound 128 (1.2 g, 5.7 mmol) and Lawesson's reagent (1.55 g, 3.8 mmol) in THF (50 mL) was stirred at room temperature for 1 h, then was concentrated and purified with silica gel column chromatography (PE:EtOAc=3:1) to give compound 137 (700 mg, 55%) as a light yellow solid. 1H NMR (400 MHz, CDCl3) δ9.25-9.45 (m, 1H), 8.36-8.46 (m, 1H), 7.35-7.45 (m, 3H), 3.04 (t, 2H, J=7.2 Hz), 2.73 (d, 2H, J=7.2 Hz), 2.18-2.35 (m, 2H).

Preparation of 2-(3-(5-nitropyridin-2-yl)propyl)thiazole 138

To a solution of the compound 137 (2.1 g, 9.3 mmol) and 2-bromo-1,1-dimethoxyethane (6.31 g, 37.3 mmol) in DME (100 mL) was added dropwise 10 drops of the concentrated HCl at room temperature. The reaction mixture was stirred at 90° C. for 5 h, treated aq. NaHCO3 and extracted with DCM. The combined organic layers was washed with brine (30 mL), dried over Na2SO4, concentrated and purified with silica gel column chromatography (PE:EtOAc=3:1) to give compound 138 (1.8 g, 76%) as a white solid. 1H NMR (400 MHz, CDCl3) δ9.33-9.38 (m, 1H), 8.34-8.40 (m, 1H), 7.65-7.70 (m, 1H), 7.32-7.36 (m, 1H), 7.18-7.23 (m, 1H), 3.12 (t, 2H, J=7.6 Hz), 3.03 (d, 2H, J=7.2 Hz), 2.25-2.35 (m, 2H).

Preparation of 6-(3-(thiazol-2-yl)propyl)pyridin-3-amine 139

A mixture of compound 138 (2.32 g, 9.3 mmol), NH4Cl (7.46 g, 140 mmol) and Iron Powder (5.19 g, 93 mmol) in water (100 mL) and CH3OH (100 mL) was stirred at 90° C. for 1 h. After cooling, the reaction mixture was filtered and the solid was washed by DCM. The filtrates were separated, the organic layer was washed with brine, dried over Na2SO4 and concentrated to dryness to give compound 139 (2.0 g, 83%) as a light yellow oil.

1H NMR (400 MHz, CDCl3) δ8.00-8.10 (m, 1H), 7.63-7.70 (m, 1H), 7.13-7.20 (m, 1H), 6.92-7.05 (m, 2H), 3.06 (t, 2H, J=7.4 Hz). 2.81 (t, 2H, J=7.4 Hz), 2.16-2.26 (m, 2H).

Preparation of 2-methyl-2-((6-(3-(thiazol-2-yl)propyl)pyridin-3-yl)amino)propanenitrile 140

TMSCN (3.7 mL, 27.9 mmol) was added to a mixture of the compound 139 (2.04 g, 9.3 mmol), acetone (4.1 mL, 55.8 mmol) and ZnCl2 (122 mg, 0.9 mmol) with stirring. The reaction mixture was stirred at 40° C. for 0.5 h, and concentrated in vacuo. The residue was diluted with water, and extracted with DCM. The combined organic layers were washed with brine, dried over Na2SO4 and concentrated to dryness to give compound 140 (2.6 g, 99%) as a light yellow oil. The crude product was used directly for the next step without purification.

1H NMR (400 MHz, CDCl3) δ8.18-8.32 (m, 1H), 7.62-7.80 (m, 1H), 7.26-7.40 (m, 1H), 7.18-7.25 (m, 1H), 7.08-7.16 (m, 1H), 3.10 (t, 2H, J=7.6 Hz), 2.87 (t, 2H, J=7.6 Hz), 2.15-2.25 (m, 2H), 1.70 (s, 6H).

Synthesis of 4-(4,4-dimethyl-5-oxo-3-(6-(3-(thiazol-2-yl)propyl)pyridin-3-yl)-2-thioxoimidazolidin-1-yl)-3-fluoro-2-(trifluoromethyl)benzonitrile

Example 67

A mixture of 140 (2.66 g, 9.3 mmol) and 3b (3.43 g, 14.0 mmol) in DMF (1 mL) was stirred at room temperature for overnight. To this mixture was added CH3OH (15 mL) and aq. 3N HCl (15 mL). The second mixture was refluxed for 2 h. After being cooled to room temperature, the reaction mixture was poured into cold water and extracted with DCM. The combined organic layers were washed with aq.NaHCO3 and brine, dried over Na2SO4 and concentrated in vacuo to dryness. The residue was purified with silica gel column chromatography (PE:EtOAc=2:1) to give the compound EXAMPLE 67 (2.0 g, 45%) as a light yellow solid. 1H NMR (400 MHz, CDCl3) δ8.50-8.55 (m, 1H), 7.72-7.85 (m, 2H), 7.68-7.72 (m, 1H), 7.57-7.65 (m, 1H), 7.37-7.44 (m, 1H), 7.22-7.26 (m, 1H), 3.20 (t, 2H, J=7.6 Hz), 3.03 (t, 2H, J=7.6 Hz), 2.32-2.42 (m, 2H), 1.59 (d, 6H, J=2.8 Hz). LCMS (M+H)+: 534.2

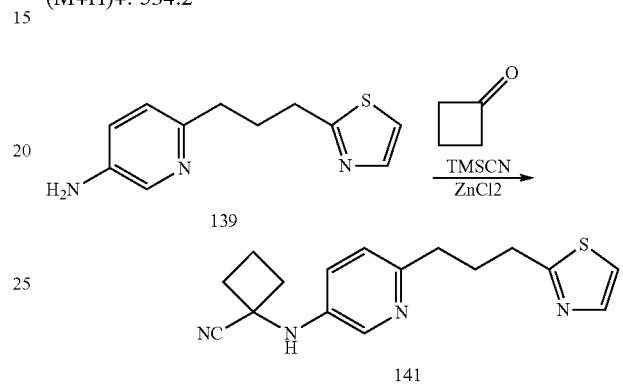

Preparation of 1-((6-(3-(thiazol-2-yl)propyl)pyridin-3-yl)amino)cyclobutanecarbonitrile 141

TMSCN (0.13 mL, 0.96 mmol) was added to a mixture of compound 139 (70 mg, 0.32 mmol), cyclobutanone (0.15 mL, 1.92 mmol) and ZnCl2 (4 mg, 0.03 mmol) with stirring. The reaction mixture was stirred at room temperature for 5 h, and concentrated in vacuo. The residue was diluted with water, and extracted with DCM. The combined organic layers were washed with brine, dried over Na2SO4 and concentrated to dryness to give compound 141 (90 mg) as a light yellow oil. The crude product was used directly for the next step without purification.

Synthesis of 3-fluoro-4-(8-oxo-5-(6-(3-(thiazol-2-yl)propyl)pyridin-3-yl)-6-thioxo-5,7-diazaspiro[3.4]octan-7-yl)-2-(trifluoromethyl)benzonitrile

Example 68

Example 68

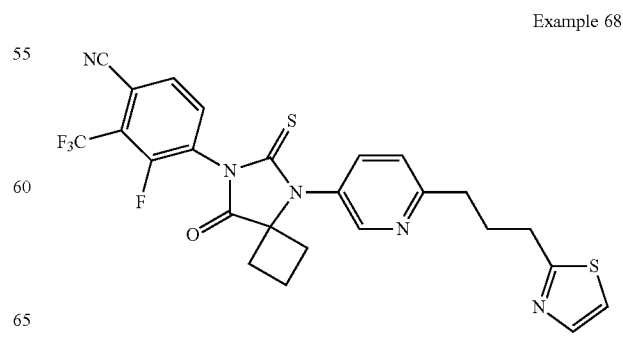

EXAMPLE 68 was synthesized via a reaction between 3b and 141 following a manner similar to the synthetic procedure of EXAMPLE 15. EXAMPLE 68 was obtained in 4% yield as a white solid.

1H NMR (400 MHz, CDCl3) δ8.50-8.55 (m, 1H), 7.72-7.85 (m, 2H), 7.68-7.72 (m, 1H), 7.57-7.65 (m, 1H), 7.38-7.44 (m, 1H), 7.18-7.22 (m, 1H), 3.19 (t, 2H, J=7.2 Hz), 3.03 (t, 2H, J=7.2 Hz), 2.64-2.76 (m, 2H), 2.44-2.56 (m, 2H), 2.32-2.42 (m, 2H), 2.20-2.30 (m, 1H), 1.65-1.76 (m, 1H). LCMS (M+H)+: 546.2.

Preparation of 3f

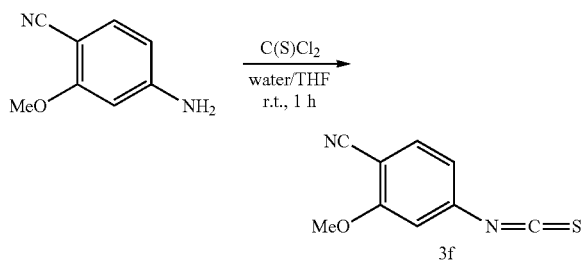

Compound 3f was prepared from 4-amino-2-methoxy-benzonitrile in a manner similar to synthesis of 3b.

Synthesis of 4-(4,4-dimethyl-5-oxo-3-(6-(3-(thiazol-2-yl)propyl)pyridin-3-yl)-2-thioxoimidazolidin-1-yl)-2-methoxybenzonitrile Example 69

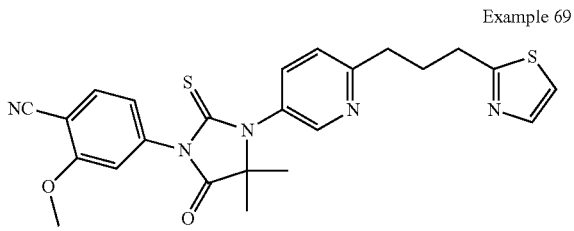 [SMILES: COc1cc(N2C(=O)C(C)(C)N(c3ccc(CCCc4nccs4)nc3)C2=S)ccc1C#N]

Example 69

EXAMPLE 69 was synthesized via a reaction between 3f and 140 following a manner similar to the synthetic procedure of EXAMPLE 15. EXAMPLE 69 was obtained in 6% yield as a white solid.

1H NMR (400 MHz, CDCl3) δ8.50-8.55 (m, 1H), 7.68-7.72 (m, 2H), 7.60-7.65 (m, 1H), 7.34-7.40 (m, 1H), 7.18-7.22 (m, 1H), 7.05-7.14 (m, 2H), 3.97 (br s, 3H), 3.17 (t, 2H, J=7.2 Hz), 3.03 (t, 2H, J=7.2 Hz), 2.32-2.42 (m, 2H), 1.59 (s, 6H). LCMS (M+H)+: 478.2

Following similar methods as above and utilizing the appropriate reagents, compounds of the invention having $Y_1$ as —S— or —NR"—, wherein R" is hydrogen, alkyl, alkenyl or alkynyl, are readily synthesized. For example, the compounds of formula (I) wherein $Y_1$ is —S— may be synthesized via a route similar to the synthesis of Example 15 or Example 17 in which the starting material 42 or 48 is replaced with 42S or 48S, respectfully.

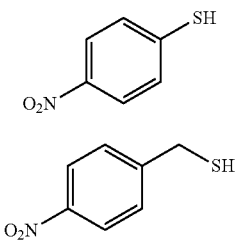

42S

48S

The compounds of formula (I) wherein $Y_1$ is —NR"— may be synthesized via a route similar to the synthesis of Example 15 or Example 17 in which the starting material 42 or 48 is replaced with 42N or 48N, respectfully. When R" is hydrogen, the nitrogen in —NH— may be protected with for example but not limited to a Boc group, which can be cleaved during the HCl treatment of the final step of the Example synthesis.

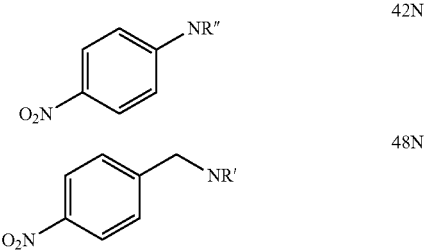

42N

48N

Test Examples

Biological Activity

The compounds of the present invention are antagonist of the androgen receptor. Certain compounds have potent antagonistic activity (IC50<1 μM) without any significant agonism. As discussed in the background section, selective antagonists are useful for treatment of androgen receptor-associated conditions, especially for prostate cancer including hormone sensitive and hormone refractory disease. The compounds of the present invention can be used alone or in combination with one or more other therapeutic agent(s).

The compounds in the present invention were screened by testing on hormone sensitive (LNCaP, LAPC4, VCAP) and hormone refractory prostate cancer cells (LNCaP-AR, LAPC4-AR, LNCaP C4-2, 22RV1, LNCaP-AI and LNCaP-abl) for antagonistic and agonistic activities. Prostate specific antigen (PSA) level can also be used as a marker for androgen receptor antagonistic activity. The MTS assay is also used to evaluate the present compounds for potency of inhibiting cell growth. The selective, potent androgen receptor antagonists with acceptable rodent oral bioavailability are further evaluated for in vivo efficacy using prostate cancer xenografts. The cell lines used can be selected from LNCaP, LAPC4, LAPC9, CWR22, LNCaP-AR, LNCaP C4-2, 22RV1, VCAP, LNCaP-abl and LNCaP-AI.

PSA Assay (Inhibition Test of the Compound of the Present Invention on Prostate-Specific Antigen (PSA) Production in Various Prostate Cancer Cells).

Androgen dependent LNCaP cells were purchased from the American Type Culture Collection (ATCC, Manassas, Va.). These cells were grown in RPMI 1640 medium supplemented with 10% fetal bovine serum (FBS), 100 U/mL penicillin, 100 µg/mL streptomycin, and 0.25 µg/mL amphotericin B. The cells were maintained at 37° C. and 5% $CO_2$. LNCaP cells between passage 20 and 35 were used for experiments. LNCaP is a hormone sensitive cell line. For the PSA assay, human prostate cancer cells LNCaP were seeded in a 96-well plate at a concentration of 5000 cells/100 µl/well. On the following day, Methyltrienolone (R1881, AR agonist) (final concentration 1 ng/ml), test compounds or bicalutamide (Casodex®, AstraZeneca) (final concentration 0.005 to 20 µM) were added. Three days after the addition, the concentration of PSA in the supernatant of the culture solution was measured by ELISA. ELISAs for human PSA in culture medium were performed using the ultra-sensitive assay procedure and reagents in the Active™ PSA assay kit (Diagnostic Systems Laboratories Inc., Webster, Tex.). Culture medium and standards (200 µl/well) were incubated in antibody-coated plates for 2 h at room temperature on a Titer plate shaker at 500-600 rpm. Wells were then washed five times. The HRP conjugate was diluted 1:20 with assay buffer, and 100 µl was added to all wells. The plates were incubated for 30 min at room temperature on the shaker and washed as before, and 100 µl TMB (3,3',5,5'-tetramethylbenzidine, 0.4 g/l) was added. The plates were incubated for 10 min on the shaker, and the reaction was terminated with 100 µl stop solution. The plates were read using a plate reader at 450 nm with a 650 nm reference filter. PSA levels were normalized for differences in growth of LNCaP cells following various treatments as determined by the MTS assay. $IC_{50}$ of PSA was calculated based on a seven point assay (concentrations of tested compound) and expressed as micromolar (uM). The results are shown in Table 1.

TABLE 1

Inhibition of PSA production in prostate cancer cells for example compounds

| Example Number | LNCAP $IC_{50}$ (uM) |
|---|---|
| Bicalutamide | 3.1 |
| 1 | 1.34 |
| 2 | 1.45 |
| 3 | 7.83 |
| 4 | 14.4 |
| 5 | 0.37 |
| 6 | 4.75 |
| 7 | 0.65 |
| 8 | 0.43 |
| 9 | 0.59 |
| 10 | 0.42 |
| 11 | 0.54 |
| 12 | 0.61 |
| 13 | 1.06 |
| 14 | 0.69 |
| 15 | 0.45 |
| 16 | 0.58 |
| 17 | 0.53 |
| 18 | 0.56 |
| 19 | 0.76 |
| 20 | 2.14 |
| 21 | 1.83 |
| 22 | 0.6 |
| 23 | 0.89 |
| 24 | 1.09 |
| 25 | 0.82 |
| 26 | 0.97 |
| 27 | 0.47 |
| 28 | 0.11 |
| 29 | 0.29 |
| 30 | 0.29 |
| 31 | 0.53 |
| 32 | 0.36 |
| 33 | 0.64 |
| 34 | 0.62 |
| 35 | 0.44 |
| 36 | 0.35 |
| 37 | 0.65 |
| 38 | 0.52 |
| 39 | 0.75 |
| 40 | 0.3 |
| 41 | 0.32 |
| 42 | 0.85 |
| 43 | 0.59 |
| 44 | 0.11 |
| 45 | 2.05 |
| 46 | 0.63 |
| 47 | 0.48 |
| 48 | 1.04 |
| 49 | 0.49 |
| 51 | 0.39 |
| 53 | 0.41 |
| 55 | 1.2 |
| 56 | 3.64 |
| 57 | 1.91 |
| 58 | 0.53 |
| 59 | 0.48 |
| 60 | 3.3 |
| 61 | 0.19 |
| 63 | 0.10 |
| 64 | 0.45 |
| 65 | 0.6 |
| 66 | 1.27 |
| 67 | 0.27 |
| 68 | 0.61 |
| 69 | 0.68 |

As is clear from Table 1, the preferred compounds of the present invention showed a higher PSA production suppressing potency in prostate cancer cells, as compared with bicalutamide.

Cell Viability Assays

LNCaP and 22RV1 cells can be maintained in RPMI 1640 medium supplemented with 10% fetal bovine serum (FBS), 100 U/mL penicillin, 100 µg/mL streptomycin, and 0.25 µg/mL amphotericin B, splitting cells when they reach 80-90% confluence. In order to test compounds, 10,000 cells/well are plated in 96 cell culture plates using 100 ul/well plating medium, are cultured overnight at 37° C. in a cell culture incubator. After carefully remove plating medium, 80 µl/well of pre-warmed assay medium is added, followed by adding 10 µl/well test compounds or bicalutamide (final concentration from 20 uM to 0.1 uM), incubated at 37° C. for 30 minutes, then adding 10 µl/well freshly prepared Methyltrienolone (R1881, AR agonist) (final concentration 1 ng/ml) to each well, incubate at 37° C. for 48-hour. At the end of incubation, 20 µl MTT (2.5 mg/ml in PBS) is added to each well, and the cells are further incubated for 2 h at 37 C to allow a complete reaction between the dye and the enzyme mitochondrial dehydrogenase in the viable cells. After removal of the residual dye and medium, 100 µA dimethylsulfoxide was added to each well, and the absorbance at 570 nm is measured with a microplate reader. The fold induction over background by 1 nM R1881 in the absence of test compounds is standardized as 100% and experimental result is expressed as percentage of inhibition by testing compounds at 2.5 micromolar (uM). Using this method, inhibition of cell growth can be determined.

Tumor Xenograft Models

More potent inhibitors in the PSA assays or cell viability assays mentioned above with appropriate pharmacokinetic properties can be further evaluated in mouse tumor xenograft models (e.g. LNCAP, 22rvl, VCAP) for in vivo efficacy. In these studies, tumor cell are implanted into immunodeficient animals, and the effect of the compound on tumor cell survival, growth and metastasis, among other properties, is evaluated by administration of the test compound to the animal, generally starting at different times after implantation. Using this assay compounds can be shown to demonstrate ability to suppress tumor growth when the mice are treated with the compounds. More preferably, compounds can prevent the regrowth growth of the tumors even after the drug treatment (4-6 weeks) has been stopped.

C57BL/6 Mouse Hair Growth Model

Six- to 8-wk-old male C57BL/6 mice in the telogen stage of the hair cycle, weighing 15-20 g, are purchased and housed in community cages under standard conditions. The growth phase of the hair cycle (anagen) is induced in the back skin of mice with all follicles in the resting phase of the hair cycle (telogen; as judged from their homogeneously pink skin color) by being shaved on the lower back using an electric shaver under mild anesthesia. Only mice in the telogen phase (pink skin) are used in the studies. Twenty microliters of test article at two concentrations in propylene glycol/ethanol (30:70, v/v) or the vehicle control is topically applied to the shaved lower back of the mice to cover an area of approximately 1 cm² (20 uL/cm²). Five mice are used in each group. The mice are treated with the compound by topical application twice daily (BID) for 4 weeks. Local irritation is recorded daily before each application, and hair growth scores are recorded twice per week. The scoring system for mouse hair growth is 0 to 4: 0=no hair growth, pink skin color; 1=skin color in shaved area changes from pink to gray without visible hair growth, indicating the onset of anagen; 2=skin color in shaved area is black with tiny hairs; 3=short black hair in shaved area; and 4=hair in shaved area is almost close to surrounding area. A reference androgen receptor antagonist (RU-58841) is included in all studies as comparison.

What we claim is:

1. A compound of formula (I):

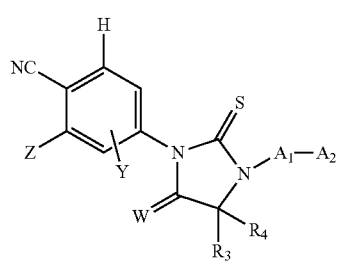

(I)

or a pharmaceutically-acceptable salt, solvate, or hydrate, prodrug or derivative thereof, wherein Z is selected from $CF_3$, $C_1$-$C_3$ alkoxy, $CF_3O$, halogen, cyano or $C_1$-$C_4$ alkyl optionally substituted with one or more halogens;

Y is selected from halogen, $C_1$-$C_3$ alkoxy, hydroxyl, $CF_3O$ or cyano;

W is selected from oxygen, sulfur and two hydrogens;

$R_3$ and $R_4$ are independently represent $C_1$-$C_4$ alkyl optionally substituted with one or more fluoro or hydroxyl groups, or alternatively, $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen;

$A_1$ is an aryl group or heteroaryl group optionally substituted with one or more $C_1$-$C_4$ alkyl, cyano, hydroxyl, methoxy, ethoxy, halogen or a 5-6 membered heteroaryl group;

$A_2$ is $(CF_2)(CH_2)_m Y_1 (CH_2)_n Q$ wherein m and n are integers independently selected from 0 to 4 and wherein at least one of m or n is not zero, or $A_2$ is $(CH_2)_m Y_1 (CH_2)_n Q$ wherein m and n are integers independently selected from 0 to 4 and wherein at least one of m or n is not zero;

wherein when $Y_1$ is —O—, —S—, or —NR", Q is C(O)NHR", C($R_x R_y$)C(O)NR"$R_1$", cyano, hydroxyl, $C_1$-$C_3$ alkoxy, C(O)OR", OC(O)NR"$R_1$", C(O)NR"$R_1$", optionally substituted 5-6 membered heteroaryl, or an optionally substituted 4-6 membered heterocycle, and wherein R" and $R_1$" are independently selected from hydrogen, $C_1$-$C_6$ alkyl, $C_1$-$C_6$ cycloalkyl and $C_1$-$C_6$ alkenyl, or NR"$R_1$" together form a 3-7 membered heterocyclic ring wherein one or more carbons may be optionally substituted with one or more hydroxyl, amino, cyano or fluoro groups; or wherein when $Y_1$ is a direct bond, Q is an optionally substituted 5-6 membered heteroaryl or an optionally substituted 4-6 membered heterocycle; or wherein when $Y_1$ is a direct bond, Q is C(O)NR"$R_1$", wherein NR"$R_1$" together form a 3-7 membered heterocyclic ring wherein one or more carbons may be optionally substituted with one or more hydroxyl, amino, cyano or fluoro groups; and $R_x$ and $R_y$ are methyl; or C($R_x R_y$) together form an optionally substituted 3-5 membered cyclic alkyl ring or a 3-5 membered cyclic ring wherein one carbon is replaced with an oxygen or an amine.

2. The compound of claim 1 wherein $A_1$ is an phenyl group or pyridyl group optionally substituted with one or more $C_1$-$C_4$ alkyl, cyano, hydroxyl, methoxy, ethoxy, halogen or a 5-6 membered heteroaryl group.

3. The compound of claim 1 wherein Q is an optionally substituted 5-6 membered heteroaryl group.

4. The compound of claim 1 wherein Q is

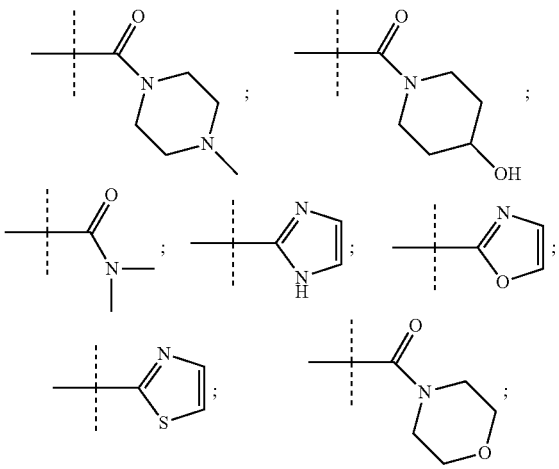

191
-continued
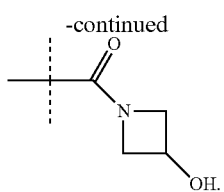
5. The compound of claim 1 wherein m+n is 2 or 3.
6. The compound of claim 1 wherein $Y_1$ is a direct bond and Q is an optionally substituted 5-6 membered heteroaryl group or an optionally substituted 4-6 membered heterocycle group.
7. The compound of claim 6 wherein Q is an optionally substituted 5-6 membered heteroaryl group.
8. The compound of claim 1 represented by
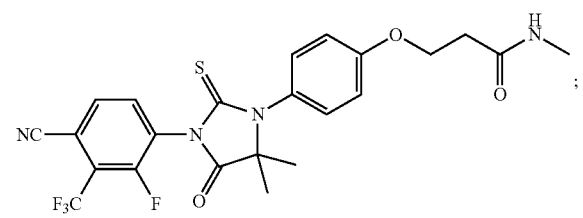
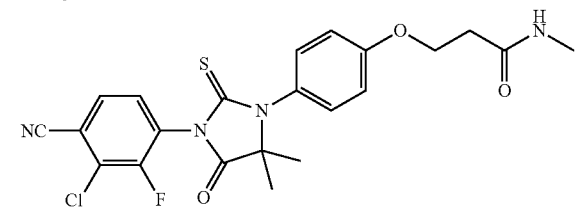
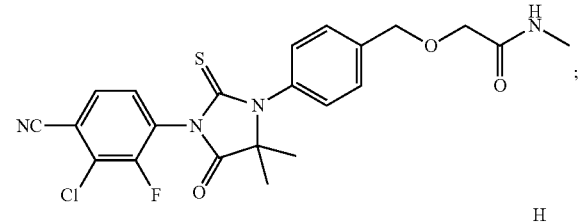
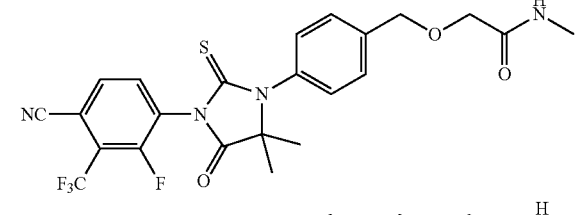
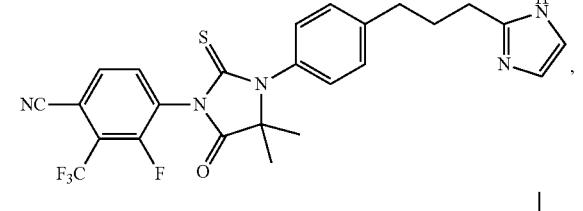
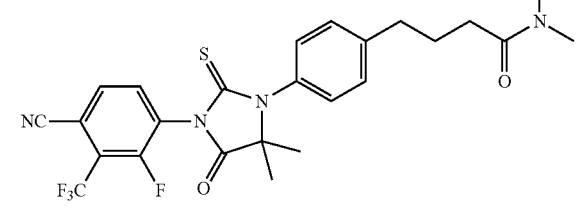
192
-continued
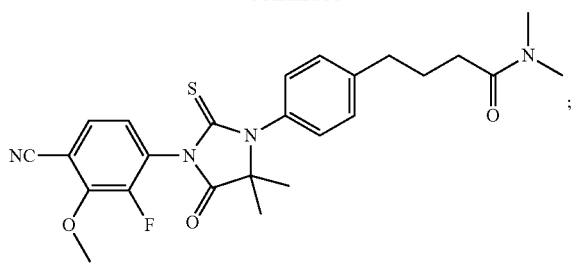
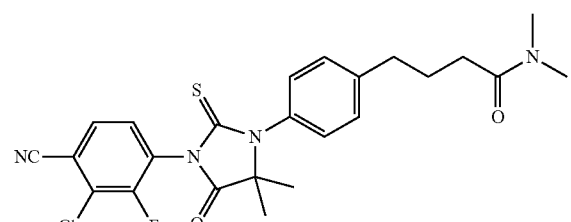
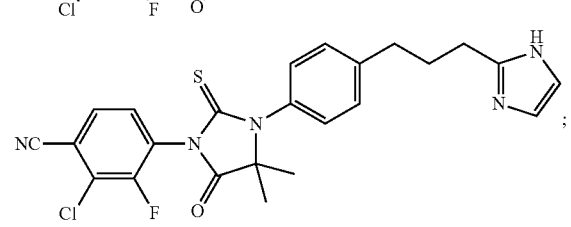
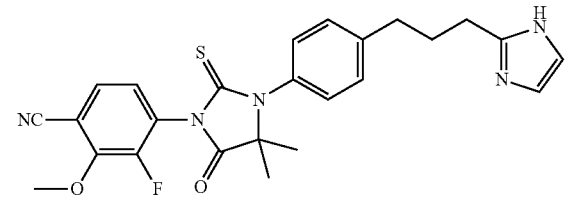
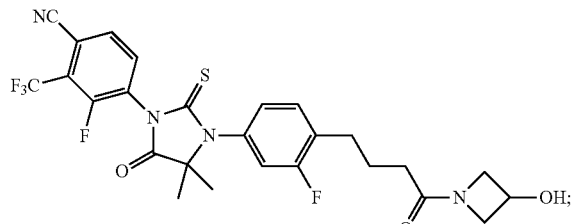
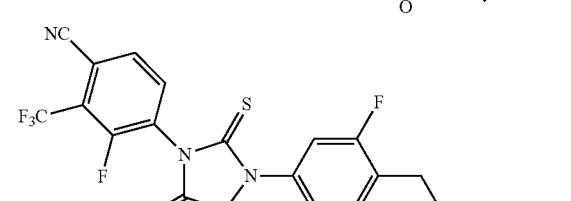
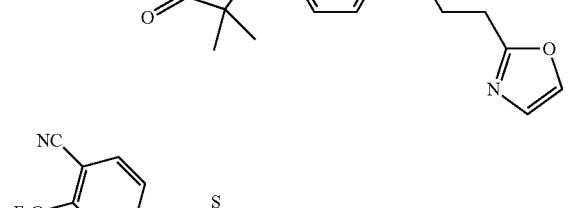
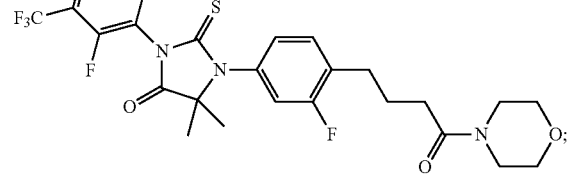

-continued

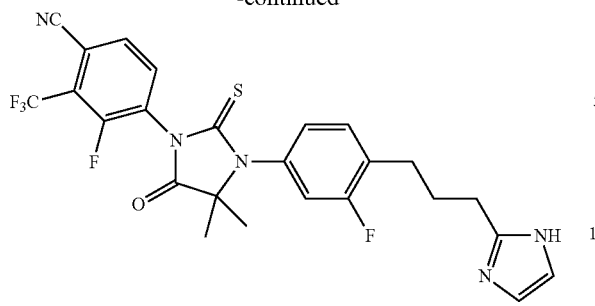

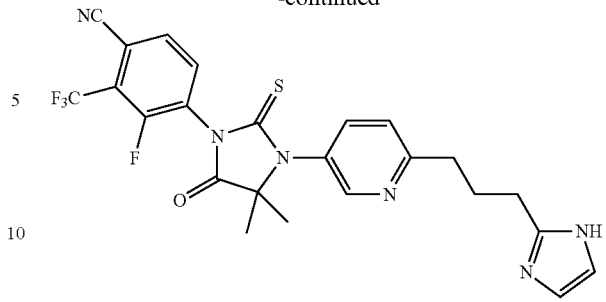

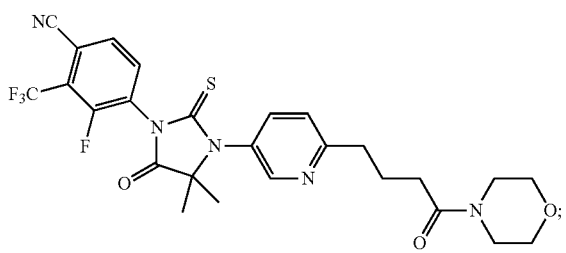

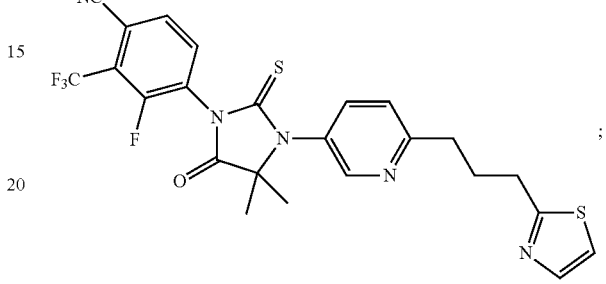

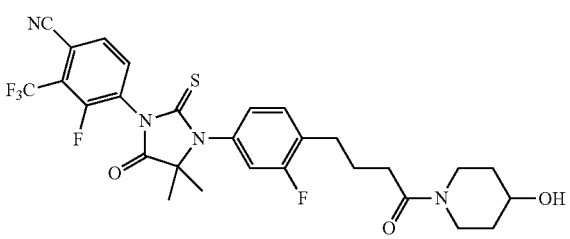

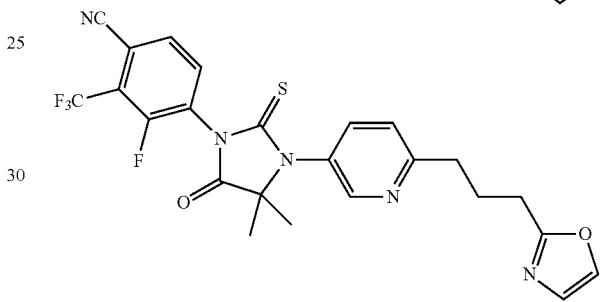

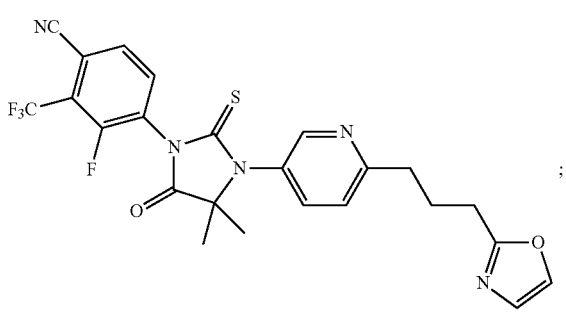

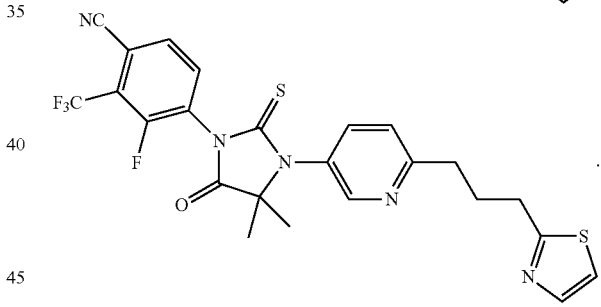

;

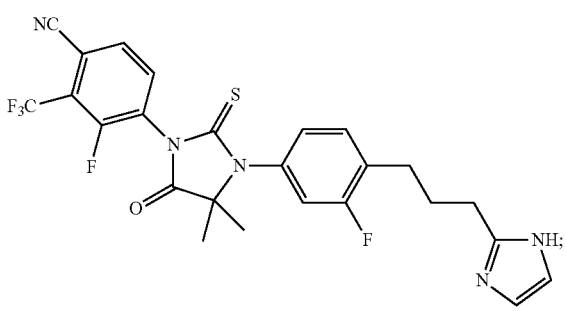

9. A pharmaceutical composition comprising a compound of claim 1 and a pharmaceutically-acceptable carrier, diluent or excipient.

10. A topical pharmaceutical formulation comprising a compound according to claim 1 for dermal applications, and a pharmaceutically acceptable carrier, diluent or excipient.

11. A method for reducing the progression of, treating or regressing a disease or disorder related to androgen receptor activity by administering to a subject afflicted therewith, a compound of claim 1 or a pharmaceutical composition thereof, wherein the disease or disorder is hormone sensitive prostate cancer or hormone refractory prostate cancer, benign prostatic hyperplasia, acne, excess sebum or alopecia.

12. A method for treating hormone sensitive prostate cancer or hormone refractory prostate cancer, benign prostatic hyperplasia, acne, excess sebum or alopecia by administering to a subject afflicted therewith, a compound of claim 1 or a pharmaceutical composition thereof.

13. A method for reducing the progression of, treating or regressing a disease or disorder selected from hormone sensitive prostate cancer or hormone refractory prostate cancer, benign prostatic hyperplasia, acne, excess sebum or alopecia, comprising administering to a subject afflicted therewith a compound of claim 1 or a pharmaceutical composition thereof.

14. A method for halting or causing a regression of prostate cancer comprising administering to a subject a compound of claim 1 or a pharmaceutical composition thereof.

\* \* \* \* \*

UNITED STATES PATENT AND TRADEMARK OFFICE
CERTIFICATE OF CORRECTION

PATENT NO. : 9,216,957 B2
APPLICATION NO. : 14/003547
DATED : December 22, 2015
INVENTOR(S) : Youzhi Tong Page 1 of 2

It is certified that error appears in the above-identified patent and that said Letters Patent is hereby corrected as shown below:

In the specification,

Column 1, line 6, delete "Aug. 3, 2012" and insert --Mar. 8, 2012-- therefor.

In the claims,

In claim 8, column 193, line 46-57, delete entire contents of line 46-57 and insert

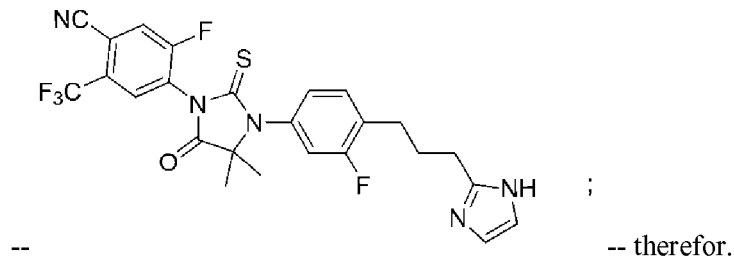

--      -- therefor.

In claim 8, column 194, line 23-34, delete entire contents of line 23-34 and insert

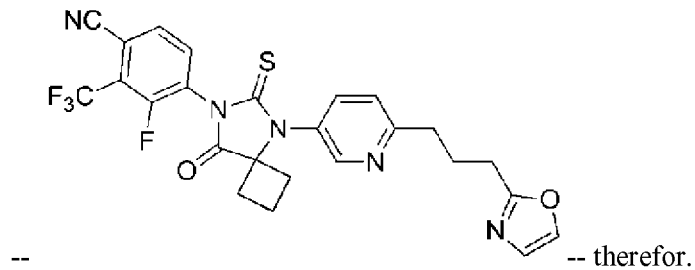

--      -- therefor.

In claim 8, column 194, line 35-46, delete entire contents of line 35-46 and insert Signed and Sealed this
Fifth Day of April, 2016

Michelle K. Lee
*Director of the United States Patent and Trademark Office*

CERTIFICATE OF CORRECTION (continued)
U.S. Pat. No. 9,216,957 B2

-- 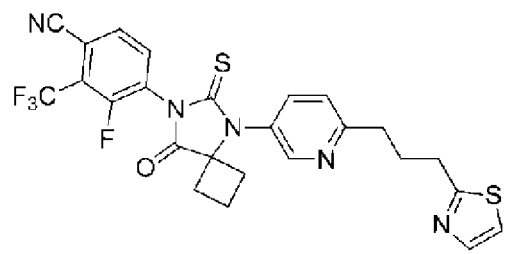 -- therefor.